(12) United States Patent
Glackin et al.

(10) Patent No.: US 10,519,442 B2
(45) Date of Patent: Dec. 31, 2019

(54) TWIST SIGNALING INHIBITOR COMPOSITIONS AND METHODS OF USING THE SAME

(71) Applicants: City of Hope, Duarte, CA (US); The Regents of the University of California, Oakland, CA (US)

(72) Inventors: Carlotta A. Glackin, Duarte, CA (US); John Rossi, Azusa, CA (US); Jeffrey I. Zink, Los Angeles, CA (US); Fuyuhiko Tamanoi, Los Angeles, CA (US); Cai M. Roberts, Duarte, CA (US); James Finlay, Duarte, CA (US)

(73) Assignee: City of Hope, Duarte, CA (US)

(*) Notice: Subject to any disclaimer, the term of this patent is extended or adjusted under 35 U.S.C. 154(b) by 0 days.

(21) Appl. No.: 15/430,372

(22) Filed: Feb. 10, 2017

(65) Prior Publication Data

US 2017/0233733 A1    Aug. 17, 2017

Related U.S. Application Data

(60) Provisional application No. 62/425,143, filed on Nov. 22, 2016, provisional application No. 62/294,229, filed on Feb. 11, 2016.

(51) Int. Cl.
*C12N 15/113* (2010.01)
*A61K 47/69* (2017.01)

(52) U.S. Cl.
CPC ........ *C12N 15/113* (2013.01); *A61K 47/6923* (2017.08); *C12N 2310/11* (2013.01); *C12N 2310/14* (2013.01); *C12N 2310/321* (2013.01); *C12N 2310/322* (2013.01); *C12N 2310/332* (2013.01); *C12N 2310/335* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,991,776 A | 11/1976 | Duffy |
| 4,076,779 A | 2/1978 | Skriletz |
| 4,093,709 A | 6/1978 | Choi et al. |
| 4,118,470 A | 10/1978 | Casey et al. |
| 4,131,648 A | 12/1978 | Choi et al. |
| 4,138,344 A | 2/1979 | Choi et al. |
| 4,293,539 A | 10/1981 | Ludwig et al. |
| 4,603,044 A | 7/1986 | Geho et al. |
| 4,675,189 A | 6/1987 | Kent et al. |
| 4,861,760 A | 8/1989 | Mazuel et al. |
| 4,911,920 A | 3/1990 | Jani et al. |
| 5,143,854 A | 9/1992 | Pirrung et al. |
| 5,212,162 A | 5/1993 | Missel et al. |
| 5,403,841 A | 4/1995 | Lang et al. |
| 2005/0246794 A1* | 11/2005 | Khvorova ............ A61K 31/713 800/286 |
| 2007/0298006 A1* | 12/2007 | Tomalia ................. A01N 25/10 424/78.03 |
| 2008/0267903 A1 | 10/2008 | Uchegbu et al. |
| 2010/0255023 A1* | 10/2010 | Chen ................... A61K 39/0011 424/192.1 |
| 2010/0286237 A1* | 11/2010 | Birrer ................... C12N 15/111 514/44 A |
| 2011/0224286 A1* | 9/2011 | Yu ........................ C12Q 1/6886 514/44 R |
| 2011/0263675 A1* | 10/2011 | Federov ................ C12N 15/111 514/44 A |
| 2012/0053079 A1* | 3/2012 | Samant .............. A61K 38/1709 506/9 |
| 2012/0207795 A1* | 8/2012 | Zink ..................... A61K 9/0019 424/400 |
| 2014/0294752 A1* | 10/2014 | Kim ....................... A61K 47/36 424/78.29 |
| 2016/0044913 A1* | 2/2016 | Deikman ................. A01N 3/02 504/115 |
| 2016/0354474 A1* | 12/2016 | Cohen ................ A61K 47/4823 |
| 2017/0143641 A1* | 5/2017 | Peer ...................... A61K 9/1272 |
| 2017/0173169 A1* | 6/2017 | Yantasee ................ A61K 48/00 |
| 2018/0028458 A1* | 2/2018 | Buschmann .......... C12N 15/111 |
| 2018/0140661 A1 | 5/2018 | Glackin et al. |

FOREIGN PATENT DOCUMENTS

| | | |
|---|---|---|
| WO | WO-96/17958 A1 | 6/1996 |
| WO | WI-2015/089419 A3 | 6/2015 |
| WO | WO-2015/089419 A2 | 6/2015 |
| WO | WO-2015-089419 A9 | 6/2015 |

OTHER PUBLICATIONS

Bramsen et al. Front. Genet. vol. 3, article 154:1-7, 2012.*
Feng, M.Y. et al. (2009, e-published Oct. 6, 2009). "Metastasis-induction and apoptosis-protection by TWIST in gastric cancer cells," *Clin Exp Metastasis* 26(8):1013-1023.
Finlay, J. et al. (2015, e-published Feb. 11, 2015). "RNA-based TWIST1 inhibition via dendrimer complex to reduce breast cancer cell metastasis," *Biomed Res Int* 2015:382745.
Finlay, J. et al. (Oct. 2015, e-published Jun. 24, 2015). "Mesoporous silica nanoparticle delivery of chemically modified siRNA against TWIST1 leads to reduced tumor burden," *Nanomedicine* 11(7):1657-1666.
Li, S et al. (Aug. 14, 2012). "TWIST1 associates with NF-κB subunit RELA via carboxyl-terminal WR domain to promote cell autonomous invasion through IL8 production.," *BMC Biol* 10:73.

(Continued)

*Primary Examiner* — Sean McGarry

(74) *Attorney, Agent, or Firm* — Mintz Levin Cohn Ferris Glovsky and Popeo, P.C.

(57) ABSTRACT

The present invention relates to compositions comprising TWIST signaling inhibitors and optionally one or more anti-cancer agents, and methods of using the compositions for the treatment of cancer.

26 Claims, 52 Drawing Sheets

Specification includes a Sequence Listing.

(56) References Cited

OTHER PUBLICATIONS

Li, C. et al. (Nov. 2012, e-published Apr. 11, 2012). "Twist overexpression promoted epithelial-to-mesenchymal transition of human peritoneal mesothelial cells under high glucose," *Nephrol Dial Treatment* 27(11):4119-4124.

Meng, H. et al. (Aug. 24, 2010). "Engineered design of mesoporous silica nanoparticles to deliver doxorubicin and P-glycoprotein siRNA to overcome drug resistance in a cancer cell line," *ACS Nano* 4(8):4539-4550.

Teng, Y. et al. (Mar. 2014, e-published Oct. 26, 2013). "The roles of HLH transcription factors in epithelial mesenchymal transition and multiple molecular mechanisms," *Clin Exp Metastasis* 31(3):367-377.

Vernon, A.E. et al. (Sep. 7, 2004). "Tumor metastasis: a new twist on epithelial-mesenchymal transitions," *Curr Biol* 14(17):R719-721.

Yang, J. et al. (Jun. 25, 2004). "Twist, a master regulator of morphogenesis, plays an essential role in tumor metastasis," *Cell* 117(7):927-939.

Zhang, J. et al. (Apr. 2012, e-published Dec. 8, 2011). "Aberrant expression of the transcriptional factor Twist1 promotes invasiveness in ALK-positive anaplastic large cell lymphoma," *Cell Signal* 24(4):852-858.

Al-Muhammed, J. et al. (May-Jun. 1996). "In-vivo studies on dexamethasone sodium phosphate liposomes," *J Microencapsul* 13(3):293-306.

Bettinger, T. et al. (Apr. 2001). "Recent developments in RNA-based strategies for cancer gene therapy," *Curr Opin Mol Ther* 3(2):116-124.

Blackman, M.L. et al. (Oct. 15, 2008, e-published Sep. 18, 2008). "Tetrazine ligation: fast bioconjugation based on inverse-electron-demand Diels-Alder reactivity," *J Am Chem Soc* 130(41):13518-13519.

Bohacek, R.S. et al. (Jan. 1996). "The art and practice of structure-based drug design: a molecular modeling perspective," *Med Res Rev* 16(1):3-50.

Bridges, R.S .et al. (Dec. 2009, e-published Nov. 5, 2009). "Gene expression profiling of pulmonary fibrosis identifies Twist1 as an antiapoptotic molecular "rectifier" of growth factor signaling," *Am J Pathol* 165(6):2351-2361.

Chang, A.T. et al. (Mar. 15, 2015, e-published Mar. 11, 2015). "An evolutionarily conserved DNA architecture determines target specificity of the TWIST family bHLH transcription factors," *Genes Dev* 29(6):603-616.

Chen, Y.Q. et al. (Jan. 1998). "A novel DNA recognition mode by the Nf-kappa B p65 homodimer," *Nat Struct Biol* 5(1):67-73.

Chonn, A. et al. (Dec. 1995). "Recent advances in liposomal drug-delivery systems," *Curr Opin Biotechnol* 6(6):698-708.

Coelho, T. et al. (Aug. 29, 2013). "Safety and efficacy of RNAi therapy for transthyretin amyloidosis," *N Engl J Med* 369(9):819-829.

Database Accession No. NM_001271893.3 (Sep. 24, 2018), 4 pages.
Database Accession No. NM_000474.3 (Nov. 10, 2018). 4 pages.
Database Accession No. NP_001258822.1 (May 1, 2019). 3 pages.
Database Accession No. NP_00465.1 (May 7, 2019). 3 pages.

Devaraj, N.K. et al. (Dec. 2008). "Tetrazine-based cycloadditions: application to pretargeted live cell imaging," *Bioconjug Chem* 19(12):2297-2299.

Elghouzzi, V. et al. (Mar. 22, 2000). "Saethre-Chotzen mutations cause TWIST protein degradation or impaired nuclear location," *Hum Mol Genet* 9(5):813-819.

Evans, R.A. (2007). "The Rise of Azide-Alkyne 1,3-Dipolar 'Click' Cycloaddition and its Application to Polymer Science and Surface Modification," *Australian Journal of Chemistry* 60(6):384-395.

Eyles, J.E. et al. (Jul. 1997). "Oral delivery and fate of poly(lactic acid) microsphere-encapsulated interferon in rats," J. Pharm. Pharmacol. 49(7):669-674.

Ferlay, J. et al. (Mar. 2010, e-published Jan. 29, 2010). "Estimates of cancer incidence and mortality in Europe in 2008," *Eur J Cancer* 46(4):765-781.

Fodor, S.P. et al. (Feb. 15, 1991). "Light-directed, spatially addressable parallel chemical synthesis," *Science* 251(4995):767-773.

Fu, J. et al. (Feb. 2011, e-published Aug. 17, 2010). "The TWIST/Mi2/NuRD protein complex and its essential role in cancer metastasis," *Cell Res* 21(2):275-289.

Gajula, R.P. et al. (Nov. 2013, e-published Aug. 27, 2013). "The twist box domain is required for Twist1-induced prostate cancer metastasis," *Mol Cancer Res* 11(11):1387-1400.

Gao, Z.H. et al. (Jun. 1995). "Controlled release of a contraceptive steroid from biodegradable and injectable gel formulations: in vitro evaluation," Pharm. Res 12(6):857-863.

Haslehurst, A.M. et al. (Mar. 19, 2012). "EMT transcription factors snail and slug directly contribute to cisplatin resistance in ovarian cancer," BMC Cancer12:91.

Hoyle, C.E. et al. (Feb. 22, 2010). "Thiol-ene click chemistry," Angew Chem Int Ed Engl 49(9):1540-1573.

Johnston, M. (Feb. 26, 1998). "Gene chips: array of hope for understanding gene regulation," *Curr Biol* 8(5):R171-174.

Journal of Polymer Science: Polymer Letters Edition (1980). "Preparation of Polyacetals by the Relaxation of Divinyl Ethers and Polyols," 18:293-297.

Kern, S. et al. (Jul. 1997). "Direct hybridization of large-insert genomic clones on high-density gridded cDNA filter arrays," Biotechniques 23(1):120-124.

Kolb, H.C. et al (Jun. 1, 2001). "Click Chemistry: Diverse Chemical Function from a Few Good Reactions," *Angewandte Chemie International Edition* 40(11):2004-2021.

Kong, D. et al. (Feb. 21, 2011). "Cancer Stem Cells and Epithelial-to-Mesenchymal Transition (EMT)-Phenotypic Cells: Are They Cousins or Twins?" Cancers 3(1):716-729.

Li, Y. et al. (Jan. 2011). "Prophylactic, therapeutic and immune enhancement effect of liposome-encapsulated PolyICLC on highly pathogenic H5N1 influenza infection," *J Gene Med* 13(1):60-72.

Little, S.R. et al. (Jun. 29, 2004, e-published Jun. 21, 2004). "Poly-β amino ester-containing microparticles enhance the activity of nonviral genetic vaccines," PNAS USA 101(26):9534-9539.

Low-Marcheli, J.M. et al. (Jan. 15, 2013). "Twist1 induces CCL2 and recruits macrophages to promote angiogenesis," *Cancer Res* 73(2):662-671.

Lu, D. et al. (Dec. 1994). "Optimization of methods to achieve mRNA-mediated transfection of tumor cells in vitro and in vivo employing cationic liposome vectors," *Cancer Gene Ther* 1(4):245-252.

McNamara. M.A. et al. (2015, e-published Nov. 19, 2015). "RNA-Based Vaccines in Cancer Immunotherapy," *J Immunol Res* 2015:794528, 9 pages.

Murray, S.S. et al. (Oct. 1992). "Expression of helix-loop-helix regulatory genes during differentiation of mouse osteoblastic cells," J Bone Miner Res 7(10):1131-1138.

Nguyen, D.X. et al. (Apr. 2009). "Metastasis: from dissemination to organ-specific colonization," *Nat Rev Cancer* 9(4):274-284.

Ostro, M.J. et al. (Aug. 1989). "Use of liposomes as injectable-drug delivery systems," *Am J Hosp Pharm* 46(8):1576-1587.

Pham, D. et al. (Jul. 15, 2012, e-published Jun. 8, 2012). "Twist1 regulates lfng expression in Th1 cells by interfering with Runx3 function," *J Immunol* 189(2):832-840.

Phua, K.K. et al. (Mar. 28, 2013, e-published Jan. 7, 2013). "Transfection efficiency and transgene expression kinetics of mRNA delivered in naked and nanoparticle format," *J Control Release* 166(3):227-233.

Phua, K.K. et al. (Jun. 4, 2014). "Intranasal mRNA nanoparticle vaccination induces prophylactic and therapeutic anti-tumor immunity," *Sci Rep* 4:5128.

Phua, K.K. et al. (Jul. 21, 2014). "Messenger RNA (mRNA) nanoparticle tumour vaccination," *Nanoscale* 6(14):7715-7729.

Piccinin, S. et al. (Sep. 11, 2012). "A "twist box" code of p53 inactivation: twist box: p53 interaction promotes p53 degradation," Cancer Cell 22(3):404-415.

(56) References Cited

OTHER PUBLICATIONS

Pichon, C. et al. (2013). "Mannosylated and histidylated LPR technology for vaccination with tumor antigen mRNA," Methods Mol Biol 969:247-274.
Rahme, G.J. et al. (Jan. 2, 2015, e-published Jan. 13, 2014). "Id4 suppresses MMP2-mediated invasion of glioblastoma-derived cells by direct inactivation of Twist1 function," Oncogene 34(1):53-62.
Rao. K.P. (1995). "Recent developments of collagen-based materials for medical applications and drug delivery systems" J. Biomater Sci. Polym. Ed. 7(7):623-645.
Sayour, E.J. et al. (2015). "Bridging infection disease vaccines with cancer immunotherapy: a role for targeted RNA based immunotherapeutics," Journal for Immunotherapy of Cancer 3:13.
Schummer, M. et al. (Dec. 1997). "Inexpensive handheld device for the construction of high-density nucleic acid arrays," Biotechniques 23(6):1087-1092.
Schwendener, R.A. et al. (Nov. 2014). "Liposomes as vaccine delivery systems: a review of the recent advances," Ther Adv Vaccines 2(6):159-182.
Simpson, P. et al. (Nov. 1983). "Maternal-Zygotic Gene Interactions during Formation of the Dorsoventral Pattern in Drosophila Embryos," Genetics 105(3):615-632.
Spiteri, C. et al. (2010). "Copper-catalyzed azide-alkyne cycloaddition: regioselective synthesis of 1,4,5-trisubstituted 1,2,3-triazoles," Angew Chem Int Ed Engl 49(1):31-33.
Stöckmann, H. et al. (Nov. 7, 2011, e-published Sep. 13, 2011). "Exploring isonitrile-based click chemistry for ligation with biomolecules," Org Biomol Chem 9(21):7303-7305.
Su, X. et al. (2011). "In Vitro and in Vivo mRNA Delivery Using Lipid-Enveloped pH-Responsive Polymer Nanoparticles," Molecular Pharmaceutics 8(3):774-787.
Tabernero, J. et al. (Apr. 2013, e-published Jan. 28, 2013). "First-in-humans trial of an RNA interference therapeutic targeting VEGF and KSP in cancer patients with liver involvement," Cancer Discov 3(4):406-417.
Trimble, E.L et al. (Aug. 2001). "Treatment of platinum-resistant ovarian cancer," Expert Opin Pharmacother 2(8):1299-1306.
Vanjaarsveld, M.T. et al. (Sep. 5, 2013, e-published Oct. 8, 2012). "miR-141 regulates KEAP1 and modulates cisplatin sensitivity in ovarian cancer cells," Oncogene 32(36):4284-4293.
Vesuna, F. et al. (Dec. 2009). "Twist modulates breast cancer stem cells by transcriptional regulation of CD24 expression," Neoplasia 11(12):1318-1328.
Vincentz, J.W. et al. (Mar. 2013, e-published Mar. 21, 2013). "Twist1 controls a cell-specification switch governing cell fate decisions within the cardiac neural crest," PLoS Genet 9(3):e1003405.
Wang, S.M .et al. (Mar. 10, 1997). "Cloning of the human twist gene: its expression is retained in adult mesodermally-derived tissues," Gene 187(1):83-92.
Wang, Y. et al. (Nov. 2011, e-published Jul. 13, 2011). "Autocrine production of interleukin-8 confers cisplatin and paclitaxel resistance in ovarian cancer cells," Cytokine 56(2)365-375.
Wasungu, L. et al. (Nov. 28, 2006, e-published Jun. 28, 2006). "Cationic lipids, lipoplexes and intracellular delivery of genes," J Control Release 116(2):255-264.
Yang, J. et al. (Apr. 2015, e-published Feb. 3, 2015). "Overexpression of inhibitor of DNA-binding 2 attenuates pulmonary fibrosis through regulation of c-Abl and Twist," Am J Pathol 185(4):1001-1011.
Zuris, J.A. et al. (Jan. 2015, e-published Oct. 30, 2014). "Cationic lipid-mediated delivery of proteins enables efficient protein-based genome editing in vitro and in vivo," Nat Biotechnol 33(1):73-80.

\* cited by examiner siTw-419H Passenger
5' - iaB rGrGrA rCrArA rGrCrU rGrArG rCrArA rGrA mU mU iaB -3' siTw-419H Guide
5' - rArArU rCrUrU rGrCrU rCrArG rCrUrU rG rUrC rCrUrU- 3'

FIG. 15A
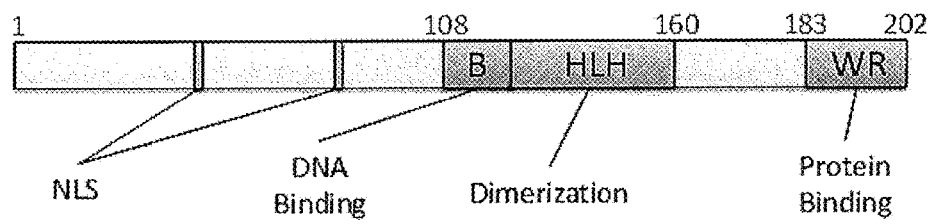
FIG. 15B
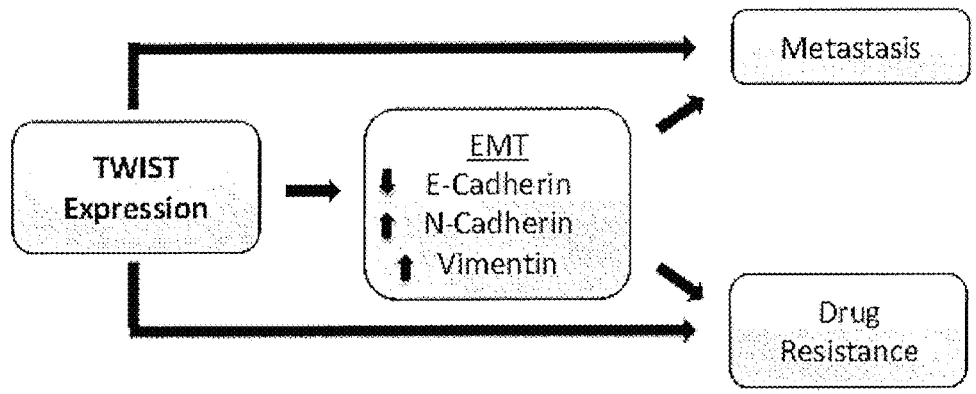
FIG. 15C
| | |
|---|---|
| si419 guide: | 5'-AAUCUUGCUCAGCUUGUCCUU-3' |
| si419 passenger: | 5'-GGACAAGCUGAGCAAGAUU-3' |
| si494 guide: | 5'-UUGGAGUCCAGCUCGUCGCUU-3' |
| si494 passenger: | 5'-GCGACGAGCUGGACUCCAA-3' |
FIG. 15D
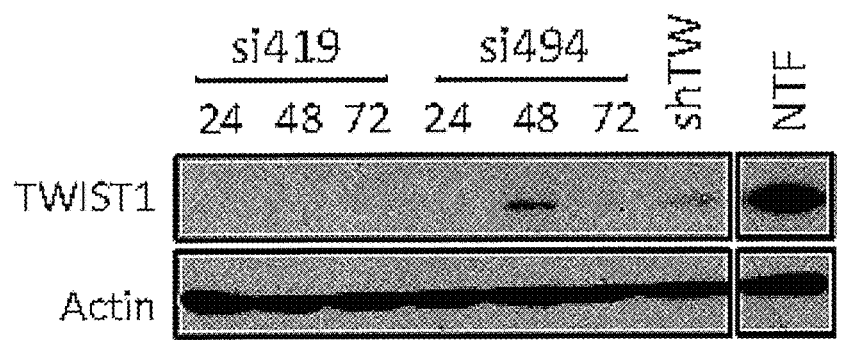

FIG. 17D
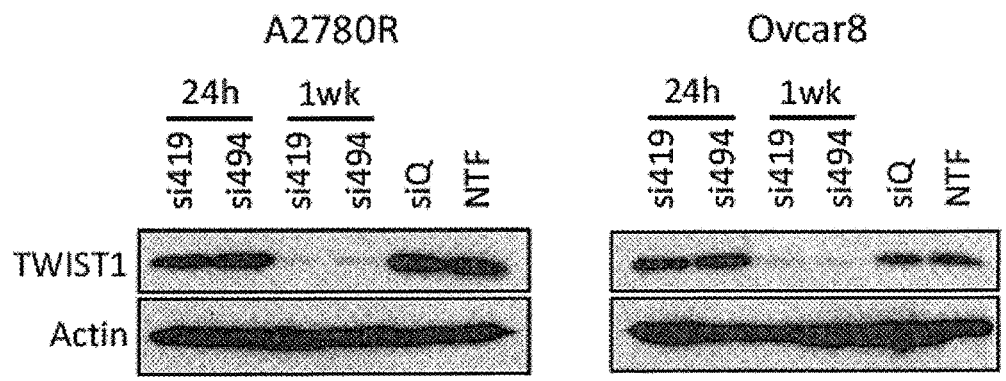
FIG. 18A
si419H Guide Strand
  5' - rArArU rCrUrU rGrCrU rCrArG rCrUrU rGrUrC rCrUrU - 3'
si419H Passenger Strand
  5' - iaB rGrGrA rCrArA rGrCrU rGrArG rCrArA rGrAmU mU iaB - 3'
  iaB = inverted abasic ribose    mU = 2'-O-methyluracil
FIG. 18B
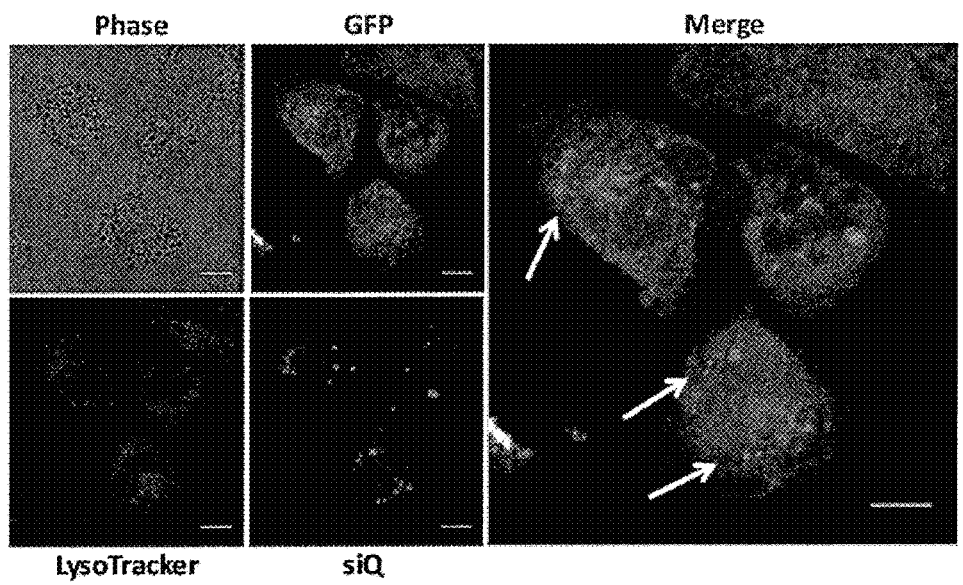

TWIST1 sh492

SEQUENCE LISTING

```
<160> NUMBER OF SEQ ID NOS: 34

<210> SEQ ID NO 1
<211> LENGTH: 19
<212> TYPE: RNA
<213> ORGANISM: Artificial Sequence
<220> FEATURE:
```

<223> OTHER INFORMATION: Synthetic polynucletoide

<400> SEQUENCE: 1
ggacaagcug agcaagauu                                                    19

<210> SEQ ID NO 2
<211> LENGTH: 21
<212> TYPE: RNA
<213> ORGANISM: Artificial Sequence
<220> FEATURE:
<223> OTHER INFORMATION: Synthetic polynucletoide

<400> SEQUENCE: 2
aaucuugcuc agcuuguccu u                                                 21

<210> SEQ ID NO 3
<211> LENGTH: 19
<212> TYPE: RNA
<213> ORGANISM: Artificial Sequence
<220> FEATURE:
<223> OTHER INFORMATION: Synthetic polynucletoide

<400> SEQUENCE: 3
gcgacgagcu ggacuccaa                                                    19

<210> SEQ ID NO 4
<211> LENGTH: 21
<212> TYPE: RNA
<213> ORGANISM: Artificial Sequence
<220> FEATURE:
<223> OTHER INFORMATION: Synthetic polynucletoide

<400> SEQUENCE: 4
uuggagucca gcucgucgcu u                                                 21

<210> SEQ ID NO 5
<211> LENGTH: 21
<212> TYPE: RNA
<213> ORGANISM: Artificial Sequence
<220> FEATURE:
<223> OTHER INFORMATION: Synthetic polynucletoide

<400> SEQUENCE: 5
gauggcaagc ugcagcuauu u                                                 21

<210> SEQ ID NO 6
<211> LENGTH: 21
<212> TYPE: RNA
<213> ORGANISM: Artificial Sequence
<220> FEATURE:
<223> OTHER INFORMATION: Synthetic polynucletoide

<400> SEQUENCE: 6
auagcugcag cuugccaucu u                                                 21

<210> SEQ ID NO 7
<211> LENGTH: 21
<212> TYPE: RNA
<213> ORGANISM: Artificial Sequence
<220> FEATURE:
<223> OTHER INFORMATION: Synthetic polynucletoide

<400> SEQUENCE: 7
gauucagacc cucaagcugu u                                                 21

<210> SEQ ID NO 8
<211> LENGTH: 21
<212> TYPE: RNA
<213> ORGANISM: Artificial Sequence
<220> FEATURE:
<223> OTHER INFORMATION: Synthetic polynucletoide

<400> SEQUENCE: 8
cagcuugagg gucugaaucu u                                            21

<210> SEQ ID NO 9
<211> LENGTH: 21
<212> TYPE: RNA
<213> ORGANISM: Artificial Sequence
<220> FEATURE:
<223> OTHER INFORMATION: Synthetic polynucletoide

<400> SEQUENCE: 9
gcugagcaag auucagaccu u                                            21

<210> SEQ ID NO 10
<211> LENGTH: 21
<212> TYPE: RNA
<213> ORGANISM: Artificial Sequence
<220> FEATURE:
<223> OTHER INFORMATION: Synthetic polynucletoide

<400> SEQUENCE: 10
ggucugaauc uugcucagcu u                                            21

<210> SEQ ID NO 11
<211> LENGTH: 19
<212> TYPE: RNA
<213> ORGANISM: Artificial Sequence
<220> FEATURE:
<223> OTHER INFORMATION: Synthetic polynucletoide
<220> FEATURE:
<221> NAME/KEY: misc_feature
<222> LOCATION: (1)..(1)
<223> OTHER INFORMATION: Residue modified at 5'-terminal with inverted
      abasic ribose
<220> FEATURE:
<221> NAME/KEY: misc_feature
<222> LOCATION: (18)..(19)
<223> OTHER INFORMATION: Residue modified to 2'-O-methyluracil
<220> FEATURE:
<221> NAME/KEY: misc_feature
<222> LOCATION: (19)..(19)
<223> OTHER INFORMATION: Residue modified at 3'-terminal with inverted
      abasic ribose

<400> SEQUENCE: 11
ggacaagcug agcaagauu                                               19

<210> SEQ ID NO 12
<211> LENGTH: 21
<212> TYPE: RNA
<213> ORGANISM: Artificial Sequence
<220> FEATURE:
<223> OTHER INFORMATION: Synthetic polynucletoide
<220> FEATURE:
<221> NAME/KEY: misc_feature
<222> LOCATION: (17)..(17)
<223> OTHER INFORMATION: Residue is 2-thio-deoxyuracil

<400> SEQUENCE: 12
aaucuugcuc agcuuguccu u                                            21

<210> SEQ ID NO 13

<211> LENGTH: 2205
<212> TYPE: DNA
<213> ORGANISM: Homo sapiens

<400> SEQUENCE: 13

```
gaggtataag agcctccaag tctgcagctc tcgcccaact cccagacacc tcgcgggctc    60
tgcagcaccg gcaccgtttc caggaggcct ggcggggtgt gcgtccagcc gttgggcgct   120
ttcttttttgg acctcggggc catccacacc gtcccctccc cctcccgcct ccctccccgc   180
ctcccccgcg cgccctcccc gcggaggtcc ctcccgtccg tcctcctgct ctctcctccg   240
cgggccgcat cgcccgggcc ggcgccgcgc gcggggggaag ctggcgggct gaggcgcccc   300
gctcttctcc tctgccccgg gcccgcgagg ccacgcgtcg ccgctcgaga gatgatgcag   360
gacgtgtcca gctcgccagt ctcgccggcc gacgacagcc tgagcaacag cgaggaagag   420
ccagaccggc agcagccgcc gagcggcaag gcgcggggac gcaagcggcg cagcagcagg   480
cgcagcgcgg gcggcggcgc ggggcccggc ggagccgcgg gtggggggcgt cggaggcggc   540
gacgagccgg gcagcccggc ccagggcaag gcgggcaaga agtctgcggg ctgtggcggc   600
ggcggcggcg cgggcggcgg cggcggcagc agcagcggcg gcgggagtcc gcagtcttac   660
gaggagctgc agacgcagcg ggtcatggcc aacgtgcggg agcgcagcg cacccagtcg   720
ctgaacgagg cgttcgccgc gctgcggaag atcatcccca cgctgccctc ggacaagctg   780
agcaagattc agaccctcaa gctggcggcc aggtacatcg acttcctcta ccaggtcctc   840
cagagcgacg agctggactc caagatggca agctgcagct atgtggctca cgagcggctc   900
agctacgcct tctcggtctg gaggatggag ggggcctggt ccatgtccgc gtcccactag   960
caggcggagc cccccacccc ctcagcaggg ccggagacct aggtaaggac cgcgccgctg   1020
cacccccttcg cctctcaggt ggcagacggc aggccggcca ggccgcggtt cccagtccac   1080
ctcgatttcc tcccctctcc cactctccgc tcagccttcc cacctcactt ggcaccgttg   1140
cctcgcgccc ccagcgtccc cggaaggccg gtctgacccc gctagggaga gcagtctcca   1200
gggggatgcg ccctggtgag gggtgtgtgt gcgcgtgagt gtgcgtgaca ggaggggaga   1260
cagagacacc cagggtcacg ggtaaggacc gttttgtcag cgccacccttt tctttcggct   1320
ttcaattttt gttctcctta aacaaatgt tttaaaacaa attccacctc ctcctccttt   1380
ccacccaccc acttcctctt gcccttgggc tgaaatcctt ccaggttgtt cagcttaatt   1440
tctcagtggt ggtgataaga acagtgctca ctagtcttag aaaacagccg cagagaccta   1500
aacaataacc gactccccc ccccctctg ggtttttgca gatgtcattg tttccagaga   1560
aggagaaaat ggacagtcta gagactctgg agctggataa ctaaaaataa aatatatgc   1620
caaagatttt cttggaaatt agaagagcaa aatccaaatt caaagaaaca gggcgtgggg   1680
cgcacttttta aaagagaaag cgagacaggc ccgtggacag tgattcccag acgggcagcg   1740
gcaccatcct cacacctctg cattctgata gaagtctgaa cagttgtttg tgttttttt   1800
ttttttttt ttgacgaaga atgttttat ttttattttt ttcatgcatg cattctcaag   1860
aggtcgtgcc aatcagccac tgaaaggaaa ggcatcacta tggactttct ctattttaaa   1920
atggtaacaa tcagaggaac tataagaaca cctttagaaa taaaaatact gggatcaaac   1980
tggcctgcaa aaccatagtc agttaattct ttttttcatc cttcctctga ggggaaaaac   2040
aaaaaaaaac ttaaaataca aaaaacaaca ttctatttat ttattgagga cccatggtaa   2100
aatgcaaata gatccggtgt ctaaatgcat tcatattttt atgattgttt tgtaaatatc   2160
tttgtatatt tttctgcaat aaataaatat aaaaaattta gagaa              2205
```

<210> SEQ ID NO 14
<211> LENGTH: 22
<212> TYPE: DNA
<213> ORGANISM: Artificial Sequence
<220> FEATURE:
<223> OTHER INFORMATION: Synthetic polynucletoide

<400> SEQUENCE: 14
ctatgtggct cacgagcggc tc                                    22

<210> SEQ ID NO 15
<211> LENGTH: 26
<212> TYPE: DNA
<213> ORGANISM: Artificial Sequence
<220> FEATURE:
<223> OTHER INFORMATION: Synthetic polynucletoide

<400> SEQUENCE: 15
ccagctccag agtctctaga ctgtcc                                26

<210> SEQ ID NO 16
<211> LENGTH: 24
<212> TYPE: DNA
<213> ORGANISM: Artificial Sequence
<220> FEATURE:
<223> OTHER INFORMATION: Synthetic polynucletoide

<400> SEQUENCE: 16
tcgtcacctt cgtgaatacc aaga                                  24

<210> SEQ ID NO 17
<211> LENGTH: 24
<212> TYPE: DNA
<213> ORGANISM: Artificial Sequence
<220> FEATURE:
<223> OTHER INFORMATION: Synthetic polynucletoide

<400> SEQUENCE: 17
cctcaggttc agggaggaaa agtt                                  24

<210> SEQ ID NO 18
<211> LENGTH: 21
<212> TYPE: DNA
<213> ORGANISM: Artificial Sequence
<220> FEATURE:
<223> OTHER INFORMATION: Synthetic polynucletoide

<400> SEQUENCE: 18
cagccagatg caatcaatgc c                                     21

<210> SEQ ID NO 19
<211> LENGTH: 21
<212> TYPE: DNA
<213> ORGANISM: Artificial Sequence
<220> FEATURE:
<223> OTHER INFORMATION: Synthetic polynucletoide

<400> SEQUENCE: 19
tggaatcctg aacccacttc t                                     21

<210> SEQ ID NO 20
<211> LENGTH: 23
<212> TYPE: DNA
<213> ORGANISM: Artificial Sequence
<220> FEATURE:

<223> OTHER INFORMATION: Synthetic polynucletoide

<400> SEQUENCE: 20
tcttacgagg agctgcagac gca                                    23

<210> SEQ ID NO 21
<211> LENGTH: 23
<212> TYPE: DNA
<213> ORGANISM: Artificial Sequence
<220> FEATURE:
<223> OTHER INFORMATION: Synthetic polynucletoide

<400> SEQUENCE: 21
atcttggagt ccagctcgtc gct                                    23

<210> SEQ ID NO 22
<211> LENGTH: 22
<212> TYPE: DNA
<213> ORGANISM: Artificial Sequence
<220> FEATURE:
<223> OTHER INFORMATION: Synthetic polynucletoide

<400> SEQUENCE: 22
gggacagttc ctgagggatc aa                                     22

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucletoide

<400> SEQUENCE: 23
tggagcctga gacacgattc tg                                     22

<210> SEQ ID NO 24
<211> LENGTH: 22
<212> TYPE: DNA
<213> ORGANISM: Artificial Sequence
<220> FEATURE:
<223> OTHER INFORMATION: Synthetic polynucletoide

<400> SEQUENCE: 24
ccgcaaagac ctgtacgcca ac                                     22

<210> SEQ ID NO 25
<211> LENGTH: 22
<212> TYPE: DNA
<213> ORGANISM: Artificial Sequence
<220> FEATURE:
<223> OTHER INFORMATION: Synthetic polynucletoide

<400> SEQUENCE: 25
ccagggcagt gatctccttc tg                                     22

<210> SEQ ID NO 26
<211> LENGTH: 26
<212> TYPE: DNA
<213> ORGANISM: Artificial Sequence
<220> FEATURE:
<223> OTHER INFORMATION: Synthetic polynucletoide

<400> SEQUENCE: 26
ctgcatcaac aagtatgggt ctccgt                                 26

<210> SEQ ID NO 27
<211> LENGTH: 23
<212> TYPE: DNA
<213> ORGANISM: Artificial Sequence
<220> FEATURE:
<223> OTHER INFORMATION: Synthetic polynucletoide

<400> SEQUENCE: 27
gttctcctgg ctgcattcgt tga                                   23

<210> SEQ ID NO 28
<211> LENGTH: 22
<212> TYPE: DNA
<213> ORGANISM: Artificial Sequence
<220> FEATURE:
<223> OTHER INFORMATION: Synthetic polynucletoide

<400> SEQUENCE: 28
cagcgcctca gaagagagga cg                                    22

<210> SEQ ID NO 29
<211> LENGTH: 25
<212> TYPE: DNA
<213> ORGANISM: Artificial Sequence
<220> FEATURE:
<223> OTHER INFORMATION: Synthetic polynucletoide

<400> SEQUENCE: 29
ccgttttcct ccagtggctt ctgct                                 25

<210> SEQ ID NO 30
<211> LENGTH: 23
<212> TYPE: DNA
<213> ORGANISM: Artificial Sequence
<220> FEATURE:
<223> OTHER INFORMATION: Synthetic polynucletoide

<400> SEQUENCE: 30
gcagcaaggg cggcaaatac tca                                   23

<210> SEQ ID NO 31
<211> LENGTH: 22
<212> TYPE: DNA
<213> ORGANISM: Artificial Sequence
<220> FEATURE:
<223> OTHER INFORMATION: Synthetic polynucletoide

<400> SEQUENCE: 31
cttgatgtcc ccgttgagcg at                                    22

<210> SEQ ID NO 32
<211> LENGTH: 22
<212> TYPE: DNA
<213> ORGANISM: Artificial Sequence
<220> FEATURE:
<223> OTHER INFORMATION: Synthetic polynucletoide

<400> SEQUENCE: 32
ccgcaaagac ctgtacgcca ac                                    22

<210> SEQ ID NO 33
<211> LENGTH: 22
<212> TYPE: DNA
<213> ORGANISM: Artificial Sequence
<220> FEATURE:
<223> OTHER INFORMATION: Synthetic polynucletoide

```
-continued

<400> SEQUENCE: 33
ccagggcagt gatctccttc tg                                                22

<210> SEQ ID NO 34
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 34
gcgacgagcu ggacuccaa                                                    19
```

TWIST SIGNALING INHIBITOR COMPOSITIONS AND METHODS OF USING THE SAME

CROSS-REFERENCES TO RELATED APPLICATIONS

This application claims the prioirty and the benefit of U.S. Provisional Application No. 62/294,229, filed Feb. 11, 2016, and U.S. Provisional Application No. 62/425,143, filed Nov. 22, 2016, the content of each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under Grant Numbers P30CA33572 and CA133697 awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 48440-614001US_ST25.TXT, created Feb. 10, 2017, 10,246 bytes, machine format IBM-PC, MS-Windows operating system, is hereby incorporated by reference.

BACKGROUND

Breast cancer is the second leading cause of cancer deaths in women in the US with over 246,660 new diagnoses expected in 2016 and almost 40,450 deaths. The "triple-negative breast cancer" (TNBC) (estrogen receptor [ER]-negative, progesterone receptor [PR]-negative, and human epidermal growth factor receptor 2 [HER2]-negative) poses a particularly difficult challenge, patients with these tumors have poor prognosis because of inherent resistance to therapy and a high incidence of metastasis. There is thus a critical need for novel efficacious therapies for patients with TNBC. Provided herein are solutions to these and other problems in the art.

SUMMARY

In a first aspect, there is provided a composition including a TWIST signaling inhibitor bound to a delivery vehicle.

In another aspect, there is provided an siRNA including a sequence of any one of SEQ ID NOs: 1-12.

In another aspect, there is provided a DNA sequence encoding an siRNA sequence including a sequence of any one of SEQ ID Nos: 1-10.

In another aspect, there is provided a method of reversing resistance to an anti-cancer drug in a subject. The method includes administering a therapeutically effective amount of a TWIST signaling inhibitor to the subject.

In another aspect, there is provided a method of treating cancer in a subject in need thereof. The method includes administering to the subject a therapeutically effective amount of a TWIST signaling inhibitor.

In another aspect, there is provided a method of inhibiting metastasis in a subject. The method includes administering a therapeutically effective amount of a TWIST signaling inhibitor to the subject.

BRIEF DESCRIPTION OF THE DRAWINGS

FIG. 1A. Individual pores are visible in TEM micrographs of ~100 nm MSNs. FIG. 1B. Particle size within a batch is uniform. FIG. 1C. Schematic of siRNA silencing via RNA induced silencing complex (RISC). siRNA contains 2-OMe-U and inverted abasic ribose modifications, to decrease degradation and immune stimulation, and to guarantee the guide strand is loaded into RISC. TWIST1 siRNA binds to TWIST1 mRNA, leading to its cleavage by Ago2. The siRNA guide strand is reused to recognize additional TWIST1 mRNAs. FIG. 1D. Sequences of si419 showing positions of 2-OMe and inverted abasic modifications. Sequences: siTw-419H Passenger (SEQ ID NO:11); siTw-419H Guide (SEQ ID NO:12).

FIG. 2A. TWIST1 siRNA delivered using LIPOFECTAMINE® 2000 decreases levels of TWIST1 protein up to 72 hours following transfection. FIG. 2B. i. Merged confocal image of GFP (grey), DAPI (white dots) and siRNA (bright white dots). ii. Magnification of cell from center right of i. siRNA shows expected perinuclear localization. iii-v. Single color images. FIG. 2C. Delivery of TWIST1 siRNA using MSNs produces significant knockdown at 72 hours post transfection, but TWIST1 protein levels stabilize after one week. FIG. 2D. qRT-PCR data demonstrate that TWIST1 mRNA levels are also reduced 72 hours following MSN+siRNA treatment.

FIG. 3A. MDA-MB-4355 cells with TWIST1 knocked down are slower to migrate and seal a scratch wound. FIG. 3B. ELISA reveals that MDA-MB-4355 cells treated with TWIST1 siRNA secrete significantly less IL-8 than nontransfected cells or those transfected with irrelevant control (siGFP).

FIG. 4A. Gross tumor images reveal smaller, less vascularized tumors in mice treated with si419H than in control mice or those given non-chemically-modified si494. Representative images shown. FIG. 4B. si419H treated tumors show a significant drop in weight compared to untreated or si494-treated tumors. FIGS. 4C-4E. qPCR results from tumors collected at necropsy. Tumors exhibit loss of TWIST1 (FIG. 4C) and its target genes Vimentin (FIG. 4D) and CCL2 (FIG. 4E). In each case, more robust knockdown is observed for si419H than si494.

FIG. 7A. Phase contrast and FIG. 7B. green channel images of MDA-MB-4355 cells. FIG. 7C. Expression of firefly luciferase is evidenced by strong signal following D-luciferin injection in mice (Xenogen IVIS, STARR).

FIG. 8A. MDA-MB-435 cells stain positive for GFP in GFP negative lung tissue. FIG. 8B. Metastases were grouped into one of four categories on the basis of cell number. No inj, no injection.

FIG. 9A. TWIST1 expression is reduced by sh419 and sh494. FIG. 9B. TWIST2 is only knocked down by sh419. FPKM, fragments per kilobase per million fragments read.

FIG. 11A. Western blot demonstrated robust TWIST1 knockdown in both shTwistA and shTwistB lines. FIG. 11B. qRT-PCR confirmed TWIST1 knockdown at the mRNA level for both stable knockdown lines. FIG. 11C. SUM 1315 cells expressing shTwistA or shTwistB exhibited decreased directional migration compared to those expressing shScram control in wound healing assays. Dashed lines indicate migratory front. Images shown are representative data from experiments performed in triplicate.

FIG. 12A. Left: non-transfected SUM 1315 cells had low background fluorescence. Right: Greater than 99% of YTZ3-15 transfected cells were positive for AlexaFluor-647 labeled siQ. FIG. 12B. Fluorescent microscopy revealed that AlexaFluor-488 labeled siQ was taken up into cells within one day, and AlexaFluor signal was still detectable in cells at seven days post-transfection. FIG. 12C. Confocal images of SUM 1315 cells stably expressing GFP and transiently transfected with AlexaFluor-647 labeled siQ using YTZ3-15. Lysotracker dye revealed that siQ colocalized with late endosomes and lysosomes after incubation with YTZ3-15 siRNA complexes.

FIG. 13A. Compared to siQ control (at seven days), siTwistA (TwA) and siTwistB (TwB) delivered via YTZ3-15 produced >90% knockdown at the mRNA level. Knockdown lasted seven days post-transfection. FIG. 13B. Compared to siQ control (at seven days), TwA and TwB delivered via YTZ3-15 produced knockdown of the TWIST1 targets N-Cadherin and Vimentin. N-Cadherin mRNA levels decreased by >40% after one day, and by approximately 90% after seven days. Vimentin mRNA was nearly undetectable after one day, and remained at <10% after seven days. FIG. 13C. YTZ3-15 transfection of siTwistA decreased directional migration compared to siQ transfected cells (control) in wound healing assays. Dashed lines indicate migratory front. Images shown are representative data from experiments performed in duplicate. FIG. 13D. Top: YTZ3-15 transfection of TwA or TwB resulted in >50% decrease in invasion of SUM1315 cells through matrigel. Cells were allowed to migrate for one day, following one day incubation with YTZ3-15-siRNA complexes. Five fields per condition were imaged (representative images shown). Bottom: Quantification of image data. Data are average of five fields per condition. Error bars represent standard deviation.

FIG. 14A. Representative animals from the mice that received YTZ3-15+siQ via intratumoral (IT) and intravenous (IV) injections. Control animals received IV injections of the dendrimer complex but had no tumors. FIG. 14B. Ex vivo imaging of spleen, kidney, liver and tumors from the three animals shown in FIG. 14A demonstrating concentration of YTZ3-15+siQ complex in the tumors but not in other organs. The units for the scale bars in this figure are p/sec/cm$^2$/sr.

FIGS. 15A to 15E. FIG. 15A. TWIST schematic showing the basic DNA binding domain, helix-loop-helix dimerization motif, and C-terminal protein-binding WR domain. FIG. 15B. Reactivation of TWIST in cancers induces an epithelial to mesenchymal transition (EMT), which in turn has been shown to lead to metastasis and acquired drug resistance. FIG. 15C. Sequences of two TWIST siRNAs targeting the coding region of TWIST mRNA (from top to bottom: SEQ ID Nos 2, 1, 4, 3, respectively). FIG. 15D. Validation of siRNA. Lipofectamine 2000 was used to transfect A2780R cells with si419 or si494. Western blot reveals robust TWIST knockdown over three days post transfection. shRNA targeting TWIST is shown as a positive control for knockdown. FIG. 15E. Without a carrier, no siRNA enters target cells.

FIG. 16A. YTZ3-15 PAMAM dendrimer used in these studies. Lipid tails encourage formation of micelle structures once dendrimers are complexed with siRNA (FIG. 16B), which is bound by terminal amines. FIG. 16C. siQ control siRNA tagged with ALEXAFLUOR® 647 is efficiently taken up by A2780R and Ovcar8 cells. Scale bar, 100 µm. FIG. 16D. Both TWIST siRNAs, when delivered using YTZ3-15, result in knockdown of TWIST in A2780R cells, but even 100 nM siRNA produces only minimal knockdown in Ovcar8. FIG. 16E. SRB assay reveals that A2780R cells are sensitized to cisplatin following treatment with YTZ3-15-si494 complexes. $IC_{50}$ is reduced from ~200 to ~20 µM.

FIGS. 17A to 17D. FIG. 17A. Schematic of an MSN with pore structure (white). MSNs used in these studies have a PEI coating (purple layer) which binds siRNA (orange). Monomer structure for PEI is shown below. FIG. 17B. Transmission electron micrograph of MSNs. Particles are of uniform diameter, ~120 nm. FIG. 17C. A2780R and Ovcar8 cells efficiently take up MSNs loaded with siQ-AlexaFluor-647. Scale bar, 100 µm. FIG. 17D. In both cell lines, si419 and si494 loaded onto MSNs produce robust TWIST knockdown lasting one week post transfection, although TWIST protein remains at 24 hours post transfection.

FIGS. 18A to 18D. FIG. 18A. In preparation for in vivo studies, si419 was chemically modified to include 2'-O-methyluracil and inverted abasic ribose caps on the passenger strand. This siRNA is termed si419H. Sequences: si419H Passenger (SEQ ID NO:11); si419H Guide (SEQ ID NO:12). FIG. 18B. Confocal microscopy demonstrates MSN delivery of siRNA to Ovcar8-IP cells. siQ-AlexaFluor-647 colocalizes with lysosomes and late endosomes, as stained by LysoTracker, reflecting proper trafficking of MSNs to allow siRNA release. FIG. 18C. Western blot confirms that si419H knocks down TWIST in Ovcar8-IP cells, including at the 24 hour timepoint. Knockdown is still effective one week post treatment. FIG. 18D. SRB cell survival assay reveals that TWIST knockdown sensitizes Ovcar8-IP cells to cisplatin. si419H performs similarly to unmodified si419. Ovcar8 is more sensitive than A2780R, hence a less pronounced effect of TWIST on drug response in Ovcar8-IP.

FIGS. 19A, 19C, 19E. Necropsy images of mice treated with siQ-AlexaFluor-647 on consecutive days reveal localization of MSN-siRNA complexes to the tumor. Bright field is shown in FIG. 19A. GFP fluorescence (FIG. 19C) shows all Ovcar8-IP tumor cells within the abdominal cavity. siQ-AlexaFluor-647 fluorescence (FIG. 19E) is concentrated in the large disseminated mass located near the stomach. FIGS. 19B, 19D, 19F. Imaging of individual organs reveals that negligible quantities of MSNs are found in the uterus, liver, kidney, or spleen. Bright field is shown in FIG. 19B. GFP fluorescence image is shown in FIG. 19D. siQ-AlexaFluor-647 fluorescence (FIG. 19F) is mostly found in disseminated tumors, including a lesion on the liver surface, with limited signal from the primary tumor. Units for luminescence are photons/sec/cm$^2$/steradian.

FIG. 20A. Bioluminescence imaging of Ovcar8-IP tumors. Tumors treated with cisplatin plus MSN-siQ emit noticeably weaker signal than MSN-siQ only control mice, while those treated with cisplatin plus MSN-si419H exhibit a further loss of signal. FIG. 20B. Quantification of bioluminescence for all four weeks of treatment as depicted in A for weeks 1 and 4. Units for luminescence are photons/sec/cm$^2$/steradian.

FIG. 21A. Mice treated with MSN-siQ only have greater numbers and sizes of tumors than TWIST knockdown mice. Cisplatin treatment eliminated much of the tumor mass, but a combination of cisplatin and TWIST knockdown yielded the cleanest peritoneal cavity at the conclusion of the experiment. Arrows indicate tumor foci. One representative image shown per group (n=4). FIG. 21B. Quantification of numbers of disseminated masses seen in images of mice, as seen in A. Cisplatin treatment reduced metastasis incidence by approximately 50%, while combination of cisplatin with MSN-si419H reduced this 75%. FIG. 21C. Quantification of tumor weight for disseminated masses only (left) and total tumor including primary in ovaries (right). Cisplatin, with or without TWIST knockdown, produced a significant drop in tumor weight. Addition of si419H led to a significant decrease in disseminated tumor mass (p=0.0084), and a drop in total tumor mass as well (p=0.1183). si419 alone did not produce a statistically significant change in tumor weight.

FIG. 22A. Western blotting demonstrates differential expression of TWIST1 between Ov8GFP stably transfected cell lines. Blots cropped for clarity; full blots are shown in FIG. 30. FIG. 22B. SRB assay demonstrates that TWIST1 expression leads to increased survival following exposure to cisplatin, particularly at lower doses (5, 10, and 20 µM, p<0.0001; 40 µM, p=0.0002). FIG. 22C. Time lapse microscopy shows that across two logs of cisplatin doses, TWIST1 expression leads to faster growth of cells. TWIST1-expressing cells achieve greater confluence over time than TWIST1 knockdown cells at corresponding drug dose. Average slopes of the lines indicate a faster rate of growth for TWIST1 cells than sh492 cells until confluence is reached. Compare curve labelled with squares (slope=1.15 over 48 hr) vs curve labelled with dots (0.66 over 48 hr) and curve labelled with up-side-down triangles (slope=0.94 over 74 hours) vs curve labelled with triangles (0.79 over 74 hr). FIG. 22D. In vivo tumorigenesis assay shows that TWIST1-expressing cells give rise to widespread disseminated tumours, especially lining the wall of the peritoneal cavity. In contrast, sh492-expressing cells do not colonize the peritoneal wall. Arrows indicate carcinomatosis in mice engrafted with Ov8GFP-TWIST1 cells. All error bars represent standard error of the mean.

FIG. 23A. RNA sequencing showed approximately 2-fold increases in GAS6 and L1CAM and a 2-fold decrease in HMGA2 mRNA when TWIST1 is overexpressed. FPKM, fragments per kilobase per million reads. FIG. 23B. Western blot confirms differential expression of L1CAM and HMGA2 found by RNA-seq. Blots cropped for clarity; full blots are shown in FIG. 30. FIG. 23C. No western blot was possible for GAS6, as the protein is secreted, but qRT-PCR shows on average a 50% decrease in GAS6 mRNA level upon TWIST1 knockdown. p=0.31, although a clear trend is present. Error bars represent standard error of the mean.

FIGS. 24A-24C. Validation of siRNAs targeting genes of interest. qRT-PCR confirms knockdown of L1CAM (FIG. 24A) (46%) and GAS6 (FIG. 24B) (90%) in Ov8GFP-TWIST1 cells treated with corresponding siRNAs, and 91% knockdown of HMGA2 (FIG. 24C) in Ov8GFP-sh492 cells treated with HMGA2 siRNAs. FIG. 24D. Western blot confirms knockdown of L1CAM and HMGA2 at the protein level (normalized results from three independent experiments, p=0.0276 for HMGA2, p=0.0042 for L1CAM). FIG. 24E. SRB assay demonstrates that knockdown of HMGA2 in Ov8GFP-sh492 cells is not sufficient to confer an increased resistance to cisplatin. FIG. 24F. Knockdown of either GAS6 or L1CAM in Ov8GFP-TWIST1 cells sensitizes this line to cisplatin, compared to treatment with non-targeting siRNA. Upper asterisks, siGAS6 (1 µM, p=0.0108, 3 µM p=0.00077, 9 µM p=0.054); lower, siL1CAM (1 µM, p=0.00077, 3 µM p<0.0001, 9 µM p=0.0064). qPCR error bars represent minimum and maximum values calculated by the StepOne software analysis. SRB error bars represent standard error of the mean.

FIG. 25A. Quantification of western blot data shows that over the course of 24 hr, 5 µM cisplatin treatment leads to increased levels of Akt in Ov8GFP-TWIST1 cells, but not in Ov8GFP-sh492 cells. Knockdown of GAS6 or L1CAM in Ov8GFP-TWIST1 cells partially abrogates the increase in Akt. NT, not treated with cisplatin. FIG. 25B. Western blot also reveals an increase in activation of Akt via phosphorylation at Ser 473 over 24 hr of 5 µM cisplatin in TWIST1 expressing cells. The opposite is true in Ov8GFP-sh492 cells, in which Akt activity is reduced over the same time period. Knockdown of GAS6 in Ov8GFP-TWIST1 cells maintains a constant pAkt/Akt ratio, while L1CAM knockdown partially prevents Akt activation. FIG. 25C. Ov8GFP-TWIST1 cells further increase their TWIST1 expression up to 2.3 fold over 24 hr of exposure to 5 µM cisplatin (p=0.0827), whereas Ov8GFP-sh492 cells show no increase. FIG. 25D. Treatment of Ov8GFP-TWIST1 cells with the PI3K inhibitor LY294002 to prevent Akt activation sensitized cells to cisplatin, compared to DMSO only control, supporting the assertion that Akt signalling is central to TWIST1-driven cisplatin resistance. p<0.0001 for both concentrations. Error bars represent standard error of the mean.

FIG. 27A. Quantification of representative western blot data demonstrating that TWIST1 expression is reduced 2-fold by sh492 and increased approximately 3.5-fold by expression of a second copy of the gene. FIG. 27B. Transfection of cells with empty pCI-Neo vector does not substantially affect TWIST1 expression levels. Representative western data shown.

FIG. 31A showed the tumor weight of each experimental group. FIG. 31B showed the tumor imaging of Group B and Group F.

DETAILED DESCRIPTION

I. Definitions

Figure 1A:
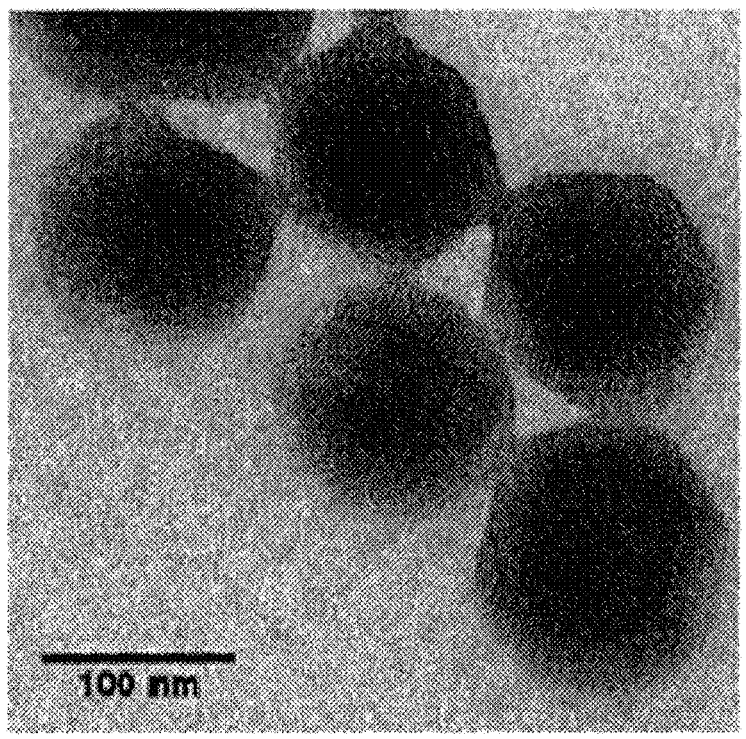
FIGS. 1A to 1D. siRNA-MSN complexes for use in vitro and in vivo.
Figure 1B:
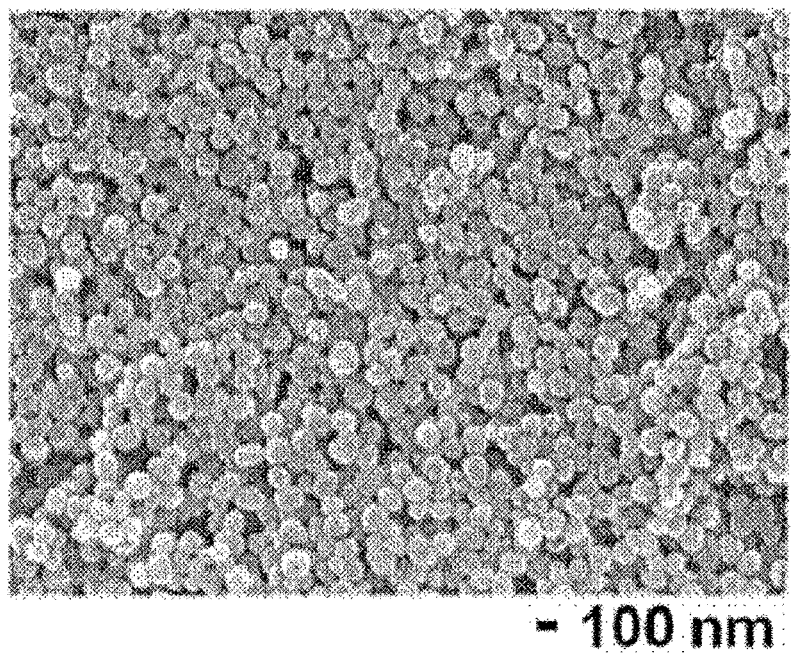

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length. The present invention includes nucleic acids sequences that are substantially identical to any of SEQ ID NOs: 1-21.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent hybridization conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent hybridization conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al., John Wiley & Sons.

For specific proteins described herein (e.g., TWIST, including TWIST1 and TWIST2; or proteins listed in Table 1), the named protein includes any of the protein's naturally occurring forms, or variants that maintain the protein transcription factor activity (e.g., within at least 50%, 80%, 90%, 95%, 96%, 97%, 98%, 99% or 100% activity compared to the native protein). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment thereof.

For specific genes described herein (e.g., TWIST, including TWIST1, TWIST2; or genes listed in Table 1), the named gene includes any of the gene's naturally occurring forms, or variants that encode proteins that maintain the protein activity (e.g., within at least 50%, 80%, 90%, 95%, 96%, 97%, 98%, 99% or 100% activity compared to the native protein). In some embodiments, variants have at least 90%, 95%, 96%, 97%, 98%, 99% or 100% nucleic acid sequence identity across the whole sequence or a portion of the sequence (e.g. a 50, 100, 150 or 200 continuous nucleic acid portion) compared to a naturally occurring form. In other embodiments, the gene is the gene as identified by its NCBI sequence reference. In other embodiments, the gene is 80%, 90%, 95%, 96%, 97%, 98%, 99% or 100% identical to the gene as identified by its NCBI sequence reference or functional fragment thereof.

A "TWIST1 gene" as referred to herein includes any of the recombinant or naturally-occurring forms of the gene encoding Twist Family BHLH Transcription Factor 1 (TWIST1), homologs or variants thereof that maintain TWIST1 protein activity (e.g. within at least 50%, 80%, 90%, 95%, 96%, 97%, 98%, 99% or 100% activity compared to TWIST1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TWIST1 polypeptide (NCBI reference number: NP_000465.1 or Gene ID: GI:4507741). In embodiments, the TWIST1 gene is 80%, 85%, 90%, 95%, 96%, 97%, 98%, 99% or 100% identical to the nucleic acid identified by the NCBI reference number Gene ID: 68160957 (NM_000474.3) or a variant having substantial identity thereto.

A "TWIST2 gene" as referred to herein includes any of the recombinant or naturally-occurring forms of the gene encoding Twist Family BHLH Transcription Factor 2 (TWIST2), homologs or variants thereof that maintain TWIST2 protein activity (e.g. within at least 50%, 80%, 90%, 95%, 96%, 97%, 98%, 99% or 100% activity compared to TWIST2). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TWIST2 polypeptide (NCBI reference number: NP_001258822.1 or Gene ID:429325228). In embodiments, the TWIST2 gene is 80%, 85%, 90%, 95%, 96%, 97%, 98%, 99% or 100% identical to the nucleic acid identified by the NCBI reference number Gene ID: 618468605 (NM_001271893.3) or a variant having substantial identity thereto.

A "HCLS1 gene" as referred to herein includes any of the recombinant or naturally-occurring forms of the gene encoding hematopoietic lineage cell-specific protein 1 (HCLS1), homologs or variants thereof that maintain HCLS1 protein activity (e.g. within at least 50%, 80%, 90%, 95%, 96%, 97%, 98%, 99% or 100% activity compared to HCLS1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring HCLS1 polypeptide (NCBI reference number: NP_001278970 or NP_005326.2). In embodiments, the HCLS1 gene is 80%, 85%, 90%, 95%, 96%, 97%, 98%, 99% or 100% identical to the nucleic acid identified by the NCBI reference number NM_001292041 or NM_005335.5 or a variant having substantial identity thereto.

A "ESM1 gene" as referred to herein includes any of the recombinant or naturally-occurring forms of the gene encoding endothelial cell specific molecule 1 (ESM1), homologs or variants thereof that maintain ESM1 protein activity (e.g. within at least 50%, 80%, 90%, 95%, 96%, 97%, 98%, 99% or 100% activity compared to ESM1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ESM1 polypeptide (NCBI reference number: NP_001129076 or NP_008967). In embodiments, the ESM1 gene is 80%, 85%, 90%, 95%, 96%, 97%, 98%, 99% or 100% identical to the nucleic acid identified by the NCBI reference number NM_001135604 or NM_007036 or a variant having substantial identity thereto.

A "GGT1 gene" as referred to herein includes any of the recombinant or naturally-occurring forms of the gene encoding gamma-glutamyltransferase 1 (GGT1), homologs or variants thereof that maintain GGT1 protein activity (e.g. within at least 50%, 80%, 90%, 95%, 96%, 97%, 98%, 99% or 100% activity compared to GGT1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring GGT1 polypeptide (NCBI reference number: NP_001275762). In embodiments, the GGT1 gene is 80%, 85%, 90%, 95%, 96%, 97%, 98%, 99% or 100% identical to the nucleic acid identified by the NCBI reference number NM_001288833 or a variant having substantial identity thereto.

A "TIE1 gene" as referred to herein includes any of the recombinant or naturally-occurring forms of the gene encoding tyrosine kinase with immunoglobulin like and EGF like domains 1 (TIE1), homologs or variants thereof that maintain TIE1 protein activity (e.g. within at least 50%, 80%, 90%, 95%, 96%, 97%, 98%, 99% or 100% activity compared to TIE1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TIE1 polypeptide (NCBI reference number: NP_001240286 or NP_005415.1). In embodiments, the TIE1 gene is 80%, 85%, 90%, 95%, 96%, 97%, 98%, 99% or 100% identical to the nucleic acid identified by the NCBI reference number NM_001253357 or NM_005424.4 or a variant having substantial identity thereto.

A "CCL20 gene" as referred to herein includes any of the recombinant or naturally-occurring forms of the gene encoding C-C motif chemokine ligand 20 (CCL20), homologs or variants thereof that maintain CCL20 protein activity (e.g. within at least 50%, 80%, 90%, 95%, 96%, 97%, 98%, 99% or 100% activity compared to CCL20). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CCL20 polypeptide (NCBI reference number: NP_001123518 or NP:_004582). In embodiments, the CCL20 gene is 80%, 85%, 90%, 95%, 96%, 97%, 98%, 99% or 100% identical to the nucleic acid identified by the NCBI reference number NM_001130046 or NM_004591 or a variant having substantial identity thereto.

An "ABCA1 gene" as referred to herein includes any of the recombinant or naturally-occurring forms of the gene encoding ATP Binding Cassette Subfamily A Member 1 (ABCA1), homologs or variants thereof that maintain ABCA1 protein activity (e.g. within at least 50%, 80%, 90%, 95%, 96%, 97%, 98%, 99% or 100% activity compared to ABCA1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ABCA1 polypeptide (NCBI reference number: NP_005493). In embodiments, the ABCA1 gene is 80%, 85%, 90%, 95%, 96%, 97%, 98%, 99% or 100% identical to the nucleic acid identified by the NCBI reference number NM_005502 or a variant having substantial identity thereto.

A "SP4 gene" as referred to herein includes any of the recombinant or naturally-occurring forms of the gene encoding Sp4 transcription factor, homologs or variants thereof that maintain SP4 protein activity (e.g. within at least 50%, 80%, 90%, 95%, 96%, 97%, 98%, 99% or 100% activity compared to SP4). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring SP4 polypeptide (NCBI reference number: NP_001313471, NP_001313472, or NP_003103). In embodiments, the SP4 gene is 80%, 85%, 90%, 95%, 96%, 97%, 98%, 99% or 100% identical to the nucleic acid identified by the NCBI reference number NM_001326542, NM_001326543, NM_003112 or a variant having substantial identity thereto.

An "ARHGDIB gene" as referred to herein includes any of the recombinant or naturally-occurring forms of the gene encoding Rho GDP-dissociation inhibitor 2 (ARHGDIB), homologs or variants thereof that maintain ARHGDIB protein activity (e.g. within at least 50%, 80%, 90%, 95%, 96%, 97%, 98%, 99% or 100% activity compared to ARHGDIB). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ARHGDIB polypeptide (NCBI reference number: N_001166). In embodiments, the ARHGDIB gene is 80%, 85%, 90%, 95%, 96%, 97%, 98%, 99% or 100% identical to the nucleic acid identified by the NCBI reference number NM_001175.6 or a variant having substantial identity thereto.

A "LSAMP gene" as referred to herein includes any of the recombinant or naturally-occurring forms of the gene encoding limbic system-associated membrane protein (LSAMP), homologs or variants thereof that maintain LSAMP protein activity (e.g. within at least 50%, 80%, 90%, 95%, 96%, 97%, 98%, 99% or 100% activity compared to LSAMP). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring LSAMP polypeptide (NCBI reference number: NP_001305844 or NP_002329). In embodiments, the LSAMP gene is 80%, 85%, 90%, 95%, 96%, 97%, 98%, 99% or 100% identical to the nucleic acid identified by the NCBI reference number NM_001318915, NM_002338 or a variant having substantial identity thereto.

An "EDN1 gene" as referred to herein includes any of the recombinant or naturally-occurring forms of the gene encoding Endothelin 1 (EDN1), homologs or variants thereof that maintain EDN1 protein activity (e.g. within at least 50%, 80%, 90%, 95%, 96%, 97%, 98%, 99% or 100% activity compared to EDN1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EDN1 polypeptide (NCBI reference number: NP_001161791 or NP_001946). In embodiments, the EDN1 gene is 80%, 85%, 90%, 95%, 96%, 97%, 98%, 99% or 100% identical to the nucleic acid identified by the NCBI reference number NM_0011683198915, NM_001955 or a variant having substantial identity thereto.

An "IL1A gene" as referred to herein includes any of the recombinant or naturally-occurring forms of the gene encoding interleukin 1 alpha (IL1A), homologs or variants thereof that maintain IL1A protein activity (e.g. within at least 50%, 80%, 90%, 95%, 96%, 97%, 98%, 99% or 100% activity compared to IL1A). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL1A polypeptide (NCBI reference number: NP_000566). In embodiments, the IL1A gene is 80%, 85%, 90%, 95%, 96%, 97%, 98%, 99% or 100% identical to the nucleic acid identified by the NCBI reference number NM_000575 or a variant having substantial identity thereto.

A "CTPS2 gene" as referred to herein includes any of the recombinant or naturally-occurring forms of the gene encoding CTP synthase 2 (CTPS2), homologs or variants thereof that maintain CTPS2 protein activity (e.g. within at least 50%, 80%, 90%, 95%, 96%, 97%, 98%, 99% or 100% activity compared to CTPS2). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTPS2 polypeptide (NCBI reference number: NP_001137474, NP_062831, or NP_787055). In embodiments, the CTPS2 gene is 80%, 85%, 90%, 95%, 96%, 97%, 98%, 99% or 100% identical to the nucleic acid identified by the NCBI reference number NM_001144002, NM_019857, NM_175859 or a variant having substantial identity thereto.

A "SERPINB2 gene" as referred to herein includes any of the recombinant or naturally-occurring forms of the gene encoding serpin family B member 2 (SERPINB2), homologs or variants thereof that maintain SERPINB2 protein activity (e.g. within at least 50%, 80%, 90%, 95%, 96%, 97%, 98%, 99% or 100% activity compared to SERPINB2). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring SERPINB2 polypeptide (NCBI reference number: NP_001137290, or NP_002566). In embodiments, the SERPINB2 gene is 80%, 85%, 90%, 95%, 96%, 97%, 98%, 99% or 100% identical to the nucleic acid identified by the NCBI reference number NM_001143818, NM_002575, or a variant having substantial identity thereto.

A "HMGA2 gene" as referred to herein includes any of the recombinant or naturally-occurring forms of the gene encoding high mobility group AT-hook 2 (HMGA2), homologs or variants thereof that maintain HMGA2 protein activity (e.g. within at least 50%, 80%, 90%, 95%, 96%, 97%, 98%, 99% or 100% activity compared to HMGA2). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring HMGA2 polypeptide (NCBI reference number: NP_001287847, NP_001287848, NP_001317119, NP_003474, or NP_003475). In embodiments, the HMGA2 gene is 80%, 85%, 90%, 95%, 96%, 97%, 98%, 99% or 100% identical to the nucleic acid identified by the NCBI reference number NM_001300918, NM_001300919, NM_001330190, NM_003483, NM_003484, or a variant having substantial identity thereto.

A "LOC643201 gene" as referred to herein includes any of the recombinant or naturally-occurring forms of the centrosomal protein 192 kDa pseudogene (LOC643201), homologs or variants thereof that maintain its protein activity (e.g. within at least 50%, 80%, 90%, 95%, 96%, 97%, 98%, 99% or 100% activity compared to LOC643201). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring LOC643201 polypeptide. In embodiments, the LOC643201 gene is 80%, 85%, 90%, 95%, 96%, 97%, 98%, 99% or 100% identical to the nucleic acid identified by the NCBI reference number NR_036494 or a variant having substantial identity thereto.

A "LPHN2 gene" as referred to herein includes any of the recombinant or naturally-occurring forms of the gene encoding adhesion G protein-coupled receptor L2 (LPHN2), homologs or variants thereof that maintain LPHN2 protein activity (e.g. within at least 50%, 80%, 90%, 95%, 96%, 97%, 98%, 99% or 100% activity compared to LPHN2). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring LPHN2 polypeptide (NCBI reference number: NP_001284633). In embodiments, the LPHN2 gene is 80%, 85%, 90%, 95%, 96%, 97%, 98%, 99% or 100% identical to the nucleic acid identified by the NCBI reference number NM_001297704 or a variant having substantial identity thereto.

A "CALB1 gene" as referred to herein includes any of the recombinant or naturally-occurring forms of the gene encoding calbindin 1 (CALB1), homologs or variants thereof that maintain CALB1 protein activity (e.g. within at least 50%, 80%, 90%, 95%, 96%, 97%, 98%, 99% or 100% activity compared to CALB1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CALB1 polypeptide (NCBI reference number: NP_004920). In embodiments, the CALB1 gene is 80%, 85%, 90%, 95%, 96%, 97%, 98%, 99% or 100% identical to the nucleic acid identified by the NCBI reference number NM_004929 or a variant having substantial identity thereto.

A "FAM129A gene" as referred to herein includes any of the recombinant or naturally-occurring forms of the gene encoding family with sequence similarity 129 member A (FAM129A), homologs or variants thereof that maintain FAM129A protein activity (e.g. within at least 50%, 80%, 90%, 95%, 96%, 97%, 98%, 99% or 100% activity compared to FAM129A). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring FAM129A polypeptide (NCBI reference number: NP_443198). In embodiments, the FAM129A gene is 80%, 85%, 90%, 95%, 96%, 97%, 98%, 99% or 100% identical to the nucleic acid identified by the NCBI reference number NM_052966 or a variant having substantial identity thereto.

A "DPYSL3 gene" as referred to herein includes any of the recombinant or naturally-occurring forms of the gene encoding dihydropyrimidinase like 3 (DPYSL3), homologs or variants thereof that maintain DPYSL3 protein activity (e.g. within at least 50%, 80%, 90%, 95%, 96%, 97%, 98%, 99% or 100% activity compared to DPYSL3). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring DPYSL3 polypeptide (NCBI reference number: NP_001184223 or NP_001378). In embodiments, the DPYSL3 gene is 80%, 85%, 90%, 95%, 96%, 97%, 98%, 99% or 100% identical to the nucleic acid identified by the NCBI reference number NM_001197294, NM_001387 or a variant having substantial identity thereto.

A "GAS6 gene" as referred to herein includes any of the recombinant or naturally-occurring forms of the gene encoding growth arrest specific 6 (GAS6), homologs or variants thereof that maintain GAS6 protein activity (e.g. within at least 50%, 80%, 90%, 95%, 96%, 97%, 98%, 99% or 100% activity compared to GAS6). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring GAS6 polypeptide (NCBI reference number: NP_000811). In embodiments, the GAS6 gene is 80%, 85%, 90%, 95%, 96%, 97%, 98%, 99% or 100% identical to the nucleic acid identified by the NCBI reference number NM_000820 or a variant having substantial identity thereto.

A "CHN1 gene" as referred to herein includes any of the recombinant or naturally-occurring forms of the gene encoding chimerin 1 (CHN1), homologs or variants thereof that maintain CHN1 protein activity (e.g. within at least 50%, 80%, 90%, 95%, 96%, 97%, 98%, 99% or 100% activity compared to CHN1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CHN1 polypeptide (NCBI reference number: NP_001020372, NP_001193531 or NP_001813). In embodiments, the CHN1 gene is 80%, 85%, 90%, 95%, 96%, 97%, 98%, 99% or 100% identical to the nucleic acid identified by the NCBI reference number NM_001025201, NM_001206602, NM_001822 or a variant having substantial identity thereto.

A "GREM1 gene" as referred to herein includes any of the recombinant or naturally-occurring forms of the gene encoding gremlin 1, DAN family BMP antagonist (GREM1), homologs or variants thereof that maintain GREM1 protein activity (e.g. within at least 50%, 80%, 90%, 95%, 96%, 97%, 98%, 99% or 100% activity compared to GREM1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring GREM1 polypeptide (NCBI reference number: NP_001178251, NP_001178252 or NP_037504). In embodiments, the GREM1 gene is 80%, 85%, 90%, 95%, 96%, 97%, 98%, 99% or 100% identical to the nucleic acid identified by the NCBI reference number NM_001191322, NM_001191323, NM_013372 or a variant having substantial identity thereto.

A "SHISA9 gene" as referred to herein includes any of the recombinant or naturally-occurring forms of the gene encoding shisa family member 9 (SHISA9), homologs or variants thereof that maintain SHISA9 protein activity (e.g. within at least 50%, 80%, 90%, 95%, 96%, 97%, 98%, 99% or 100% activity compared to SHISA9). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring SHISA9 polypeptide (NCBI reference number: NP_001138676, or NP_001138677). In embodiments, the SHISA9 gene is 80%, 85%, 90%, 95%, 96%, 97%, 98%, 99% or 100% identical to the nucleic acid identified by the NCBI reference number NM_001145204, NM_001145205 or a variant having substantial identity thereto.

An "EPHB1 gene" as referred to herein includes any of the recombinant or naturally-occurring forms of the gene encoding Ephrin type-B receptor 1 (EPHB1), homologs or variants thereof that maintain EPHB1 protein activity (e.g. within at least 50%, 80%, 90%, 95%, 96%, 97%, 98%, 99% or 100% activity compared to EPHB1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EPHB1 polypeptide (NCBI reference number: NM_004441). In embodiments, the EPHB1 gene is 80%, 85%, 90%, 95%, 96%, 97%, 98%, 99% or 100% identical to the nucleic acid identified by the NCBI reference number NM_004441 or a variant having substantial identity thereto.

A "RHOBTB1 gene" as referred to herein includes any of the recombinant or naturally-occurring forms of the gene encoding Rho-related BTB domain-containing protein 1 (RHOBTB1), homologs or variants thereof that maintain RHOBTB1 protein activity (e.g. within at least 50%, 80%, 90%, 95%, 96%, 97%, 98%, 99% or 100% activity compared to RHOBTB1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring RHOBTB1 polypeptide (NCBI reference number: NP_001229288). In embodiments, the RHOBTB1 gene is 80%, 85%, 90%, 95%, 96%, 97%, 98%, 99% or 100% identical to the nucleic acid identified by the NCBI reference number NM_001242359 or a variant having substantial identity thereto.

A "L1CAM gene" as referred to herein includes any of the recombinant or naturally-occurring forms of the gene encoding L1 cell adhesion molecule (L1CAM), homologs or variants thereof that maintain L1CAM protein activity (e.g. within at least 50%, 80%, 90%, 95%, 96%, 97%, 98%, 99% or 100% activity compared to L1CAM). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring L1CAM polypeptide (NCBI reference number: NP_000416.1, NP_001137435.1, NP_001265045.1 or NP_076493.1). In embodiments, the L1CAM gene is 80%, 85%, 90%, 95%, 96%, 97%, 98%, 99% or 100% identical to the nucleic acid identified by the NCBI reference number NM_000425.4, NM_001143963.2, NM_001278116.1, NM_024003.3 or a variant having substantial identity thereto.

A "PCSK9 gene" as referred to herein includes any of the recombinant or naturally-occurring forms of the gene encoding proprotein convertase subtilisin/kexin type 9 (PCSK9), homologs or variants thereof that maintain PCSK9 protein activity (e.g. within at least 50%, 80%, 90%, 95%, 96%, 97%, 98%, 99% or 100% activity compared to PCSK9). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PCSK9 polypeptide (NCBI reference number: NP_777596). In embodiments, the PCSK9 gene is 80%, 85%, 90%, 95%, 96%, 97%, 98%, 99% or 100% identical to the nucleic acid identified by the NCBI reference number NM_174936 or a variant having substantial identity thereto.

An "OAS3 gene" as referred to herein includes any of the recombinant or naturally-occurring forms of the gene encoding 2'-5'-oligoadenylate synthase 3 (OAS3), homologs or variants thereof that maintain OAS3 protein activity (e.g. within at least 50%, 80%, 90%, 95%, 96%, 97%, 98%, 99% or 100% activity compared to OAS3). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring OAS3 polypeptide (NCBI reference number: NP_006178). In embodiments, the OAS3 gene is 80%, 85%, 90%, 95%, 96%, 97%, 98%, 99% or 100% identical to the nucleic acid identified by the NCBI reference number NM_006187 or a variant having substantial identity thereto.

A "LOX gene" as referred to herein includes any of the recombinant or naturally-occurring forms of the gene encoding protein-lysine 6-oxidase (LOX), homologs or variants thereof that maintain LOX protein activity (e.g. within at least 50%, 80%, 90%, 95%, 96%, 97%, 98%, 99% or 100% activity compared to LOX). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring LOX polypeptide (NCBI reference number: NP_002308). In embodiments, the LOX gene is 80%, 85%, 90%, 95%, 96%, 97%, 98%, 99% or 100% identical to the nucleic acid identified by the NCBI reference number NM_002317 or a variant having substantial identity thereto.

A "DOK7 gene" as referred to herein includes any of the recombinant or naturally-occurring forms of the gene encoding protein docking protein 7 (DOK7), homologs or variants thereof that maintain DOK7 protein activity (e.g. within at least 50%, 80%, 90%, 95%, 96%, 97%, 98%, 99% or 100% activity compared to DOK7). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring DOK7 polypeptide (NCBI reference number: NP_001158145). In embodiments, the DOK7 gene is 80%, 85%, 90%, 95%, 96%, 97%, 98%, 99% or 100% identical to the nucleic acid identified by the NCBI reference number NM_001164673 or a variant having substantial identity thereto.

An "ID3 gene" as referred to herein includes any of the recombinant or naturally-occurring forms of the gene encoding inhibitor of DNA binding 3 (ID3), homologs or variants thereof that maintain ID3 protein activity (e.g. within at least 50%, 80%, 90%, 95%, 96%, 97%, 98%, 99% or 100% activity compared to ID3). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ID3 polypeptide (NCBI reference number: NP_002158). In embodiments, the ID3 gene is 80%, 85%, 90%, 95%, 96%, 97%, 98%, 99% or 100% identical to the nucleic acid identified by the NCBI reference number NM_002167 or a variant having substantial identity thereto.

A "LEPREL1 gene" as referred to herein includes any of the recombinant or naturally-occurring forms of the gene encoding prolyl 3-hydroxylase 2 (LEPREL1), homologs or variants thereof that maintain LEPREL1 protein activity (e.g. within at least 50%, 80%, 90%, 95%, 96%, 97%, 98%, 99% or 100% activity compared to LEPREL1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring LEPREL1 polypeptide (NCBI reference number: NP_001127890). In embodiments, the LEPREL1 gene is 80%, 85%, 90%, 95%, 96%, 97%, 98%, 99% or 100% identical to the nucleic acid identified by the NCBI reference number NM_001134418 or a variant having substantial identity thereto.

A "CAPN6 gene" as referred to herein includes any of the recombinant or naturally-occurring forms of the gene encoding calpain-6 (CAPN6), homologs or variants thereof that maintain CAPN6 protein activity (e.g. within at least 50%, 80%, 90%, 95%, 96%, 97%, 98%, 99% or 100% activity compared to CAPN6). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CAPN6 polypeptide (NCBI reference number: NP_055104). In embodiments, the CAPN6 gene is 80%, 85%, 90%, 95%, 96%, 97%, 98%, 99% or 100% identical to the nucleic acid identified by the NCBI reference number NM_014289 or a variant having substantial identity thereto.

A "FN1 gene" as referred to herein includes any of the recombinant or naturally-occurring forms of the gene encoding fibronectin 1 (FN1), homologs or variants thereof that maintain FN1 protein activity (e.g. within at least 50%, 80%, 90%, 95%, 96%, 97%, 98%, 99% or 100% activity compared to FN1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring FN1 polypeptide (NCBI reference number: NP_001293058). In embodiments, the FN1 gene is 80%, 85%, 90%, 95%, 96%, 97%, 98%, 99% or 100% identical to the nucleic acid identified by the NCBI reference number NM_001306129 or a variant having substantial identity thereto.

A "COL12A1 gene" as referred to herein includes any of the recombinant or naturally-occurring forms of the gene encoding collagen alpha-1(XII) chain (COL12A1), homologs or variants thereof that maintain COL12A1 protein activity (e.g. within at least 50%, 80%, 90%, 95%, 96%, 97%, 98%, 99% or 100% activity compared to COL12A1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring COL12A1 polypeptide (NCBI reference number: NP_004361). In embodiments, the COL12A1 gene is 80%, 85%, 90%, 95%, 96%, 97%, 98%, 99% or 100% identical to the nucleic acid identified by the NCBI reference number NM_004370 or a variant having substantial identity thereto.

An "AMIGO2 gene" as referred to herein includes any of the recombinant or naturally-occurring forms of the gene encoding amphoterin-induced protein 2 (AMIGO2), homologs or variants thereof that maintain AMIGO2 protein activity (e.g. within at least 50%, 80%, 90%, 95%, 96%, 97%, 98%, 99% or 100% activity compared to AMIGO2). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring AMIGO2 polypeptide (NCBI reference number: NP_001137140). In embodiments, the AMIGO2 gene is 80%, 85%, 90%, 95%, 96%, 97%, 98%, 99% or 100% identical to the nucleic acid identified by the NCBI reference number NM_001143668 or a variant having substantial identity thereto.

A "GALNT3 gene" as referred to herein includes any of the recombinant or naturally-occurring forms of the gene encoding polypeptide N-acetylgalactosaminyltransferase 3 (GALNT3), homologs or variants thereof that maintain GALNT3 protein activity (e.g. within at least 50%, 80%, 90%, 95%, 96%, 97%, 98%, 99% or 100% activity compared to GALNT3). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring GALNT3 polypeptide (NCBI reference number: NP_004473). In embodiments, the GALNT3 gene is 80%, 85%, 90%, 95%, 96%, 97%, 98%, 99% or 100% identical to the nucleic acid identified by the NCBI reference number NM_004482 or a variant having substantial identity thereto.

A "COL4A4 gene" as referred to herein includes any of the recombinant or naturally-occurring forms of the gene encoding collagen alpha-4(IV) chain (COL4A4), homologs or variants thereof that maintain COL4A4 protein activity (e.g. within at least 50%, 80%, 90%, 95%, 96%, 97%, 98%, 99% or 100% activity compared to COL4A4). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring COL4A4 polypeptide (NCBI reference number: NP_000083). In embodiments, the COL4A4 gene is 80%, 85%, 90%, 95%, 96%, 97%, 98%, 99% or 100% identical to the nucleic acid identified by the NCBI reference number NM_000092 or a variant having substantial identity thereto.

A "HOXA3 gene" as referred to herein includes any of the recombinant or naturally-occurring forms of the gene encoding homeobox protein Hox-A3 (HOXA3), homologs or variants thereof that maintain HOXA3 protein activity (e.g. within at least 50%, 80%, 90%, 95%, 96%, 97%, 98%, 99% or 100% activity compared to HOXA3). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring HOXA3 polypeptide (NCBI reference number: NP_109377). In embodiments, the HOXA3 gene is 80%, 85%, 90%, 95%, 96%, 97%, 98%, 99% or 100% identical to the nucleic acid identified by the NCBI reference number NM_030661 or a variant having substantial identity thereto.

An "ATOH8 gene" as referred to herein includes any of the recombinant or naturally-occurring forms of the gene encoding protein atonal homolog 8 (ATOH8), homologs or variants thereof that maintain ATOH8 protein activity (e.g. within at least 50%, 80%, 90%, 95%, 96%, 97%, 98%, 99% or 100% activity compared to ATOH8). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ATOH8 polypeptide (NCBI reference number: NP_116216). In embodiments, the ATOH8 gene is 80%, 85%, 90%, 95%, 96%, 97%, 98%, 99% or 100% identical to the nucleic acid identified by the NCBI reference number NM_032827 or a variant having substantial identity thereto.

A "GDF6 gene" as referred to herein includes any of the recombinant or naturally-occurring forms of the gene encoding growth/differentiation factor 6 (GDF6), homologs or variants thereof that maintain GDF6 protein activity (e.g. within at least 50%, 80%, 90%, 95%, 96%, 97%, 98%, 99% or 100% activity compared to GDF6). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring GDF6 polypeptide (NCBI reference number: NP_001001557). In embodiments, the GDF6 gene is 80%, 85%, 90%, 95%, 96%, 97%, 98%, 99% or 100% identical to the nucleic acid identified by the NCBI reference number NM_001001557 or a variant having substantial identity thereto.

A "PXDNL gene" as referred to herein includes any of the recombinant or naturally-occurring forms of the gene encoding peroxidasin-like protein (PXDNL), homologs or variants thereof that maintain PXDNL protein activity (e.g. within at least 50%, 80%, 90%, 95%, 96%, 97%, 98%, 99% or 100% activity compared to PXDNL). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PXDNL polypeptide (NCBI reference number: NP_653252). In embodiments, the PXDNL gene is 80%, 85%, 90%, 95%, 96%, 97%, 98%, 99% or 100% identical to the nucleic acid identified by the NCBI reference number NM_144651 or a variant having substantial identity thereto.

A "BDKRB1 gene" as referred to herein includes any of the recombinant or naturally-occurring forms of the gene encoding B1 bradykinin receptor 1 (BDKRB1), homologs or variants thereof that maintain BDKRB1 protein activity (e.g. within at least 50%, 80%, 90%, 95%, 96%, 97%, 98%, 99% or 100% activity compared to BDKRB1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring BDKRB1 polypeptide (NCBI reference number: NP_000701). In embodiments, the BDKRB1 gene is 80%, 85%, 90%, 95%, 96%, 97%, 98%, 99% or 100% identical to the nucleic acid identified by the NCBI reference number NM_000710 or a variant having substantial identity thereto.

A "LINC00452 gene" as referred to herein includes any of the recombinant or naturally-occurring forms of the gene long intergenic non-protein coding RNA 452 (LINC00452), homologs or variants thereof that maintain its protein activity (e.g. within at least 50%, 80%, 90%, 95%, 96%, 97%, 98%, 99% or 100% activity compared to wild type protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring LINC00452 polypeptide (NCBI reference number: NP_001265603). In embodiments, the LINC00452 gene is 80%, 85%, 90%, 95%, 96%, 97%, 98%, 99% or 100% identical to the nucleic acid identified by the NCBI reference number NM_001278674 or a variant having substantial identity thereto.

A "VIP gene" as referred to herein includes any of the recombinant or naturally-occurring forms of the gene encoding vasoactive intestinal peptide (VIP), homologs or variants thereof that maintain VIP protein activity (e.g. within at least 50%, 80%, 90%, 95%, 96%, 97%, 98%, 99% or 100% activity compared to VIP). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring VIP polypeptide (NCBI reference number: NP_003372 or NP_919416.1). In embodiments, the VIP gene is 80%, 85%, 90%, 95%, 96%, 97%, 98%, 99% or 100% identical to the nucleic acid identified by the NCBI reference number NM_003381, NM_194435.2, or a variant having substantial identity thereto.

A "DPT gene" as referred to herein includes any of the recombinant or naturally-occurring forms of the gene encoding dermatopontin (DPT), homologs or variants thereof that maintain DPT protein activity (e.g. within at least 50%, 80%, 90%, 95%, 96%, 97%, 98%, 99% or 100% activity compared to DPT). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring DPT polypeptide (NCBI reference number: NP_001928). In embodiments, the DPT gene is 80%, 85%, 90%, 95%, 96%, 97%, 98%, 99% or 100% identical to the nucleic acid identified by the NCBI reference number NM_001937 or a variant having substantial identity thereto.

A "KCNA10 gene" as referred to herein includes any of the recombinant or naturally-occurring forms of the gene encoding B1 bradykinin receptor 1 (KCNA10), homologs or variants thereof that maintain KCNA10 protein activity (e.g. within at least 50%, 80%, 90%, 95%, 96%, 97%, 98%, 99% or 100% activity compared to KCNA10). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring KCNA10 polypeptide (NCBI reference number: NP_005540). In embodiments, the KCNA10 gene is 80%, 85%, 90%, 95%, 96%, 97%, 98%, 99% or 100% identical to the nucleic acid identified by the NCBI reference number NM_005549 or a variant having substantial identity thereto.

A "microRNA," "microRNA nucleic acid sequence," "miR," "miRNA" as used herein, refers to a nucleic acid that functions in RNA silencing and post-transcriptional regulation of gene expression. The term includes all forms of a miRNA, such as the pri-, pre-, and mature forms of the miRNA. In embodiments, microRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA. In embodiments, a miRNA nucleic acid sequence described herein is about 10 to 80 nucleotides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 nucleotides) in length. In embodiments, a miRNA nucleic acid sequence described herein is about 15 to 50 nucleotides (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides) in length. In embodiments, a miRNA nucleic acid sequence described herein is about 18 to 25 nucleotides (e.g., 18, 19, 20, 21, 22, 23, 24, 25 nucleotides) in length.

As used herein, the term "miR484" or "miR484 nucleic acid sequence" includes all forms of miR484 including the pri-, pre-, and mature forms of miR484, as well as variants, homologues, modifications, and derivatives thereof (e.g., within at least 50%, 80%, 90%, 95%, 96%, 97%, 98%, 99% or 100% activity compared to the native miR484). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR484 is the miRNA as identified by NCBI Reference Sequence: NR_030159.

As used herein, the term "miR1909" or "miR1909 nucleic acid sequence" includes all forms of miR1909 including the pri-, pre-, and mature forms of miR1909, as well as variants, homologues, modifications, and derivatives thereof (e.g., within at least 50%, 80%, 90%, 95%, 96%, 97%, 98%, 99% or 100% activity compared to the native miR1909). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR1909 is the miRNA as identified by NCBI Reference Sequence: NR_031730.

As used herein, the term "miR5193" or "miR5193 nucleic acid sequence" includes all forms of miR5193 including the pri-, pre-, and mature forms of miR5193, as well as variants, homologues, modifications, and derivatives thereof (e.g., within at least 50%, 80%, 90%, 95%, 96%, 97%, 98%, 99% or 100% activity compared to the native miR5193). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR5193 is the miRNA as identified by NCBI Reference Sequence: NR_049825.

As used herein, the term "miR4324" or "miR4324 nucleic acid sequence" includes all forms of miR4324 including the pri-, pre-, and mature forms of miR4324, as well as variants, homologues, modifications, and derivatives thereof (e.g., within at least 50%, 80%, 90%, 95%, 96%, 97%, 98%, 99% or 100% activity compared to the native miR4324). In embodiments, the variants or homologues or derivatives have at least 50%, 80%, 85%, 90%, 91%, 92%, 93%, 94%, 95%, 96%, 97%, 98%, 99% or 100% sequence identity across the whole sequence or a portion of the sequence (e.g. a 10, 15, 20, 25, 30, 40, 45, 50, 55, 60, 65, 70, 75, or 80 continuous nucleotides portion) compared to a naturally occurring form. In embodiments, the miR4324 is the miRNA as identified by NCBI Reference Sequence: NR_036209.

An "siRNA" refers to a nucleic acid that forms a double stranded RNA, which double stranded RNA has the ability to reduce or inhibit expression of a gene or target gene when the siRNA is present (e.g. expressed) in the same cell as the gene or target gene. The siRNA is typically about 5 to about 100 nucleotides in length, more typically about 10 to about 50 nucleotides in length, more typically about 15 to about 30 nucleotides in length, most typically about 20-30 base nucleotides, or about 20-25 or about 24-29 nucleotides in length, e.g., 20, 21, 22, 23, 24, 25, 26, 27, 28, 29, or 30 nucleotides in length. siRNA molecules and methods of generating them are described in, e.g., Bass, 2001, Nature, 411, 428-429; Elbashir et al., 2001, Nature, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, Molecular Interventions, 2:158 (2002).

Of the double stranded RNA of an siRNA, the strand that is at least partially complementary to at least a portion of a specific target nucleic acid (e.g. a target nucleic acid sequence), such as an mRNA molecule (e.g. a target mRNA molecule), is called the antisense (or guide strand; and the other strand is called sense (or passenger strand). The passenger strand is degraded and the guide strand is incorporated into the RNA-induced silencing complex (RISC).

The siRNA can be administered directly or siRNA expression vectors can be used to induce RNAi that have different design criteria. A vector can have inserted two inverted repeats separated by a short spacer sequence and ending with a string of T's which serve to terminate transcription.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

The compositions described herein can be purified. Purified compositions are at least about 60% by weight (dry weight) the compound of interest. Preferably, the preparation is at least about 75%, more preferably at least about 90%, and most preferably at least about 99% or higher by weight the compound of interest. Purity is measured by any appropriate standard method, for example, by High-performance liquid chromatography, polyacrylamide gel electrophoresis.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a siRNA, (e.g., shRNA, miRNA, snoRNA), compound or small molecule that inhibits cellular function (e.g., replication) e.g., by binding, partially or totally blocking stimulation, decrease, prevent, or delay activation, or inactivate, desensitize, or down-regulate signal transduction, gene expression or enzymatic activity necessary for protein activity. A "TWIST inhibitor" refers to a substance that results in a detectably lower expression of TWIST (TWIST1, TWIST2 or both) genes or TWIST (TWIST1, TWIST2 or both) proteins or lower activity level of TWIST (TWIST1, TWIST2 or both) proteins as compared to those levels without such substance. In some embodiments, a TWIST inhibitor is an inhibitor for both TWIST1 and TWIST2. In some embodiments, a TWIST inhibitor is an anti-TWIST siRNA. In some embodiments, a TWIST inhibitor is a composition (e.g., an anti-TWIST siRNA bound to a nanoparticle) described herein. In some embodiments, a TWIST inhibitor is a pharmaceutical composition described herein.

"TWIST signaling" or "TWIST signaling pathway" used herein refers to the intracellular signaling pathway activated when TWIST (TWIST1 or TWIST2 or both TWIST1 and TWIST2) binds to DNA and initiates its transcriptional activity. Activation of TWIST initiates functioning of many downstream factors and signaling pathways. "TWIST signaling gene" refers to a gene in the TWIST signaling. In embodiments, TWIST signaling genes include TWIST1, TWIST2, genes listed in Table 1 and an Akt (or Akt/PI3K) signaling gene. "TWIST signaling protein" refers to a protein in the TWIST signaling protein. In embodiments, TWIST signaling proteins include TWIST1, TWIST2, proteins listed in Table 1 and an Akt (or Akt/PI3K) signaling protein.

"Akt (or Akt/PI3K) signaling" or "Akt (or Akt/PI3K) signaling pathway" used herein refers to intracellular signaling pathway activated when growth factor causes activation of a cell surface receptor and phosphorylation of PI3K. Activated PI3K then phosphorylates lipids on the plasma membrane, forming second messenger phosphatidylinositol (3,4,5)-trisphosphate (PIP3). Akt, a serine/threonine kinase, is recruited to the membrane by interaction with these phosphoinositide docking sites, so that it can be fully activated. Activated Akt mediates downstream responses, including cell survival, growth, proliferation, cell migration and angiogenesis, by phosphorylating a range of intracellular proteins. "Akt/PI3K signaling gene" refers to a gene in the Akt/PI3K signaling. In embodiments, Akt/PI3K signaling genes include Akt (e.g., Akt1, Akt2, or Akt3) and PI3K genes. "Akt/PI3K signaling protein" refers to a protein in the Akt/PI3K signaling. In embodiments, Akt/PI3K signaling proteins include Akt (e.g., Akt1, Akt2, or Akt3) and PI3K proteins.

An "Akt1 gene" as referred to herein includes any of the recombinant or naturally-occurring forms of the gene encoding RAC-alpha serine/threonine-protein kinase (Akt1), homologs or variants thereof that maintain Akt1protein activity (e.g. within at least 50%, 80%, 90%, 95%, 96%, 97%, 98%, 99% or 100% activity compared to Akt1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Akt1 polypeptide (NCBI reference number: NP_001014432.1 or NP_005154.2). In embodiments, the Akt1 gene is 80%, 85%, 90%, 95%, 96%, 97%, 98%, 99% or 100% identical to the nucleic acid identified by the NCBI reference number NM_001014432.1, NM_005163.2 or a variant having substantial identity thereto.

An "Akt1" as referred to herein includes any of the recombinant or naturally-occurring forms of RAC-alpha serine/threonine-protein kinase (Akt1), homologs or variants thereof that maintain Akt1 protein activity (e.g. within at least 50%, 80%, 90%, 95%, 96%, 97%, 98%, 99% or 100% activity compared to Akt1). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Akt1 protein. In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to amino acid sequence identified by NCBI reference number: NP_001014432.1 or NP_005154.2.

An "Akt2 gene" as referred to herein includes any of the recombinant or naturally-occurring forms of the gene encoding RAC-beta serine/threonine-protein kinase (Akt2), homologs or variants thereof that maintain Akt2 protein activity (e.g. within at least 50%, 80%, 90%, 95%, 96%, 97%, 98%, 99% or 100% activity compared to Akt2). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Akt2 polypeptide (NCBI reference number: NP_001229956.1 or NP_001229957.1, NP_001317440.1, NP_001617.1). In embodiments, the Akt2 gene is 80%, 85%, 90%, 95%, 96%, 97%, 98%, 99% or 100% identical to the nucleic acid identified by the NCBI reference number NM_001243027.2, NM_001243028.2, NM_001330511.1, NM_001626.5 or a variant having substantial identity thereto.

An "Akt2" as referred to herein includes any of the recombinant or naturally-occurring forms of RAC-beta serine/threonine-protein kinase (Akt2), homologs or variants thereof that maintain Akt2 protein activity (e.g. within at least 50%, 80%, 90%, 95%, 96%, 97%, 98%, 99% or 100% activity compared to Akt2). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Akt2 protein. In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to amino acid sequence identified by NCBI reference number: NM_001243027.2, NM_001243028.2, NM_001330511.1, or NM_001626.5.

An "Akt3 gene" as referred to herein includes any of the recombinant or naturally-occurring forms of the gene encoding RAC-gamma serine/threonine-protein kinase (Akt3), homologs or variants thereof that maintain Akt2 protein activity (e.g. within at least 50%, 80%, 90%, 95%, 96%, 97%, 98%, 99% or 100% activity compared to Akt3). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Akt3 polypeptide (NCBI reference number: NP_001193658.1, NP_005456.1, NP_859029.1, or NP_001617.1). In embodiments, the Akt3 gene is 80%, 85%, 90%, 95%, 96%, 97%, 98%, 99% or 100% identical to the nucleic acid identified by the NCBI reference number NM_001206729.1, NM_005465.4, NM_181690.2 or a variant having substantial identity thereto.

An "Akt3" as referred to herein includes any of the recombinant or naturally-occurring forms of RAC-gamma serine/threonine-protein kinase (Akt3), homologs or variants thereof that maintain Akt3 protein activity (e.g. within at least 50%, 80%, 90%, 95%, 96%, 97%, 98%, 99% or 100% activity compared to Akt3). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Akt3 protein. In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to amino acid sequence identified by NCBI reference number: NP_001193658.1, NP_005456.1, NP_859029.1, or NP_001617.1.

A "PI3K" as referred to herein includes any of the recombinant or naturally-occurring forms of phosphatidylinositide 3-kinases (PI3K), homologs or variants thereof that maintain Akt3 protein activity (e.g. within at least 50%, 80%, 90%, 95%, 96%, 97%, 98%, 99% or 100% activity compared to PI3K). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PI3K protein.

In embodiments, PI3K is class I PI3K. Class I PI3Ks are responsible for the production of phosphatidylinositol 3-phosphate (PI(3)P), phosphatidylinositol (3,4)-bisphosphate (PI(3,4)P2), and phosphatidylinositol (3,4,5)-trisphosphate (PI(3,4,5)P3). Class I PI3K are heterodimeric molecules composed of a regulatory and a catalytic subunit; they are further divided between IA and IB subsets on sequence similarity. Class IA PI3K is composed of a heterodimer between a p110 catalytic subunit and a p85 regulatory subunit. There are five variants of the p85 regulatory subunit, designated p85α, p55α, p50α, p85β, and p55γ. There are also three variants of the p110 catalytic subunit designated p110α, β, or δ catalytic subunit. The first three regulatory subunits are all splice variants of the same gene (Pik3r1), the other two being expressed by other genes (Pik3r2 and Pik3r3, p85β, and p55γ, respectively). The most highly expressed regulatory subunit is p85α; all three catalytic subunits are expressed by separate genes (Pik3ca, Pik3cb, and Pik3cd for p110α, p110β, and p110δ, respectively). The first two p110 isoforms (α and β) are expressed in all cells, but p110δ is expressed primarily in leukocytes, and it has been suggested that it evolved in parallel with the adaptive immune system. The regulatory p101 and catalytic p110γ subunits comprise the class IB PI3Ks and are encoded by a single gene each. The p85 subunits contain SH2 and SH3 domains. The SH2 domains bind preferentially to phosphorylated tyrosine residues in the amino acid sequence context Y-X-X-M.

In embodiments, PI3K is class II and III PI3K. Class II and III PI3K are differentiated from the Class I by their structure and function. The distinct feature of Class II PI3Ks is the C-terminal C2 domain. This domain lacks critical Asp residues to coordinate binding of Ca2+, which suggests class II PI3Ks bind lipids in a Ca2+-independent manner. Class II comprises three catalytic isoforms (C2α, C2β, and C2γ), but, unlike Classes I and III, no regulatory proteins. Class II catalyzes the production of PI(3)P from PI and PI(3,4)P2 from PIP; however, little is known about their role in immune cells. C2α and C2β are expressed through the body, but expression of C2γ is limited to hepatocytes. Class III produces only PI(3)P from PI but are more similar to Class I in structure, as they exist as heterodimers of a catalytic (Vps34) and a regulatory (Vps15/p150) subunits. Class III seems to be primarily involved in the trafficking of proteins and vesicles.

Exemplary PI3K genes/proteins include:

A "TWIST signaling inhibitor" refers to a substance that results in a detectably lower expression and/or activity of one or more TWIST signaling genes/proteins as compared to those levels without such substance. In embodiments, a TWIST signaling inhibitor results in a detectably lower gene expression of one or more TWIST signaling genes. In embodiments, a TWIST signaling inhibitor results in a detectably lower protein expression of one or more TWIST signaling proteins. In embodiments, a TWIST signaling inhibitor results in lower activity level of one or more TWIST signaling proteins compared to those levels without such inhibitor. In some embodiments, a TWIST signaling inhibitor is a siRNA inhibitor. In some embodiments, a TWIST signaling inhibitor is a small molecule inhibitor. In embodiments, a TWIST signaling inhibitor is a TWIST inhibitor, an inhibitor of genes/proteins listed in Table 1 and/or an Akt signaling genes/proteins. In embodiments, a TWIST signaling inhibitor is a TWIST inhibitor, an inhibitor of GAS6, L1CAM, PI3K or protein kinase B (also known as Akt). In some embodiments, a TWIST signaling inhibitor is a composition (e.g., an inhibitor bound to a delivery vehicle) described herein. In some embodiments, a TWIST signaling inhibitor is a pharmaceutical composition described herein.

A "pharmaceutical composition" is a formulation containing the composition (e.g., an siRNA inhibitor, a small molecule inhibitor, or an siRNA inhibitor bound to a nanoparticle) described herein in a form suitable for administration to a subject. In embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., an siRNA inhibitor, a small molecule inhibitor, or an siRNA inhibitor bound to a nanoparticle) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In embodiments, the active TWIST signaling inhibitor is mixed under sterile

| group | gene | protein | aliases | EC number |
|---|---|---|---|---|
| class 1 catalytic | PIK3CA | PI3K, catalytic, alpha polypeptide | p110-α | 2.7.1.153 |
| | PIK3CB | PI3K, catalytic, beta polypeptide | p110-β | |
| | PIK3CG | PI3K, catalytic, gamma polypeptide | p110-γ | |
| | PIK3CD | PI3K, catalytic, delta polypeptide | p110-δ | |
| class 1 regulatory | PIK3R1 | PI3K, regulatory subunit 1 (alpha) | p85-α | N/A |
| | PIK3R2 | PI3K, regulatory subunit 2 (beta) | p85-β | |
| | PIK3R3 | PI3K, regulatory subunit 3 (gamma) | p55-γ | |
| | PIK3R4 | PI3K, regulatory subunit 4 | p150 | |
| | PIK3R5 | PI3K, regulatory subunit 5 | p101 | |
| | PIK3R6 | PI3K, regulatory subunit 6 | p87 | |
| class 2 | PIK3C2A | PI3K, class 2, alpha polypeptide | PI3K-C2α | 2.7.1.154 |
| | PIK3C2B | PI3K, class 2, beta polypeptide | PI3K-C2β | |
| | PIK3C2G | PI3K, class 2, gamma polypeptide | PI3K-C2γ | |
| class 3 | PIK3C3 | PI3K, class 3 | Vps34 | 2.7.1.137 | conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. A thorough discussion of pharmaceutically acceptable excipients is available in REMINGTON'S PHARMACEUTICAL SCIENCES (Mack Pub. Co., N.J. 1991). Pharmaceutically acceptable excipients in therapeutic compositions may contain liquids such as water, saline, glycerol and ethanol. Additionally, auxiliary substances, such as wetting or emulsifying agents, pH buffering substances, and the like, may be present in such vehicles.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized sepharose(TM), agarose, cellulose, and the like), polymeric amino acids, amino acid copolymers, and lipid aggregates (such as oil droplets or liposomes). Additionally, these carriers can function as immunostimulating agents (i.e., adjuvants).

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A pharmaceutical composition of the invention can be administered to a subject in many of the well-known methods currently used for chemotherapeutic treatment. For example, for treatment of cancers, a composition of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

As used herein, "monotherapy" refers to the administration of a single active or therapeutic compound to a subject in need thereof. Preferably, monotherapy will involve administration of a therapeutically effective amount of an active composition (e.g., an anti-TWIST siRNA or any composition described herein). For example, described herein can be a cancer monotherapy with one of compositions of the present invention to a subject in need of treatment of cancer. Monotherapy may be contrasted with combination therapy, in which a combination of multiple active compositions (e.g., multiple anti-TWIST siRNAs) is administered, preferably with each component of the combination present in a therapeutically effective amount. Monotherapy with a composition of the present invention may be more effective than combination therapy in inducing a desired biological effect.

As used herein, "combination therapy" or "co-therapy" includes the administration of a composition of the present invention and at least a second agent as part of a specific treatment regimen intended to provide the beneficial effect from the co-action of these therapeutic agents. The beneficial effect of the combination may include, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A composition of the present invention may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The anti-cancer agents set forth below are for illustrative purposes and not intended to be limiting. The present invention includes at least one anti-cancer agent selected from the lists below. The present invention can include more than one anti-cancer agent, e.g., two, three, four, or five anti-cancer agents such that the composition of the present invention can perform its intended function.

In embodiments, the anticancer agent is a compound that affects histone modifications, such as an HDAC inhibitor. In certain embodiments, an anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologics (such as Alpha Interferon, Bacillus Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Tykerb®, Velcade® and Zevalin™); corticosteroids, (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

In embodiments, the anti-cancer agent is a chemotherapeutic agent (also referred to as an anti-neoplastic agent or anti-proliferative agent), selected from the group including an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/odine131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; Pkc412; bryostatin; KAI-9803;SF1126; or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristine, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur −0.4 M 5-chloro-2,4-dihydroxypyrimidine −1 M potassium oxonate), or lovastatin.

In embodiments, the anti-cancer agent is a chemotherapeutic agent or a cytokine such as G-CSF (granulocyte colony stimulating factor).

In embodiments, the anti-cancer agents can be standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), or CMFP (cyclophosphamide, methotrexate, 5-fluorouracil and prednisone).

In embodiments, the anti-cancer agents can be an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies. Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Ab1), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Ab1), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

Additionally, the siRNA compound described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the siRNA compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In embodiments, the anti-cancer agent used herein refers to doxorubicin, cisplatin, carboplatin, a taxane, camptothecin or any combination thereof.

As used herein, a "subject in need thereof" or "a patient" is a subject having cancer or a subject having a precancerous condition. In embodiments, a subject in need thereof has cancer. In embodiments, a subject in need thereof has ovarian cancer. In embodiments, a subject in need thereof has breast cancer. A "subject" or a "patient" includes a mammal. The mammal can be e.g., a human or appropriate non-human mammal, such as primate, mouse, rat, dog, cat, cow, horse, goat, camel, sheep or a pig. The subject can also be a bird or fowl. In embodiments, the mammal is a human. Thus the methods are applicable to both human therapy and veterinary applications.

In embodiments, a "subject in need thereof" is a subject that has breast cancer. Subjects with breast cancer includes subject with one or more signs or symptoms of breast cancer. Signs and symptoms of breast cancer include lumps found in breast tissue, lumps found in the lymph nodes, thickening of breast tissue, one breast becoming larger or lower, a nipple changing position or shape or becoming inverted, breast skin puckering or dimpling, a rash on or around a nipple, discharge from one or both nipples, constant pain in part of the breast or armpit, and swelling beneath the armpit or around the collarbone.

In embodiments, a "subject in need thereof" can also refer to a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

In embodiments, a "subject in need thereof" is a subject that has ovarian cancer. Subjects with ovarian cancer includes subject with one or more signs or symptoms of ovarian cancer. Signs and symptoms of ovarian cancer include bloating, pelvic or abdominal pain, trouble eating or feeling full quickly, urinary symptoms such as urgency or frequency, fatigue, upset stomach, back pain, constipation, menstrual changes, and/or abdominal swelling with weight loss.

In embodiments, a "subject in need thereof" can also refer to a subject having an increased risk of developing ovarian cancer relative to the population at large. A subject with an increased risk of developing ovarian cancer relative to the population at large is a female subject with older age (e.g., 40 years old or older), obesity, no reproductive history, using fertility drug for longer than one year, using androgens, using estrogen therapy and hormone therapy, a family history or personal history of ovarian cancer, breast cancer or colorectal cancer.

In embodiments, a "subject in need thereof" has already undergone, is undergoing or will undergo, at least one therapeutic intervention for the cancer or precancerous condition.

A subject in need thereof may have refractory cancer on most recent therapy. "Refractory cancer" means cancer that does not respond to treatment. The cancer may be resistant at the beginning of treatment or it may become resistant during treatment. Refractory cancer is also called resistant cancer. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a composition, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a composition, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a composition, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a composition, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

"Breast cancer" includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both. A breast cancer that is to be treated can be "triple-negative breast cancer" (TNBC) (estrogen receptor [ER]-negative, progesterone receptor [PR]-negative, and human epidermal growth factor receptor 2 [HER2]-negative).

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

The term "carcinoma" refers to a malignant new growth made up of epithelial cells tending to infiltrate the surrounding tissues and give rise to metastases. Exemplary carcinomas that may be treated with a composition, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having about 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

"An effective amount" or "a therapeutically effective amount" as provided herein refers to an amount effective to achieve its intended purpose. The actual amount effective for a particular application will depend, inter alia, on the condition being treated. When administered in methods to treat a disease, the pharmaceutical compositions described herein will contain an amount of anti-TWIST siRNA and optionally at least one anti-cancer agent to achieve the desired result, e.g., reducing, eliminating, or slowing the progression of disease symptoms (e.g., cancer), or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer.

As used herein, "treating" or "treat" describes the management and care of a patient for the purpose of combating a disease, condition, or disorder and includes the administration of a composition of the present invention to alleviate the symptoms or complications of a disease, condition or disorder, or to eliminate the disease, condition or disorder. The term "treat" can also include treatment of a cell in vitro or an animal model.

As used herein, the term "alleviate" is meant to describe a process by which the severity of a sign or symptom of a disorder is decreased. Importantly, a sign or symptom can be alleviated without being eliminated. The administration of compositions or pharmaceutical compositions of the invention may or can lead to the elimination of a sign or symptom, however, elimination is not required. Effective dosages should be expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer.

Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

Severity can also describe the degree to which a tumor has secreted growth factors, degraded the extracellular matrix, become vascularized, lost adhesion to juxtaposed tissues, or metastasized. Moreover, severity can describe the number of locations to which a primary tumor has metastasized. Finally, severity can include the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body. For example, a cancer may also cause symptoms such as fever, fatigue, or weight loss. Pain may be an early symptom with some cancers such as bone cancers or testicular cancer. But most often pain is a symptom of advanced disease. Along with cancers of the skin, some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here.

Treating cancer may result in or can result in a reduction in size of a tumor. A reduction in size of a tumor may also be referred to as "tumor regression". Preferably, after treatment, tumor size would be reduced by about 5% or greater relative to its size prior to treatment; more preferably, tumor size is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75% or greater. Size of a tumor may be measured by any reproducible means of measurement. The size of a tumor may be measured as a diameter of the tumor.

Treating cancer may result in or can result in a reduction in tumor volume. Preferably, after treatment, tumor volume would be reduced by about 5% or greater relative to its size prior to treatment; more preferably, tumor volume is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75% or greater. Tumor volume may be measured by any reproducible means of measurement.

Treating cancer may result in or can result in a decrease in number of tumors. Preferably, after treatment, tumor number would be reduced by about 5% or greater relative to number prior to treatment; more preferably, tumor number is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer may result in or can result in a decrease in number of metastatic lesions in other tissues or organs distant from the primary tumor site. Preferably, after treatment, the number of metastatic lesions would be reduced by about 5% or greater relative to number prior to treatment; more preferably, the number of metastatic lesions is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer may result in or can result in an increase in average survival time of a population of treated subjects in comparison to a population receiving carrier alone. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active composition. An increase in average survival time of a population may also be measured, for example, by calculating for a population the average length of survival following completion of a first round of treatment with an active composition.

Treating cancer may result in or can result in an increase in average survival time of a population of treated subjects in comparison to a population of untreated subjects. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active composition. An increase in average survival time of a population may also be measured, for example, by calculating for a population the average length of survival following completion of a first round of treatment with an active composition.

Treating cancer may result in or can result in increase in average survival time of a population of treated subjects in comparison to a population receiving monotherapy with a drug that is not a composition of the present invention. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active composition. An increase in average survival time of a population may also be measured, for example, by calculating for a population the average length of survival following completion of a first round of treatment with an active composition.

Treating cancer may result in or can result in a decrease in the mortality rate of a population of treated subjects in comparison to a population receiving carrier alone. Treating cancer may result in or can result in a decrease in the mortality rate of a population of treated subjects in comparison to an untreated population. Treating cancer may result in or can result in a decrease in the mortality rate of a population of treated subjects in comparison to a population receiving monotherapy with a drug that is not a composition of the present invention, or a pharmaceutically acceptable salt, prodrug, metabolite, analog or derivative thereof. Preferably, the mortality rate would be decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active composition. A decrease in the mortality rate of a population may also be measured, for example, by calculating for a population the average number of disease-related deaths per unit time following completion of a first round of treatment with an active composition.

Treating cancer may result in or can result in a decrease in tumor growth rate. Preferably, after treatment, tumor growth rate would be reduced by at least 5% relative to number prior to treatment; more preferably, tumor growth rate would be reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer may result in or can result in a decrease in tumor regrowth. Preferably, after treatment, tumor regrowth would be less than 5%; more preferably, tumor regrowth would be less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

II. Compositions

In one aspect, provided herein are TWIST signaling inhibitors. In embodiments, TWIST signaling inhibitors described herein are TWIST inhibitors and/or inhibitors of TWIST signaling genes or protein. In embodiments, TWIST signaling inhibitors provided herein include TWIST1 inhibitor and TWIST1 signaling inhibitors. In embodiments, In embodiments, TWIST signaling inhibitors provided herein include TWIST2 inhibitors and TWIST2 signaling inhibitors. In embodiments, TWIST signaling inhibitors provided herein include TWIST1 and TWIST2 inhibitors and TWIST1 and TWIST2 signaling inhibitors. In embodiments, TWIST signaling inhibitors provided herein include TWIST inhibitors and inhibitors of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52) genes/proteins listed in Table 1 and one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52) genes/proteins of Akt/PI3K signaling. In embodiments, TWIST signaling inhibitors provided herein include inhibitors of TWIST1, TWIST2, GAS6, L1CAM, PI3K, Akt, or any combination thereof.

In embodiments, TWIST signaling inhibitors provided herein are siRNA inhibitors. In embodiments, TWIST signaling inhibitors provided herein are siRNAs against TWIST1, TWIST2, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52) genes listed in Table 1 and Akt signaling genes. In embodiments, TWIST signaling inhibitors provided herein are siRNAs against TWIST1, TWIST2, GAS6, L1CAM, PI3K, and/or Akt.

In embodiments, TWIST inhibitors are siRNA molecules (e.g., anti-TWIST siRNAs). The siRNA molecule of the invention is an isolated siRNA molecule that binds to a single stranded RNA molecule, which is a messenger RNA (mRNA) that encodes at least part of a peptide or protein of TWIST1 or TWIST2.

TWIST1 and TWSIT2 are basic helix-loop-helix (bHLH) transcription factors. TWIST1 and TWIST2 sequences are publicly available. For example, nucleotide sequence of TWSIST1 can be found at NM_000474.3: and nucleotide sequence of TWSIST1 can be found at: NP_000465.1. For example, amino acid sequences of TWIST2 can be found at NP_001258822.1: and amino acid sequences of TWIST2 can be found at NM_001271893.3.

One exemplary nucleic acid sequence of TWIST1 is provided below:

(SEQ ID NO: 13)

```
GAGGTATAAGAGCCTCCAAGTCTGCAGCTCTCGCCCAACTCCCAGACACCTCGCGGGCTCTGCAGCACCG
GCACCGTTTCCAGGAGGCCTGGCGGGGTGTGCGTCCAGCCGTTGGGCGCTTTCTTTTTGGACCTCGGGGC
CATCCACACCGTCCCCTCCCCCTCCCGCCTCCCTCCCCGCCTCCCCGCGCGCCCTCCCCGCGGAGGTCC
CTCCCGTCCGTCCTCCTGCTCTCTCCTCCGCGGGCCGCATCGCCCGGGCCGGCGCCGCGCGCGGGGGAAG
CTGGCGGGCTGAGGCGCCCCGCTCTTCTCCTCTGCCCCGGGCCCGCGAGGCCACGCGTCGCCGCTCGAGA
GATGATGCAGGACGTGTCCAGCTCGCCAGTCTCGCCGGCCGACGACAGCCTGAGCAACAGCGAGGAAGAG
CCAGACCGGCAGCAGCCGCCGAGCGGCAAGCGCGGGGGACGCAAGCGGCGCAGCAGCAGGCGCAGCGCGG
GCGGCGGCGCGGGGCCCGGCGGAGCCGCGGGTGGGGCGTCGGAGGCGGCGACGAGCCGGGCAGCCCGGC
CCAGGGCAAGCGCGGCAAGAAGTCTGCGGGCTGTGGCGGCGGCGGCGGCGCGGGCGGCGGCGGCGGCAGC
AGCAGCGGCGGCGGGAGTCCGCAGTCTTACGAGGAGCTGCAGACGCAGCGGGTCATGGCCAACGTGCGGG
AGCGCCAGCGCACCCAGTCGCTGAACGAGGCGTTCGCCGCGCTGCGGAAGATCATCCCCACGCTGCCCTC
GGACAAGCTGAGCAAGATTCAGACCCTCAAGCTGGCGGCCAGGTACATCGACTTCCTCTACCAGGTCCTC
CAGAGCGACGAGCTGGACTCCAAGATGGCAAGCTGCAGCTATGTGGCTCACGAGCGGCTCAGCTACGCCT
TCTCGGTCTGGAGGATGGAGGGGCCTGGTCCATGTCCGCGTCCCACTAGCAGGCGGAGCCCCCACCCC
CTCAGCAGGGCCGGAGACCTAGGTAAGGACCGCGCCGCTGCACCCCTTCGCCTCTCAGGTGGCAGACGGC
AGGCCGGCCAGGCCGCGGTTCCCAGTCCACCTCGATTTCCTCCCCTCTCCCACTCTCCGCTCAGCCTTCC
CACCTCACTTGGCACCGTTGCCTCGCGCCCCAGCGTCCCCGGAAGGCCGGTCTGACCCCGCTAGGGAGA
GCAGTCTCCAGGGGGATGCGCCCTGGTGAGGGGTGTGTGTGCGCGTGAGTGTGCGTGACAGGAGGGGAGA
CAGAGACACCCAGGGTCACGGGTAAGGACCGTTTTGTCAGCGCCACCCTTTCTTTCGGCTTTCAATTTTT
GTTCTCCTTAAAACAAATGTTTTAAAACAAATTCCACCTCCTCCTCCTTTCCACCCACCCACTTCCTCTT
GCCCTTGGGCTGAAATCCTTCCAGGTTGTTCAGCTTAATTTCTCAGTGGTGGTGATAAGAACAGTGCTCA
CTAGTCTTAGAAAACAGCCGCAGAGACCTAAACAATAACCGACTCCCCCCCCCCCCCTCTGGGTTTTTGCA
GATGTCATTGTTTCCAGAGAAGGAGAAAATGGACAGTCTAGAGACTCTGGAGCTGGATAACTAAAAATAA
AAATATATGCCAAAGATTTTCTTGGAAATTAGAAGAGCAAAATCCAAATTCAAAGAAACAGGGCGTGGGG
CGCACTTTTAAAAGAGAAAGCGAGACAGGCCCGTGGACAGTGATTCCCAGACGGGCAGCGGCACCATCCT
CACACCTCTGCATTCTGATAGAAGTCTGAACAGTTGTTTGTGTTTTTTTTTTTTTTTTTTGACGAAGA
ATGTTTTTATTTTTATTTTTTTCATGCATGCATTCTCAAGAGGTCGTGCCAATCAGCCACTGAAAGGAAA
```

-continued

```
GGCATCACTATGGACTTTCTCTATTTTAAAATGGTAACAATCAGAGGAACTATAAGAACACCTTTAGAAA

TAAAAATACTGGGATCAAACTGGCCTGCAAAACCATAGTCAGTTAATTCTTTTTTTCATCCTTCCTCTGA

GGGGAAAAACAAAAAAAAACTTAAAATACAAAAAACAACATTCTATTTATTTATTGAGGACCCATGGTAA

AATGCAAATAGATCCGGTGTCTAAATGCATTCATATTTTTATGATTGTTTTGTAAATATCTTTGTATATT

TTTCTGCAATAAATAAATATAAAAAATTTAGAGAA
```

Underlined: transcription starting codes
Double underlined: translation starting codes
Wave underlined: bHLH domain
Italic and underlined: stop codon One skilled in the art will appreciate that TWIST (including TWIST1 and TWIST2) nucleic acid and protein molecules can vary from those publicly available, such as polymorphisms resulting in one or more substitutions, deletions, insertions, or combinations thereof, while still retaining TWIST biological activity. Accordingly, in various embodiments, the amino acid sequence of the TWIST may be about 95%, about 96%, about 97%, about 98%, about 99% identical to the TWIST1 or TWIST2 sequence publicly available, or fragment thereof. A fragment can be between 3-10 amino acids, 10-20 amino acids, 20-40 amino acids, 40-56 amino acids in length or even longer. Amino acid sequences having about 95%, about 96%, about 97%, about 98%, about 99% identity to the fragments described herein are also included within the scope of the present invention.

In embodiments, the nucleic acid sequence of the TWIST may be about 95%, about 96%, about 97%, about 98%, about 99% identical to the TWIST1 or TWIST2 sequence publicly available, or fragment thereof. A fragment can be between 3-10 nucleotides, 10-20 nucleotides, 20-40 nucleotides, 40-56 nucleotides in length or even longer. Nucleic acid sequences having about 95%, about 96%, about 97%, about 98%, about 99% identity to the fragments described herein are also included within the scope of the present invention.

In embodiments, a TWIST signaling inhibitor is an anti-TWIST siRNA. As used herein, the term "anti-TWIST siRNA" includes all forms of anti-TWIST siRNA, including variants, modifications and derivatives thereof. In embodiments, the siRNA molecule is an oligonucleotide with a length of about 19 to about 35 base pairs (e.g., about 19, 20, 21, 22, 23, 24, 25, 26 27, 28, 29, 30, 31, 32 33, 34, 35 base pairs). In another embodiment, the molecule is an oligonucleotide with a length of about 19 to about 27 base pairs. In embodiments, the molecule is an oligonucleotide with a length of about 21 to about 25 base pairs. In embodiments, the molecule may have blunt ends at both ends, or sticky ends at both ends, or a blunt end at one end and a sticky end at the other. In embodiments, an anti-TWIST siRNA targets TWIST1 or variants and homologues. In embodiments, an anti-TWIST siRNA targets TWIST2 or variants and homologues. In embodiments, an anti-TWIST siRNA targets both TWIST1 and TWIST2 or their variants and homologues.

Exemplary anti-TWIST siRNA sequences include, but are not limited to:

| Name | | Sequence | |
|---|---|---|---|
| siTWIST 419 | Passenger: | 5'-GGACAAGCUGAGCAAGAUU-3' | (SEQ ID No: 1) |
| | Guide: | 5'-AAUCUUGCUCAGCUUGUCCUU-3' | (SEQ ID No: 2) |
| siTWIST494 | Passenger: | 5'-GCGACGAGCUGGACUCCAA-3' | (SEQ ID No: 3) |
| | Guide: | 5'-UUGGAGUCCAGCUCGUCGCUU-3' | (SEQ ID No: 4) |
| TW511 | Passenger: | 5'-GAUGGCAAGCUGCAGCUAUUU-3' | (SEQ ID No: 5) |
| | Guide: | 5'-AUAGCUGCAGCUUGCCAUCUU-3' | (SEQ ID No: 6) |
| TW433 | Passenger: | 5'-GAUUCAGACCCUCAAGCUGUU-3' | (SEQ ID No: 7) |
| | Guide: | 5'-CAGCUUGAGGGUCUGAAUCUU-3' | (SEQ ID No: 8) |
| TW424 | Passenger: | 5'-GCUGAGCAAGAUUCGACCUU-3' | (SEQ ID No: 9) |
| | Guide: | 5'-GGUCUGAAUCUUGCUCAGCUU-3' | (SEQ ID No: 10) |

One skilled in the art will appreciate that anti-TWIST siRNAs of the invention also include sequences having about 95%, about 96%, about 97%, about 98%, about 99% identity to any one of SEQ ID No: 1-10.

As described above, antisense nucleic acids are capable of hybridizing to (e.g. selectively hybridizing to) a target nucleic acid (e.g. target mRNA). In some embodiments, the antisense nucleic acid hybridizes to the target nucleic acid sequence (e.g. mRNA) under stringent hybridization conditions. In some embodiments, the antisense nucleic acid hybridizes to the target nucleic acid (e.g. mRNA) under moderately stringent hybridization conditions.

An siRNA sequence (including antisense or sense sequence) may comprise naturally occurring nucleotides or modified nucleotides. Examples of such modifications include chemical substitutions at the ribose and/or phosphate and/or base positions. Modified nucleotides are described in U.S. Pat. No. 5,660,985, which describes oligonucleotides containing nucleotide derivatives chemically modified at the 2' position of ribose, 5 position of pyrimidines, and 8 position of purines. U.S. Pat. No. 5,756,703 describes oligonucleotides containing various 2'-modified pyrimidines. U.S. Pat. No. 5,580,737 describes highly specific nucleic acid ligands containing one or more nucleotides modified with 2'-amino (2'-NH.sub.2), 2'-fluoro (2'-F), and/or 2'-O-methyl (2'-OMe) substituents.

Modifications of the siRNA sequences contemplated in this invention include, but are not limited to, those which provide other chemical groups that incorporate additional charge, polarizability, hydrophobicity, hydrogen bonding, electrostatic interaction, and fluxionality to the siRNA bases or to the siRNA sequences as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil; backbone modifications, phosphorothioate or alkyl phosphate modifications, methylations, unusual base-pairing combinations such as the isobases isocytidine and isoguanidine and the like. Modifications may also include 2'-O-methyl modifications, 2'-O-methyl modified ribose sugars with terminal phosphorothioates and a cholesterol group at the 3' end, 2'-O-methoxyethyl (2'-MOE) modifications, 2'-fluoro modifications, and 2',4' methylene modifications (referred to as "locked nucleic acids" or LNAs). Modifications can also include 3' and 5' modifications such as capping.

In embodiments, antisense sequence (guide strand) and the sense (passenger strand) contain different modification(s). In embodiments, passenger strand may contain modifications that promote loading of the guide strand onto the mRNA cleavage machinery, modifications that prevent the passenger sequence loading into RISC complex, modifications that prevent nuclease-mediated degradation, modifications that reduce immunogenicity mediated by toll-like receptors and RIG-I, or any combinations thereof. In embodiments, the passenger strand may contain inverted abasic riboses, 2'-O-methyluracil, or combination thereof. Guide strand may contain modifications that increase their loading efficiency to RISC complex. In embodiments, guide strand may contain 2-thio-deoxyuracil. Exemplary chemically modified anti-TWIST siRNA sequences include, but are not limited to:

12, 13, 14, 15, 16, 17, 18, 19, 20 or more) anti-L1CAM siRNAs. As used herein, the term "anti-L1CAM siRNA" includes all forms of anti-L1CAM siRNA, including variants, modifications and derivatives thereof. In embodiments, the siRNA molecule is an oligonucleotide with a length of about 19 to about 35 base pairs (e.g., about 19, 20, 21, 22, 23, 24, 25, 26 27, 28, 29, 30, 31, 32 33, 34, 35 base pairs). In another embodiment, the molecule is an oligonucleotide with a length of about 19 to about 27 base pairs. In still another embodiment, the molecule is an oligonucleotide with a length of about 21 to about 25 base pairs. In all of these embodiments, the molecule may have blunt ends at both ends, or sticky ends at both ends, or a blunt end at one end and a sticky end at the other.

A siRNA sequence against a specific gene can be designed according to any method known in the art. In embodiments, siRNAs against GAS6, L1CAM, and HMGA2 were obtained from Santa Cruz Biotechnology (Dallas, Tex.; item numbers sc-35450, sc-43172, and sc-37994, respectively).

In embodiments, TWIST signaling inhibitors provided herein are small molecule inhibitors. In embodiments, TWIST signaling inhibitors provided herein are small molecule inhibitors against TWIST1, TWIST2, one or more proteins listed in Table 1 and/or one or more proteins of Akt/PI3K signaling. In embodiments, TWIST signaling inhibitors provided herein include a plurality of small molecule inhibitors. In embodiments, TWIST signaling inhibitors provided herein are small molecule inhibitors against TWIST1, TWIST2, GAS6, L1CAM, PI3K, and/or Akt. In embodiments, small molecule inhibitors against PI3K/Akt signaling include, but are not limited to, Wortmannin, demethoxyviridin, LY294002, perifosine, idelalisib, buparlisib (BKM120), duvelisib, alpelisib (BYL719), TGR 1202,

| Name | Sequence | |
|---|---|---|
| Modified siTWIST419 | Passenger: | 5'-iaBrGrGrArCrArArGrCrUrGrArGrCrArArGrAmUmUiaB-3' (SEQ ID No: 11) iaB = inverted abasic ribose mU = 2'-O-methyluracil |
| | Guide: | 5'-rArArUrCrUrUrGrCrUrCrArGrCrUrUrG2thio-dUrCrCrUrU-3' (SEQ ID No: 12) 2thio-dU =2-thio-deoxyuracil |

It is noted that the guide strand sequence of siTWIST419 has the fewest immunogenic hits, after scanning for RNA sequence motifs that stimulate TLR8-dependent immune responses.

In embodiments, TWIST signaling inhibitors provided herein are one or more (e.g., 1, 2, 3, 4, 5, 6, 7, 8, 9, 10, 11, 12, 13, 14, 15, 16, 17, 18, 19, 20 or more) anti-GAS6 siRNAs. As used herein, the term "anti-GAS6 siRNA" includes all forms of anti-GAS6 siRNA, including variants, modifications and derivatives thereof. In embodiments, the siRNA molecule is an oligonucleotide with a length of about 19 to about 35 base pairs (e.g., about 19, 20, 21, 22, 23, 24, 25, 26 27, 28, 29, 30, 31, 32 33, 34, 35 base pairs). In another embodiment, the molecule is an oligonucleotide with a length of about 19 to about 27 base pairs. In still another embodiment, the molecule is an oligonucleotide with a length of about 21 to about 25 base pairs. In all of these embodiments, the molecule may have blunt ends at both ends, or sticky ends at both ends, or a blunt end at one end and a sticky end at the other.

In embodiments, TWIST signaling inhibitors provided herein are one or more (e.g., 1, 2, 3, 4, 5, 6, 7, 8, 9, 10, 11, copanlisib (BAY 80-6946), PX-866, dactolisib, RP6530, SF1126, INK1117, pictilisib, XL147 (also known as SAR245408), XL765 (also known as SAR245409), palomid 529, GSK1059615, ZSTK474, PWT33597, CUDC-907, ME-401, IPI-549, IC87114, TG100-115, CAL263, RP6503, PI-103, GNE-477, and AEZS-136.

In embodiments, TWIST signaling inhibitors provided herein include one or more (e.g., 1, 2, 3, 4, 5, 6, 7, 8, 9, 10, 11, 12, 13, 14, 15, 16, 17, 18, 19, 20 or more) siRNA inhibitors and one or more (e.g., 1, 2, 3, 4, 5, 6, 7, 8, 9, 10, 11, 12, 13, 14, 15, 16, 17, 18, 19, 20 or more) small molecule inhibitors. In embodiments, TWIST signaling inhibitors provided herein include one or more (e.g., 1, 2, 3, 4, 5, 6, 7, 8, 9, 10, 11, 12, 13, 14, 15, 16, 17, 18, 19, 20 or more) anti-TWIST siRNAs and/or one or more (e.g., 1, 2, 3, 4, 5, 6, 7, 8, 9, 10, 11, 12, 13, 14, 15, 16, 17, 18, 19, 20 or more) anti-GAS6 siRNAs and/or one or more (e.g., 1, 2, 3, 4, 5, 6, 7, 8, 9, 10, 11, 12, 13, 14, 15, 16, 17, 18, 19, 20 or more) anti-L1CAM siRNAs and/or one or more (e.g., 1, 2, 3, 4, 5, 6, 7, 8, 9, 10, 11, 12, 13, 14, 15, 16, 17, 18, 19, 20 or more) PI3K small molecule inhibitors and/or one or more (e.g., 1, 2, 3, 4, 5, 6, 7, 8, 9, 10, 11, 12, 13, 14, 15, 16, 17, 18, 19, 20 or more) Akt small molecule inhibitors.

The invention also provides a composition that includes a TWIST signaling inhibitor described herein bound to a delivery vehicle.

In embodiments, the delivery vehicle is a nanoparticle. In embodiments, the delivery vehicle is a lipid particle (or lipid vehicle). The term "delivery vehicle" or "carrier" refers to any support structure that brings about the transfer of a component of genetic material or a protein. Genetic material includes but is not limited to DNA, RNA or fragments thereof and proteins or polypeptides comprise amino acids and include but are not limited to antigens, antibodies, ligands, receptors or fragments thereof. Delivery vehicles include but are not limited to vectors such as viruses (examples include but are not limited to retroviruses, adenoviruses, adeno-associated viruses, pseudotyped viruses, replication competent viruses, herpes simplex virus), virus capsids, liposomes or liposomal vesicles, lipoplexes, polyplexes, dendrimers, macrophages, artificial chromosomes, nanoparticles, polymers and also hybrid particles, examples of which include virosomes. Delivery vehicles may have multiple surfaces and compartments for attachment and storage of components. These include but are not limited to outer surfaces and inner compartments.

In embodiments, the delivery vehicle is a nanoparticle or a lipid particle or a viral vector. Any nanoparticles known for siRNA/small molecule delivery can be used for the invention described herein. Recent dramatic advances in nanotechnology have led to the development of a variety of nanoparticles (NPs) that provide valuable tools. Numerous nanomaterials such as polymers, liposomes, protein based NPs and inorganic NPs have been developed and a variety of particles are currently being evaluated in clinical studies with promising initial results; and some liposomal NPs are approved by the FDA. One of the major advantages of using these NPs is that they offer targeted tissue/site delivery. Their small size allows NPs to escape through blood vessels at the tissue site through the leaky vascular structure (Enhanced permeability and retention effect). In addition to this passive mechanism, a variety of targeting moieties can be attached to NPs to confer active targeting capability. The ability of nanoparticles to target delivery of anticancer drugs to tumors also results in decreased chemotherapy-related off-target toxicity for patients. Exemplary nanoparticles that can be used for delivering compositions described herein include, but are not limited to, solid nanoparticles (e.g., metals such as silver, gold, iron, titanium), non-metal, lipid-based solids (e.g., liposome), polymers (e.g., polyethylenimene, dendrimer), suspensions of nanoparticles, or combinations thereof (e.g., polyethylenimene-liposome, dendrisome). Any compositions described herein (such as Mito-Cas9, mito-Cpf1, or other mito-RNA guided nucleases (mito-RGN)) may be delivered in nanopoarticle complexes in the form of protein, DNA, or mRNA. Additional information about nanoparticles that can be used by the compositions described herein can be found in Coelho et al., N Engl J Med 2013; 369:819-29, Tabernero et al., Cancer Discovery, April 2013, Vol. 3, No. 4, pages 363-470, Zhang et al., WO2015089419 A2. and Zuris J A et al., Nat Biotechnol. 2015; 33(1):73-80, each of which is incorporated herein by reference.

In embodiments, the nanoparticle used herein is mesoporous silica nanoparticle (MSN). MSNs are inorganic NPs that have developed as a delivery system for anticancer drugs and siRNA (silencing small interfering RNA). MSNs are synthesized by the sol-gel method, which enables preparation of homogeneous particles with diameters as small as 40 nm or as large as desired. They contain thousands of pores that provide a large storage space for drugs and other reagents. These nanomaterials are biocompatible and their safety has been demonstrated in a number of animal experiments. MSNs are taken up by endocytosis, localized first to lysosomes, deliver drugs, and are eventually exocytosed out of cells. MSNs can be coated with targeting moieties that bind to receptors on cancer cells, thereby greatly enhancing particle uptake, and with valves that control the release of drug cargo resulting in apoptosis. Additional information about the making and use of MSNs can be found in the U.S. Patent Publication 2012/0207795, the content of which is incorporated herein as entirety.

In embodiments, the surface of the nanoparticle (e.g. MSNs) are chemically modified. To maximize the delivery of negatively charged nucleic acids to cells, the silica surface may be converted into positive charge in order to bind DNA and siRNA. Some of the methods for introducing cationic charge on inorganic materials, which include silica, iron oxide, and gold, typically involve surface grafting with amine groups and coating with cationic polymers (e.g. polyethyleneimine, polyamidoamine, polylysine) through either covalent or non-covalent (e.g. electrostatic) association (Radu et al., J. Am. Chem. Soc., vol. 126, pp. 13216-13217, 2004; Bharali et al., Proc. Natl. Acad. Sci. U.S.A., vol., 102, pp. 11539-11544, 2005; Bonoiu et al., Proc. Natl. Acad. Sci. U.S.A., vol. 106, pp. 5546-5550, 2009; Elbakry et al., Nano Lett., vol. 9, pp. 2059-2064, 2009; Fuller et al., Biomaterials, vol. 29, pp. 1526-1532, 2008; Kneuer et al., Bioconjugate Chem., vol. 11, pp. 926-932, 2000; McBain et al., J. Mater. Chem., vol. 17, pp. 2561-2565, 2007; Zhu et al., Biotechnol. Appl. Biochem., vol. 39, pp. 179-187, 2004). In embodiments, the nanoparticle (e.g. MSN) is bound to polyethyleneimine (PEI). The PEI may be referred to herein as a non-covalent linker.

As used herein, the term "bioconjugate" or "bioconjugate reactive group" or "bioconjugate linker" refers to the association between atoms or molecules. The association can be direct or indirect. For example, a conjugate between a first moiety (e.g. $-NH_2$, $-COOH$, $-N$-hydroxysuccinimide, or -maleimide) and a second moiety (e.g., sulfhydryl, sulfur-containing amino acid) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first moiety (e.g., a TWIST signaling inhibitor) is non-covalently attached to the second moiety on the nanoparticle through a non-covalent chemical linker or covalent chemical linker formed by a reaction between a component of the first moiety (e.g., a TWIST signaling inhibitor) and a component of the second moiety on the delivery vehicle (e.g., nanoparticle or lipid particle). In embodiments, the first moiety (e.g., a TWIST signaling inhibitor) includes one or more reactive moieties, e.g., a covalent reactive moiety, as described herein (e.g., alkyne, azide, amine, ester, N-hydroxy-succinimide, maleimide or thiol reactive moiety). In embodiments, the first moiety (e.g., a TWIST signaling inhibitor) includes a linker (e.g., first linker) with one or more reactive moieties, e.g., a covalent reactive moiety, as described herein (e.g., alkyne, azide, amine, ester, N-hydroxy-succinimide, maleimide or thiol reactive moiety). In embodiments, the delivery vehicle (e.g., nanoparticle or lipid particle) includes one or more reactive moieties, e.g., a covalent reactive moiety, as described herein (e.g., alkyne, azide, amine, ester, N-hydroxy-succinimide, maleimide or thiol reactive moiety). In embodiments, the delivery vehicle (e.g., nanoparticle or lipid particle) includes a linker with one or more reactive moieties, e.g., a covalent reactive moiety, as described herein (e.g., alkyne, azide, amine, ester, N-hydroxy-succinimide, maleimide or thiol reactive moiety).

Useful reactive functional groups (e.g., reactive groups such as bioconjugate or bioconjugate reactive groups) used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

The reactive functional groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

In embodiments, the surface of the nanoparticle (e.g. MSNs) are bound (e.g., coated) with positively charged compound or chemical moiety (e.g. polyethyleneimine (PEI)), which non-covalently binds to negatively charged nucleic acid (e.g., anti-TWIST signaling siRNA) via electrostatic interaction. In embodiments the positively charged compound (also referred to herein a a positively charged non-covalent linker) is a synthetic cationic polymer. In embodiments, the positively charged non-covalent linker compacts DNA and siRNA into complexes that are effectively taken up in cells. In embodiments, the non-covalent linker (e.g. positively charged non-covalent linker) is attached to nanoparticle surfaces through covalent (e.g. using boiconjugate techniques as disclosed herein and known in the art) and electrostatic interactions. For example, PEIs are synthetic cationic polymers that compact DNA and siRNA into complexes that are effectively taken up in cells. In embodiments, the PEI is attached to nanoparticle surfaces through covalent and electrostatic interactions. Several PEI polymer sizes ranging from MW of 0.6 to 25 KD can be used in the invention. The surface of nanoparticle (e.g. MSNs) may be modified using low molecular weight multi-branched PEI (e.g., less than or equal to MW 1200) due to their low toxicity.

In embodiments, the nanoparticle (e.g. MSNs) contain one or more nanodevices called "nanovalves." Nanovalves are made of chemical moieties (e.g. rotaxanes and pseudorotaxanes) that include a stalk and a moving part. The moving part acts as a gatekeeper of the pores' openings. The opening can be triggered by recognition events (pH, redox, charge, metal ions and biomolecules such as enzymes) and external control (magnetic field, light). One type of nanovalve is triggered by low pH (around pH 6). This consists of a stalk that has cyclodextrin attached. The cyclodextrin binding causes the nanovalve to be closed. Upon exposure to low pH (such as in tumor tissue), cyclodextrin comes off thus releasing the contents of the pores. The pH threshold can be adjusted by chemically modifying the valve. Additional information about nanovalve that is triggered by low pH can be found in the U.S. Patent Publication 2010/0310465, the content of which is incorporated herein as entirety.

In embodiments, the nanoparticle (e.g. MSNs) have nanovalves that are activated by an external stimulus. For example, the MSNs include thermo sensitive nanovalves. Nanoparticles (such as MSNs) containing nanovalves that are activated by an external stimulus are an attractive method for drug delivery as they provide non-invasive treatment that has refined control over a selected area, the exposure time, and hence the dosage. In some embodiments, magnetic core-shell nanoparticles (e.g. MSNs such as mag@MSN or Magnet-MSN, referred to herein as MSN-B) are utilized. For example, when exposed to an oscillating magnetic field, the magnetic nanocrystal (NC) cores produce heat (T>42° C.) that can be used to stimulate a thermally responsive nanovalve (note that the nanovalve is made up of a thermo sensitive pseudorotaxane). Additional information about MSN-B can be found in the U.S. Patent Publication 2010/0255103, the content of which is incorporated herein as entirety. Additional information about nanovalve that is triggered by light can be found in the U.S. Patent Publication 2010/0284924, the content of which is incorporated herein as entirety.

In embodiments, the nanoparticle is porous. The porous structure of nanoparticles (e.g. MSNs) may allow both the binding of nucleotides on the surface as well as the encapsulation of small molecules within the particles. In embodiments, one or more anti-cancer agents are encapsulated in within the pores of the nanoparticles (e.g. MSNs) that have nanovalves. The release of the anti-cancer agent may be controlled by nanovalves within the nanoparticle (e.g. MSNs). In particular, nanovalves may provide an open/close function so that anti-cancer agent stored in the pores of the nanoparticles (e.g. MSNs) can only be released when they encounter conditions (such as low pH, magnetic field, light) that allow nanovalves to open.

In embodiments, the nanoparticle (e.g. MSN) has surface modifications including the attachment of tumor targeting moieties. In embodiments, the nanoparticle (e.g. MSN) have surface modifications including the attachment of PEI and tumor targeting moieties. In some embodiments, the tumor targeting moiety is hyaluronic acid (HA).

In embodiments, composition of the invention includes an anti-TWIST signaling siRNA described herein bound to MSN via PEI that is attached to MSN surface (PEI-MSN). In embodiments, such PEI-MSN also includes nanovavles (low pH, magnetic field, or light triggered). In embodiments, such PEI-MSN containing nanovalves also encapsulates one or more anti-cancer agents.

In embodiments, composition of the invention includes an anti-TWIST signaling siRNA described herein bound to PEI-MSN that also has HA attached to its surface (PEI-MSN-HA). In embodiments, such PEI-MSN-HA also includes nanovavles (low pH, magnetic field, or light triggered). In embodiments, such PEI-MSN-HA containing nanovalves also encapsulates one or more anti-cancer agents.

Figure 10:
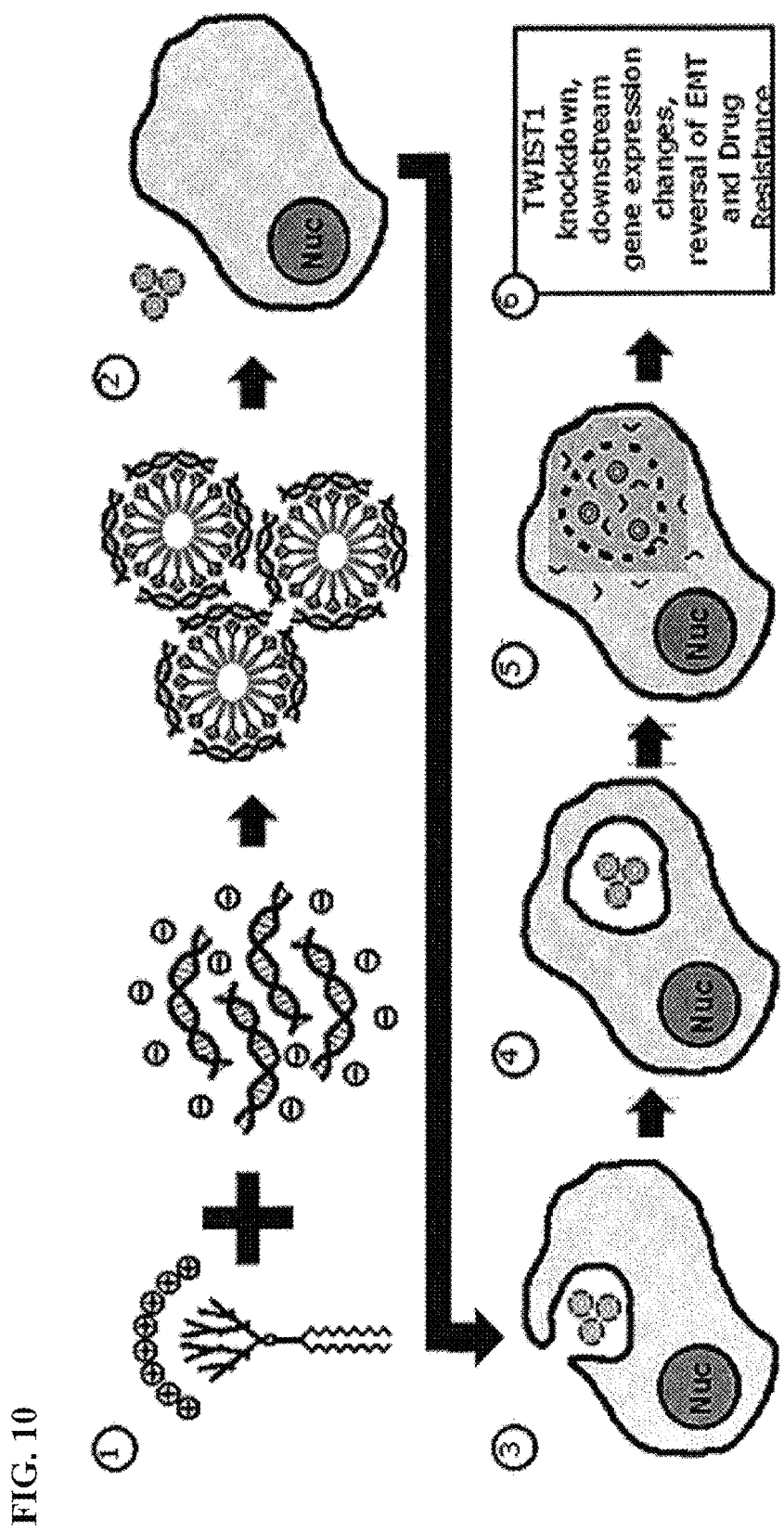
FIG. 10. Mechanism of dendrimer-mediated siRNA delivery and TWIST1 knockdown. 1. siRNA adheres to positive charges on the YTZ3-15 dendrimer, and the dendrimer-siRNA complex is administered to tumor cells. 2. Complexes are taken up via macropinocytosis. 3. Complexes are trafficked to late endosomes. 4. Due to the proton sponge effect, electrostatic interactions between the dendrimer and siRNA are disrupted and siRNA escapes from the disrupted endosome into the cytosol. 5. Once in the cytosol, siRNA recruits the endogenous RNAi machinery to degrade TWIST1 mRNA. siRNA guide strand is conserved, and the RISC complex is free to recognize and degrade subsequent TWIST1 mRNAs.

In embodiments, an anti-TWIST signaling siRNA described herein is bound to a dendrimer-based nanoparticle. In embodiment, the nanoparticle is YTZ3-15 dendrimer. In embodiment, the nanoparticle is polyamidoamine dendrimer. Dendrimers are repetitively branched molecules. Nanoparticles based on the dendritic polymer or dendrimer are referred as dendrimer-based nanoparticles. The chemical formula for each YTZ3-15 dendrimer is $C_{125}H_{247}N_{37}O_{20}$ with a molecular weight of 2586.9448 Daltons. They are formed by click chemistry and consist of two lipid tails at one end and a dendron with eight terminal amines on the opposite end. The dendrimer was purified by column chromatography on silica gel with Petroleum ether/EtOAc. These dendrimers spontaneously aggregate to form micelles ranging in size from 100 nm to 200 nm. When in the presence of siRNA, these dendrimers rearrange into smaller (6-8 nm) substructures as part of the larger micelles in order to allow for more electrostatic interactions between the negatively charged siRNA and the positively charged amines on the dendrimer (see FIG. 10).

In embodiments, a dendrimer-based nanoparticle bound (covalently or non-covalently) to an anti-TWIST signaling siRNA described herein may be further bound (covalently or non-covalently) to an anti-cancer agent.

In embodiments, an anti-cancer agent used herein is doxorubicin, cisplatin, carboplatin, a taxane, camptothecin or any combination thereof.

In embodiments, the delivery vehicle used herein is a vector. In embodiments, the vector is a replication-incompetent viral vector. For example, the replication-incompetent viral vector is a replication-incompetent DNA viral vector (including, but is not limited to, adenoviruses, adeno-associated viruses). For example, the replication-incompetent viral vector is a replication-incompetent RNA viral vector (including, but is not limited to, replication defective retroviruses, lentiviruses, and rabies viruses).

In embodiments, the delivery vehicle used herein is a lipid particle-a particle having lipid as a component, such as liposomes or liposomal vesicles or lipoplexes. Liposomes, also known as vesicles, are generally composed of phospholipids and other lipid components such as cholesterol. They can function as carriers whose essential structural feature is a bipolar lipid membrane which envelops an aqueous core volume in which pharmacological agents are solubilized and therefore encapsulated. Various lipid formulations and methods for their preparation have been described for the delivery of pharmaceutically active agents to a host. For example, Geho and Lau in U.S. Pat. No. 4,603,044 describe a targeted liposomal delivery system for delivery of a drug to the hepatobiliary receptors of the liver. The system is composed of a drug or diagnostic agent encapsulated in or associated with lipid membrane structures in the form of vesicles or liposomes, and a molecule having a fatty substituent attached to the vesicle wall and a target substituent which is a biliary attracted chemical, such as a substituted iminodiacetate complex. The system is particularly useful for the delivery of insulin and serotonin in the treatment of Types I and II diabetes, respectively. Several cationic lipid reagents have become commercially available for transfecting eukaryotic cells. These examples include Lipofectin® (DOTMA:DOPE) (Invitrogen, Carlsbad, Calif.), LipofectAmine™ (DOSPA:DOPE)(Invitrogen). LipofectAmine2000™ (Invitrogen), LipofectAmine 3000™ (Invitrogen), Lipofectamine RNAiMax™ (Invitrogen), Lipofectamme LTX™ (Thermo Fisher Scientific), Fugene®, Transfectam® (DOGS), Effectene®, DC-Chol. US Patent Publication No. 20050019923 involves cationic dendrimers for delivering bioactive molecules, such as polynucleotide molecules, peptides and polypeptides and/or pharmaceutical agents, to a mammalian body, given the low toxicity and targeting specificity. Other derivatives of cationic d ndrimer mentioned in Bioactive Polymers, US published application 20080267903, may also be suitable delivery vehicles for mitoCas9 gene therapy.

Various polymeric formulations of biologically active agents and methods for their preparation have been described. U.S. Patent Nos. 3,773,919, 3,991,776, 4,076, 779, 4,093,709, 4,118,470, 4,131,648, 4,138,344, 4,293,539 and 4,675,189, inter alia, disclose the preparation and use of biocompatible, biodegradable polymers, such as poly (lactic acid), poly(glycolic acid), copolymers of glycolic and lactic acids, poly (o-hydroxycarboxy lie acid), polylactones, polyacetals, polyorthoesters and polyorthocarbonates, for the encapsulation of drugs and medicaments. These polymers mechanically entrap the active constituents and later provide controlled release of the active ingredient via polymer dissolution or degradation. Certain condensation polymers formed from divinyl ethers and polyols are described in Polymer Letters, 18, 293 (1980). Polymers have proven to be successful controlled-release drug delivery devices.

More information about liposomal constructs or polymeric constructs that can be used for the present invention can be found at Schwendener R A et al., Ther Adv Vaccines. 2014 Nov; 2(6): 159-182; Li Y et al., J Gene 2011, Med 13: 60-72; Pichon C et al., Methods Mol Biol 2013 969: 247-274; McNamara MA et al., J Immunol Res. 2015; 2015: 794528; Sayour E. J. et al., *Journal for Immunotherapy of Cancer.* 2015;3, article 13; Bettinger T. et al, *Current Opinion in Molecular Therapeutics.* 2001;3(2):116-124; Lu D. et al., *Cancer Gene Therapy.* 1994; 1(4):245-252; Wasungu L.

et al., *Journal of Controlled Release*. 2006; 116(2):255-264; Little S. et al., *Proceedings of the National Academy of Sciences of the United States of America*. 2004; 101(26): 9534-9539; Phua K. et al., *Journal of Controlled Release*. 2013; 166(3):227-233; Su X et al., *Molecular Pharmaceutics*.2011; 8(3):774-787; Phua K. K. L. et al., *Nanoscale*. 2014; 6(14):7715-7729; Phua K. K. L. et al., *Scientific Reports*.2014;4, article 5128, the content of each of which is incorporated herein as entirety.

The present invention also provides a DNA sequence encoding an anti-TWIST siRNA sequence of any one of SEQ ID Nos: 1-10. Such DNA sequence can be further included to a vector for transfection and expression of the anti-TWIST siRNA.

The present invention further provides pharmaceutical compositions/formulations that include a composition disclosed herein in combination with at least one pharmaceutically acceptable excipient or carrier.

Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids such as glycine, carbohydrates, chelating agents, sugars, and other standard ingredients known to those skilled in the art (Remington's Pharmaceutical Science 16$^{th}$ edition, Osol, A. Ed. 1980).

A pharmaceutical formulation including a composition as described herein can be administered by a variety of methods known in the art. The route and/or mode of administration vary depending upon the desired results. In embodiments, administration is intravenous, intramuscular, intraperitoneal, or subcutaneous, or administered proximal to the site of the target. Pharmaceutically acceptable excipients can be suitable for intravenous, intramuscular, subcutaneous, parenteral, spinal or epidermal administration (e.g., by injection or infusion).

Pharmaceutical formulations of the nucleic acid as described herein can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions.

Actual dosage levels of the active ingredients (i.e., the compositions described herein) in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, the route of administration, the time of administration, the rate of excretion of the particular composition (e.g., the nucleic acid described herein) being employed, the duration of the treatment, other drugs, compounds and/or materials used in combination with the particular compositions employed, the age, sex, weight, condition, general health and prior medical history of the patient being treated, and like factors.

A physician or veterinarian can start doses of the nucleic acid (e.g., anti-TWIST siRNA) of the invention employed in the pharmaceutical formulation at levels lower than that required to achieve the desired therapeutic effect and gradually increase the dosage until the desired effect is achieved. In general, effective doses of the compositions of the present invention vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with a pharmaceutical formulation of the invention, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

The compositions provided herein can be administered on multiple occasions. Intervals between single dosages can be weekly, monthly or yearly. Intervals can also be irregular as indicated by measuring immune response to the neo-antigen. Alternatively, composition can be administered as a sustained release formulation, in which case less frequent administration is required. Dosage and frequency vary depending on the half-life of the composition in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

A composition or a pharmaceutical composition provided herein may, if desired, be presented in a kit (e.g., a pack or dispenser device) which may contain one or more unit dosage forms containing the composition or the pharmaceutical composition, for example (1) a TWIST signaling inhibitor, (2) a composition including a TWIST signaling inhibitor bound to a delivery vehicle, (3) a composition including an anti-cancer drug and a TWIST signaling inhibitor that is optionally bound to a delivery vehicle, or (4) a pharmaceutical composition including a pharmaceutically acceptable excipient and a composition described herein. The pack may for example comprise metal or plastic foil, such as a blister pack. The pack or dispenser device may be accompanied by instructions for administration. Compositions comprising a composition described herein formulated in a compatible pharmaceutical carrier may also be prepared, placed in an appropriate container, and labeled for treatment of an indicated condition. Instructions for use may also be provided.

Instructions (e.g., written, tape, VCR, CD-ROM, etc.) for carrying out the assay may be included in the kit. The assay may for example be in the form of q-PCR, Western Blot analysis, Immunohistochemistry (IHC), immunofluorescence (IF), sequencing and Mass spectrometry (MS) as known in the art.

III. Methods

The invention further provides methods of using the compositions described herein.

In one aspect, the invention relates to a method of reversing to an anti-cancer drug (e.g., doxorubicin, cisplatin, carboplatin, a taxane, camptothecin or any combination thereof) in a subject by administering a therapeutically effective amount of a TWIST signaling inhibitor described herein to the subject.

In one aspect, the invention relates to a method of treating cancer in a subject in need thereof by administering to the subject a therapeutically effective amount of a TWIST signaling inhibitor described herein.

In another aspect of the invention relates to a method of inhibiting metastasis in a subject in need thereof by administering to the subject a therapeutically effective amount of a TWIST signaling inhibitor described herein.

In embodiments, a subject in need thereof of the method described herein may be resistant to an anti-cancer drug (e.g., doxorubicin, cisplatin, carboplatin, a taxane, camptothecin or any combination thereof).

In embodiments, any method described herein may also include administering to the subject an effective amount of an anti-cancer agent, simultaneously as the TWSIT signaling inhibitor or subsequently (after the administration of the TWIST signaling inhibitor). An anti-cancer agent can be any anti-cancer agent described herein. In embodiments, an anti-cancer agent is doxorubicin, cisplatin, carboplatin, a taxane, camptothecin or any combination thereof.

In embodiments, the TWIST signaling inhibitor used in any method described herein is a TWIST inhibitor described herein. In embodiments, the TWIST signaling inhibitor is a TWIST1 signaling inhibitor. In embodiments, the TWIST signaling inhibitor is a TWIST2 signaling inhibitor. In embodiments, the TWIST signaling inhibitor is a TWIST1 and TWIST2 signaling inhibitor. In embodiments, TWIST signaling inhibitors include inhibitors of TWIST1, TWIST2, one or more genes/proteins listed in Table 1 and Akt signaling genes/proteins. In embodiments, TWIST signaling inhibitors include inhibitors of TWIST1, TWIST2, GAS6, L1CAM, PI3K, Akt, or any combination thereof. In embodiments, the TWIST signaling inhibitor used in any method described herein includes a plurality of TWIST signaling inhibitors provided herein.

In embodiments, TWIST signaling inhibitors used in any method described herein are siRNA inhibitors. In embodiments, TWIST signaling inhibitors are siRNAs against TWIST1, TWIST2, one or more genes listed in Table 1 and Akt signaling genes. In embodiments, TWIST signaling inhibitors are siRNAs against TWIST1, TWIST2, GAS6, L1CAM, PI3K, and/or Akt. A siRNA sequence against a specific gene can be designed according to any method known in the art. In embodiments, the siRNA inhibitor used in any method described herein includes a plurality of siRNAs (i.e., a pooled siRNAs) against TWIST1, TWIST2, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52) of the genes listed in Table 1 and Akt signaling genes.

In embodiments, the TWIST signaling inhibitor used in any method described herein is a TWIST1 inhibitor. In embodiments, the TWIST signaling inhibitor used in any method described herein is an anti-TWIST siRNA. In embodiments, the TWIST signaling inhibitor used in any method described herein is an anti-TWIST siRNA having a sequence of any one of SEQ ID Nos: 1-12. In embodiments, the TWIST signaling inhibitor used in any method described herein is a composition including a nanoparticle bound with an anti-TWIST siRNA. In embodiments, the TWIST signaling inhibitor used in any method described herein is a pharmaceutical composition described herein.

In embodiments, pooled siRNAs against GAS6, L1CAM, and HMGA2 were obtained from Santa Cruz Biotechnology (Dallas, Tex.; item numbers sc-35450, sc-43172, and sc-37994, respectively).

In embodiments, TWIST signaling inhibitors are small molecule inhibitors. In embodiments, TWIST signaling inhibitors are small molecule inhibitors against one or more proteins listed in Table 1 and Akt/PI3K signaling proteins. In embodiments, TWIST signaling inhibitors are small molecule inhibitors against TWIST1, TWIST2, GAS6, L1CAM, PI3K, and/or Akt. In embodiments, the small molecule inhibitor used in any method described herein includes a plurality of small molecule inhibitors (i.e., a pooled small molecule inhibitors) against one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52) of TWIST1, TWIST2, the proteins listed in Table 1 and Akt signaling proteins. In embodiments, small molecule inhibitors against PI3K/Akt signaling include, but are not limited to, Wortmannin, demethoxyviridin, LY294002, perifosine, idelalisib, buparlisib (BKM120), duvelisib, alpelisib (BYL719), TGR 1202, copanlisib (BAY 80-6946), PX-866, dactolisib, RP6530, SF1126, INK1117, pictilisib, XL147 (also known as SAR245408), XL765 (also known as SAR245409), palomid 529, GSK1059615, ZSTK474, PWT33597, CUDC-907, ME-401, IPI-549, IC87114, TG100-115, CAL263, RP6503, PI-103, GNE-477, and AEZS-136.

In embodiments, TWIST signaling inhibitor used in any method described herein is within a composition described herein. In embodiments, TWIST signaling inhibitor used in any method described herein is within a pharmaceutical composition described herein.

According to the methods provided herein, cancer is any type of cancer. In embodiments, the cancer to be treated is melanoma, ovarian cancer, breast cancer, prostate cancer, lung cancer, glioblastoma multiforme, neuroblastoma, kidney cancer and more. In embodiments, the cancer to be treated is a metastatic cancer. In embodiments, the cancer to be treated is metastatic melanoma, metastatic ovarian cancer, metastatic breast cancer, metastatic prostate cancer, metastatic lung cancer, metastatic glioblastoma multiforme, metastatic neuroblastoma, metastatic kidney cancer and more.

The terms effective amount and effective dosage are used interchangeably. The term effective amount is defined as any amount necessary to produce a desired physiologic response. In this case, for example, a desired physiologic response includes a subject being more (e.g., about 5%, 10%, 15%, 20%, 25%, 30%, 35%, 40%, 45%, 50%, 75%, 100% or more) responsive to the anti-cancer agent when administered with a TWIST signaling inhibitor compared to the response level of the subject without taking the TWIST signaling inhibitor. A skilled artisan would readily determine the signs of being responsive (such as, slower progression of cancer, smaller size of the cancer tissue, etc.). Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

A therapeutically effective amount used herein also refers to an amount of TWIST signaling inhibitor that is sufficient to re-sensitize the subject to a subsequent or co-treatment with an anti-cancer agent. In embodiments, the amount of the TWIST signaling inhibitor used herein is sufficient to make the subject become responsive to the anti-cancer agent that is administered simultaneously or subsequently or in alteration.

In embodiments, the TWIST signaling inhibitor and the anti-cancer agent are administered in a single composition. In embodiments, the TWIST signaling inhibitor and the anti-cancer agent are both bound to a same delivery vehicle (e.g., a nanoparticle).

In embodiments, the TWIST signaling inhibitor and the anti-cancer agent are administered in two or more compositions. In embodiments, the TWIST signaling inhibitor and the anti-cancer agent are bound to different delivery vehicles (e.g., different nanoparticles).

In some embodiments, the release of the anti-cancer agent is controlled by nanovalves of the nanoparticle. In particular, either an internal or an external stimulus (such as lower pH, magnetic field or light) triggers the opening of the nanovalves, thus controlling the release of the anti-cancer drug.

In embodiments, the TWIST signaling inhibitor and the anti-cancer agent are administered in a single composition, as being bound to the same delivery vehicle (e.g., a nanoparticle). In embodiments, the TWIST signaling inhibitor and the anti-cancer agent are released simultaneously. In embodiments, the anti-cancer agent is released after the TWIST signaling inhibitor takes effect. In embodiments, the anti-cancer agent is released one or more hours, or one or more days after the TWIST signaling inhibitor takes effect. In embodiments, the anti-cancer drug is released about 30 min, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or more after the TWIST signaling inhibitor takes effect.

In some embodiments, the TWIST signaling inhibitor and the anti-cancer agent are administered in two or more compositions, as being bound to different delivery vehicles (e.g., different nanoparticles).

In embodiments, the compositions containing TWIST signaling inhibitor and the anti-cancer agent are administered simultaneously. In embodiments, the anti-cancer agent is released simultaneously as the TWIST signaling inhibitor takes effect. In embodiments, the anti-cancer agent is released about 30 min, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or more after the TWIST signaling inhibitor takes effect.

In embodiments, the composition(s) containing the anti-cancer agent is administered after the administration of the composition containing the TWIST signaling inhibitor. In embodiments, the composition(s) containing the anti-cancer agent is administered and released about 30 min, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or more after the TWIST signaling inhibitor is administered and takes effect.

The TWIST signaling inhibitor takes effect when the expression level of TWIST signaling gene or TWIST signaling protein or the activity level of TWIST signaling protein is less than 90% of the initial level, less than 80% of the initial level, less than 70% of the initial level, less than 60% of the initial level, less than 50% of the initial level, less than 40% of the initial level, less than 30% of the initial level, less than 20% of the initial level or less than 10% of the initial level. Methods for determining the expression level of TWIST signaling gene or TWIST signaling protein or the activity level of TWIST signaling protein is well known in the art.

In embodiments, the nanoparticle utilized in these methods are further bound with one or more tumor targeting moieties (such as HA) to enhance the tumor-targeting specificity of the nanoparticle.

Embodiments

Embodiments contemplated herein include embodiments P1 to P41 following.

Embodiment P1. A composition comprising an anti-TWIST siRNA bound to a nanoparticle.

Embodiment P2. The composition of embodiment P1, wherein said anti-TWIST siRNA comprises a sequence of any one of SEQ ID Nos: 1-10, or a complementary sequence thereof.

Embodiment P3. The composition of embodiment P2, wherein said sequence comprises a nucleic acid modification.

Embodiment P4. The composition of embodiment P3, wherein said nucleic acid modification is a 2'-O-methyluracil or inverted abasic deoxyribose.

Embodiment P5. The composition of embodiment P4, wherein said anti-TWIST siRNA comprises a sequence of SEQ ID NO: 11.

Embodiment P6. The composition of embodiment P3, wherein said modification is a 2-thio-deoxyuracil.

Embodiment P7. The composition of embodiment P6, wherein said anti-TWIST siRNA comprises a sequence of SEQ ID NO: 12.

Embodiment P8. The composition of embodiment P1, wherein said nanoparticle is a mesoporous silica nanoparticle (MSN).

Embodiment P9. The composition of embodiment P8, wherein said MSN is bound to polyethyleneimine (PEI).

Embodiment P10. The composition of embodiment P9, wherein said MSN is further bound to a tumor targeting moiety.

Embodiment P11. The composition of embodiment P10, wherein said tumor targeting moiety is hyarulonic acid (HA).

Embodiment P12. The composition of embodiment P8, wherein said MSN is bound to a tumor targeting moiety.

Embodiment P13. The composition of embodiment P12, wherein said tumor targeting moiety is HA.

Embodiment P14. The composition of embodiment P8, wherein said MSN comprises a low pH activated nanovalve.

Embodiment P15. The composition of embodiment P14, wherein said MSN is further bound with an anti-cancer agent.

Embodiment P16. The composition of embodiment P8, wherein said MSN is a magnetic core-shell MSN.

Embodiment P17. The composition of embodiment P16, wherein said MSN is further bound with an anti-cancer agent .

Embodiment P18. The composition of embodiment P1, wherein said nanoparticle is a dendrimer-based nanoparticle.

Embodiment P19. The composition of embodiment P18, wherein said dendrimer-based nanoparticle is YTZ3-15.

Embodiment P20. The composition of embodiment P19, wherein said anti-cancer agent is Doxorubicin, Cisplatin, Carboplatin, Taxanes, Camptothecin or any combination thereof.

Embodiment P21 . The composition of embodiment P1, further comprising a pharmaceutically acceptable excipient to form a pharmaceutical composition.

Embodiment P22. An siRNA comprising a sequence of any one of SEQ ID NOs: 1-12.

Embodiment P23. A DNA sequence encoding an siRNA sequence comprising a sequence of any one of SEQ ID Nos: 1-10.

Embodiment P24. A pharmaceutical composition, comprising a pharmaceutically acceptable excipient and said siRNA of embodiment P22.

Embodiment P25. A method of reversing resistance to an anti-cancer drug in a subject, the method comprising administering an effective amount of a TWIST inhibitor to said subject.

Embodiment P26. The method of embodiment P25, wherein said TWIST inhibitor is a TWIST1 inhibitor.

Embodiment P27. The method of embodiment P25, wherein said TWIST inhibitor is an anti-TWIST siRNA.

Embodiment P28. The method of embodiment P25, wherein said TWIST inhibitor is the composition of one of embodiments P1 to P24.

Embodiment P29. A method of treating cancer in a subject in need thereof, the method comprising administering to said subject a therapeutically effective amount of a TWIST inhibitor.

Embodiment P30. The method of embodiment P29, wherein said TWIST inhibitor is an anti-TWIST siRNA.

Embodiment P31. The method of embodiment P29, wherein said TWIST inhibitor is the composition of one of embodiments P1 to P24.

Embodiment P32. The method of embodiment P29, wherein said therapeutically effective amount is an amount sufficient to sensitize the subject to subsequent treatment with an anti-cancer agent.

Embodiment P33. The method of embodiment P29, further comprising administering to said subject a therapeutically effective amount of said anti-cancer agent.

Embodiment P34. The method of embodiment P33, wherein said anti-cancer agent is Doxorubicin, Cisplatin, Carboplatin, Taxanes, Camptothecin or any combination thereof.

Embodiment P35. The method of embodiment P33, wherein said anti-cancer agent is bound to a nanoparticle.

Embodiment P36. The method of embodiment P35, wherein said nanoparticle is MSN.

Embodiment P37. The method of embodiment P36, wherein said MSN comprises a low pH activated nanovalve or is a magnetic core-shell MSN.

Embodiment P38. The method of embodiment P29, wherein said subject is resistant to said anti-cancer agent.

Embodiment P39. A method of inhibiting metastasis in a subject in need thereof, the method comprising administering to said subject a therapeutically effective amount of a TWIST inhibitor.

Embodiment P40. The method of embodiment P39, wherein said TWIST inhibitor is an anti-TWIST siRNA.

Embodiment P41. The method of embodiment P39, wherein said TWIST inhibitor is the composition of one of embodiments P1 to P24.

Embodiment P42. The method of embodiment P39, further comprising administering to said subject a therapeutically effective amount of an anti-cancer agent.

Embodiment P43. The method of embodiment P42, wherein said anti-cancer agent is bound to a nanoparticle.

Further embodiments include embodiments Q1 to Q19 following.

Embodiment Q1. A method of treating cancer in a subject in need thereof, the method comprising administering to said subject a therapeutically effective amount of a TWIST signaling inhibitor.

Embodiment Q2. A method of inhibiting metastasis in a subject in need thereof, the method comprising administering to said subject a therapeutically effective amount of a TWIST signaling inhibitor.

Embodiment Q3. A method of reversing resistance to an anti-cancer drug in a subject, the method comprising administering to said subject a therapeutically effective amount of a TWIST signaling inhibitor.

Embodiment Q4. The method of any one of embodiments Q1 to Q3, wherein said TWIST signaling inhibitor is an inhibitor of growth arrest-specific 6 (GAS6), L1 cell adhesion molecule (L1CAM) or an Akt signaling factor.

Embodiment Q5. The method of embodiment Q4, wherein said Akt signaling factor is phosphatidylinositol 3-kinase (PI3K) or protein kinase B (Akt).

Embodiment Q6. The method of any one of embodiments Q1 to Q5, wherein said TWIST signaling inhibitor is a siRNA inhibitor or a small molecule inhibitor.

Embodiment Q7. The method of any one of embodiments Q1 to Q6, wherein said TWIST signaling inhibitor is bound to a delivery vehicle.

Embodiment 18. The method of embodiment 7, wherein said delivery vehicle is a nanoparticle or a lipid particle.

Embodiment Q9. The method of embodiment Q1 or embodiment Q2, wherein said subject is resistant to an anti-cancer drug.

Embodiment Q10. The method of embodiment Q1 or embodiment Q2, wherein said therapeutically effective amount is an amount sufficient to re-sensitize the subject to subsequent treatment with an anti-cancer agent.

Embodiment Q11. The method of any one of embodiments Q1 to Q10, further comprising administering to said subject a therapeutically effective amount of an anti-cancer agent.

Embodiment Q12. The method of any one of embodiments Q1 to Q11, wherein said anti-cancer agent is doxorubicin, cisplatin, carboplatin, a taxane, camptothecin or any combination thereof.

Embodiment Q13. The method of any one of embodiments Q1 to Q12, wherein said inhibitor is within a pharmaceutical composition comprising said inhibitor and a pharmaceutically acceptable excipient.

Embodiment Q14. A composition comprising a TWIST signaling inhibitor bound to a delivery vehicle.

Embodiment Q15. The composition of embodiment Q14, wherein said delivery vehicle is a nanoparticle or a lipid particle.

Embodiment Q16. The composition of embodiment Q14, wherein said TWIST signaling inhibitor is an inhibitor of growth arrest-specific 6 (GAS6), L1 cell adhesion molecule (L1CAM) or an Akt signaling factor.

Embodiment Q17. The composition of embodiment Q16, wherein said Akt signaling factor is phosphatidylinositol 3-kinase (PI3K) or protein kinase B (Akt).

Embodiment Q18. A pharmaceutical composition, comprising a pharmaceutically acceptable excipient and a composition of embodiment Q14.

Embodiment Q19. A kit, comprising an instruction manual and a composition of embodiment Q14 or a pharmaceutical composition of embodiment Q18.

Further embodiments contemplated herein include embodiments 1 to 55 following.

Embodiment 1. A composition comprising a TWIST signaling inhibitor bound to a delivery vehicle.

Embodiment 2. The composition of embodiment 1, wherein said TWIST signaling inhibitor is an siRNA inhibitor or a small molecule inhibitor.

Embodiment 3. The composition of embodiment 1, wherein said delivery vehicle is a nanoparticle or a lipid particle.

Embodiment 4. The composition of embodiment 2, wherein said siRNA inhibitor is an anti-TWIST siRNA.

Embodiment 5. The composition of embodiment 4, wherein said anti-TWIST siRNA comprises a sequence of any one of SEQ ID Nos: 1-10, or a complementary sequence thereof.

Embodiment 6. The composition of embodiment 5, wherein said sequence comprises a nucleic acid modification.

Embodiment 7. The composition of embodiment 6, wherein said nucleic acid modification is a 2'-O-methyluracil or inverted abasic deoxyribose.

Embodiment 8. The composition of embodiment 7, wherein said anti-TWIST siRNA comprises a sequence of SEQ ID NO: 11.

Embodiment 9. The composition of embodiment 6, wherein said modification is a 2-thio-deoxyuracil.

Embodiment 10. The composition of embodiment 9, wherein said anti-TWIST siRNA comprises a sequence of SEQ ID NO: 12.

Embodiment 11. The composition of embodiment 3, wherein said nanoparticle is a mesoporous silica nanoparticle (MSN).

Embodiment 12. The composition of embodiment 11, wherein said MSN is bound to polyethyleneimine (PEI).

Embodiment 13. The composition of embodiment 12, wherein said MSN is further bound to a tumor targeting moiety.

Embodiment 14. The composition of embodiment 13, wherein said tumor targeting moiety is hyarulonic acid (HA).

Embodiment 15. The composition of embodiment 11, wherein said MSN is bound to a tumor targeting moiety.

Embodiment 16. The composition of embodiment 15, wherein said tumor targeting moiety is HA.

Embodiment 17. The composition of embodiment 11, wherein said MSN comprises a low pH activated nanovalve.

Embodiment 18. The composition of embodiment 17, wherein said MSN is further bound with an anti-cancer agent.

Embodiment 19. The composition of embodiment 11, wherein said MSN is a magnetic core-shell MSN.

Embodiment 20. The composition of embodiment 19, wherein said MSN is further bound with an anti-cancer agent.

Embodiment 21. The composition of embodiment 3, wherein said nanoparticle is a dendrimer-based nanoparticle.

Embodiment 22. The composition of embodiment 21, wherein said dendrimer-based nanoparticle is YTZ3-15.

Embodiment 23. The composition of embodiment 20, wherein said anti-cancer agent is doxorubicin, cisplatin, carboplatin, a taxane, camptothecin or any combination thereof.

Embodiment 24. The composition of embodiment 1, wherein said TWIST signaling inhibitor is an inhibitor of growth arrest-specific 6 (GAS6), L1 cell adhesion molecule (L1CAM) or an Akt signaling factor.

Embodiment 25. The composition of embodiment 24, wherein said Akt signaling factor is phosphatidylinositol 3-kinase (PI3K) or protein kinase B (Akt).

Embodiment 26. The composition of embodiment 1, further comprising a pharmaceutically acceptable excipient to form a pharmaceutical composition.

Embodiment 27. An siRNA comprising a sequence of any one of SEQ ID NOs: 1-12.

Embodiment 28. A DNA sequence encoding an siRNA sequence comprising a sequence of any one of SEQ ID Nos: 1-10.

Embodiment 29. A pharmaceutical composition, comprising a pharmaceutically acceptable excipient and said siRNA of embodiment 27.

Embodiment 30. A method of reversing resistance to an anti-cancer drug in a subject, the method comprising administering an effective amount of a TWIST signaling inhibitor to said subject.

Embodiment 31. The method of embodiment 30, wherein said TWIST signaling inhibitor is a TWIST1 inhibitor.

Embodiment 32. The method of embodiment 30, wherein said TWIST signaling inhibitor is an anti-TWIST siRNA.

Embodiment 33. The method of embodiment 30, wherein said TWIST signaling inhibitor is an inhibitor of growth arrest-specific 6 (GAS6), L1 cell adhesion molecule (L1CAM) or an Akt signaling factor.

Embodiment 34. The method of embodiment 33, wherein said Akt signaling factor is phosphatidylinositol 3-kinase (PI3K) or protein kinase B (Akt).

Embodiment 35. The method of embodiment 30, wherein said TWIST signaling inhibitor is the composition of embodiment 1.

Embodiment 36. A method of treating cancer in a subject in need thereof, the method comprising administering to said subject a therapeutically effective amount of a TWIST signaling inhibitor.

Embodiment 37. The method of embodiment 36, wherein said TWIST signaling inhibitor is an anti-TWIST siRNA.

Embodiment 38. The method of embodiment 36, wherein said TWIST signaling inhibitor is an inhibitor of growth arrest-specific 6 (GAS6), L1 cell adhesion molecule (L1CAM) or an Akt signaling factor.

Embodiment 39. The method of embodiment 38, wherein said Akt signaling factor is phosphatidylinositol 3-kinase (PI3K) or protein kinase B (Akt).

Embodiment 40. The method of embodiment 36, wherein said TWIST signaling inhibitor is the composition of embodiment 1.

Embodiment 41. The method of embodiment 36, wherein said therapeutically effective amount is an amount sufficient to sensitize the subject to subsequent treatment with an anti-cancer agent.

Embodiment 42. The method of embodiment 36, further comprising administering to said subject a therapeutically effective amount of said anti-cancer agent.

Embodiment 43. The method of embodiment 42, wherein said anti-cancer agent is doxorubicin, cisplatin, carboplatin, a taxane, camptothecin or any combination thereof.

Embodiment 44. The method of embodiment 42, wherein said anti-cancer agent is bound to a nanoparticle.

Embodiment 45. The method of embodiment 44, wherein said nanoparticle is MSN.

Embodiment 46. The method of embodiment 45, wherein said MSN comprises a low pH activated nanovalve or is a magnetic core-shell MSN.

Embodiment 47. The method of embodiment 36, wherein said subject is resistant to an anti-cancer agent.

Embodiment 48. A method of inhibiting metastasis in a subject in need thereof, the method comprising administering to said subject a therapeutically effective amount of a TWIST signaling inhibitor.

Embodiment 49. The method of embodiment 48, wherein said TWIST signaling inhibitor is an anti-TWIST siRNA Embodiment 50. The method of embodiment 48, wherein said TWIST signaling inhibitor is an inhibitor of growth arrest-specific 6 (GAS6), L1 cell adhesion molecule (L1CAM) or an Akt signaling factor.

Embodiment 51. The method of embodiment 50, wherein said Akt signaling factor is phosphatidylinositol 3-kinase (PI3K) or protein kinase B (Akt).

Embodiment 52. The method of embodiment 48, wherein said TWIST signaling inhibitor is the composition of embodiment 1.

Embodiment 53. The method of embodiment 48, further comprising administering to said subject a therapeutically effective amount of an anti-cancer agent.

Embodiment 54. The method of embodiment 53, wherein said anti-cancer agent is bound to a nanoparticle.

Embodiment 55. A kit, comprising an instruction manual and a composition of embodiment 1 or a pharmaceutical composition of embodiment 29.

EXAMPLES

Example 1

Mesoporous Silica Nanoparticle Delivery of Chemically Modified siRNA Against TWIST1 Leads to Reduced Tumor Burden Abstract. Growth and progression of solid tumors depends on the integration of multiple pro-growth and survival signals, including the induction of angiogenesis. TWIST1 is a transcription factor whose reactivation in tumors leads to epithelial to mesenchymal transition (EMT), including increased cancer cell stemness, survival, and invasiveness. Additionally, TWIST1 drives angiogenesis via activation of IL-8 and CCL2, independent of VEGF signaling. In this work, results suggest that chemically modified siRNA against TWIST1 reverses EMT both in vitro and in vivo. siRNA delivery with a polyethyleneimine-coated mesoporous silica nanoparticle (MSN) led to reduction of TWIST1 target genes and migratory potential in vitro. In mice bearing xenograft tumors, weekly intravenous injections of the siRNA-nanoparticle complexes resulted in decreased tumor burden together with a loss of CCL2 suggesting a possible anti-angiogenic response. Therapeutic use of TWIST1 siRNA delivered via MSNs has the potential to inhibit tumor growth and progression in many solid tumor types.

In this disclosure we demonstrate siRNA delivery via a (polyethyleneimine) PEI coated MSN. We show that the siRNA is able to knock down the expression of TWIST1 both in vitro and in vivo following MSN delivery. The knockdown of TWIST1 resulted in a functional change in the expression of TWIST1 targets and ultimately leads to decreased tumor burden in a xenograft mouse model.

Methods.

MSN Production. The 100 nm MSNs used were produced using the sol-gel method as described previously.[33] The addition of the cationic PEI coating to the MSNs has previously been described.[40]

Cell Culture and Transfection. MDA-MB-4355 melanoma cancer cells were obtained from ATCC (Manassas, Va.). These cells were maintained at 37° C., 5% $CO_2$, and 90% humidity in a standard tissue culture incubator. Media for the MDA-MB-4355 cells consisted of RPMI 1640 media (Genesee Scientific, San Diego, Calif.) supplemented with 10% fetal bovine serum and 1% penicillin/streptomycin. Cells were passaged using 0.25% trypsin (Genesee Scientific, San Diego, Calif.) every 3-4 days as they became confluent.

To allow for imaging of cells in a xenograft model, it was necessary to create a stable line of MDA-MB-4355 that expressed GFP and firefly luciferase (ffluc). These cells were created by with the aid of a CMV lentiviral construct that encodes a fusion protein of GFP and ffluc separated by a three glycine linker.[41] This stable cell line was maintained and used for all experiments (in vitro and in vivo).

Figures 1C, 1D:
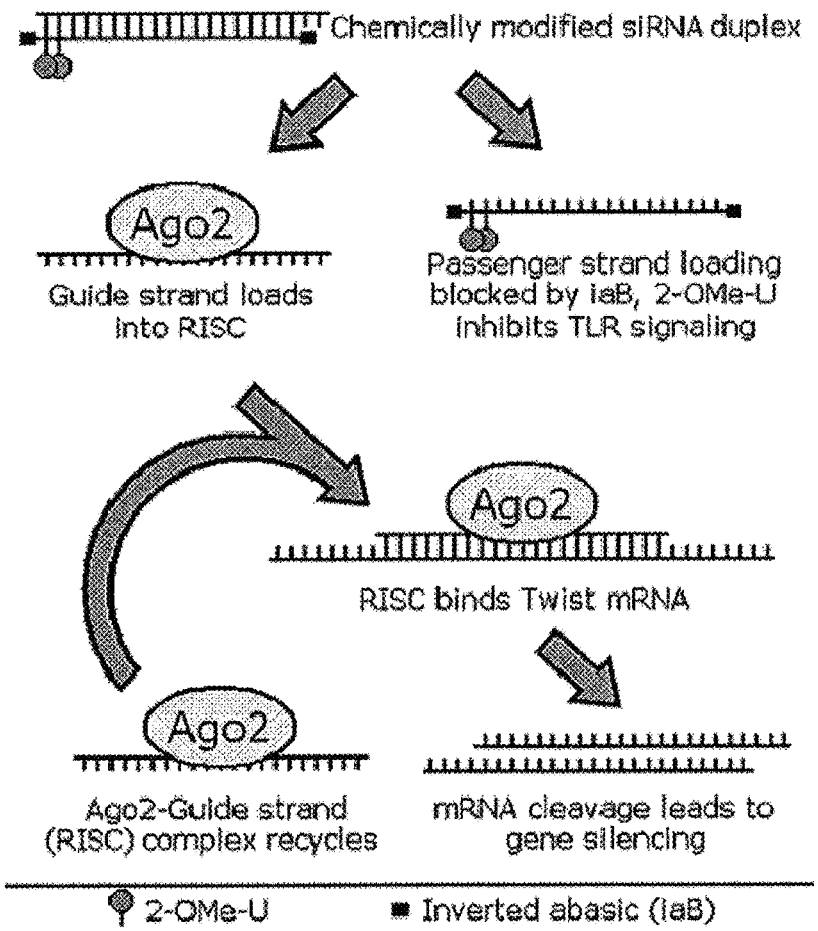

Previously published siRNA sequences against TWIST1 were used (si419-passenger, 5'-GGACAAGCUGAG-CAAGAUU-3'(SEQ ID NO: 1); si419-guide, 5'-AAUC-UUGCUCAGCUUGUCCUU-3'(SEQ ID NO: 2); si494-passenger, 5'-GCGACGAGCUGGACUCCAA-3'(SEQ ID No: 3); si494-guide, 5'-UUGGAGUCCAGCUCGU-CGCUU-3'(SEQ ID No: 4)).[42] Two chemical modifications (addition of 2'-O-methyl and inverted abasic reoxyribose, see FIG. 1D) were made to the si419 passenger/sense strand for all experiments except for those involving LIPOFECTAMINE® 2000 transfection. The chemically modified si419 duplex is referred to as si419Hybrid or si419H. No chemical modifications were made to the si494 sequences. siRNA duplexes were formed by placing equal molar volumes together and heating them in a hot block (100° C.) for 10 minutes followed by removal of the aluminum block from the heat source. Block and duplexes were then allowed to cool to room temperature over several hours. The negative control siRNA (siQ, labeled with ALEXAFLUOR® 647) was AllStars Negative Control siRNA from Qiagen (Valencia, Calif.; proprietary sequence).

Transient transfection of MDA-MB-435S GFP+ffluc was carried out using LIPOFECTAMINE® 2000 (Thermo Fisher Scientific, Waltham, Mass.) according to the manufacturer's instructions. LIPOFECTAMINE® 2000 transfection was used to confirm the functionality of the siRNA (si419 and si494) prior to testing their efficacy with MSNs. Transfection of siRNA with MSNs was carried out by incubating the MSNs with the siRNA overnight at 4° C. while rotating the tube constantly. The mixture consisted of 7 parts MSN (diluted to 500 ng/ul in sterile PBS) to 1 part siRNA (diluted to 10 uM). The final concentration for of MSNs and siRNA applied to cells was 17.5 ng/ul and 50 nM, respectively.

ELISA Assay. Expression of Interleukin 8 (IL-8) is known to be mediated by TWIST1. Therefore, we used an ELISA assay to measure the amount of IL-8 secreted by MDA-MB-4355 GFP+ffluc cells following treatment with MSN+siRNA (si419H and si494). MSNs complexed with siRNA against GFP (siGFP) was used as a control. In a 6-well tissue culture plate, 250,000 MDA-MB-435S GFP+ffluc cells were seeded and allowed to adhere for 24 hours. Following this acclimatization period, cells were incubated with the MSN+siRNA complexes for 72 hours at standard tissue culture conditions. After 72 hours, a sample of the conditioned media was collected for secreted IL-8 quantification. The IL-8 Human ELISA Kit (Thermo Fisher Scientific Inc., Waltham, Mass.) was used according to the manufacturer's specifications.

Western Blot. Following siRNA treatment described above, cells were lifted from tissue culture wells with 0.25% trypsin, pelleted, and lysed in RIPA buffer. Protein concentration was determined using a BCA Assay (Thermo Fisher Scientific). A total of 30 μg of protein per lane was run on 4% stacking and 12% resolving polyacrylamide gels. Following gel electrophoresis, protein was transferred to Immobilon-P PVDF membrane (Millipore, Billerica, Mass.) using a Trans-Blot SD Semi-Dry Transfer Cell (Bio-Rad, Hercules, Calif.). Membranes were then blocked with 5% dry milk dissolved in 1×PBS with 0.1% Tween-20. Antibodies were diluted in blocking buffer (1:250 for anti-TWIST1 and 1:2,500 for anti-Actin). Antibodies used were: anti-TWIST, TWIST 2c1a (Santa Cruz Biotech, Dallas, Tex.); anti-β-Actin, A1978 (Sigma Aldrich, St. Louis, Mo.); and Horse Radish Peroxidase (HRP)-conjugated anti-mouse secondary antibody (Li-Cor, Lincoln, Nebr.). ECL Plus chemiluminescent substrate (Pierce, Thermo Fisher Scientific, Waltham, Mass.) and Blue Devil Film (Genesee Scientific, San Diego, Calif.) were used for the development of images.

Wound Healing Assay. In vitro wound healing assays were performed to examine directional cell migration.[43] MDA-MB-4355 GFP+ffluc cells were grown in the tissue culture conditions described previously in 6-well tissue culture plates. Cells were treated with MSN+siQ, MSN+si419H, or MSN+si494 for 24 hours (as described earlier in this section) prior to being scratched. A sterile 200 μl pipette tip was used with consistent pressure to scratch a line in the monolayer of cells. Images were taken at several time points thereafter using a Nikon TE-2000S microscope (Nikon, Tokyo, Japan) and SPOT Advanced software (Diagnostic Instruments, Sterling Heights, Mich.). Markings were made on the lid of the tissue culture plate to ensure that the same location along the scratch was imaged at each time point. Cells were incubated with MSN+siRNA complexes at 37° C., 5% $CO_2$, and 90% humidity in a tissue culture incubator at all times except for the imaging time points.

Quantitative PCR. Total cellular RNA was isolated using the RNeasy Plus kit (Qiagen, Valencia, Calif.). Synthesis of cDNA from total RNA was carried out using the iScript cDNA Synthesis kit (Bio-Rad, Hercules, Calif.) with an equal amount of RNA used for all samples. Quantitative RT-PCR was performed using Maxima SYBR Green Master Mix (Thermo Fisher Scientific, Waltham, Mass.) in 25 μl reactions. Thermocycling was conducted in a Bio-Rad iQ5 thermal cycler for 40 cycles (95° C., 15s; 57° C., 60s; 79° C., 30s) followed by melt curve analysis. Data were analyzed using Bio-Rad iQ5 software. Primers used were: TWIST1 forward, 5'-CTATGTGGCTCACGAGCGGCTC-3'(SEQ ID No: 14); TWIST1 reverse, 5'-CCAGCTCCA-GAGTCTCTAGACTGTCC-3' (SEQ ID No: 15); Vimentin forward, 5'-TCGTCACCTTCGTGAATACCAAGA-3' (SEQ ID NO: 16), Vimentin reverse, 5'-CCTCAGGTTCA-GGGAGGAAAAGTT-3'(SEQ ID NO: 17); CCL2 forward, 5'-CAGCCAGATGCAATCAATGCC-3'(SEQ ID NO: 18); CCL2 reverse, 5'-TGGAATCCTGAACCCACTTCT-3' (SEQ ID NO: 19).[18].

Confocal Microscopy. MDA-MB-4355 GFP+ffluc cells were seeded into a 3.5 cm glass bottom tissue culture dish and allowed to attach over a 24 hour period. At that time, 2 ml of fresh media was added following the removal of old media. Next, MSN+siQ complexes (labeled with ALEX-AFLUOR® 647) were added to the dish for a 24 hour period at the final concentrations of 17.5 ng/μl (MSN) and 50 μM (siQ). Following fixation with 4% paraformaldehyde cells were counterstained with DAPI (300 nM for 2 min) and then mounted using PROLONG® Gold (Thermo Fisher Scientific, Waltham, Mass.). Confocal images were obtained using the Zeiss LSM 700 Confocal Microscope and ZEN 2012 microscopy software (Zeiss AG, Oberkochen, Germany).

Tumor Engraftment and In vivo Imaging. All animal work was done following protocol approval by the Institutional Animal Care and Use Committee of the City of Hope Beckman Research Institute. A total of 18 female NOD.Cg-Prkdc$^{scid}$ Il2rg$^{tm1Wjl}$/SzJ (NSG) mice (The Jackson Laboratory, Bar Harbor, Me.) were used. All mice were approximately 10 weeks old at the time of the inoculation of tumor cells. Mice were randomly divided into four groups: control mice (no xenografts, 2 mice); negative control (MSN+siQ, 4 mice); si419H treatment group (MSN+si419H, 6 mice); and si494 treatment group (MSN+si494, 6 mice). Mice (other than the no xenograft controls) received bilateral inoculations into the 4$^{th}$ mammary fat pad set immediately adjacent to the nipple. Inoculation was carried out while mice were fully anesthetized using isoflurane (2-5%) delivered via a vaporizer. Inoculum for each mammary fat pad consisted of $3.2 \times 10^6$ MDA-MB-4355 GFP+ffluc cells suspended in 75 μl PBS. Following injections, mice were allowed to fully recover in a clean cage before being placed back in their home cage.

Bioluminescent imaging of mice began 12 days after initial inoculation of tumor cells and occurred every week for six weeks. Images were captured using the Xenogen IVIS 100 biophotonic imaging system (STTARR, Toronto, Ontario, Canada) in order to follow xenograft growth. Prior to being fully anesthetized with isoflurane (2-4%), mice were given a 200 μl intraperitoneal injection of 25 mg/ml D-Luciferin (PerkinElmer, Waltham, Mass.). Ten minutes after the D-luciferin injection, mice were placed in a black box inside of the biophotonic imager. Images were captured over a period of one minute.

Intravenous (IV) injections of MSN+siRNA (siQ, si419H, or si494; siQ fluorescently labeled with ALEXAFLUOR® 647, si419H and si494 labeled with Cy5) were started two weeks after the inoculation of MDA-MB-435S GFP+ffluc cells and done weekly for six weeks. Prior to IV injections, mice were briefly warmed with a heat lamp and then placed in a restrainer. A 120 μl volume of MSN+siRNA was given in the lateral tail vein of each mouse (excluding no-tumor controls). The injection consisted of 105 μl of 500 ng/μl MSN complexed with 15 μl of 10 μM siRNA (complexing took place overnight at 4° C.). Ten minutes after the IV injection animals were fully anesthetized (2-4% isoflurane)

and underwent infrared imaging using the Xenogen IVIS 100 biophotonic imaging system (STTARR, Toronto, Ontario, Canada).

At the end of the experiments, all animals were euthanized via $CO_2$ asphyxiation followed by a complete necropsy. Tumors were carefully dissected away from any adherent tissue and weighed and then placed in 10% formalin along with the heart, lungs, spleen, kidney, and liver for histological evaluation. Histopathological examination of tissues was interpreted by a board certified veterinary pathologist who was blinded to the treatment groups.

Statistical Analysis. Data were analyzed using Prism 6 (GraphPad Software, La Jolla, Calif.). All qPCR data were analyzed by a one-tailed unpaired t-test with Welch's correction, separately comparing si419H to siQ and si494 to siQ. As data were analyzed as mean, standard deviation, and n, no correction for multiple comparisions was performed. ELISA data were analyzed by Kruskal-Wallis non-parametric test and Dunn's test for multiple comparisons. Data represents normalized data from two runs, each in duplicate, for a total n of 4. Tumor growth data were analyzed by Kruskal-Wallis and Dunn's test as described above, and represent all single tumors in each group (grown as 2 tumors per mouse). Exact p values are given on figures where applicable (*=p<0.05 and **=p<0.01).

SUM1315 Cell Culture. SUM 1315 breast cancer cells were obtained from ATCC (Manassas, Va.). Tissue culture incubator environment was maintained at 37° C., 5% $CO_2$, with 90% humidity. Cells were grown in media consisting of a 50-50 mixture of DMEM and F12 media, supplemented with 5% fetal bovine serum, 10 ng/ml EGF, 5 µg/ml insulin, and 1% penicillin/streptomycin. Upon reaching confluency cells were passaged every 2-3 days using 0.25% trypsin (Genesee Scientific, San Diego, Calif.).

Stable SUM1315 cell lines were developed that reliably expressed a short hairpin RNA (shRNA) against TWIST1 (shTwist419, shTwist494), or a scrambled control shRNA (shScram) as a negative control. These SUM1315 cell lines were created as previously described. See e.g, Li S, et al., BMC Biology. 2012; 10: 73

RNA-Seq. Cell pellets from SUM1315-shTwist419, SUM1315-shTwist494, and SUM1315-shScram were collected and immediately processed for RNA extraction. Total cellular RNA was isolated using the RNeasy Plus kit (Qiagen, Valencia, Calif.). 10 µg of total RNA was then resuspended in nuclease free water and poly (A) enriched to remove ribosomal RNA. Samples were processed using the Illumina HiSeq 2500 (Illumina, San Diego, Calif.). Resulting raw RNA-seq data was first aligned using TopHat (version 2.0.8, Center for Computational Biology, Johns Hopkins University) followed by counting and expression scoring with Cufflinks (version 2.02) as described previously. See e.g., Trapnell C, et al. Nature protocols. 2012; 7: 562-78.

Immunohistochemistry. To confirm that nests of cells in lung fields were metastatic lesions 5 µm sections of all paraffin imbedded tissues were cut and stained with 1:3000 rabbit polyclonal GFP antibodies (Ab290, Abcam, Cambridge, Mass.). Sections were incubated at room temperature for 30 minutes. An HRP-conjugated goat anti-rabbit IgG was used as the secondary antibody.

MTT Assay. The tetrazolium dye MTT [3-(4,5-dimethylthiazol-2-yl)-2,5-diphenyltetrazolium bromide] was used to assess cell death following treatment with various concentrations of MSN+siRNA. A total of 5,000 MDA-MB-4355 GFP+ffluc were placed in each well of a 96-well tissue culture plate and allowed to attach over 24 hours. Next the cells were treated with either ½×, 1×, 2', 5×, or 10× the typical MSN+siRNA concentration (final concentration for of MSNs and siRNA applied to cells was 17.5 ng/ul and 50 nM, respectively) for 24 hours. Following this incubation period media was removed from each well and 110 µl MTT diluted in complete media (0.45 mg/ml) was added. Incubation lasted for 3 hoursat 37° C., 5% $CO_2$, with 90% humidity. Following the incubation period the MTT media was removed and 110 µl DMSO was added to each well and the plate was gentle shaken for 15 mins. Dye intensity for each well was then read at a wavelength of 580 nm.

Figure 2A:
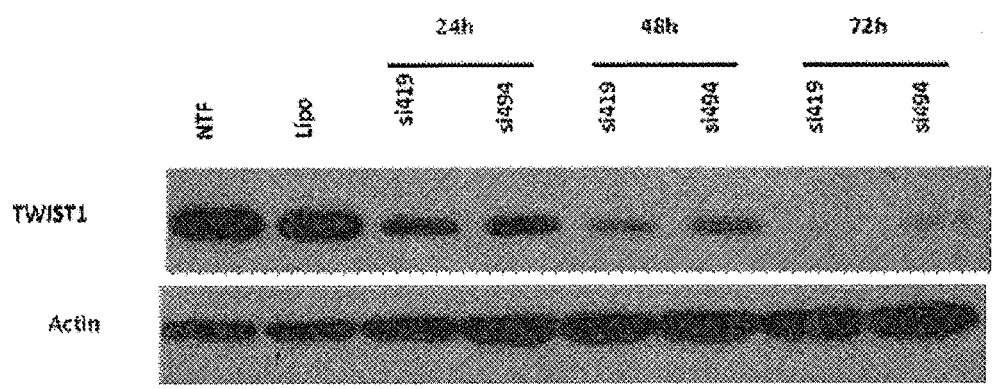
FIGS. 2A to 2D. siRNA enters cells and knocks down TWIST1 in vitro.
Figure 6:
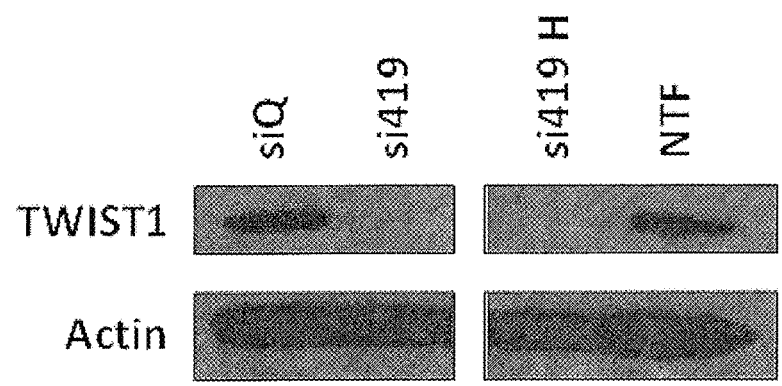
FIG. 6. Chemical modification of si419 does not significantly change knockdown efficiency. Unmodified si419 and hybrid si419 containing only the passenger strand modifications (H) each show approximately 80% knockdown. Therefore, si419 hybrid was used throughout this work.

Results.

siRNA design and loading onto mesoporous silica nanoparticles. We have designed and synthesized siRNA to inhibit TWIST expression, by incorporating various chemical modifications to increase resistance to nuclease activity, decrease immunogenicity and to promote efficient loading of the guide strand into RISC (FIG. 1C). Our previous studies with a breast cancer cell line (SUM 1315) demonstrated the efficacy of the si419H and si494.[42] To confirm efficacy of si419 and si494 (with/without chemical modifications) in MDA-MB-4355 cells, Lipofectamine® 2000 transfection was performed. A time dependent TWIST1 knockdown, was observed with greater than 90% TWIST1 protein reduction at 72 hours following transfection (FIG. 2A). Chemical modifications (2'-O-methyl and inverted abasic reoxyribose on passenger/sense strand) did not impact the efficacy of TWIST1 knock down (FIG. 6).

The above siRNAs were loaded onto mesoporous silica nanoparticles (MSNs) that have a PEI coated cationic surface. Mixing of PEI+siRNA enables tight binding of siRNA to positively charged MSNs. Thus, PEI provides protection of siRNA and efficient delivery of siRNA to cancer cells.

Figure 2B:
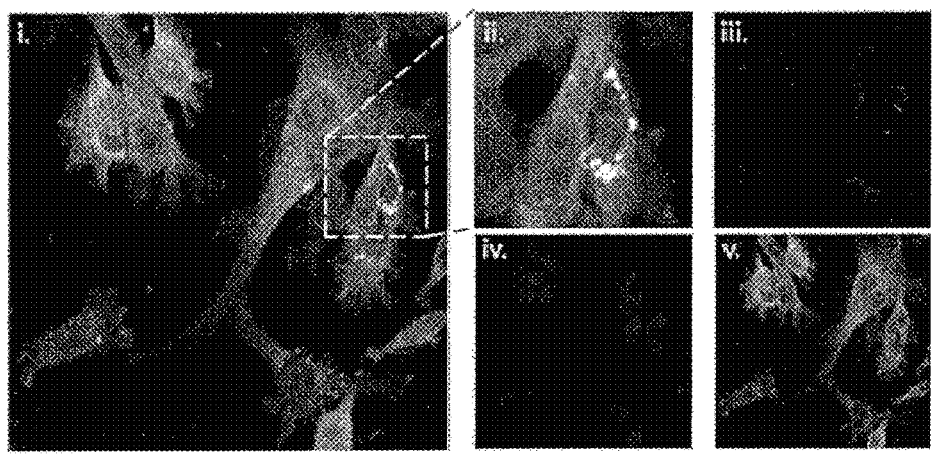
Figure 5:
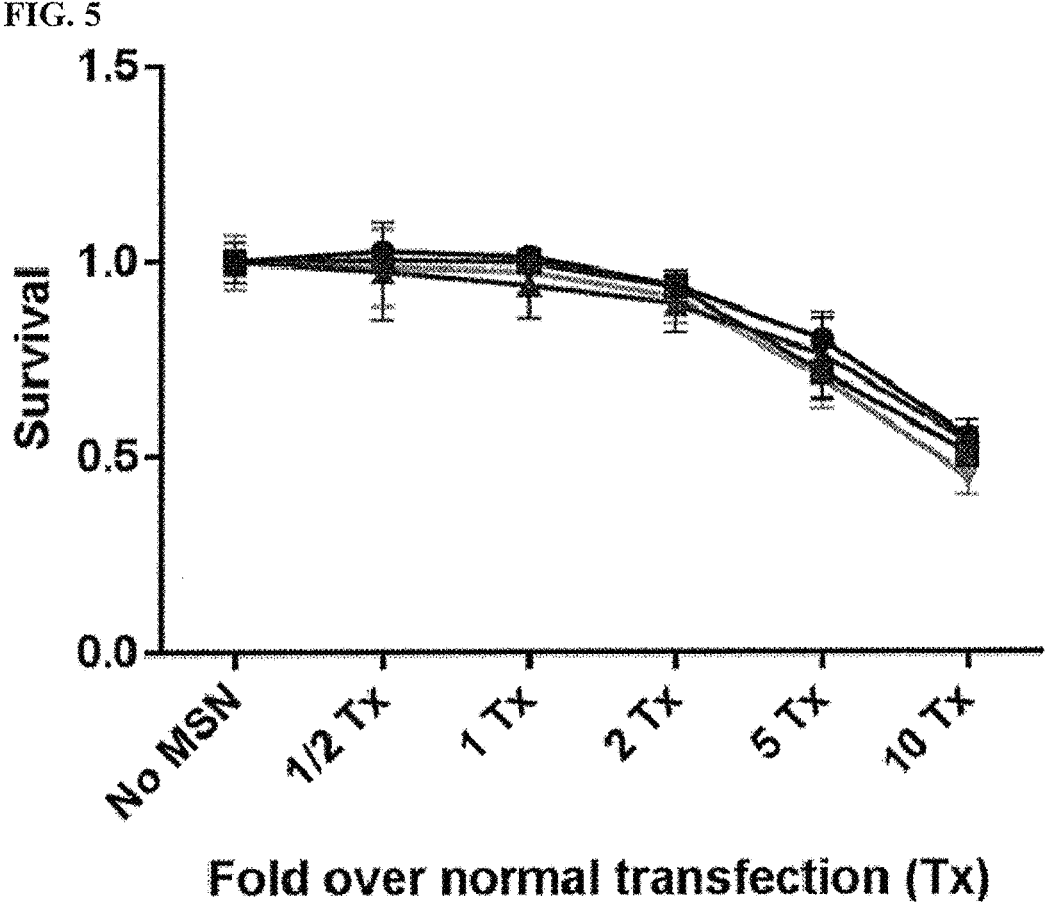
FIG. 5. MTT assay demonstrates that at concentrations used for transfection in vitro (1 Tx) siRNA-MSN complexes are not inherently cytotoxic, and do not show appreciable cell death until dose is increased five-fold. This phenomenon was independent of siRNA sequence.
Figure 7A:
FIGS. 7A to 7C. MDA-MB-4355 cells express GFP and firefly luciferase.
Figure 7B:
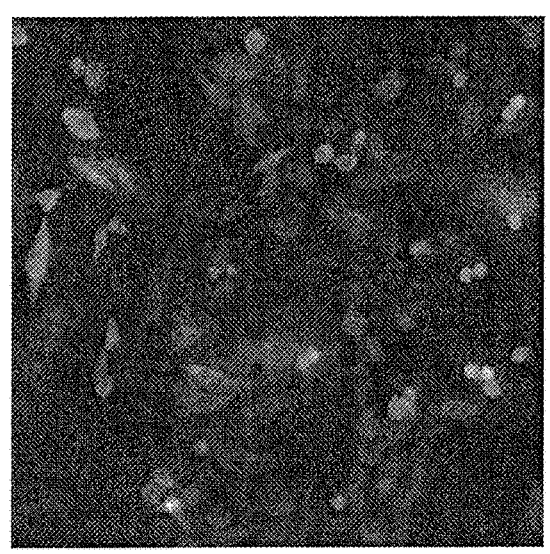
Figure 7C:
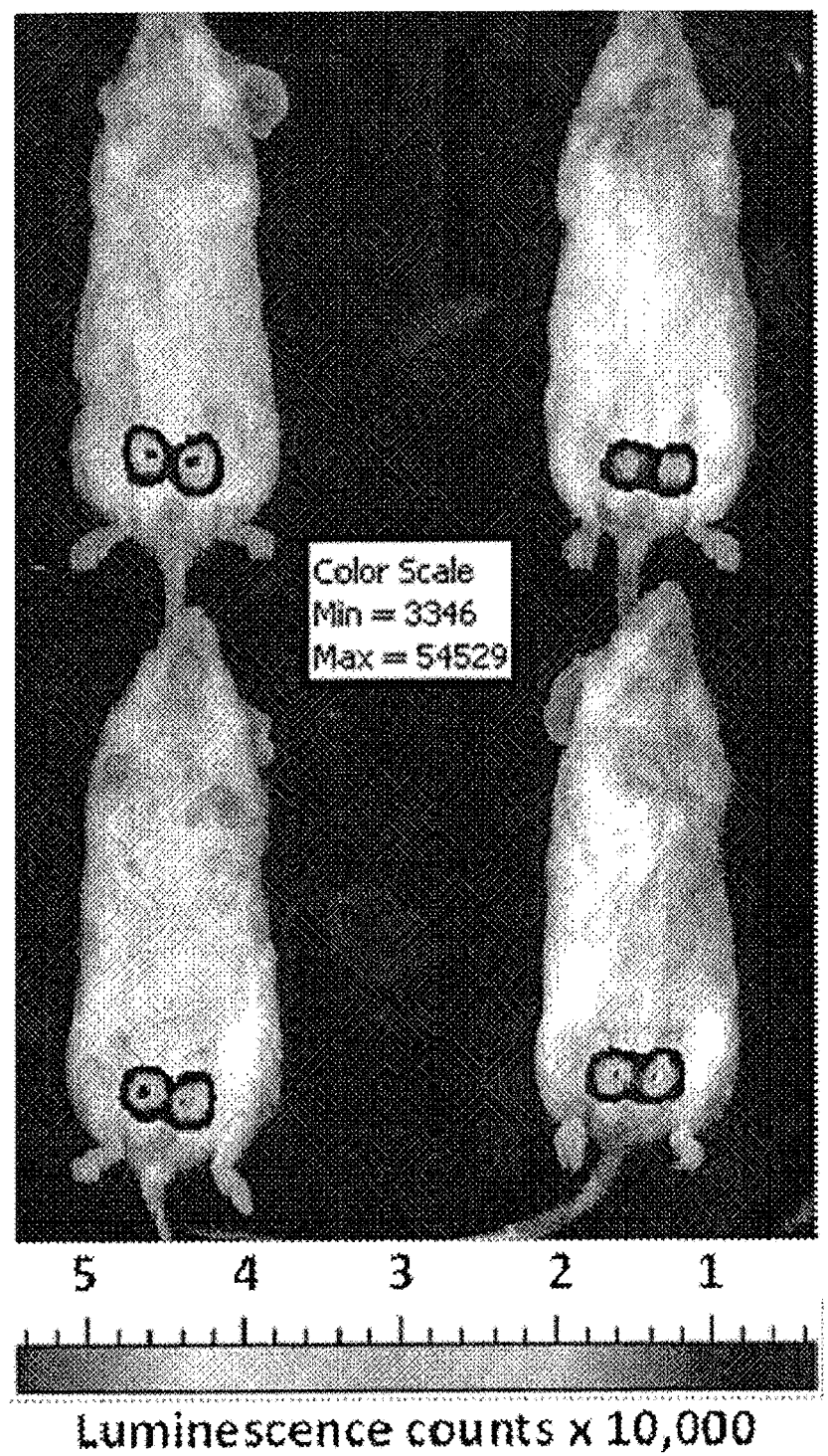

MSN+siRNA delivery and TWIST1 silencing. A stable line of MDA-MB-435S that expresses GFP and ffluc was successfully produced via lentiviral transduction. Both GFP and ffluc were shown to be fully functional in vitro and in vivo (FIGS. 7A-7C). Confocal microscopy of MDA-MB-4355 GFP+ffluc cells following incubation with fluorescently labeled MSN+siQ resulted in correct perinuclear localization of the siRNA (FIG. 2B). No noticeable cellular death was observed. MTT assays confirmed that significant cell death did not occur until MSN+siRNA treatment was 2-5 times the usual concentration (i.e. MSNs=17.5 ng/µl and siRNA=50 nM) (FIG. 5).

TWIST1 knock down in MDA-MB-4355 GFP+ffluc cells was observed at 72 hours post MSN+siRNA treatment. A 90% decrease in TWIST1 was observed in both RNA and protein measurements (FIG. 2C), whereas basal levels of TWIST1 expression returned by one week.

Figure 3A:
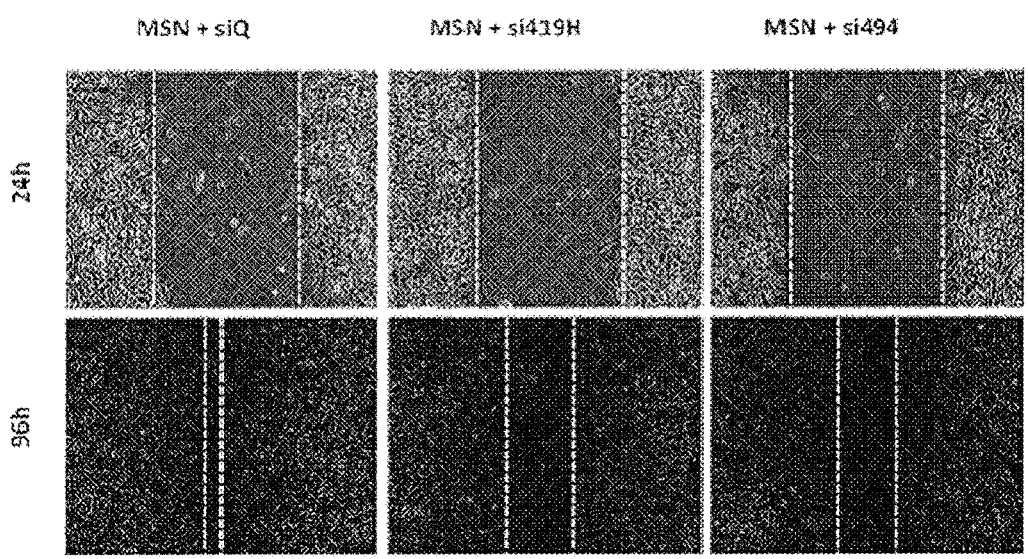
FIGS. 3A to 3B. TWIST1 knockdown reduces downstream pathways in vitro.
Figure 3B:
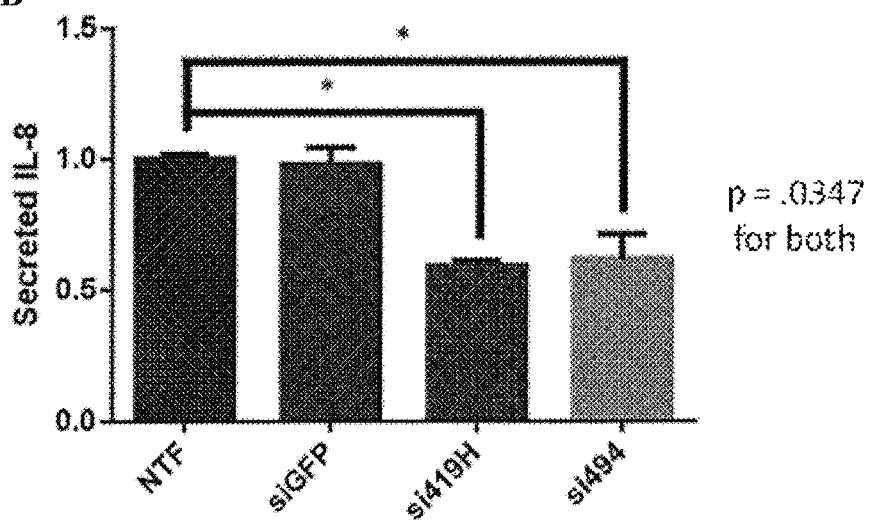

TWIST knockdown results in decreased migration and decrease in the secretion of IL8. TWIST1 knock down resulted in downstream effects to functional phenotypes following MSN+siRNA treatment. A wound healing assay showed an appreciable difference in the migration capabilities of MDA MB 435S GFP+ffluc cells following treatment with MSN+si419H and MSN+si494 when compared to the MSN+siQ control (FIG. 3A). IL-8 ELISA assays also demonstrated significant reduction in human IL-8 secretion from the MDA-MB-435S GFP+ffluc cells following 72 hours of treatment with MSN+si419H or MSN+494 when compared to MSN+siQ negative control (FIG. 3B). Reduction of IL-8 secretion was also observed at 48 and 96 hours posttransfection, however, no IL-8 changes observed at 24 hours.

Tumor Burden Decreased Following Treatment with MSN+Chemically Modified siRNA. All mice that received an inoculation of tumor cells developed bilateral tumors in the area of the mammary fat pad in the 4$^{th}$ mammary set. All tumors were palpable and emitted a robust bioluminescent signal following IP injection of D-Luciferin. Following histopathological examination, no changes were observed in the heart, lungs, liver, spleen, and kidneys, in mice receiving MSN+siRNA treatments when compared to controls that did not receive any treatment.

Figure 2C:
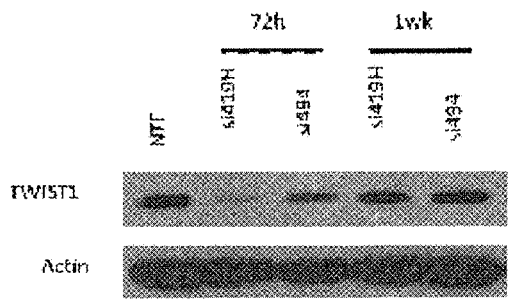
Figure 2D:
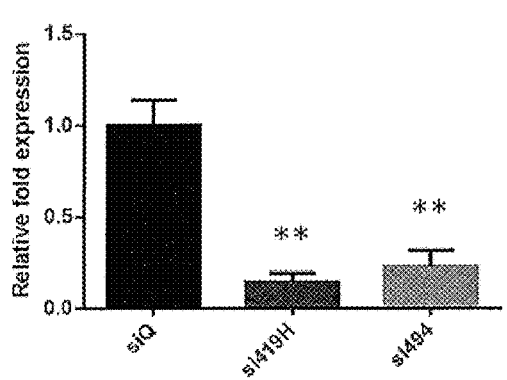
Figure 4A:
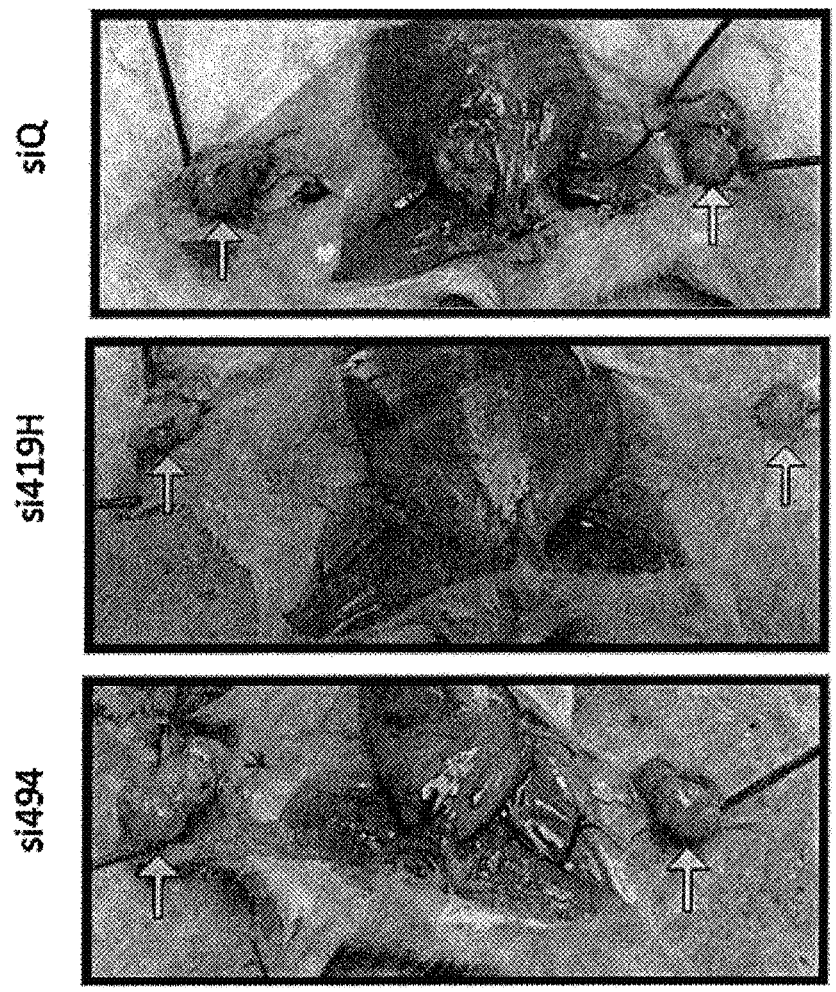
FIGS. 4A to 4E. MSN+siRNA therapy reduces TWIST expression and tumor growth in vivo.
Figure 4B:
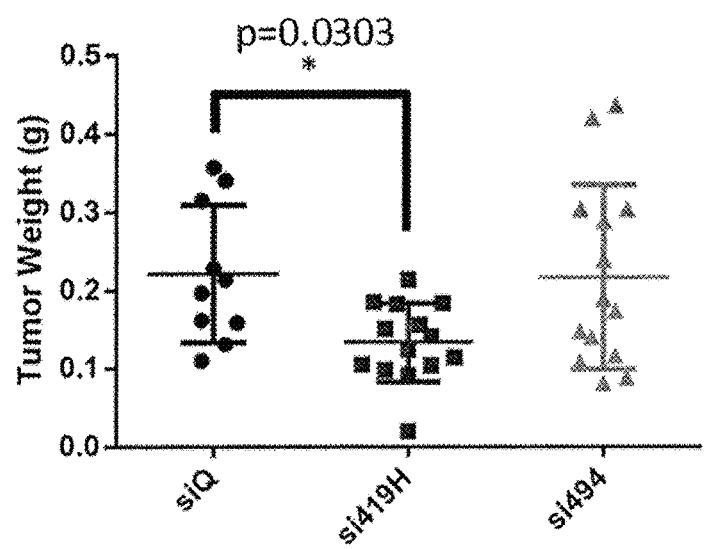

However, tumors collected from the MSN+si419H mice were significantly smaller when compared to the weights of the tumors from the MSN+siQ control mice (FIGS. 4A-4B). Furthermore, by visual inspection, the blood vessels supplying the tumors of MSN+si419H treated mice were smaller and appeared less hemorrhagic than those of the other two groups (FIG. 4A). However, the tumors from mice treated with MSN+si494 without chemical modifications were not significantly smaller than tumors of the control mice as would be expected from the in vitro TWIST1 knockdown studies for both si419H and si494 in (FIG. 2C).

Figure 4C:
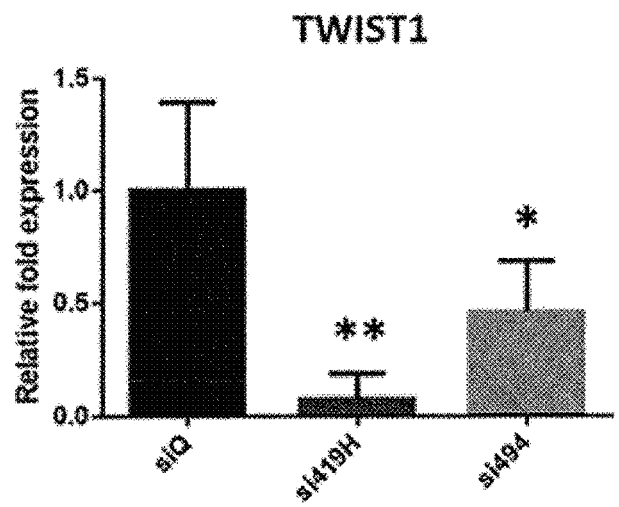
Figure 4D:
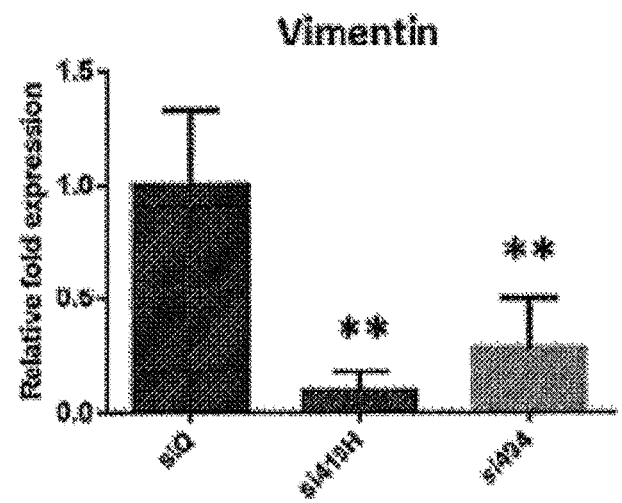
Figure 4E:
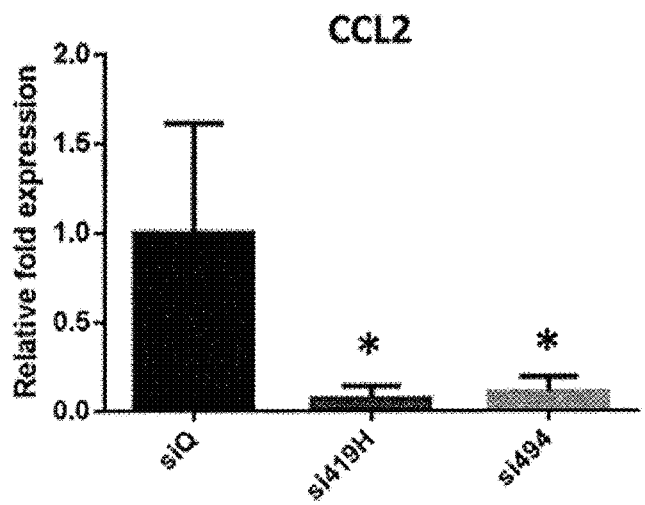

Tumor Characterization Demonstrated EMT Inhibition. mRNA isolated from collected tumors were analyzed for relative quantities of TWIST1, Vimentin (an EMT marker), and CCL2 (chemokine involved in angiogenesis). A significant reduction in the amount of TWIST1, Vimentin, and CCL2 mRNA was observed in the MSN+si419H and MSN+si494 treated mice when compared to the control mice (MSN+siQ) (FIGS. 4C-4E). The average relative reduction of TWIST1 for MSN+si494 treated mice was less than that of those treated with MSN+si419H (p=0.0067), though no significant difference was observed for Vimentin or CCL2. Thus, these data suggest inhibition of EMT/angiogenesis through the delivery of TWIST1 siRNA.

Figure 8A:
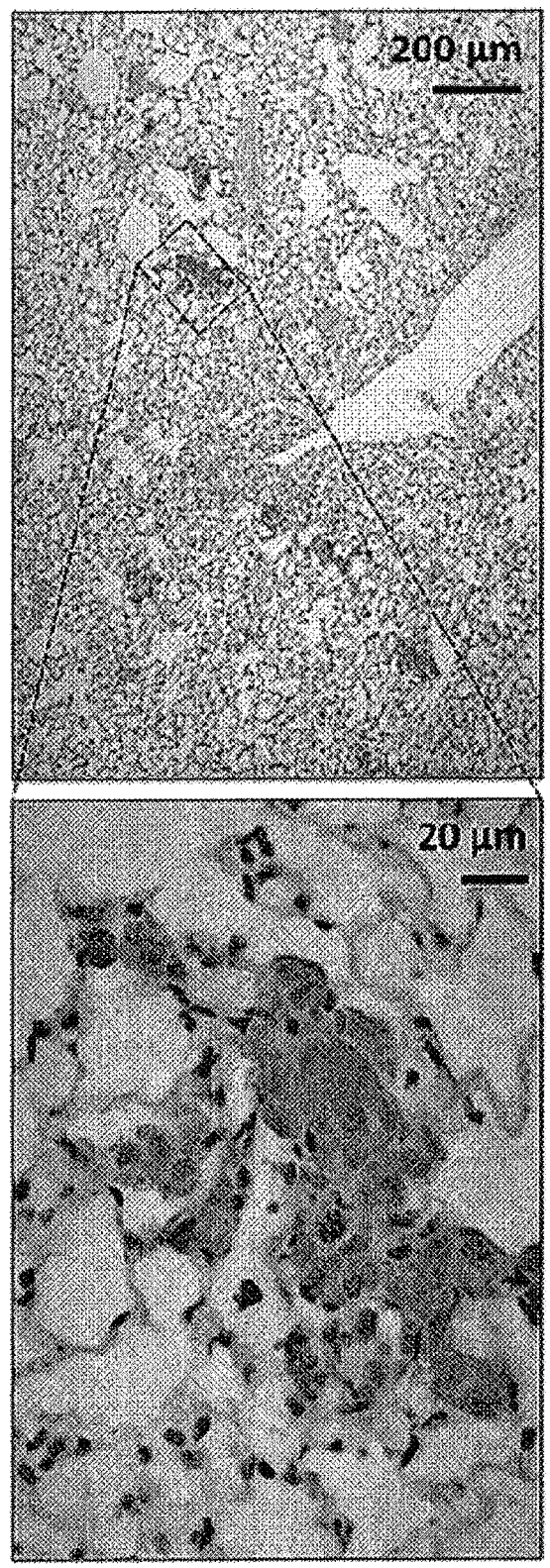
FIGS. 8A to 8B. MDA-MB-4355 cells metastasized to the lungs in mice.
Figure 8B:
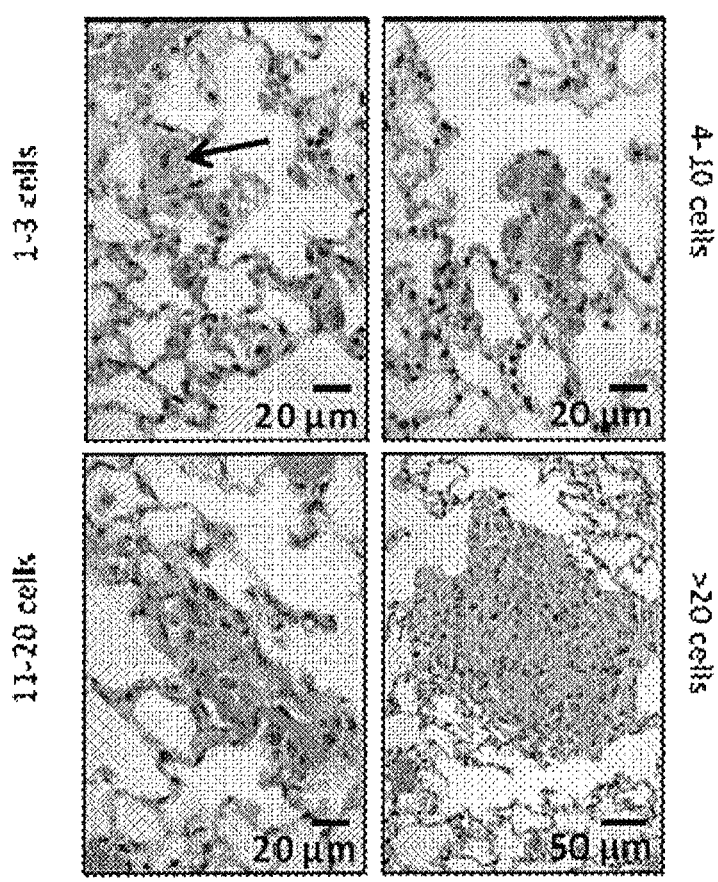
Figure 9A:
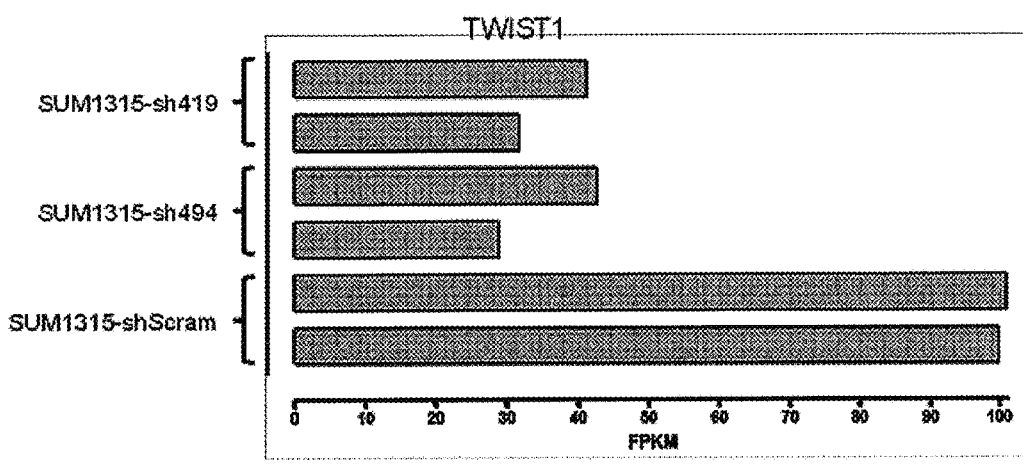
FIGS. 9A to 9B. RNA-seq performed on SUM1315 triple negative breast cancer cells stably expressing shRNA against TWIST or control (shScram).
Figure 9B:
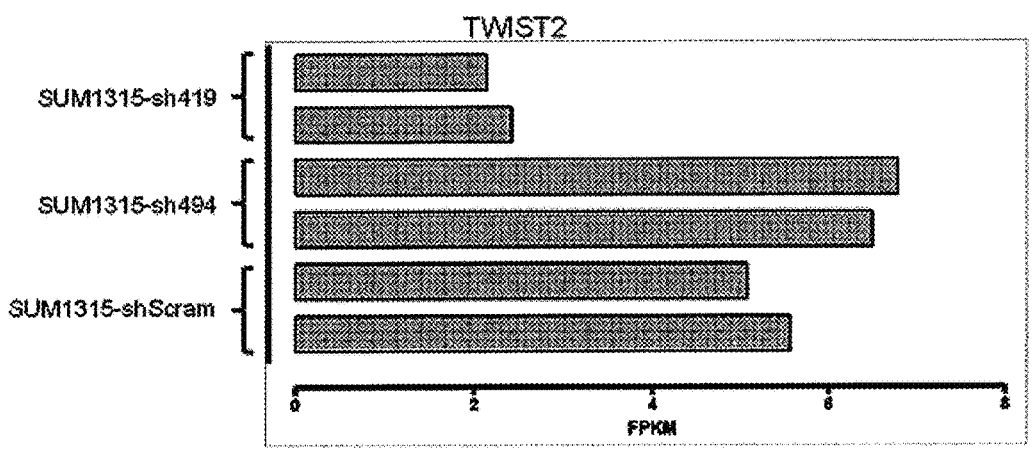

No Evidence of Decreased Metastatic Lesions. Contrary to what would be expected with significant TWIST1 knock down, there was no reduction in the number of metastatic lung lesions (FIGS. 8A-8C). Metastatic lesions were categorized into 4 groups based on size, and no significant difference was seen among the MSN+siQ, MSN+si419H, and MSN+si494 treatment groups. The cause for this finding could be attributed to two possible elements in the experimental design. First, the initial MSN treatment occurred two weeks after the MDA-MB-4355 GFP+ffluc were inoculated. This period of time was designed to allow for the tumor cells to engraft unencumbered by any treatment. However, it is possible that the tumor cells from this highly metastatic cell line spread to the lungs and engrafted before MSN treatments were initiated. Although less clinically relevant, future studies with this cell line might benefit from beginning MSN+siRNA treatments simultaneously with tumor cell inoculation. Second, just because the in vitro data demonstrated TWIST1 protein levels following MSN+siRNA treatment were reduced at 72 hours, but returned by 7 days (FIG. 2C); it is possible that in vivo levels of TWIST1 (and its target genes) are higher and for effective knocked down it would have been necessary to provide MSN+siRNA treatments at more frequent intervals (e.g. twice per week rather than once). Metastatic disease is the ultimate cause of mortality in the vast majority of cancer related deaths. For this reason there are great efforts being made in understanding the mechanisms underlying metastasis as well as developing therapies to exploit these mechanisms to prevent the spread of cancer cells.[44,45]

Discussion

Here, we demonstrate the effective delivery of a chemically modified siRNA therapy via a silica nanoparticle carrier. Following delivery of the siRNA, there is significant knockdown of the transcription factor TWIST1, a known regulator of EMT and angiogenesis.[46] TWIST1 knockdown was associated with decreased tumor burden in vivo as well as a reduction in the TWIST1-mediated targets-Vimentin (EMT) and CCL2 (angiogenesis) (FIGS. 4C-4E).

Our results demonstrate that nanoparticle delivery of TWIST1 siRNA leads to a decrease in tumor burden supporting the idea that TWIST1 is an important therapeutic target. TWIST1 was selected as a target for siRNA therapy because it is highly associated with metastasis, EMT, and a poor prognosis.[46] TWIST1 is also an attractive therapeutic target because it is not expressed in most adult tissues, and therefore most normal tissues would not be negatively impacted by an siRNA silencing strategy.[47]

The observed decrease of tumor burden appears to be due to the effect of reduced TWIST expression on EMT-mediated angiogenesis. Angiogenesis in cancer occurs following a variety of complex signaling pathways that ultimately result in increased blood supply to the tumor, thus allowing for continued growth and metastasis. Two key components of angiogenesis that were examined here are CCL2 and IL-8. CCL2 is a monocyte chemotactic protein secreted by tumor cells responsible for recruiting macrophages to aid in establishing new blood vessels in the tumor.[18,49] IL-8 is a pro-inflammatory cytokine that is known to work synergistically with VEGF to stimulate vessel growth in tumors.[50] Furthermore, IL-8 is known to promote angiogenesis independent of VEGF and can cause anti-VEGF therapies to fail.[51] Reduction of both IL-8 (in vitro, secreted) and CCL2 (in vivo) were observed following treatment with MSN+si419H and MSN+si494 (FIGS. 3B and 4E). While reduction of these two promoters of angiogenesis was evident for both types of MSN+siTWIST treatment groups, reduced tumor burden was only observed with MSN+si419H.

In our experiments, we found that si419H exhibited excellent efficacy in vitro and in vivo.

Our results show that mesoporous silica nanoparticles provide efficient vehicle delivery of siRNA in vitro and in vivo. The MSNs developed for this project were shown in vitro to successfully deliver their siRNA payload into melanoma cells (FIG. 2B) and that this delivery resulted in significant knockdown of TWIST1 (FIG. 2C). These results further establish that MSNs are viable carriers for siRNA. [36,54] The PEI coated 130 nm MSNs used in this project were shown to cause no cellular death in vitro (at normal concentrations, FIG. 5). Following weekly IV injections of MSN+siRNA there was no observable histopathologic evidence of tissue damage in any of the examined organ tissues. Taken together, this would indicate that MSNs are efficacious and safe as reported previously.[55,56] MSNs provide a number of advantages for future development as a siRNA vehicle. First, MSNs are highly customizable in both their size and shape, thus allowing for a finely tuned nanoparticle which can be optimized to specific delivery needs. Modification to the size and structure of the MSN allows for increased biocompatibility and safety.[55] The porous nature of the MSN allows for the internal loading of therapies in addition to the siRNA demonstrated here and elsewhere, thus enabling a multimodal approach to cancer therapy.[54] Finally, MSNs can be modified to carry targeting moieties that allow them to home to specific tissues or tumors.[57] The porous nature of the MSNs used in this research is an untapped nanoparticle characteristic that should be explored in conjunction with the observed knockdown of TWIST1. Drug resistance is a major hindrance to the treatment of cancer and often results in a more aggressive phenotype. Therefore, a MSN based co-delivery strategy of anti-TWIST1 siRNA together with chemotherapy could result in more pronounced tumor reduction. Increased efficacy and reduced dosage would also be possible with tumor targeting moieties as previously described.[54]

These data support continued development and optimization of MSNs as a delivery platform for the treatment of cancer. This research represents the first example of silencing an EMT regulating transcription factor following siRNA delivery using MSNs.

References (Example 1)

[1] Nguyen D X, et al., Nature reviews Cancer. 2009; 9: 274-84; [2] Coghlin C. & Murray G I, J Pathol. 2010; 222: 1-15; [3] Lee J M, et al., J Cell Biol. 2006; 172: 973-81; [4] Kalluri R. & Weinberg R A, J Clin Invest. 2009; 119: 1420-8; [5] Vernon A E & LaBonne C., Curr Biol. 2004; 14: R719-21; [6] Niu R F, et al., J Exp Clin Cancer Res. 2007; 26: 385-94; [7] Carmeliet P., Nature. 2005; 438: 932-6; [8] Risau W., Nature. 1997; 386: 671-4; [9] Pralhad T, et al., The Journal of pharmacy and pharmacology. 2003; 55: 1045-53; [10] Carmeliet P. & Jain R K, Nature. 2000; 407: 249-57; [11] Hanahan D. & Weinberg R A, Cell. 2011; 144: 646-74; [12] Spano D. & Zollo M., Clin Exp Metastasis. 2012; 29: 381-95; [13] Gotink K J & Verheul H M, Angiogenesis. 2010; 13: 1-14; [14] Choi S H, et al., Liver international: official journal of the International Association for the [Study of the Liver. 2014; 34: 632-42; [15] Semenza G L, Journal of cellular biochemistry. 2007; 102: 840-7; [16] Yancopoulos GD, et al., Nature. 2000; 407: 242-8; [17] Linardou H, et al., Breast Cancer Res. 2012; 14: R145; [18] Low-Marchelli J M, et al., Cancer Res. 2013; 73: 662-71; [19] Bialek P, et al., Dev Cell. 2004; 6: 423-35; [20] Khan M A, et al., Tumour biology: the journal of the International Society for Oncodevelopmental Biology and Medicine. 2013; 34: 2497-506; [21] El Ghouzzi V, et al., Eur J Hum Genet. 1999; 7: 27-33; [22] Xu Y, et al., Am J Pathol. 2013; 183: 1281-92; [23] Kong D, et al., Cancers (Basel). 2011; 3: 716-29; [24] Vesuna F, et al., Neoplasia. 2009; 11: 1318-28; [25] Li J, et al., Investigative ophthalmology & visual science. 2014; 55: 8267-77; [26] Shalini Singh I W Y M, et al., Advances in Biology. 2014; 2014: 8 Pages; [27] Mironchik Y, et al., Cancer Res. 2005; 65: 10801-9; [28] Li S, et al., BMC Biol. 2012; 10: 73; [29] Lu J, et al., Small. 2007; 3: 1341-6; [30] Liong M, et al., ACS nano. 2008; 2: 889-96; [31] Greish K., Methods Mol Biol. 2010; 624: 25-37; [32] Castanotto D. & Rossi J J, Nature. 2009; 457: 426-33; [33] Horn C., et al., Small. 2010; 6: 1185-90; [34] David S., et al., Pharmacol Res. 2010; 62: 100-14; [35] Yamazaki Y., et al., Gene therapy. 2000; 7: 1148-55; [36] Xia T, et al., ACS nano. 2009; 3: 3273-86; [37] Guo P, et al., Adv Drug Deliv Rev. 2010; 62: 650-66; [38] Behlke M A, Oligonucleotides. 2008; 18: 305-19; [39] Czauderna F, et al., Nucleic Acids Res. 2003; 31: 2705-16; [40] Meng H, et al., ACS nano. 2011; 5: 4131-44; [41] Brown C E, et al., Cancer Res. 2009; 69: 8886-93; [42] Finlay J., et al., BioMed research international. 2015; 2015: 382745; [43] Liang C C, et al., Nature protocols. 2007; 2: 329-33; [44] Vernon A E, et al., Rev Endocr Metab Disord. 2007; 8: 199-213; [45] Kuperwasser C., et al., Cancer Res. 2005; 65: 6130-8; [46] Yang J., et al., Cell. 2004; 117: 927-39; [47] Wang S M, et al., Gene. 1997; 187: 83-92; [48] Dykxhoorn D M & Lieberman J., Cell. 2006; 126: 231-5; [49] Bonapace L., et al., Nature. 2014; 515: 130-3; [50] Martin D., et al., J Biol Chem. 2009; 284: 6038-42; [51] Huang D., et al., Cancer Res. 2010; 70: 1063-71; [52] Teng Y. & Li X., Clin Exp Metastasis. 2014; 31: 367-77; [53] Forsbach A, et al., J Immunol. 2008; 180: 3729-38; [54] Meng H, et al., ACS nano. 2013; 7: 994-1005; [55] Lu J., et al., Small. 2010; 6: 1794-805; [56] Ferris D P, et al., Small. 2011; 7: 1816-26; [57] Tarn D. et al.., Accounts of chemical research. 2013; 46: 792-801; [58] Vesuna F., et al., Oncogene. 2011; [59] Wang X, et al., Oncogene. 2004; 23: 474-82; [60] Yanes R E & Tamanoi F., Therapeutic delivery. 2012; 3: 389-404;

Example 2

RNA-Based TWIST1 Inhibition via Dendrimer Complex to Reduce Breast Cancer Cell Metastasis Abstract. Breast cancer is the leading cause of cancer-related deaths among women in the United States, and five-year survival rates for patients with metastases are drastically lower than for patients with localized disease. This is especially true for patients with triple-negative breast cancer (TNBC; ER, PR, Her2 negative) tumors. Understanding the metastatic mechanisms of aberrant cancer cells is therefore crucial to identify new therapeutic targets and develop novel therapies to use in conjunction with current therapies to prevent metastasis and improve patient outcomes. A potential target is the TWIST1 transcription factor, a master regulator of cellular migration through epithelial-mesenchymal transition (EMT), which is often overexpressed in aggressive breast cancers. Here, we demonstrate an siRNA-based TWIST1 silencing approach with delivery using a modified poly(amidoamine) (PAMAM) dendrimer. Our results demonstrate that SUM1315 TNBC cells efficiently take up PAMAM-siRNA complexes, leading to significant knock down of TWIST1 and EMT-related target genes. Knockdown lasts up to one week post transfection and leads to a reduction in the migratory and invasive nature of breast cancer cells, as determined by in vitro wound healing and transwell assays. Furthermore, we demonstrate that PAMAM dendrimers can deliver siRNA to xenograft orthotopic tumors with a high degree of specificity. These results suggest that dendrimer-based delivery of siRNA for TWIST1 silencing may be a valuable adjunctive therapy for patients with TNBC.

In the current study, we investigated whether anti-TWIST1 siRNA could be functionally delivered to metastatic breast cancer cells (SUM 1315 cells) using YTZ3-15. We tested the ability of the YTZ3-15-delivered siRNA to knock down TWIST1, reduce expression of EMT-related target genes, and alter the phenotypic characteristics associated with cancer cell migration (metastasis). We also evaluated the tumor-specific delivery capability of YTZ3-15 using a mouse breast cancer model.

Materials and Methods.

Cell Culture, Transfection, and Stable Cell Line Production. SUM 1315 breast cancer cells were obtained from ATCC (Manassas, Va.). Cells were maintained at 37° C., 5% $CO_2$, and 90% humidity in a tissue culture incubator. Media for SUM 1315 cells consisted of a 50-50 mixture of DMEM and F12 media, supplemented with 5 µg/ml insulin, 10 ng/ml EGF, 5% fetal bovine serum, and 1% penicillin/streptomycin. Cells were passaged using 0.25% trypsin (Genesee Scientific, San Diego, Calif.) every 2-3 days as they reached confluency. Transient transfection of SUM 1315 cells was performed using Lipofectamine 2000 (Thermo Fisher Scientific, Waltham, Mass.) or YTZ3-15 (obtained from Dr. Ling Peng, Centre Interdisciplinaire de Nanoscience de Marseille, France). siRNA sequences were as follows: siTwistA-sense, 5'-GGACAAGCUGAGCAAGAUU-3'(SEQ ID NO: 1); siTwistA-antisense, 5'-AAUCUUGCUCAGC- UUGUCCUU-3'(SEQ ID NO:2); siTwistB-sense, 5'-GC-GACGAGCUGGACUCCAA-3'(SEQ ID No: 3); siTwistB-antisense, 5'-UUGGAGUCCAGCUCGUCGCUU-3'(SEQ ID No: 4). All custom siRNAs were synthesized by IDT (Integrated DNA Technologies, Inc., Skokie, Ill.) and arrived lyophilized and were resuspened in H2O prior to being reannealed. Negative control siRNA (siQ, labeled with either AlexaFluor® 488 or 647) was AllStars Negative Control siRNA from Qiagen (Valencia, Calif.). Lipofectamine 2000 was diluted fifty-fold in OptiMEM® (Thermo Fisher Scientific; Waltham, Mass.) and incubated with 10 uM siRNA for 20 min at room temperature. YTZ3-15 was diluted to 1.75 uM in Opti-MEM® and mixed with 10 uM siRNA at an N/P ratio of 5, for a final dendrimer-siRNA complex concentration of 50 nM. Complexes were incubated 20 min at room temperature which resulted in dendriplexes of roughly 100 nm in size. Incubation of the YTZ3-15 dendriplexes with SUM 1315 cells was done at the tissue culture conditions described previously for up to 7 days with fresh media being added to existing media as needed. Stable transfections of SUM 1315 cells were performed using lentivirus. Cells expressing eGFP-firefly luciferase fusion protein were created by transfecting the CMV cassette as described previously [39].

To examine the effects of TWIST1 knock down in SUM 1315 cells without the possible confounding variables of the delivery mechanism itself, we developed cell lines that stably expressed a short hairpin RNA (shRNA) against TWIST1 (shTwistA, shTwistB), or a scrambled control shRNA (shScram) as a negative control. Cells were alternatively stably transfected with shTwistA, shTwistB or shScram as described previously [40]. Immortalized human mesenchymal stem cells (hMSCs) were used as described previously [41].

Wound Healing Assay. To examine direction cell migration in vitro wound healing assays were performed as described previously [42]. In summary, SUM 1315 cells (parental, eGFP+luc, shScram, shTwistA, and shTwistB) were grown in the conditions described above (2.1) in 6-well tissue culture plates. Once cells reached 80% confluency, a sterile 200 µl pipette tip was used to scratch a line in the monolayer of cells. Images were taken immediately after the scratch and at several time points thereafter using a Nikon TE-2000S microscope and SPOT Advanced software (Diagnostic Instruments, Sterling Heights, Mich.). Care was taken to always capture images in the same location for each time point. Additionally, SUM 1315 cells were transfected with siQ, siTwistA, or siTwistB using YTZ3-15 at a 50 nM final concentration. Cells were incubated with YTZ3-15+siRNA for 24 hours at 37° C., 5% $CO_2$, and 90% humidity in a tissue culture incubator; the plates were then scratched with the 200 µl pipette tip.

Invasion Assay. $2.5 \times 10^5$ SUM 1315 cells were transfected using YTZ3-15 complexed with siQ, siTwistA, or siTwistB as described above (2.2). After 24 hours incubation, $2.5 \times 10^5$ SUM 1315 cells were lifted from the plate with 0.25% trypsin, washed, and seeded onto transwell inserts (8 µm pore diameter; Millipore, Darmstadt, Germany). Inserts (which nest inside of wells in a 24-well tissue culture plate) were pre-coated with Matrigel® (3 mg/ml, 60 µl, diluted with serum-free medium) (BD Biosciences, San Jose, Calif.), which was allowed to solidify in a tissue culture incubator for 30 minutes prior to the addition of the transfected cells. In order to stimulate cell invasion the top chamber containing the transfected SUM 1315 cells contained 1% FBS (400 µl) while the lower chamber contained 600 µl of complete media with 20% FBS. Cells were permitted to invade for 24 hours in a tissue culture incubator. After this period the MatriGel® and any remaining cells in the upper chamber were removed with a cotton-tipped swab. Transwell membranes were then washed twice in PBS and stained with Crystal Violet. Five images of each membrane were taken and cells were counted manually. Graphs were created to show an average count from each of the five images.

Quantitative PCR. Total cellular RNA was isolated using the RNeasy Plus kit (Qiagen, Valencia, Calif.). RNA quantity and quality was measured and analyzed (with 260/280 nm and 260/230 nm spectra measurements) using a Nano-Drop ND-1000 (Thermo Fisher Scientific, Waltham, Mass.). An equal amount of RNA for all conditions was used as a template for cDNA synthesis using the iScript cDNA Synthesis kit (Bio-Rad, Hercules, Calif.). Quantitative RT-PCR was performed in quadruplicate using Maxima SYBR Green Master Mix (Thermo Fisher Scientific, Waltham, Mass.) in 25 µl reactions. Cycling was conducted in a Bio-Rad iQ5 thermal cycler for 40 cycles (95° C., 15s; 57° C., 60s; 79° C., 30s) followed by melt curve analysis. Data were analyzed using Bio-Rad iQ5 software using the $2^{-\Delta\Delta C_t}$ method and normalized to Actin. Primers used were: Twist forward #1, 5'-CTATGTGGCTCACGAGCGGCTC-3'(SEQ ID No: 14); Twist reverse #1, 5'-CCAGCTCCAGAGTCTCTA-GACTGTCC-3'(SEQ ID No: 15); Twist forward #2, 5'-TCT-TACGAGGAGCTGCAGACGCA-3'(SEQ ID NO: 20); Twist reverse #2, 5'-ATCTTGGAGTCCAGCTCGTCGCT-3'(SEQ ID NO: 21); N-cadherin forward, 5'-GGGACAGT-TCCTGAGGGATCAA-3'(SEQ ID NO: 22), N-cadherin reverse, 5'-TGGAGCCTGAGACACGATTCTG-3'(SEQ ID NO: 23), Vimentin forward, 5'-TCGTCACCTTCGT-GAATACCAAGA-3'(SEQ ID NO: 16), Vimentin reverse, 5'-CCTCAGGTTCAGGGAGGAAAAGTT-3'(SEQ ID NO: 17), β Actin forward, 5'-CCGCAAAGACCTGTACGC-CAAC-3' (SEQ ID NO: 24); β Actin reverse, 5'-CCA-GGGCAGTGATCTCCTTCTG-3' (SEQ ID NO: 25).

Western Blot. Cells were seeded at 250,000 cells per well in 6-well tissue culture plates and treated as described in section 2.1. Cells were pelleted, lysed in RIPA buffer, and protein concentration was determined using the BCA Assay (Thermo Fisher Scientific, Waltham, Mass.). 30 µg total protein per lane was run on 4% stacking and 10-12% resolving polyacrylamide gels and transferred to Immobilon-P PVDF membrane (Millipore, Billerica, Mass.). Membranes were blocked with 5% dry milk dissolved in 1×PBS with 0.1% Tween-20. Antibodies were diluted in blocking buffer. Antibodies used were: anti-Twist, Twist 2c1a (Santa Cruz Biotech, Dallas, Tex.); anti-β-actin, A1978 (Sigma Aldrich, St. Louis, Mo.); and HRP-conjugated anti-mouse secondary antibodies. ECL Plus chemiluminescent substrate (Pierce, Thermo Fisher Scientific, Waltham, Mass.) and Blue Devil Film (Genesee Scientific, San Diego, Calif.) were used.

Confocal Microscopy. SUM 1315 cells were transfected with siQ siRNA (labeled with AlexaFluor® 647) using YTZ3-15 and incubated for 24 hours in a tissue culture incubator. Cells were then treated with LysoTracker® Red (Thermo Fisher Scientific, Waltham, Mass.) according to the manufacturer's conditions. Confocal images were obtained using the Zeiss LSM 700 Confocal Microscope and the ZEN 2012 microscopy software (Zeiss AG, Oberkochen, Germany).

Tumor Engraftment. A total of nine female NOD.Cg-Prkdc$^{scid}$ Il2rg$^{tm1Wjl}$/SzJ (NSG) mice (The Jackson Laboratory, Bar Harbor, Me.) were used to engraft the SUM 1315 eGFP+luc breast cancer cells (8 weeks old at time of inoculation). The nine mice were to be divided into three groups; intratumoral (IT), intravenous (IV), and IV long term. While under anesthesia (Isoflurane, 2.5-4%), mice received bilateral inoculations of cells into the 4$^{th}$ mammary fat pad. Inoculum for each mammary fat pad consisted of 1×10$^6$ SUM 1315 eGFP+luc cells together with 2×10$^5$ hMSCs resuspended in 50 μl Matrigel®. Injections were delivered into the mammary fat pad adjacent to the nipple. Mice were then allowed to recover in a clean cage. Two NSG mice receiving no cells were used as controls.

In Vivo Imaging. After tumor cell inoculations, the mice were imaged every two weeks using the Xenogen IVIS 100 biophotonic imaging system (STTARR, Toronto, Ontario, Canada) to monitor tumor growth. To obtain in vivo images, mice were given a 200 μl intraperitoneal (IP) injection of 25 mg/ml D-Luciferin (PerkinElmer, Waltham, Mass.). After a 10-minute waiting period, animals were anesthetized using Isoflurane (2-5%) and placed in a black box in the biophotonic imager. Bioluminescent images were captured over a period of one minute. Once tumors had reached 0.5-0.75 cm, three mice were given a single intravenous (IV) injection of the YTZ3-15+siQ complex diluted in 200 μl PBS. A separate group of three animals was given intratumoral injections of the YTZ3-15+siQ complex. Three additional tumor bearing animals received IV injections of YTZ3-15+siQ to be used for longer term imaging studies with the final images being captured 14 days post injection. After the injections, animals underwent in vivo fluorescent imaging using the biophotonic imager (Cy5.5 filter). Images were captured at 5, 10, 15, and 240 minutes after injection of the dendrimer complex. After the final time point (4 hours), all animals were euthanized and tissues were collected. Tumors, spleen, kidney, and liver from each animal were imaged ex vivo using the IVIS 100 to detect the AlexaFluor® 647-labeled siRNA without the hindrance of the skin and fur. Two NSG mice receiving no cells were used as controls for in vivo imaging.

Statistics and Replications. Wound healing assays were repeated three times as were the western blot analyses. Invasion assay was repeated twice with identical conditions. Five images were captured for each invasion assay condition and the numbers of cells were counted manually and standard deviations were calculated using Excel (Microsoft, Redman, Wash.). Quantitative PCR experiments were done in quadruplicate and analyzed using the 2$^{-\Delta\Delta C_t}$ method in the Bio-Rad iQ5 software. Three animals per group (along with two control animals) were used for biodistribution purposes and no statistical analyses were performed with in vivo imaging data.

Results and Discussion.

Figure 11A:
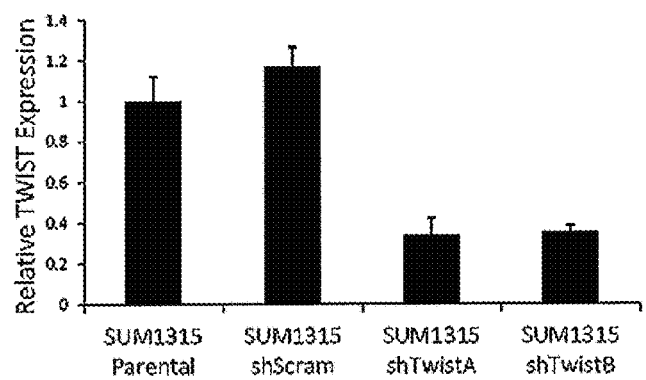
FIGS. 11A to 11C. Stable shRNA-mediated TWIST1 knockdown in SUM 1315.
Figure 11B:
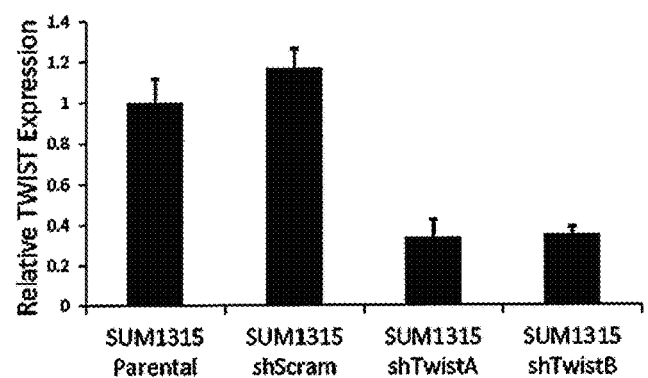

Stable TWIST1 Knock Down in SUM 1315 Cells. The relationship between TWIST1 expression and EMT has been established for breast cancer [43]. To examine the effects of TWIST1 knock down in SUM 1315 cells without the possible confounding variables that a delivery mechanism may cause, we developed cell lines that stably expressed a shRNA against TWIST1 (shTwistA and shTwistB) and a scrambled shRNA (shScram) as a negative control. TWIST1 expression in the SUM 1315 shTwistA and shTwistB cell lines demonstrated excellent knock down of TWIST1 compared to the parental line and the shScram line (FIGS. 11A-11B).

Figure 11C:
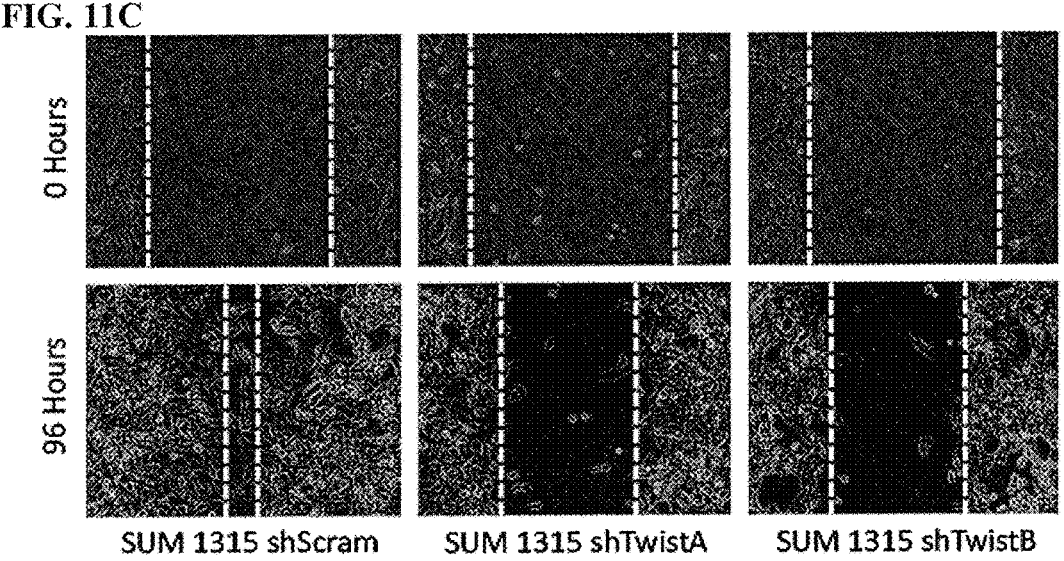
Figure 12A:
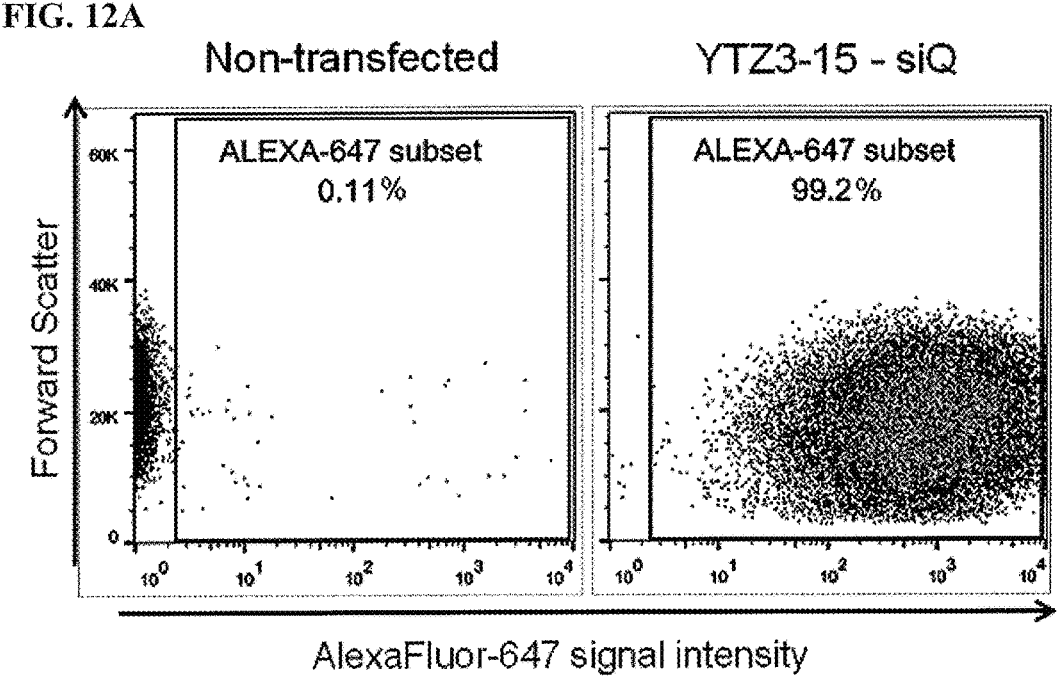
FIGS. 12A to 12C. YTZ3-15 efficiently delivers siRNA to SUM 1315 cells.
Figure 12B:
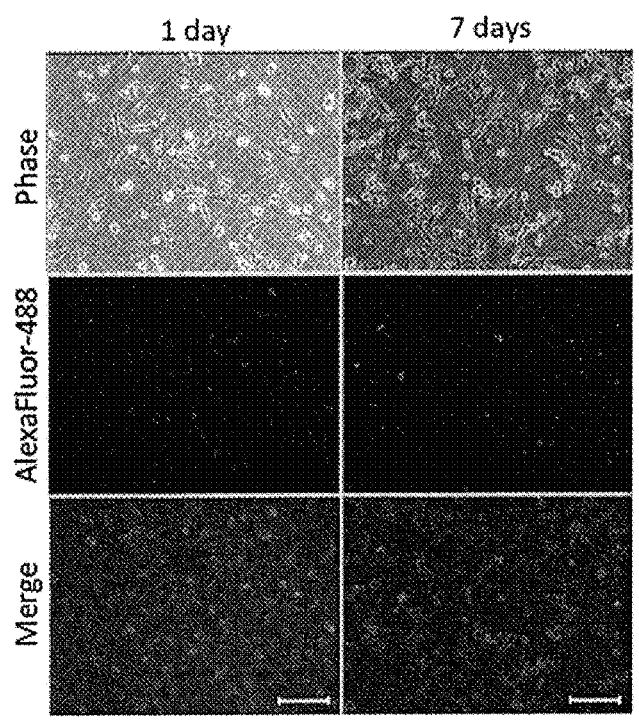

To test the effect of TWIST1 knock down on cell movement, we performed a wound healing assay. Our results demonstrated that the SUM 1315 shTwistA and shTwistB cell lines had reduced directional migratory abilities compared to the SUM 1315 shScram cell line (FIG. 11C). Taken together, these data suggest that shTwistA and shTwistB not only significantly knock down expression of TWIST1 in SUM 1315 cells, but also that the down regulation of TWIST1 results in a phenotypic change consistent with diminished migratory ability.

siRNA-Mediated TWIST1 Knock Down in SUM 1315 Cells. The SUM 1315 shRNA results described above not only demonstrate a significant reduction in the amount of TWIST1 expression, but also a phenotypic change in cell migration, suggesting that these shRNA sequences were effective in knocking down TWIST1 expression. We thus designed siRNA sequences (siTwistA and siTwistB) based on these shRNA sequences. To test the efficacy of siTwistA and siTwistB, SUM 1315 cells were transfected using LIPOFECTAMINE® 2000. Transfection with both siTwistA and siTwistB resulted in knockdown of TWIST1, with siTwistB giving slightly more knockdown than siTwistA in both protein and mRNA levels. Next, we tested the delivery of siRNA into SUM 1315 cells using the YTZ3-15 dendrimer. Cellular uptake efficiency of AlexaFluor® 647 labeled siQ (acting as a surrogate for unlabeled siTwistA and siTwistB) was greater than 90% after 24 hours, as measured with flow cytometry and fluorescent microscopy (FIGS. 12A-12B). The presence of siQ transfected using YTZ3-15 was confirmed as far out as 7 days from the time of transfection (FIG. 12B). These findings confirm previous work [38] performed with this PAMAM dendrimer and demonstrate its ability to safely deliver siRNA across the cell membrane because we did not appreciate any increase in cell death. Cellular uptake efficiency using YTZ3-15+siQ was comparable when tested in other cell lines including other breast, ovarian, uterine, and prostate cancer cell lines (data not shown).

Figure 12C:
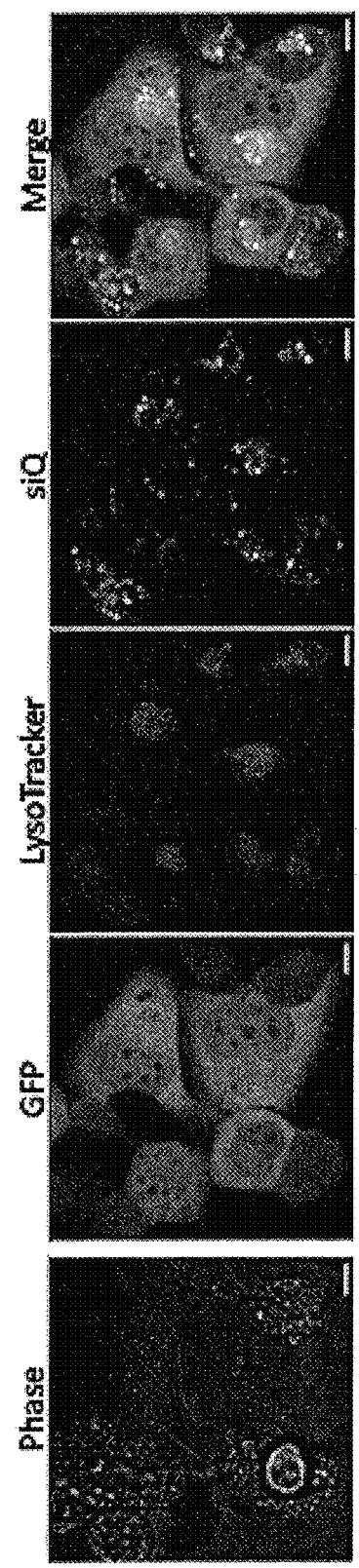

While uptake of the dendrimer complex can be appreciated with fluorescent microscopy and flow cytometry, these methods do not indicate the location of the siRNA within the cell. To examine this, we used LysoTracker® Red (dye taken up into acidic organelles) to show where siQ is colocalized. Our results show that much of the siQ signal colocalizes with the mid to late endosome in the SUM 1315 eGFP+luc cell line (FIG. 12C). This colocalization is desirable to take advantage of the "proton sponge effect", which is thought to be essential for siRNA release [44,45].

Figure 13A:
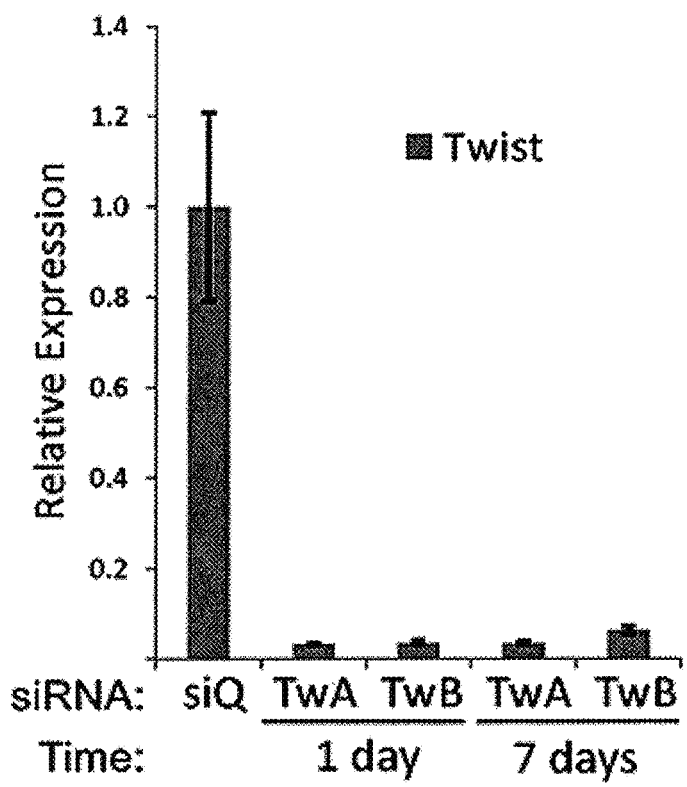
FIGS. 13A to 13D. TWIST1 knockdown following YTZ3-15 delivery of siTwist decreases cell motility and downstream EMT marker expression.
Figure 13B:
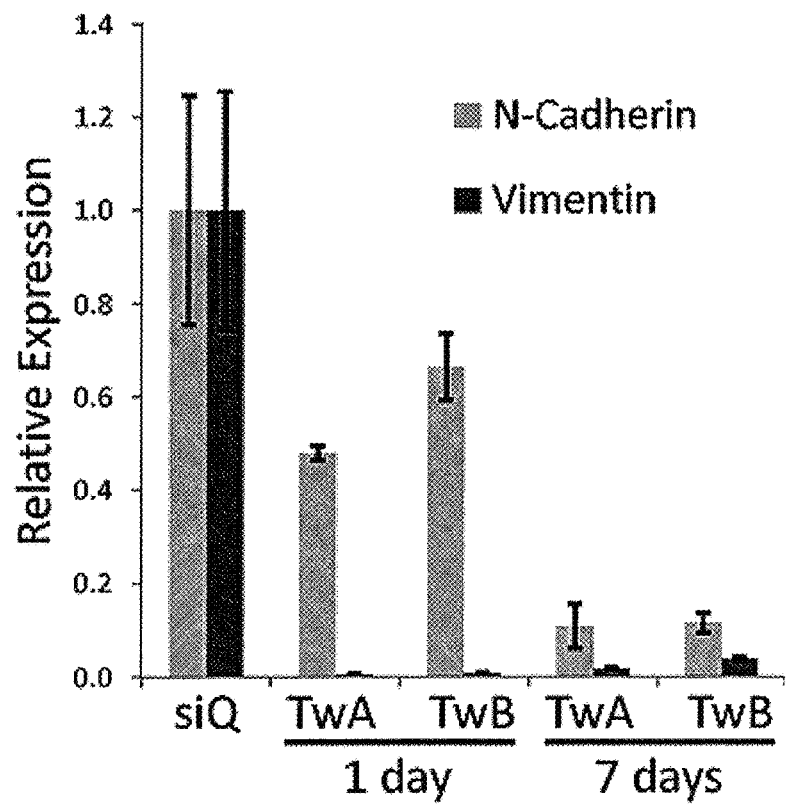

After confirming the function of siTwistA and siTwistB with Lipofectamine 2000 and the cellular uptake efficiency of siQ using YTZ3-15, we tested siTwistA and siTwistB with YTZ3-15-based delivery. TWIST1 levels were measured using qPCR and found to be significantly reduced at 24 hours and one week post transfection (FIG. 13A). Two EMT-related TWIST1 target genes (Vimentin and N-Cadherin) also showed reduced mRNA expression. Vimentin and N-Cadherin were both substantially reduced at the 24 hour time point; however, Vimentin showed a slight return at the one week time point whereas N-Cadherin continued to decrease at one week (FIG. 13B). While reduced expression of these genes was noted, renewed expression of the epithelial marker E-Cadherin was not observed (data not shown). This is a noted difference from previous studies [4]. The possible causes for this discrepancy are the different cell lines used between ours and previous studies, and that E-Cadherin is not entirely controlled by TWIST1 [19,46]. Reduced expression of these EMT-related genes is a positive indication that migration and invasion would be hindered.

Figure 13C:
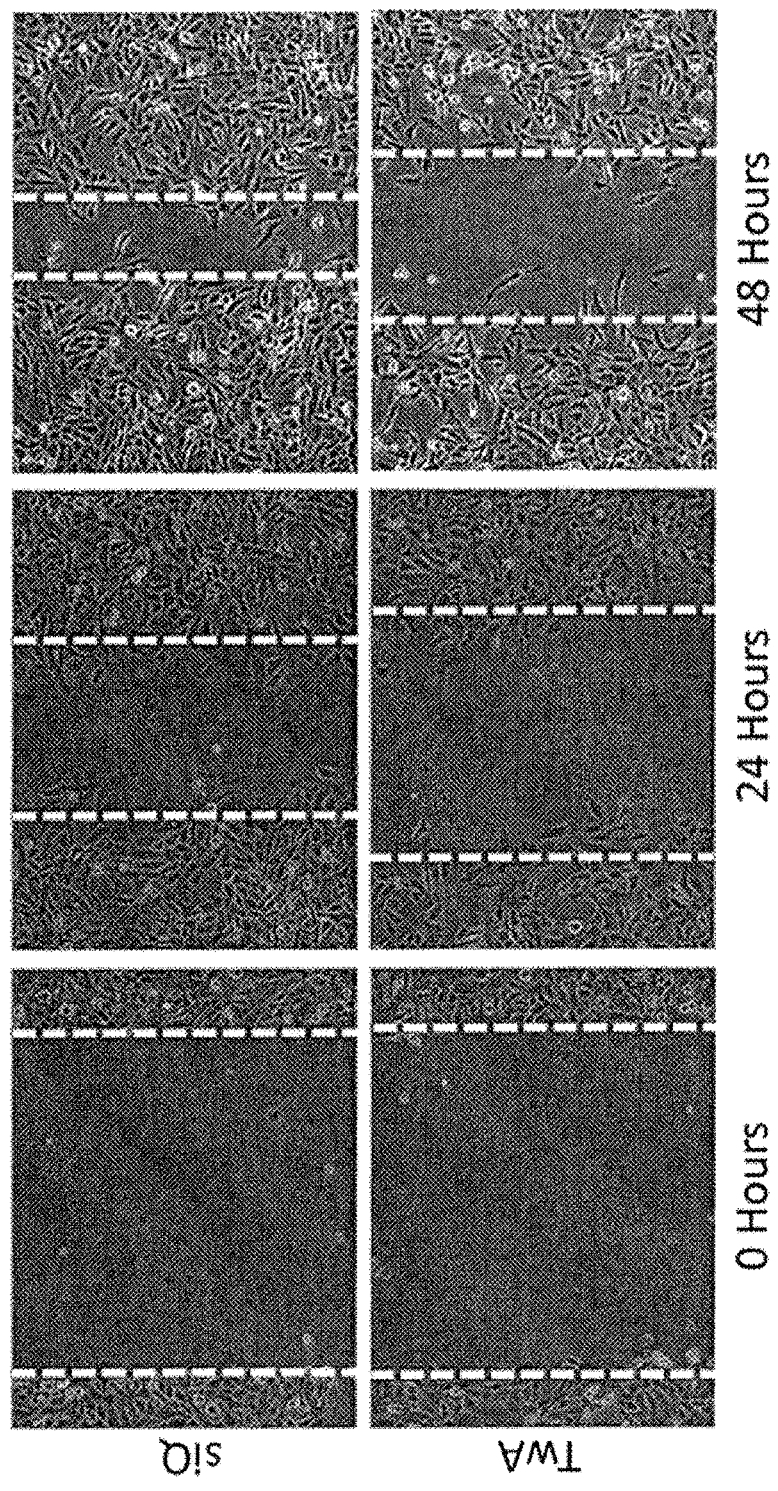

Next, we performed a wound healing assay to validate that YTZ3-15-delivered siTwistA and siTwistB not only reduces TWIST1 and its target genes, but also inhibits the migratory action of SUM 1315 cells. This assay demonstrated decreased directional migration of SUM 1315 cells transfected with siTwistA (FIG. 13C).

Figure 13D:
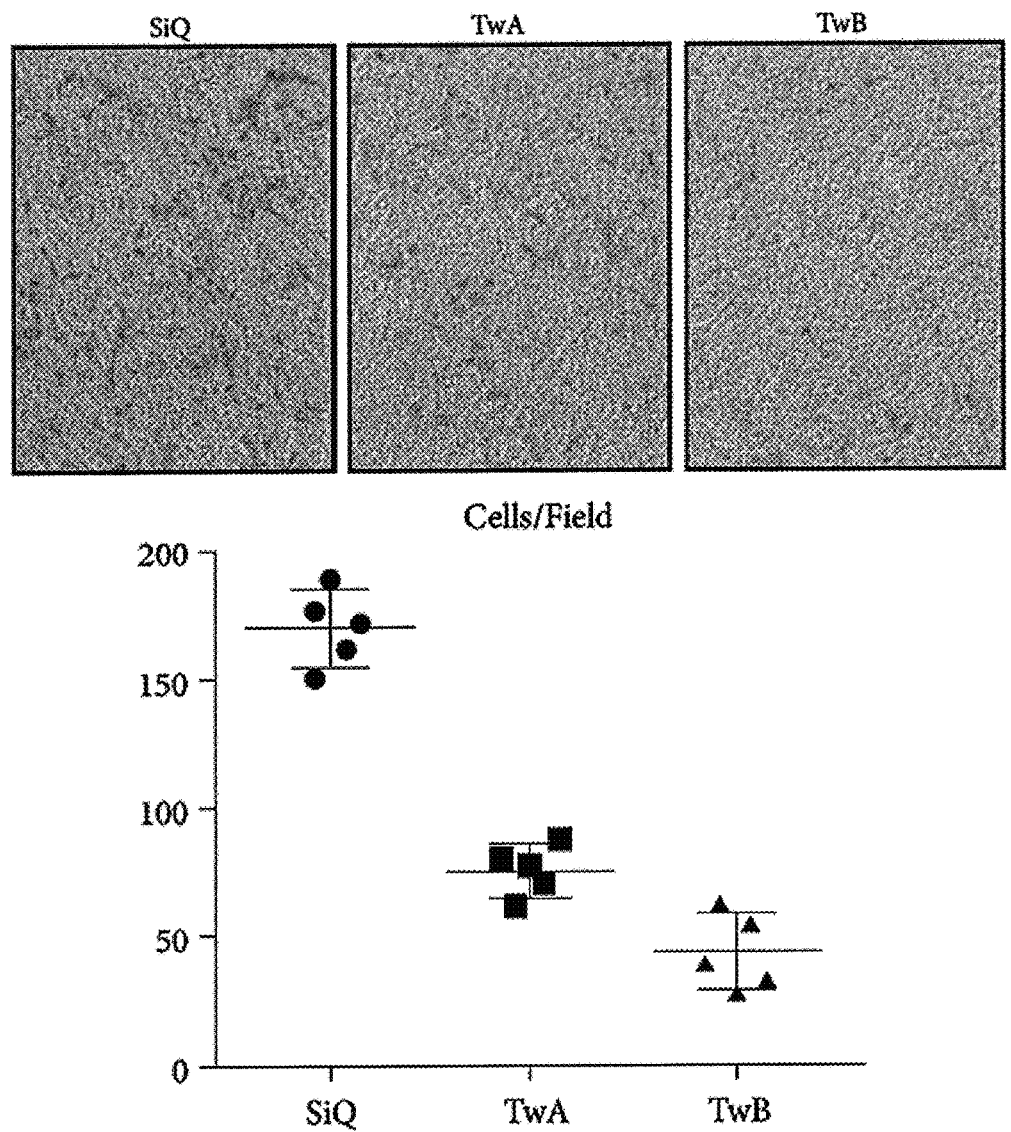

The EMT process consists of migration and invasion, and TWIST1 is a major player in allowing cancer cells to infiltrate surrounding tissues, blood vessels and the lymphatic system [40,47]. To investigate whether the invasive phenotype is reduced following siRNA-mediated TWIST1 knock down, we performed a transwell invasion assay. Results indicate that the YTZ3-15+siRNA-treated cells have diminished abilities to invade the MATRIGEL® Matrix and pass through the porous membrane, thus indicating a reduction in the invasive phenotype (FIG. 13D). TWIST1 overexpression is associated with cancers that are more metastatic and therefore invasive [22], and these data show that TWIST1 silencing following PAMAM dendrimer delivery of siRNA decreases metastatic potential. This in turn suggests that as a therapeutic approach for patients with MBC, this delivery method and target could have a significant impact on improving survival and outcomes for MBC patients if pre-clinical and clinical trials show similar results.

A TWIST1 siRNA therapeutic approach to assist in the treatment of MBC is also attractive because it could complement and augment current treatment regimens. The data suggest that siRNA-based knock down of TWIST1 could be used in conjunction with hormonal therapy or chemotherapy to achieve a synergistic effect.

Figure 14A:
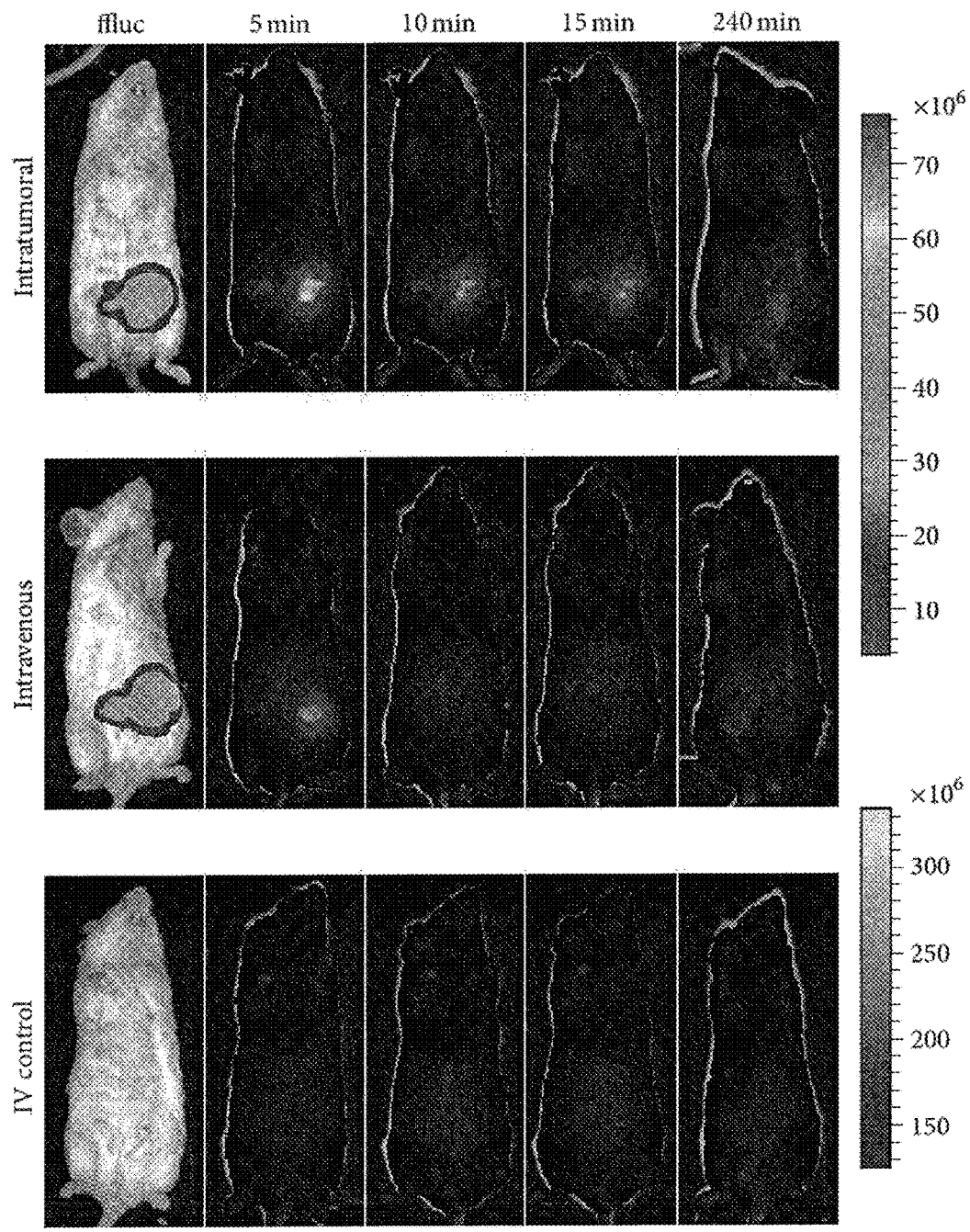
FIGS. 14A to 14B. YTZ3-15 concentrates in orthotopic breast cancer tumors in vivo.
Figure 14B:
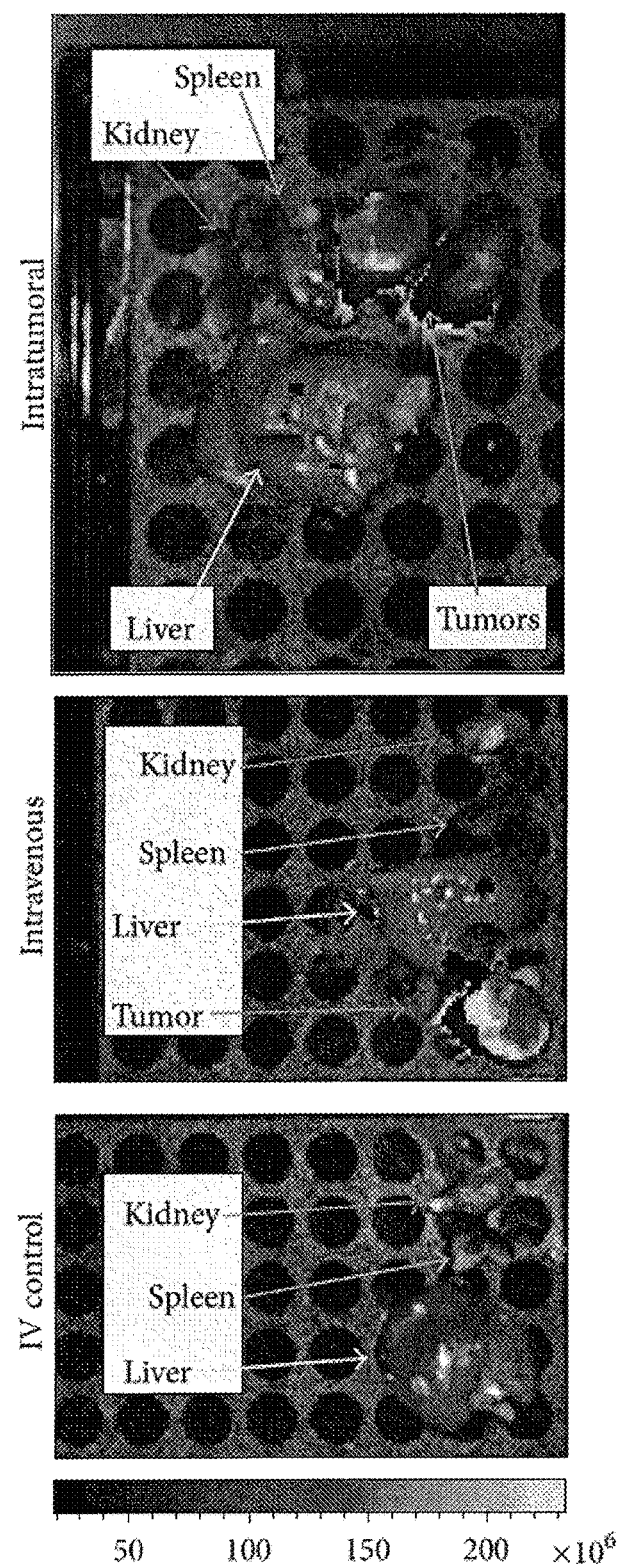

In vivo Distribution of PAMAM Dendrimers. In vivo studies were completed to determine the optimum delivery route (IV versus IT) of siQ using YTZ3-15. Five minutes after the IV and IT injection of the YTZ3-15+siQ complex, a bright signal was noted at the site of the tumor (FIG. 14A). The signal at the tumor site continued to be evident in mice that received IT injections at 10, 15, and 240 minutes, whereas no signal was seen at the tumor site after 5 minutes in mice that received IV injections (FIG. 14A). Ex vivo imaging of tumors, spleen, liver, and kidneys revealed a robust ALEXAFLUOR® 647 signal in the tumors but little to no signal in other examined organs (FIG. 14B). This ex vivo tumor-centric signal was evident for all mice, regardless of the route of administration (IV versus IT).

While the YTZ3-15 dendrimer does not have any inherent tumor-targeting capabilities, our in vivo studies demonstrate that this PAMAM dendrimer does accumulate preferentially in the orthotopic breast cancer tumors. It is possible that localization to the tumor is due to the Enhanced Permeability and Rentention (EPR) effect, which has been seen with other PAMAM dendrimers and nanoparticle delivery vehicles [58-60]. The inherent leakiness of tumor vasculature coupled with minimal lymphatic drainage results in particles becoming trapped and consequently concentrated in the tumor environment. This effect is magnified as the tumor enlarges and promotes angiogenesis, which may explain why siQ concentration was noted only after orthotopic tumors reached 0.5×0.5 cm in size (data not shown).

Conclusions

These studies demonstrate successful delivery and utilization of two siRNAs against TWIST1. Delivery was realized using a modified third generation PAMAM dendrimer and resulted in significant knock down of TWIST1 and other EMT-related target genes. TWIST1 knock down resulted in a reduction in cellular migration and invasion as has been observed previously [9,11,40,47,61]. Finally, delivery of an siRNA by YTZ3-15 was shown to have a specific concentrating ability in orthotopic tumors in a triple negative (ER-negative, progesterone receptor [PR]-negative and HER2-negative) breast cancer mouse model.

These data demonstrated that TWIST1 is an important and potentially clinically significant therapeutic target for the treatment of MBC as well as other solid tumor cancers [62-64]. These data further demonstrated that TWIST1 knock down via PAMAM dendrimer-delivered siRNA could serve as a valuable tool and adjuvant therapy to reduce migration/invasion, chemoresistance, and anti-apoptotic tendencies. Novel results from this study serve to validate a multimodal approach to cancer treatment by focusing on a transcription factor associated with breast cancer tumor types that have minimal treatment options. Furthermore, these data demonstrated (both in vitro and in vivo) the use of siRNA coupled with nanoparticles to treat malignant breast cancer by knocking down Twist1 and its associated EMT targets.

REFERENCES (EXAMPLE 2)

[1] Siegel R, et al., 2014. CA Cancer J Clin 2014, 64(1):9-29; [2] Hussein O & Komarova S V, J Cell Commun Signal 2011, 5(2):85-99; [3] Lin N U, et al., Cancer 2008, 113(10):2638-2645; [4] Vesuna F, et al., Biochem Biophys Res Commun 2008, 367(2):235-241; [5] Hollier B G, et al., J Mammary Gland Biol Neoplasia 2009, 14(1):29-43; [6] Kong D, et al., Cancers (Basel) 2011, 3(1):716-729; [7] Takebe N, et all., Breast Cancer Res 2011, 13(3):211; [8] Watanabe O, et al., Anticancer Res 2004, 24(6):3851-3856; [9] Vernon A E & LaBonne C, Curr Biol 2004, 14(17):R719-721; [10] Vesuna F, et al., Neoplasia 2009, 11(12):1318-1328; [11] Feng M Y, et al., Clin Exp Metastasis 2009, 26(8):1013-1023; [12] Maestro R, et al., Genes Dev 1999, 13(17):2207-2217; [13] Fu J, et al., Int J Biol Sci 2012, 8(4):522-532; [14] Vesuna F, et al., Oncogene 2011; [15] Chen Y, et al., Chemotherapy 2012, 58(4):264-272; [16] Elias M C, et al., Neoplasia 2005, 7(9):824-837; [17] Matsuo N, et al., BMC Cancer 2009, 9:240; [18] Yuen H F, et al., J Clin Pathol 2007, 60(5):510-514; [19] Yuen H F, et al., Histopathology 2007, 50(5):648-658; [20] Martin T A, et al., Ann Surg Oncol 2005, 12(6):488-496; [21] van Nes J G, et al., Breast Cancer Res Treat 2012, 133(1):49-59; [22] Yang J, et al., Cell 2004, 117(7):927-939; [23] Khan M A, et al., Tumour biology: the journal of the International Society for Oncodevelopmental Biology and Medicine 2013; [24] Fire A, et al., Nature 1998, 391(6669):806-811; [25] Whitehead K A, et al.,Nature reviews Drug discovery 2009, 8(2):129-138; [26] Hamilton A J & Baulcombe D C, Science 1999, 286(5441):950-952; [27] Guo P, et al., Adv Drug Deliv Rev 2010, 62(6):650-666; [28] Aagaard L & Rossi J J, Adv Drug Deliv Rev 2007, 59(2-3):75-86; [29] Behlke M A, Mol Ther 2006, 13(4):644-670; [30] Gavrilov K, et al., The Yale journal of biology and medicine 2012, 85(2):187-200; [31] Snead N M & Rossi J J, Wiley interdisciplinary reviews RNA 2010, 1(1):117-131; [32] Castanotto D & Rossi J J, Nature 2009, 457(7228):426-433; [33] Wang J, et al., AAPS J 2010, 12(4):492-503; [34] David S, et al., Pharmacol Res 2010, 62(2):100-114; [35] Foged C, Curr Top Med Chem 2012, 12(2):97-107; [36] Tang Y, et al., Mol Pharm 2012; [37] Zhou J, et al., Mol Ther 2011, 19(12):2228-2238; [38] Yu T, et al., Angew Chem Int Ed Engl 2012, 51(34):8478-8484; [39] Brown C E, et al., Cancer Res 2009, 69(23):8886-8893; [40] Li S, Kendall S E, Raices R, Finlay J, Covarrubias M, Liu Z, Lowe G, Lin Y, Teh Y H, Leigh V et al: TWIST1 Associates with NF-KB Subunit RELA via Carboxyl-Terminal WR Domain to Promote Cell Autonomous Invasion through IL8 Production. 2012; [41] Samineni S, et al., International journal of breast cancer 2011, 2011:381080; [42] Liang C C, et al., Nature protocols 2007, 2(2):329-333; [43] Teng Y ^ Li X, Clin Exp Metastasis 2014, 31(3):367-377; [44] Ouyang D, et al., Biophys Chem 2011, 158(2-3):126-133; [45] Benjaminsen R V, et al., Mol Ther 2013, 21(1):149-157; [46] Zhang C H, et al., J Surg Res 2012, 174(1):120-129; [47] Li C, et al., Nephrology, dialysis, transplantation: official publication of the European Dialysis and Transplant Association—European Renal Association 2012, 27(11):4119-4124; [48] Kress W, et al., European journal of human genetics: EJHG 2006, 14(1):39-48; [49] El Ghouzzi V, et al., European journal of human genetics: EJHG 1999, 7(1):27-33; [50] Bialek P, et al., Developmental cell 2004, 6(3):423-435; [51] Soo K, et al., Developmental biology 2002, 247(2):251-270; [52] Isenmann S, et al., Stem Cells 2009, 27(10):2457-2468; [53] Wang X, et al., Oncogene 2004, 23(2):474-482; [54] Li Q Q, et al., Clin Cancer Res 2009, 15(8):2657-2665; [55] Meng H, et al., ACS nano 2011, 5(5):4131-4144; [56] Lu J, et al., Small 2010, 6(16):1794-1805; [57] Meng H, et al., J Am Chem Soc 2010, 132(36):12690-12697; [58] Kobayashi H, et al., Theranostics 2013, 4(1):81-89; [59] Greish K, Methods Mol Biol 2010, 624:25-37; [60] Biswas S &Torchilin V P, Pharmaceuticals (Basel) 2013, 6(2):161-183; [61] Zhang J, et al., Cell Signal 2012, 24(4):852-858; [62] Khan M A, et al., Tumour biology: the journal of the International Society for Oncodevelopmental Biology and Medicine 2013, 34(5):2497-2506; [63] Kwok W K, et al., Cancer Res 2005, 65(12):5153-5162; [64] Wallerand H, et al., Urol Oncol 2010, 28(5):473-479;

Example 3

Nanoparticle Delivery of siRNA Against TWIST to Reduce Drug Resistance and Tumor Growth in Ovarian Cancer Models Abstract. Epithelial ovarian cancer (EOC) is the most deadly gynecologic malignancy on account of its late stage at diagnosis and frequency of drug resistant recurrences. Novel therapies to overcome these barriers are urgently needed. TWIST is a developmental transcription factor reactivated in cancers and linked to angiogenesis, metastasis, cancer stem cell phenotype, and drug resistance, making it a promising therapeutic target. In this work, we demonstrate the efficacy of TWIST siRNA (siTWIST) and two nanoparticle delivery platforms to reverse chemoresistance in EOC models. Polyamidoamine dendrimers and mesoporous silica nanoparticles (MSNs) carried siTWIST into target cells and led to sustained TWIST knockdown in vitro. Mice treated with cisplatin plus MSN-siTWIST exhibited lower tumor burden than mice treated with cisplatin alone, with most of the effect coming from reduction in disseminated tumors. This platform has potential application for overcoming the clinical challenges of metastasis and chemoresistance in EOC and other TWIST overexpressing cancers.

Background.

Epithelial ovarian cancer (EOC) is one of the leading causes of cancer-related deaths among women worldwide, representing a significant unmet therapeutic challenge [1-3]. EOC accounts for 90% of all ovarian cancers [1]; additionally, 70% of women with EOC are not diagnosed until the disease is advanced stage [1]. The majority of EOC patients respond well to first line chemotherapy consisting of a platinum drug and/or paclitaxel. Unfortunately, most of these patients relapse with disease that is both metastatic and drug resistant, with a five-year survival rate of approximately 20% [3-5]. There is therefore an urgent need for therapies to prevent both metastatic spread and acquired drug resistance in EOC.

EOC tumors are characterized by high expression levels of epithelial-to-mesenchymal transition (EMT) markers such as TWIST, which plays an essential role in cancer metastasis (FIG. 15A) [6,7]. However, transcription factors such as TWIST are difficult to target with small molecule drugs due to their nuclear localization [16]. To circumvent this issue, small interfering RNAs (siRNAs) have become increasingly popular. We have designed and validated two therapeutic siRNAs against TWIST (FIG. 15C), and have evaluated two nanoparticle-based delivery platforms. First, we used third generation polyamidoamine (PAMAM) dendrimers, and second, we created polyethylenimine (PEI) coated mesoporous silica nanoparticles (MSNs). We have previously shown effective delivery to tumor cells using both of these modalities, both in vitro and in mouse models of melanoma and breast cancer [14,15].

In this study we applied our siRNA-nanoparticle technologies to EOC. We hypothesized that nanoparticle delivered anti-TWIST siRNAs would knock down TWIST and sensitize cells to chemotherapeutics. We also evaluated the tumor-specific delivery capability of our MSNs. By evaluating the effects of TWIST knockdown using MSNs in animal models of a metastatic and chemoresistant phenotype, we present an MSN delivery platform for siRNA and drug combination therapies to prevent both metastatic spread and acquired drug resistance in ovarian and other cancers.

Methods.

Cell Culture. A2780R and all derivatives of Ovcar8 were grown in RPMI 1640 (Genesee Scientific, San Diego, Calif.) in a tissue culture incubator at 37° C., 5% $CO_2$, and 90% humidity. Growth medium was supplemented with 10% fetal bovine serum and 1% penicillin/streptomycin. Cells were passaged every 2-4 days using 0.25% trypsin (Genesee Scientific). Where indicated, cells were transfected with Lipofectamine 2000 (Thermo Fisher, Waltham, Mass.) according to the manufacturer's instructions. A2780R cells are a cisplatin resistant derivative of A2780.

Optimization of Ovcar8 for in vivo use. For mouse experiments, Ovcar8 cells were stably transfected with CMV-p:EGFP-ffluc pHIV7 as has been described previously [17]. This resulted in expression of an eGFP-firefly luciferase (ffluc) fusion protein. To increase engraftment efficiency and homogeneity of the cell population, Ovcar8 cells were passaged through mice. Ovcar8-GFP+ffluc cells were injected intraperitoneally (IP) and allowed to form tumors. Cells were harvested after 37 days and used to establish the Ovcar8-IP line.

siRNA design. siRNAs against TWIST were designed based on shRNAs that were previously validated [13,15]. Sequences are: si419 guide, 5'-AAUCUUGCUCAGCUU-GUCCUU-3' (SEQ ID NO:2); si419 passenger, 5'-GGA-CAAGCUGAGCAAGAUU-3' (SEQ ID NO:1); si494 guide, 5'-UUGGAGUCCAGCUCGUCGCUU-3' (SEQ ID NO:4); si494 passenger, 5'-GCGACGAGCUGGACUC-CAA-3' (SEQ ID NO:3). Non-targeting control siRNA (siQ) was AllStars Negative Control siRNA, labeled with AlexaFluor-647, from Qiagen (Valencia, Calif.). For in vivo studies, 2'-O-methyluracil and inverted abasic ribose chemical modifications were made to the si419 passenger strand, as illustrated in FIG. 18A.

Figure 16A:
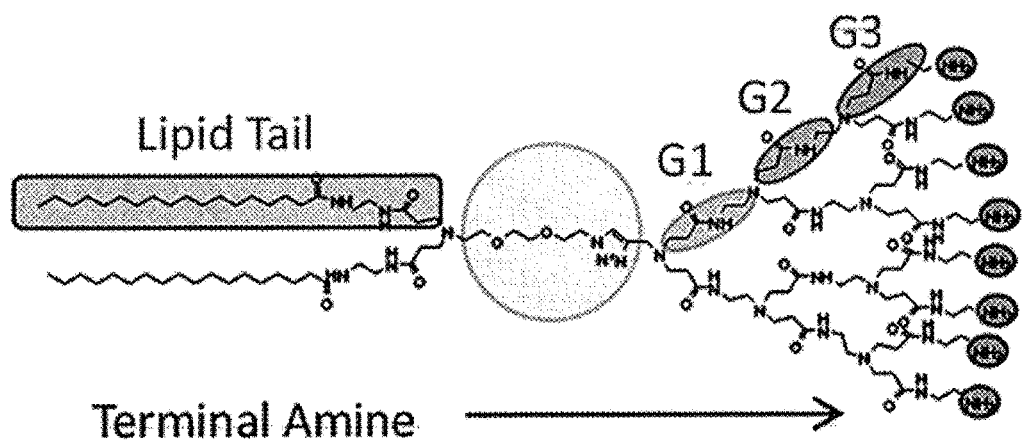
FIGS. 16A to 16E.
Figure 16B:
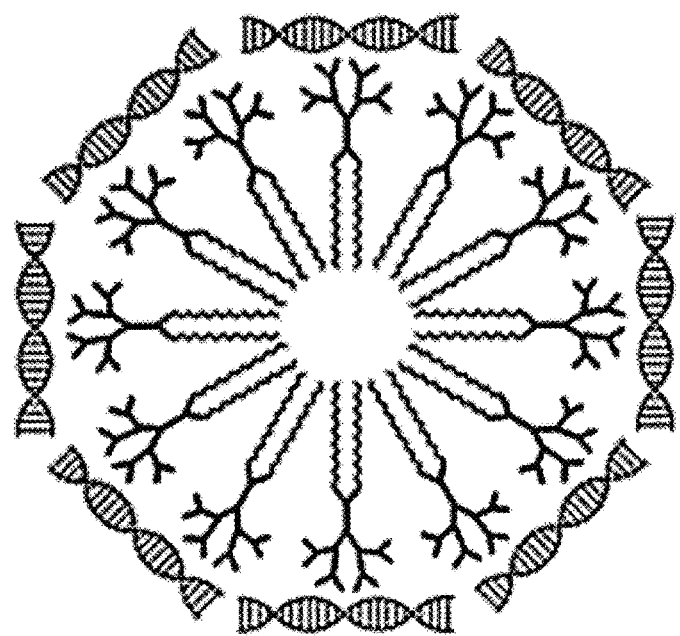

PAMAM dendrimer design and delivery. The polyamidoamine (PAMAM) dendrimer used in this study is the YTZ3-5 third generation dendrimer, illustrated in FIG. 16A and previously described [15,18]. To complex the dendrimer with siRNA, YTZ3-15 at 240 μM was mixed with 10 μM siRNA in OptiMEM Low Serum Medium (Thermo Fisher). Upon complexing with siRNA, dendrimers form micelle structures with siRNA at the surface and the hydrophobic tails sequestered in the core (FIG. 16B) [19]. 14.6 μl YTZ3-15 and 10 μl siRNA were used per well of a 6-well plate. Final concentrations of YTZ3-15 and siRNA once added to cells were 1.75 μM and 50 nm, respectively. Where indicated, 3.5 μM YTZ3-15 and 100 nm siRNA were used for Ovcar8.

MSN design and delivery. Mesoporous silica nanoparticles (MSNs) were synthesized utilizing the sol-gel method as described previously [14,20]. First, 250 mg 95% cetyltrimethylammonium bromide (CTAB) was dissolved in 120 ml of water with 875 μl 2M sodium hydroxide solution, at 80° C. Next, 1.2 ml of 98% tetraethylorthosilicate was added. After 15 min, 300 μl of 42% 3-(trihydroxysilyl) propyl methylphosphonate was added, and the mixture was stirred 2 hr. Particles were collected using centrifugation and washed with methanol. Acidic methanol was then used to remove any remaining CTAB surfactants. Zeta potential at 50 μg/mL was 43.75 mV [14]. All chemicals were obtained from Aldrich (St. Louis, Mo.). Particles were ~120 nm in diameter, with 2.5 nm pores. Low molecular weight (1.8 kD branched polymer) polyethyleneimine (PEI) was electrostatically attached to the particle surface to provide a positive change to attract negatively charged siRNA [21]. To complex siRNA for in vitro experiments, 10 μl siRNA at 10 μM was mixed with 70 ul MSNs at 500 μg/ml and 20 μl water, and the mixture was incubated overnight at 4° C. on a roller. The following day, 100 μl of the MSN-siRNA complexes was added to each well of a 6-well plate containing 1900 μl normal medium.

Fluorescence Microscopy. To verify cell uptake of the nanoparticle-siRNA complexes, cells were imaged immediately before harvesting. Phase images were acquired, as well as fluorescent images to detect siQ-AlexaFluor-647. Images were acquired using a Nikon TE-20005 microscope and SPOT Advanced software (Diagnostic Instruments, Sterling Heights, Mich.).

Confocal Microscopy. Ovcar8-IP cells were seeded into a 3.5 cm glass bottom tissue culture dish. Following attachment (24 hr), 2 ml of fresh medium replaced the old medium. Next, MSN+siQ complexes (labeled with ALEXAFLUOR® 647) were added to the cells in the dish at final concentrations of 17.5 ng/μl (MSN) and 50 nM (siQ) and incubated for an additional 48 hours in a tissue culture incubator. Cells were then treated with LysoTracker Red (Thermo Fisher Scientific, Waltham, Mass,) according to the manufacturer's protocol. Confocal images were obtained using the Zeiss LSM700 Confocal Microscope and ZEN 2012 microscopy software (Zeiss AG, Oberkochen, Germany).

Western Blotting. Following siRNA treatment, cells were pelleted and lysed in RIPA buffer. Protein concentration was determined by BCA assay (Thermo Fisher). Following SDS-PAGE, protein was transferred to Amersham PVDF membrane (Genesee Scientific) using a BioRad Trans-Blot SD semi-dry transfer unit. Blots were then blocked in milk for one hour at room temperature or overnight at 4° C. Incubation with primary antibody took place for one hour at room temperature or overnight at 4° C. Antibodies were diluted in 5% milk, with 0.1-0.2% Tween-20. Antibodies used were TWIST 2c1a (Santa Cruz Biotechnology, Dallas, Tex.) at 1:250-1:500 dilution, (3-Actin, A1978 (Sigma Aldrich, St. Louis, Mo.) at 1:2500-1:5000 dilution; and Horseradish Peroxidase (HRP) conjugated anti-mouse secondary antibodies. For film-based westerns, Blue Devil film (Genesee Scientific) and ECL Plus chemiluminescent substrate (Thermo Fisher) were used to detect protein. For digital westerns, the Syngene Pxi4 digital blot imager and Michigan Diagnostics FemtoGlow chemilumescent substrate were used.

Sulphorhodamine B Cell Survival Assays. A2780R or Ovcar8-IP cells were plated in 6 well plates and allowed to adhere overnight. The following day, cells were transfected with siQ, si419, or si494 as described above—A2780R cells using YTZ3-15 and Ovcar8-IP cells using MSNs. After 48-72 hours, cells were transferred to 96 well plates at 5,000 cells per well and allowed to adhere overnight. The following day cells were treated with cisplatin at a series of concentrations (cells not treated with cisplatin served as controls). After 72 hours, cells were fixed in 10% trichloroacetic acid for 1 hour at 4° C., washed with water, and dried. Cells were stained in 0.4% sulphorhodamine B (SRB) in 1% acetic acid for 15 minutes at room temperature and then washed 3-4 times with 1% acetic acid until no further color was present in the wash. Any stray SRB on the walls of the wells was removed, and stained cells were dried for 10 minutes. SRB was solubilized in 10 mM Tris base and color intensity was quantified by absorbance at 570 nm. Each condition was normalized to its own untreated control.

Animal Studies. The animal studies conducted in these experiments were done in accordance with a protocol approved by the Institutional Animal Care and Use Committee at the City of Hope Beckman Research Institute. A total of 48 female NOD.Cg-Prkdc$^{scid}$Il2rg$^{tm1Wjl}$/SzJ (NSG) mice (The Jackson Laboratory, Bar Harbor, Me.) were used. Ten week old (on average) mice were administered an intraperitoneal injection (IP) of $2.5 \times 10^6$ Ovcar8-IP cells in 200 μl of RPMI media. For all studies, mice were placed into four groups: MSN-siQ, MSN-siQ+cisplatin, MSN-si419H, and MSN-si419H+cisplatin (n=4 or n=8). Previous reports show no cellular uptake without MSNs[14], thus a siRNA-only group was not added to this study.

Bioluminescent imaging of mice (using Xenogen IVIS 100 biophotonic imaging system, STTARR, Toronto, Ontario, Canada) commenced seven days after injection of tumor cells in order to ensure engraftment, and continued once a week for four weeks. Mice were given a 100 μl IP injection of 20 mg/ml D-Luciferin (PerkinElmer, Waltham, Mass.). Ten minutes after the D-luciferin injection, mice were anesthetized with isoflurane (2%-5%) and placed in the biophotonic imager, and images were taken within two minutes. An alfalfa-free version of the regular rodent diet (alfalfa-free CA-1) was administered to the siQ mice to prevent autofluorescence from the regular diet.

IP injections of MSN+siRNA (siQ fluorescently labeled with ALEXAFLUOR® 647 or si419H) were conducted one week after the inoculation of Ovcar8-IP cells and done once or twice per week for a total of four weeks. Mice received 105 μl of 500 ng/μl MSN complexed with 15 μl of 10 μM siRNA per week, divided into one full or two half doses (n=4 and n=8, respectively). This is equivalent to 0.04 mg/kg MSN/week. Weekly 3 mg/kg IP cisplatin injections were given starting two weeks after initial inoculation of cells.

At completion of the experiment, all animals were euthanized via $CO_2$ asphyxiation. Both primary tumors and disseminated masses were carefully dissected from adjacent tissue and weighed. Mice treated twice weekly with siQ only were imaged for biodistribution studies. Tumors, spleen, kidney, uterus and liver were imaged ex vivo to detect the location of both the Ovcar8-IP cells and AlexaFluor 647- labeled siQ without the hindrance of the skin and fur. Efficacy data is presented from mice dosed once per week with MSN-siRNA.

Statistics. All in vivo data was analyzed using one-way ANOVA with correction for multiple comparisons, comparing all groups to MSN-siQ treatment group. Additionally, an unpaired t-test with Welch's correction was used to compare tumor number and weight between cisplatin alone and the combination cisplatin +MSN-si419H treatment groups. All analyses were done using Prism 6 software (GraphPad Software, La Jolla, Calif.). *p<0.05, p<0.01, *p<0.001, **** p<0.0001 throughout. Power analysis demonstrates that 4 mice per group has 99% power to detect a 50% difference in means, assuming 25% standard deviation and a one-tailed test (alpha=0.05).

Results.

Figure 15E:
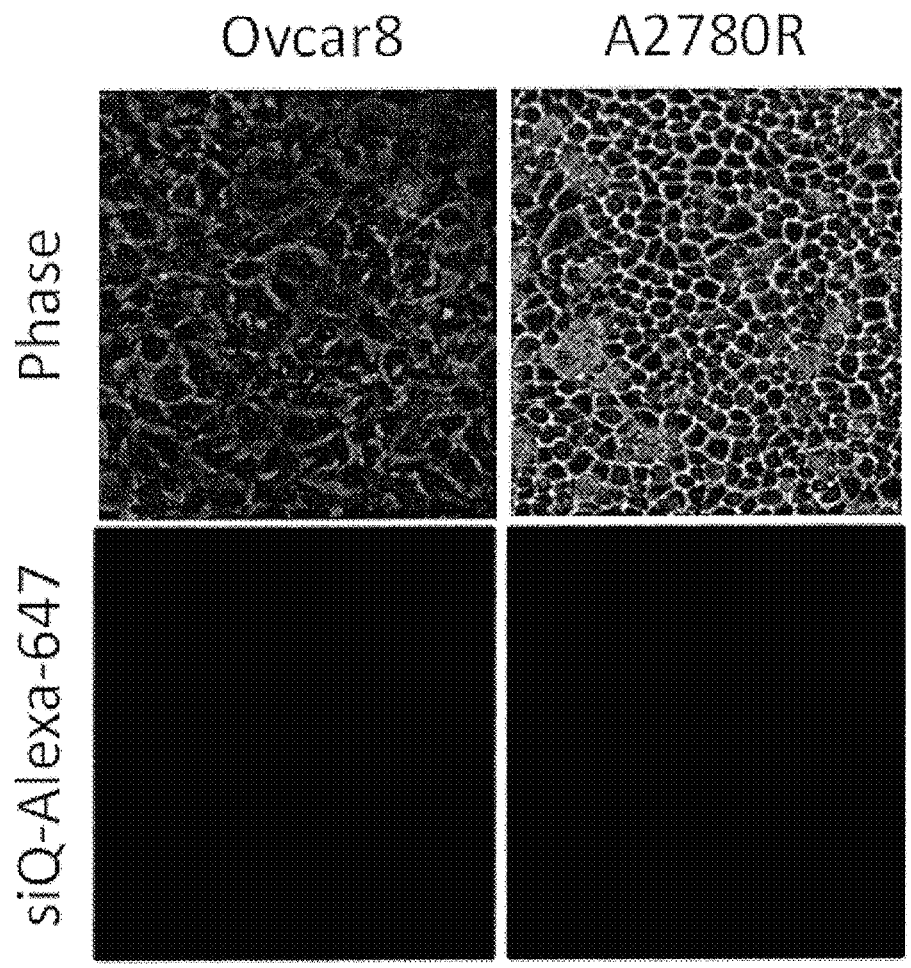
Figure 16C:
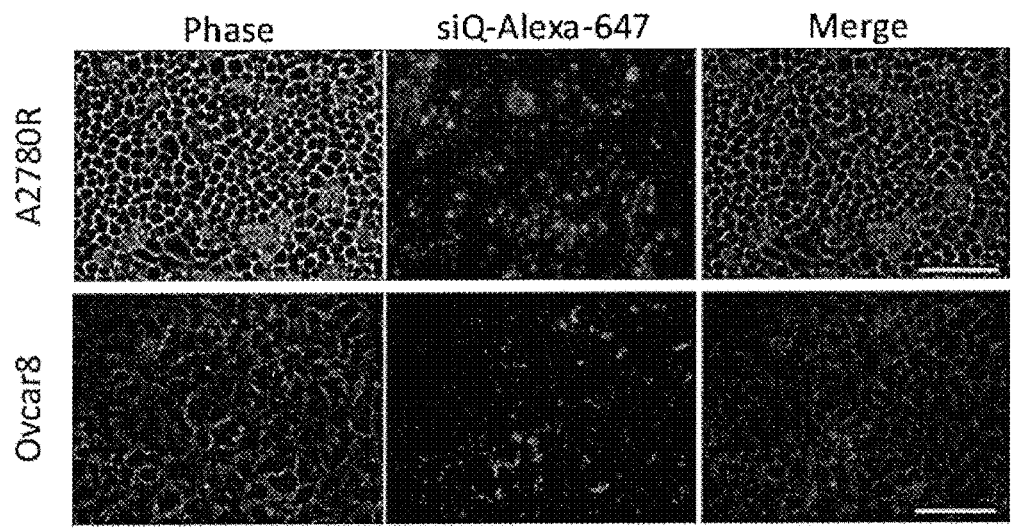
Figure 16D:
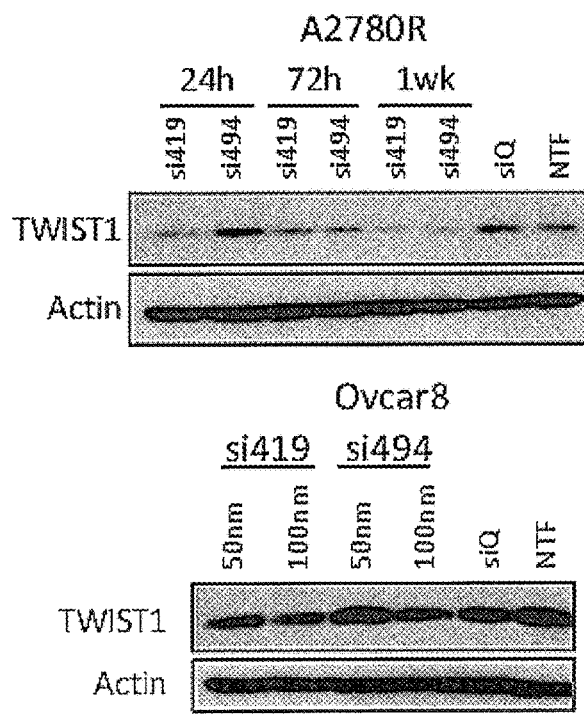

Dendrimer delivered siRNA knocks down TWIST in ovarian cancer cell lines. We have previously showed the efficacy of our siRNAs targeting TWIST (si419 and si494, FIG. 15C) [14,15]. We used Lipofectamine 2000 transfection to test si419 and si494 in A2780R cells. Both were able to completely inhibit TWIST expression over the course of three days (FIG. 15D). In the absence of a carrier, no siRNA enters cells (FIG. 15E), therefore once siRNAs had been validated, we introduced the amphiphilic PAMAM dendrimer YTZ3-15 as a delivery vehicle. YTZ3-15 electrostatically attracts negatively charged siRNA using the cationic terminal amines (FIG. 16A), while the lipid tails mediate arrangement into micelles (FIG. 16B) [19]. In order to verify that dendrimers successfully delivered siRNA into target cells, we conjugated YTZ3-15 with AlexaFluor-647 tagged siQ control siRNA. Micrographs revealed robust cell uptake of labeled siRNA in both A2780R and Ovcar8 cells (FIG. 16C). Furthermore, YTZ3-15 delivery of si419 and si494 successfully knocked down TWIST in both lines, although knockdown in Ovcar8 was minimal and required double the usual siRNA-YTZ3-15 dose (FIG. 16D).

Figure 16E:
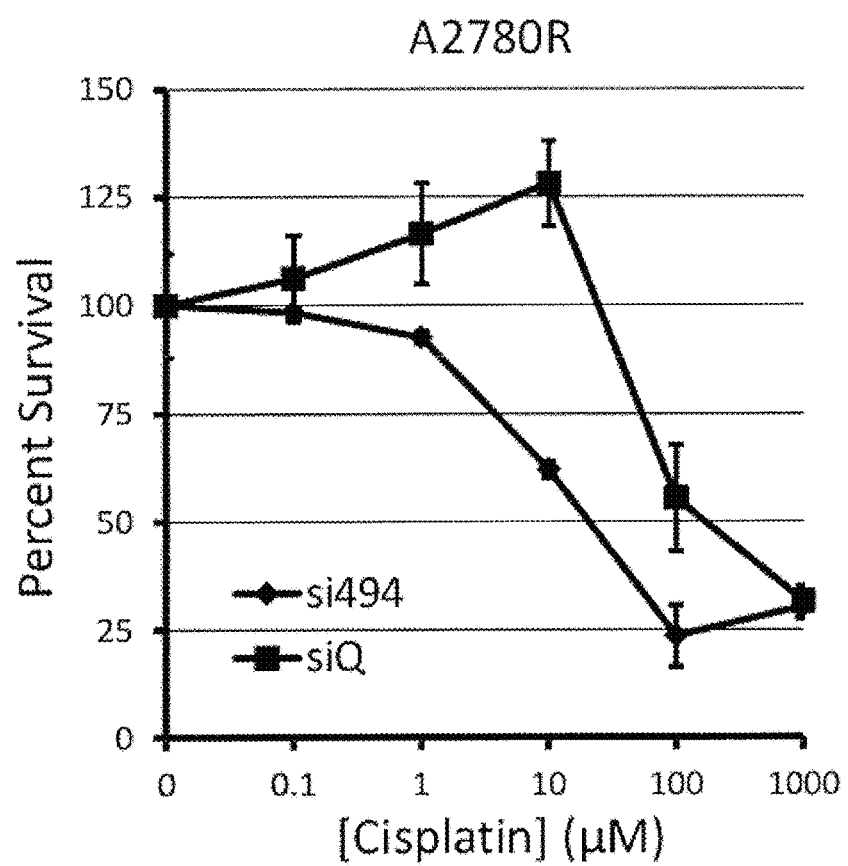

TWIST knockdown impacts cisplatin resistance. In order to determine the effect of TWIST knockdown on cisplatin resistance, we performed a sulphorhodamine B (SRB) cell survival assay. Following treatment with YTZ3-15-si494, cisplatin resistant A2780R cells were sensitized to cisplatin, with approximately one log difference in $IC_{50}$ (FIG. 16E).

Figure 17A:
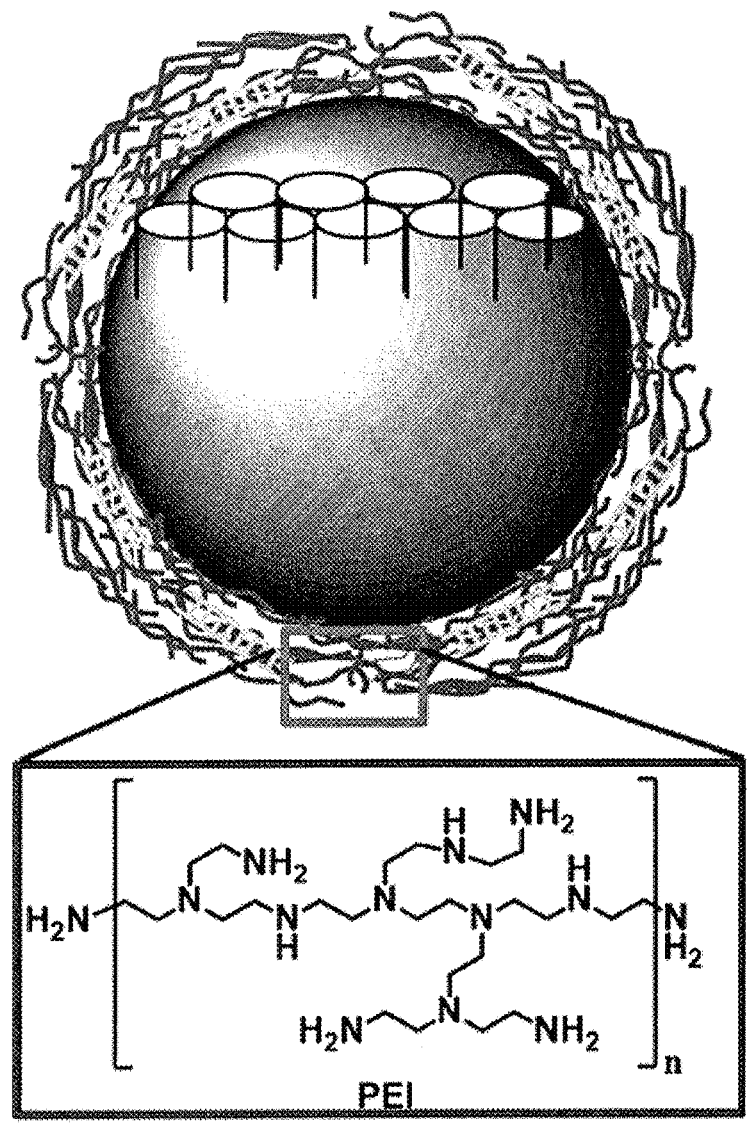
Figure 17B:
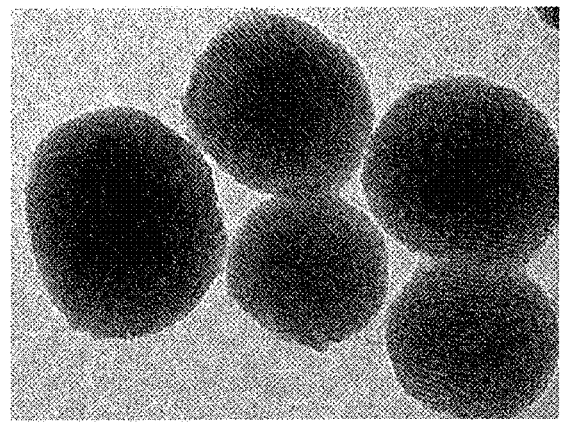
Figure 17C:
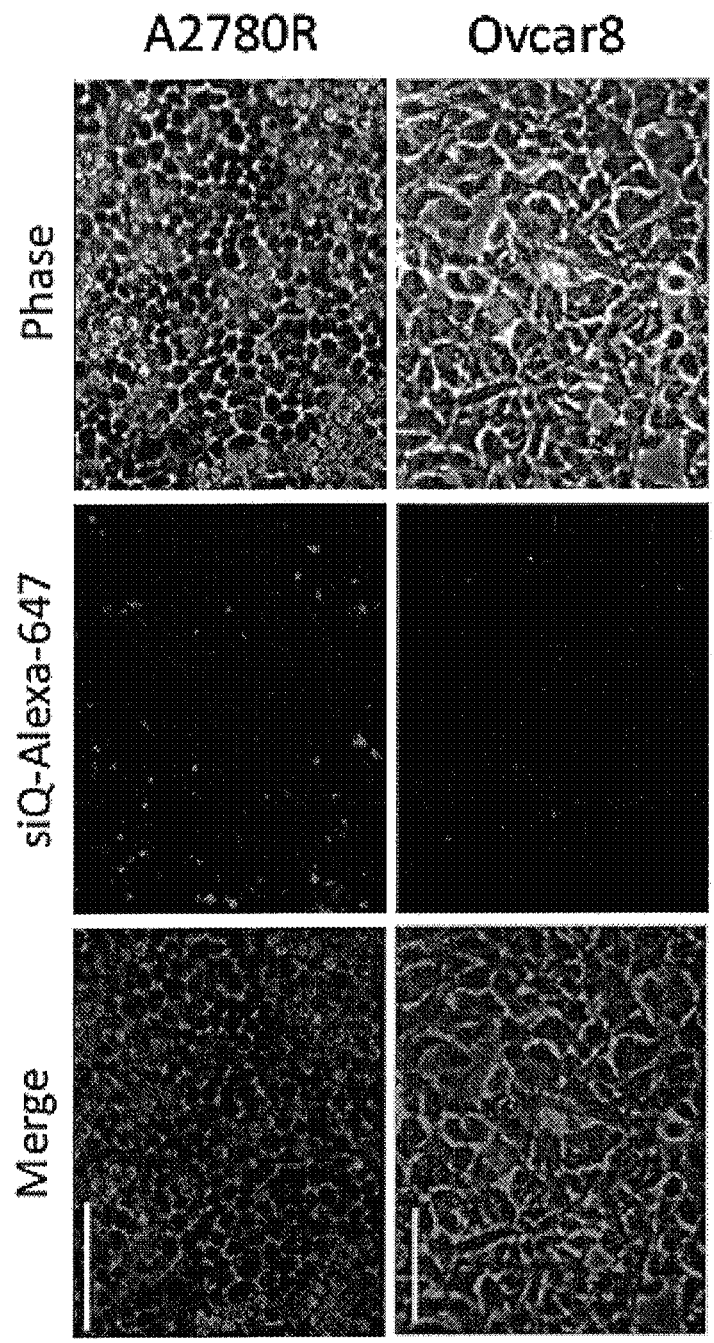

Mesoporous Silica Nanoparticles as siRNA delivery vehicles. While YTZ3-15 treatment yielded significant TWIST knockdown in A2780R, we wanted to explore additional nanocarriers which would be capable of multiple functions (i.e. drug delivery and targeting via surface moieties) and have increased efficacy in Ovcar8. Following our recent success using mesoporous silica nanoparticles (MSNs) to target TWIST in vitro and in vivo in melanoma [14], we elected to apply these particles to EOC. MSNs coated with polyethyleneimine (PEI) can carry siRNA on their outer surface, and contain a pore structure capable of carrying additional cargo, such as cytotoxic drugs (FIG. 17A) [20-22]. In addition, MSNs can be modified with controlled release valves and targeting moieties, further increasing their appeal [23-28]. For the present study, we used PEI coated MSNs without additional modifications or drug loading. These particles were of ~120 nm diameter with highly uniform size (FIG. 17B). We first confirmed that PEI-coated MSNs could effectively deliver AlexaFluor-647 labeled siQ to both A2780R and Ovcar8 cells (FIG. 17C). We found that MSNs required extended incubation with cells to produce knockdown as compared to YTZ3-15, but MSN knockdown lasted longer. With MSNs, we observed little effect at 24 hours but robust knockdown of TWIST lasting up to one week post transfection in both cell lines tested (FIG. 17D).

Optimization of siRNAs for in vivo use by chemical modifications. In order to maximize siRNA efficacy in vivo, nuclease degradation of siRNA and immune activation by siRNAs must be reduced. Immune reactions are mediated largely by toll-like receptors, which respond to varying degrees to different RNA sequence motifs [29]. Analysis of these motifs revealed that si419's passenger strand, which would not be incorporated into RISC, contained no immune-activating sequences, and this siRNA was therefore selected for in vivo experiments. We added additional chemical modifications to the si419 passenger strand to create si419 hybrid siRNA (si419H, FIG. 18A). In order to promote nuclease resistance of the siRNA duplex, 2'-O-methyl and inverted abasic ribose (iaB) modifications were added [30, 31]. iaB also prevents the loading of the passenger strand into RISC, effectively increasing the potency of siRNA by ensuring that all duplexes result in binding to TWIST mRNA, improving silencing [30].

Figure 18C:
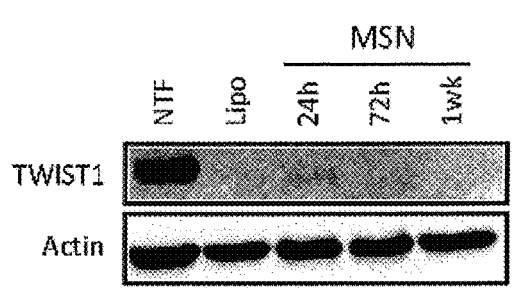
Figure 18D:
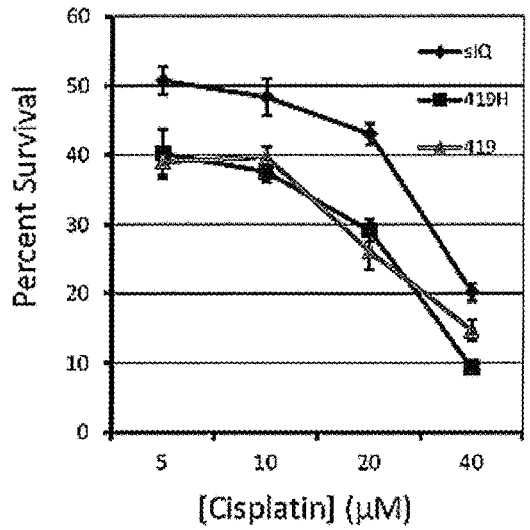

MSNs deliver siRNA to correct cellular compartment of Ovcar8-IP cells. Ovcar8 cells were selected for further study as their genetic makeup more closely resembles that of the typical clinical high grade serous ovarian carcinoma, than the A2780 cell line family [32]. In order to improve uniform tumor cell engraftment in mice and enable tracking of cells in vivo, we passaged Ovcar8 cells through mice and used lentiviral transduction to stably express an eGFP firefly luciferase fusion protein (see Methods). This line is hereafter referred to as Ovcar8-IP. Confocal microscopy revealed that MSN treatment of Ovcar8-IP cells resulted in siQ accumulating in the late endosomes and lysosomes of the cells, as evidenced by colocalization with LysoTracker dye (FIG. 18B). These structures are located in the perinuclear space, as we have shown previously [14,15]. Transfection of Ovcar8-IP cells using MSNs and si419H resulted in robust knockdown of TWIST even after 24 hours of treatment (FIG. 18C). Furthermore, SRB assays revealed sensitization of Ovcar8-IP cells to cisplatin following MSN-419H or MSN-419 treatment (FIG. 18D). Ovcar8 cells are not as cisplatin resistant as A2780R, hence a smaller effect size compared to that seen in FIG. 16E.

Figure 19A:
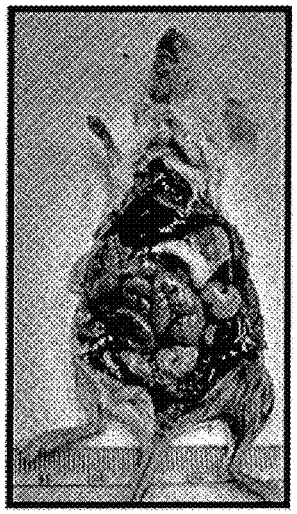
FIGS. 19A to 19F.
Figure 19B:
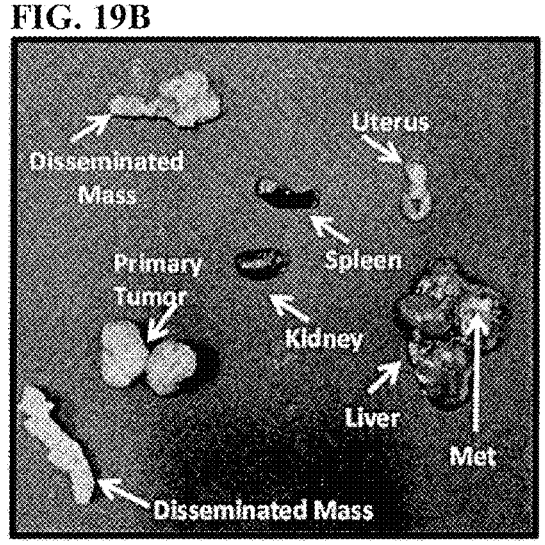
Figure 19C:
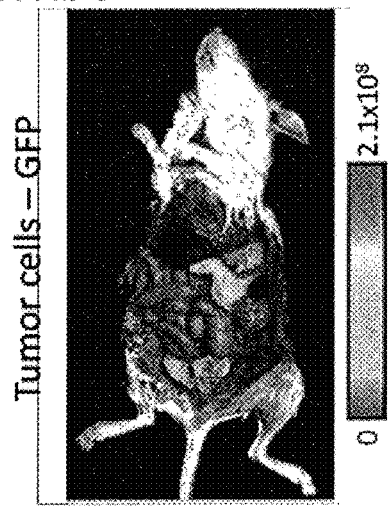
Figure 19D:
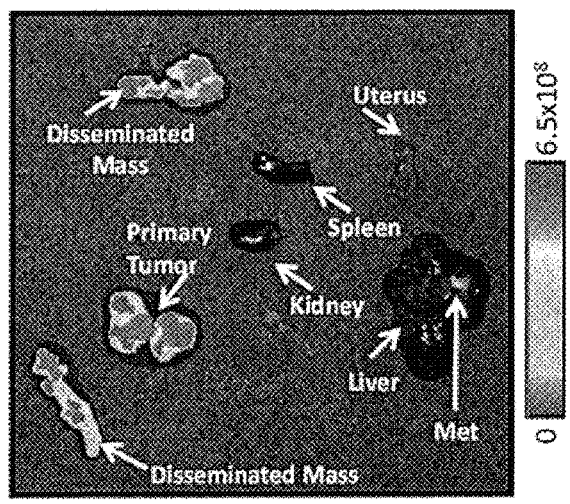
Figure 19E:
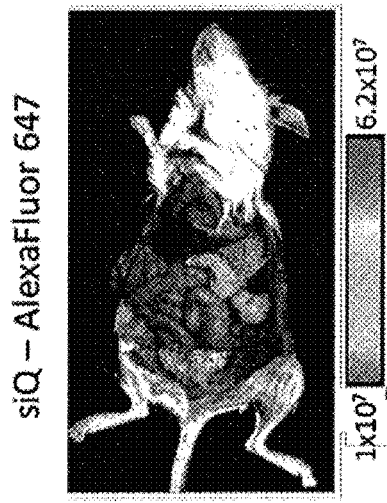
Figure 19F:
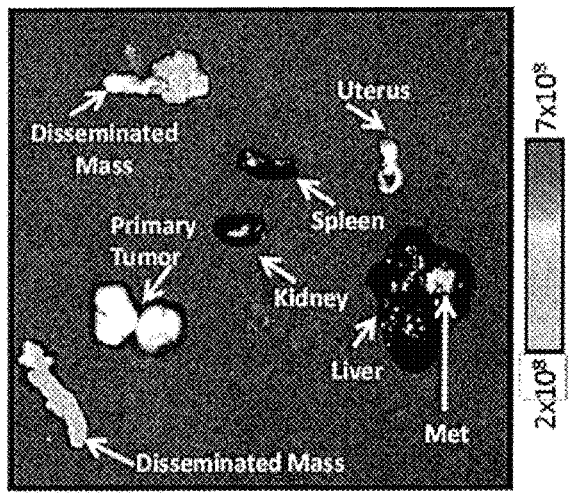

MSNs selectively accumulate in disseminated Ovcar8-IP masses. In order to determine if our MSNs targeted tumors in vivo, we performed fluorescent imaging of siQ treated mice. Ovcar8-IP cells successfully produced primary tumors (defined as those localized to the ovary) and disseminated masses (FIGS. 19C-19D). This pattern of engraftment following IP administration of cells is consistent with the current prevailing theory that the site of origin for EOC is the fallopian tube epithelium, and that cells migrate to the ovary and peritoneal cavity, giving rise to both large ovarian tumors and widely disseminated tumor foci [33-35]. MSNs carrying siRNA selectively penetrated and accumulated at these primary tumors and disseminated masses, but not in any other peritoneal tissue or organ examined (FIGS. 19E-19F). Note that a tumor focus also appears on the liver of this control mouse, to which the MSN-siQ also homed (FIGS. 19D-19F). Tumor uptake of MSN-siQ was greater in disseminated masses than in ovaries, but signal is visible on the primary tumors.

Figure 20A:
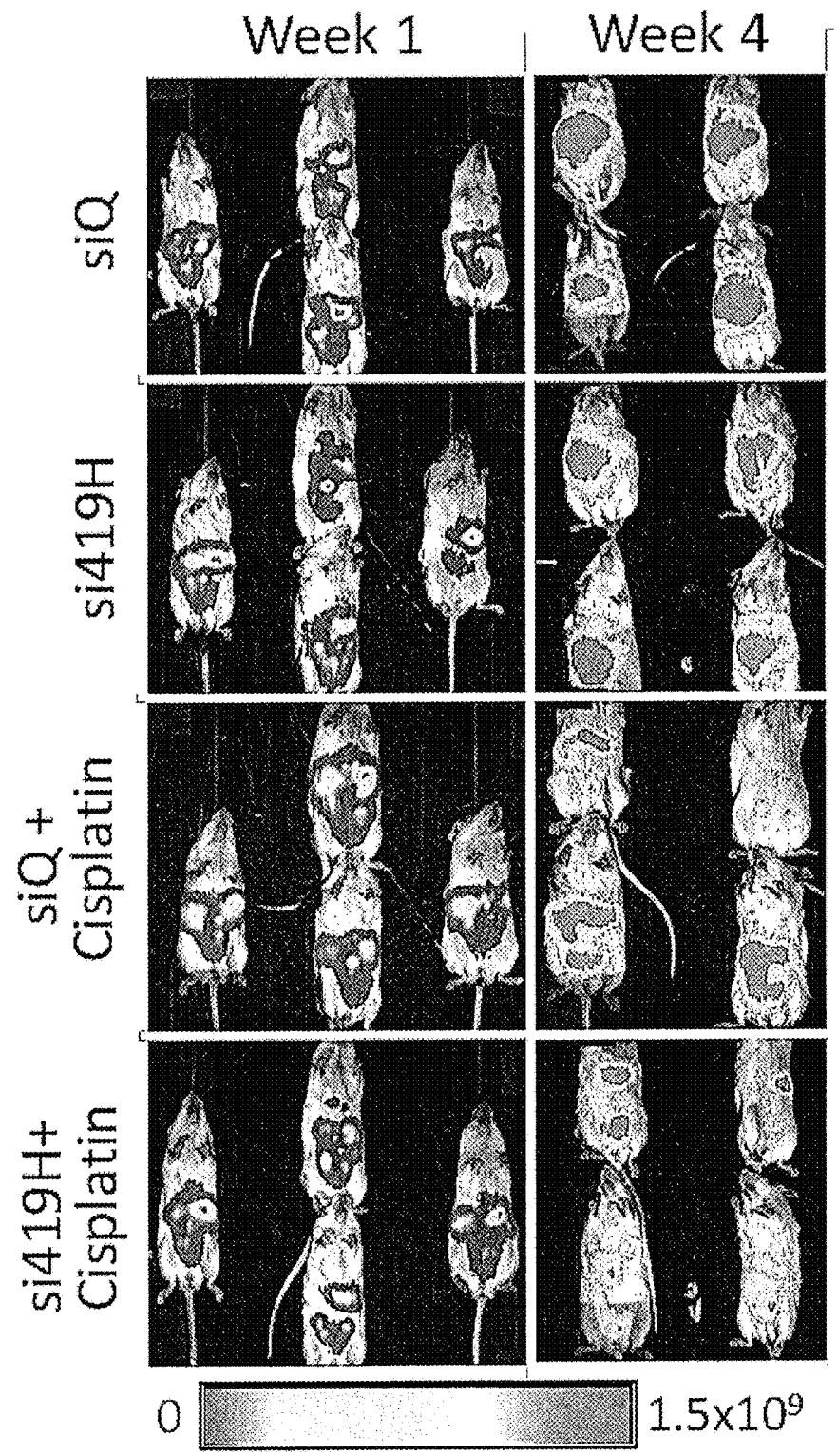
FIGS. 20A to 20B.
Figure 20B:
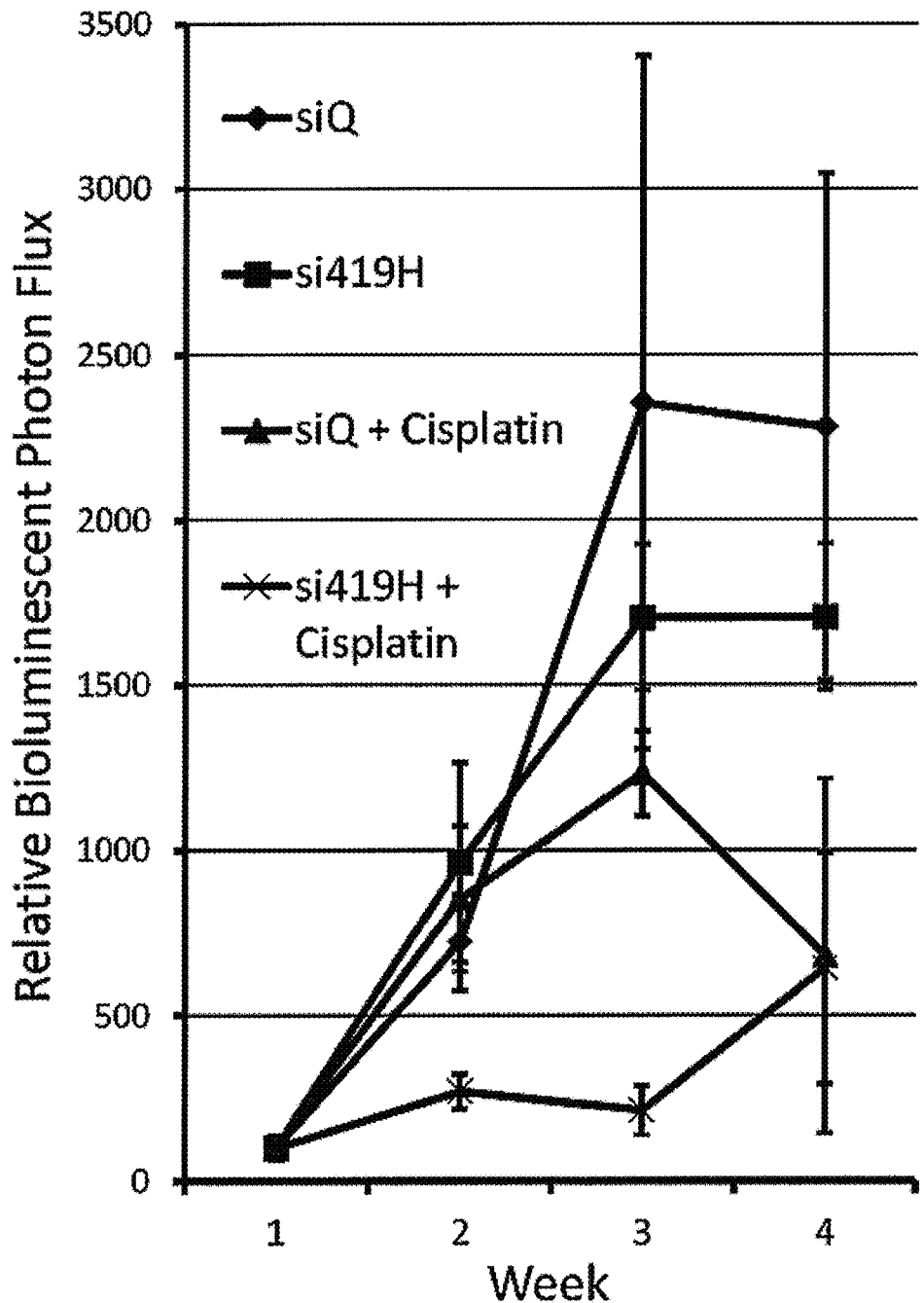

Ovcar8-IP tumor growth is inhibited by siTWIST and cisplatin combination therapy. Mice were treated weekly for four weeks with MSN-siQ or MSN-si419H, with or without cisplatin. After four weeks of therapy, the negative control (MSN-siQ weekly) mice developed significant tumors and produced disseminated masses as shown by relative bioluminescent photon flux measurements (FIGS. 20A-20B). The si419H treatment group (MSN-si419H weekly) produced relatively smaller tumors, with a 30% drop in bioluminescent signal after four weeks of therapy in comparison to the controls. The chemotherapy only treatment group (MSN-siQ and cisplatin weekly) had a reduction rate of about 50%, whereas the si419H with cisplatin chemotherapy treatment group (MSN-si419H and cisplatin weekly) exhibited an almost 85% decrease in tumor burden as measured by bioluminescence (FIGS. 20A-20B). Mice treated with MSN-siRNA twice weekly at half the dose failed to show these differences (data not shown).

Figure 21A:
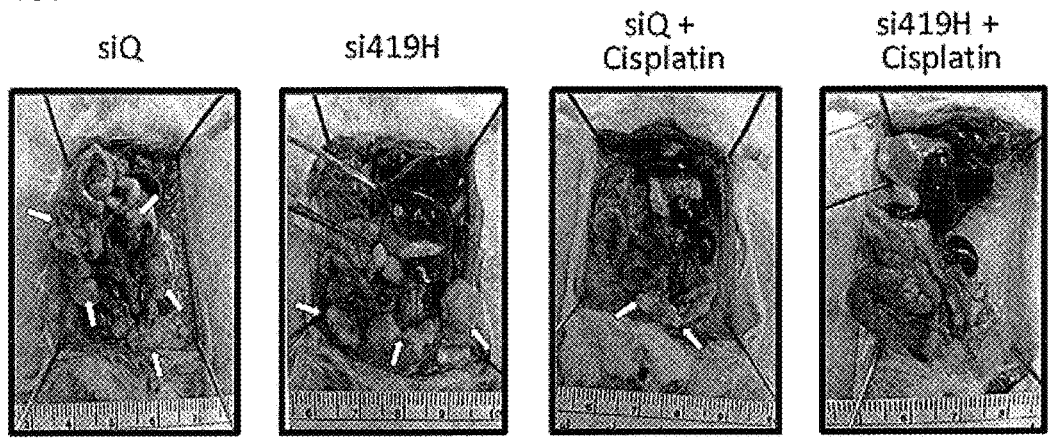
FIGS. 21A to 21C.
Figure 21B:
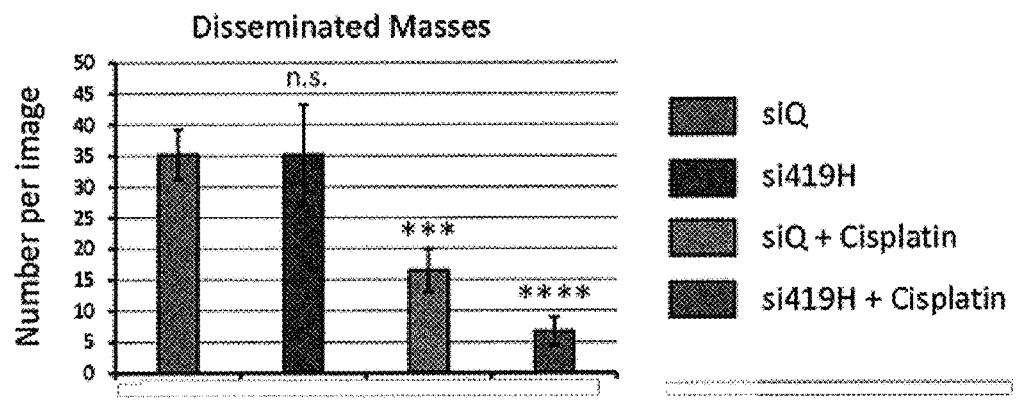
Figure 21C:
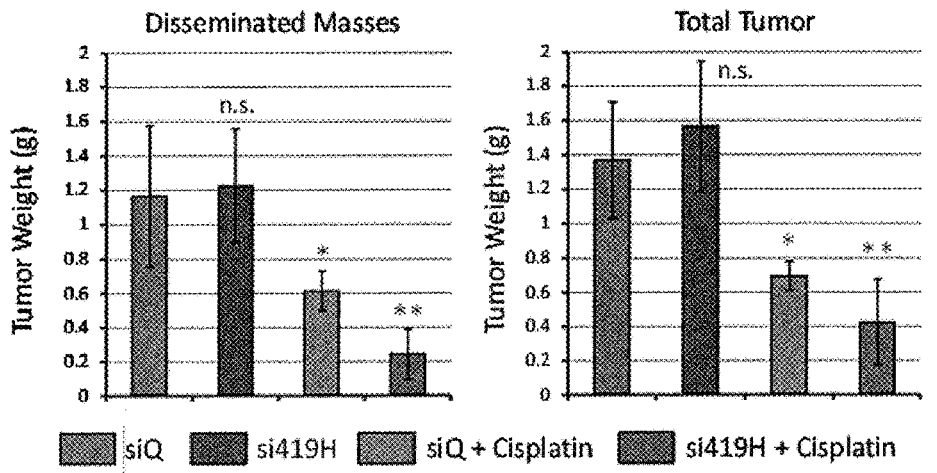

Tumors collected from the MSN-si419H+cisplatin mice were significantly smaller when compared to the tumors from the MSN-siQ control mice (FIGS. 21A and 21C). Furthermore, MSN-siQ control mice produced large numbers of disseminated masses and had enlarged primary tumors (FIGS. 21A-21B) in comparison to the MSN-si419H+cisplatin treated mice that exhibited no large disseminated lesions. It is important to note that cisplatin+MSN-siQ hindered tumor growth by more than 50% (FIGS. 21B-21C). However, si419H and cisplatin combination therapy inhibited Ovcar8-IP tumor growth to an even greater degree, with almost a 75% drop in number of foci and tumor weight in comparison to the controls (FIGS. 21B-21C). A similar trend was seen for proportion of mice developing ascites, with 4/4 MSN-siQ and MSN-si419H treated mice, 2/4 cisplatin treated mice, and 1/4 combination treated mouse developing ascites. There was significant reduction in weight (p=0.0084) and number (p=0.0046) of disseminated masses between cisplatin +MSN-siQ and cisplatin+MSN-si419H treated mice, but this trend did not reach statistical significance for total tumor weight (p=0.1183). This is likely the result of greater MSN-siRNA uptake by the disseminated masses than primary tumor (FIG. 20B).

Discussion.

To our knowledge, this is the first example of silencing TWIST utilizing a nanoparticle delivery system in EOC. We demonstrate delivery and efficacy of chemically modified siRNA against TWIST in EOC; significant TWIST knockdown was achieved with a modified third generation PAMAM dendrimer and a silica nanoparticle in vitro. The delivery of our siRNA by YTZ3-15 was shown to have a profound effect on both TWIST silencing and chemoresistance in the EOC model. Silencing TWIST via the YTZ3-15 dendrimer substantially increased chemosensitivity, decreasing cell survival by more than 50% (FIG. 16E). These data demonstrated that TWIST is a clinically significant therapeutic target.

The PEI coated MSNs developed for this study successfully delivered siRNA into Ovcar8-IP ovarian cancer cells in vitro (FIGS. 18B-18D). This delivery also led to substantial knockdown of TWIST (FIG. 18C). Our results demonstrate si419H's efficacy both in vitro and in vivo. Fluorescence microscopy demonstrated appropriate localization of MSN+Alexa-647 labeled siRNA in the lysosomes of EOC cells (FIG. 18B), which lead to successful silencing of TWIST within 24 hours and complete absence of expression within one week (FIG. 18C). As with YTZ3-15 delivery, MSN-delivered si419H sensitized EOC cells to cisplatin treatment (FIG. 18D). In vivo, delivery of TWIST siRNA leads to significant impediment of metastatic growth in siTWIST treated mice in combination with cisplatin, reducing tumor weight almost 80% (FIGS. 21A-21C), compared to the siQ control. The observed decrease in tumor burden is mostly due to abrogated TWIST expression in EMT-mediated disseminated masses. These findings strongly support our assertion that TWIST is an important therapeutic target in EOC.

One of the main advantages of our system is its safety and specificity. The MSN-siRNA only localized to tumor sites and no other tissues or organs.

The potential for these MSNs is vast due to their mesoporous nature as compared to other dense nanoparticles, such as gold or carbon. MSNs can also be modified with targeting moieties such as hyaluronic acid (HA). Since HA is a native ligand for CD44, which is overexpressed and correlates with worse prognosis in EOC [48,49], addition of HA will lead to enhanced uptake into tumors, especially in primary tumors, which in this study showed limited siRNA uptake in vivo.

Overall, without wishing to be bound by theory, it is believe that this disclosure serves to demonstrate that an MSN-siRNA approach can provide significant benefit in an EOC model, and multifunctional MSNs incorporating cytotoxic drug delivery and targeting moieties, in multiple cancer models.

REFERENCED (EXAMPLE 3)

[1] Siegel, R. L., Miller, K. D. & Jemal, A. Cancer statistics, 2016. CA: a cancer journal for clinicians 66, 7-30 (2016); [2] Khalil, I., Brewer, M. A., Neyarapally, T. & Runowicz, C. D. The potential of biologic network models in understanding the etiopathogenesis of ovarian cancer. Gynecol Oncol 116, 282-285 (2010); [3] Visintin, I. et al. Diagnostic markers for early detection of ovarian cancer. Clin Cancer Res 14, 1065-107 (2008); [4] Karimi-Zarchi, M. et al. The Clinicopathologic Characteristics and 5-year Survival Rate of Epithelial Ovarian Cancer in Yazd, Iran. Electronic physician 7, 1399-1406 (2015); [5] Holschneider, C. H. & Berek, J. S. Ovarian cancer: epidemiology, biology, and prognostic factors. Seminars in surgical oncology 19, 3-10 (2000); [6] Terauchi, M. et al. Possible involvement of TWIST in enhanced peritoneal metastasis of epithelial ovarian carcinoma. Clin Exp Metastasis 24, 329-339 (2007); [7] Yang, J. et al. Twist, a master regulator of morphogenesis, plays an essential role in tumor metastasis. Cell 117, 927-939 (2004); [8] Yin, G. et al. Constitutive proteasomal degradation of TWIST-1 in epithelial-ovarian cancer stem cells impacts differentiation and metastatic potential. Oncogene 32, 39-49 (2013); [9] Gort, E. H. et al. Methylation of the TWIST1 promoter, TWIST1 mRNA levels, and immunohistochemical expression of TWIST1 in breast cancer. Cancer epidemiology, biomarkers & prevention: a publication of the American Association for Cancer Research, cosponsored by the American Society of Preventive Oncology 17, 3325-3330 (2008); [10] Vesuna, F., Lisok, A., Kimble, B. & Raman, V. Twist modulates breast cancer stem cells by transcriptional regulation of CD24 expression. Neoplasia (New York, N.Y.) 11, 1318-1328 (2009); [11] Yin, G. et al. TWISTing stemness, inflammation and proliferation of epithelial ovarian cancer cells through MIR199A2/214. Oncogene 29, 3545-3553 (2010); [12] Ahmed, N., Abubaker, K., Findlay, J. & Quinn, M. Epithelial mesenchymal transition and cancer stem cell-like phenotypes facilitate chemoresistance in recurrent ovarian cancer. Current cancer drug targets 10, 268-278 (2010); [13] Li, S. et al. TWIST1 associates with NF-kappaB subunit RELA via carboxyl-terminal WR domain to promote cell autonomous invasion through IL8 production. BMC Biol 10, 73 (2012); [14] Finlay, J. et al. Mesoporous silica nanoparticle delivery of chemically modified siRNA against TWIST1 leads to reduced tumor burden. Nanomedicine: nanotechnology, biology, and medicine 11, 1657-1666 (2015); [15] Finlay, J. et al. RNA-based TWIST1 inhibition via dendrimer complex to reduce breast cancer cell metastasis. BioMed research international 2015, 382745 (2015); [16] Bobbin, M. L. & Rossi, J. J. RNA Interference (RNAi)-Based Therapeutics: Delivering on the Promise? Annual review of pharmacology and toxicology 56, 103-122 (2016); [17] Brown, C. E. et al. Recognition and killing of brain tumor stem-like initiating cells by CD8+ cytolytic T cells. Cancer Res 69, 8886-8893 (2009); [18] Yu, T. et al. An amphiphilic dendrimer for effective delivery of small interfering RNA and gene silencing in vitro and in vivo. Angew Chem Int Ed Engl 51, 8478-8484 (2012); [19] Liu, X. et al. Adaptive amphiphilic dendrimer-based nanoassemblies as robust and versatile siRNA delivery systems. Angew Chem Int Ed Engl 53, 11822-11827 (2014); [20] Hom, C. et al. Mesoporous silica nanoparticles facilitate delivery of siRNA to shutdown signaling pathways in mammalian cells. Small (Weinheim an der Bergstrasse, Germany) 6, 1185-1190 (2010); [21] Meng, H. et al. Use of size and a copolymer design feature to improve the biodistribution and the enhanced permeability and retention effect of doxorubicin-loaded mesoporous silica nanoparticles in a murine xenograft tumor model. ACS nano 5, 4131-4144 (2011); [22] Liong, M. et al. Multifunctional inorganic nanoparticles for imaging, targeting, and drug delivery. ACS nano 2, 889-896 (2008); [23] Tarn, D., Xue, M. & Zink, J. I. pH-responsive dual cargo delivery from mesoporous silica nanoparticles with a metal-latched nanogate. Inorganic chemistry 52, 2044-2049 (2013); [24] Ambrogio, M. W., Thomas, C. R., Zhao, Y. L., Zink, J. I. & Stoddart, J. F. Mechanized silica nanoparticles: a new frontier in theranostic nanomedicine. Accounts of chemical research 44, 903-913 (2011); [25] Lu, J., Li, Z., Zink, J. I. & Tamanoi, F. In vivo tumor suppression efficacy of mesoporous silica nanoparticles-based drug-delivery system: enhanced efficacy by folate modification. Nanomedicine: nanotechnology, biology, and medicine 8, 212-220 (2012); [26] Thomas, C. R. et al. Noninvasive remote-controlled release of drug molecules in vitro using magnetic actuation of mechanized nanoparticles. Journal of the American Chemical Society 132, 10623-10625 (2010); [27] Dong, J., Xue, M. & Zink, J. I. Functioning of nanovalves on polymer coated mesoporous silica Nanoparticles. Nanoscale 5, 10300-10306 (2013); [28] Deng, Z. J. et al. Layer-by-layer nanoparticles for systemic codelivery of an anticancer drug and siRNA for potential triple-negative breast cancer treatment. ACS nano 7, 9571-9584 (2013); [29] Forsbach, A. et al. Identification of RNA sequence motifs stimulating sequence-specific TLR8-dependent immune responses. Journal of immunology (Baltimore, Md.: 1950) 180, 3729-3738 (2008); [30] Behlke, M. A. Chemical modification of siRNAs for in vivo use. Oligonucleotides 18, 305-319 (2008); [31] Czauderna, F. et al. Structural variations and stabilising modifications of synthetic siRNAs in mammalian cells. Nucleic Acids Res 31, 2705-2716 (2003); [32] Domcke, S., Sinha, R., Levine, D. A., Sander, C. & Schultz, N. Evaluating cell lines as tumour models by comparison of genomic profiles. Nat Commun 4, 2126 (2013); [33] Lee, Y. et al. A candidate precursor to serous carcinoma that originates in the distal fallopian tube. The Journal of pathology 211, 26-35 (2007); [34] Medeiros, F. et al. The tubal fimbria is a preferred site for early adenocarcinoma in women with familial ovarian cancer syndrome. The American journal of surgical pathology 30, 230-236 (2006); [35] Morin, P. J. & Weeraratna, A. T. Genetically-defined ovarian cancer mouse models. The Journal of pathology 238, 180-184 (2016); [36] Helleman, J., Smid, M., Jansen, M. P., van der Burg, M. E. & Berns, E. M. Pathway analysis of gene lists associated with platinum-based chemotherapy resistance in ovarian cancer: the big picture. Gynecol Oncol 117, 170-176 (2010); [37] Yoshida, J. et al. Changes in the expression of E-cadherin repressors, Snail, Slug, SIP1, and Twist, in the development and progression of ovarian carcinoma: the important role of Snail in ovarian tumorigenesis and progression. Medical molecular morphology 42, 82-91 (2009); [38] Zhu, D. J. et al. Twist1 is a potential prognostic marker for colorectal cancer and associated with chemoresistance. American journal of cancer research 5, 2000-2011 (2015); [39] Zhu, X. et al. miR-186 regulation of Twist1 and ovarian cancer sensitivity to cisplatin. Oncogene 35, 323-332 (2016); [40] Cheng, G. Z. et al. Twist transcriptionally up-regulates AKT2 in breast cancer cells leading to increased migration, invasion, and resistance to paclitaxel. Cancer Res 67, 1979-1987 (2007); [41] Greish, K. Enhanced permeability and retention (EPR) effect for anticancer nanomedicine drug targeting. Methods Mol Biol 624, 25-37 (2010); [42] Biswas, S. & Torchilin, V. P. Dendrimers for siRNA Delivery. Pharmaceuticals (Basel, Switzerland) 6, 161-183 (2013); [43] Maeda, H., Sawa, T. & Konno, T. Mechanism of tumor-targeted delivery of macromolecular drugs, including the EPR effect in solid tumor and clinical overview of the prototype polymeric drug SMANCS. Journal of controlled release: official journal of the Controlled Release Society 74, 47-61 (2001); [44] Xia, T. et al. Polyethyleneimine coating enhances the cellular uptake of mesoporous silica nanoparticles and allows safe delivery of siRNA and DNA constructs. ACS nano 3, 3273-3286 (2009); [45] Ferris, D. P. et al. Synthesis of biomolecule-modified mesoporous silica nanoparticles for targeted hydrophobic drug delivery to cancer cells. Small (Weinheim an der Bergstrasse, Germany) 7, 1816-1826 (2011); [46] Lu, J., Liong, M., Zink, J. I. & Tamanoi, F. Mesoporous silica nanoparticles as a delivery system for hydrophobic anticancer drugs. Small (Weinheim an der Bergstrasse, Germany) 3, 1341-1346 (2007); [47] Gaglione, M. & Messere, A. Recent progress in chemically modified siRNAs. Mini reviews in medicinal chemistry 10, 578-595 (2010); [48] Elzarkaa, A. A. et al. Clinical relevance of CD44 surface expression in advanced stage serous epithelial ovarian cancer: a prospective study. Journal of cancer research and clinical oncology 142, 949-958 (2016); [49] Kayastha, S. et al. Expression of the hyaluronan receptor, CD44S, in epithelial ovarian cancer is an independent predictor of survival. Clin Cancer Res 5, 1073-1076 (1999).

Example 4

TWIST1 Drives Cisplatin Resistance and Cell Survival in an Ovarian Cancer Model, Via Upregulation of GAS6, L1CAM, and Akt Signalling Abstract. Epithelial ovarian cancer (EOC) is the most deadly gynaecologic malignancy due to late onset of symptoms and propensity towards drug resistance. Epithelial-mesenchymal transition (EMT) has been linked to the development of chemoresistance in other cancers, yet little is known regarding its role in EOC. In this study, we sought to determine the role of the transcription factor TWIST1, a master regulator of EMT, on cisplatin resistance in an EOC model. We created two Ovcar8-derived cell lines that differed only in their TWIST1 expression. TWIST1 expression led to increased tumour engraftment in mice, as well as cisplatin resistance in vitro. RNA sequencing analysis revealed that TWIST1 expression resulted in upregulation of GAS6 and L1CAM and downregulation of HMGA2. Knockdown studies of these genes demonstrated that loss of GAS6 or L1CAM sensitized cells to cisplatin, but that loss of HMGA2 did not give rise to chemoresistance. TWIST1, in part via GAS6 and L1CAM, led to higher expression and activation of Akt upon cisplatin treatment, and inhibition of Akt activation sensitized cells to cisplatin. These results suggest TWIST1—and EMT-driven increase in Akt activation, and thus tumour cell proliferation, as a potential mechanism of drug resistance in EOC.

Introduction. Epithelial ovarian cancer (EOC), which accounts for over 90% of ovarian tumours, is the most lethal gynaecologic malignancy [1,2,3]. A significant challenge in the treatment of EOC is the frequent development of tumour recurrence and chemoresistance. We and others have previously shown that ovarian cancer stem cells (CSCs) that survive initial rounds of chemotherapy facilitate this tumour recurrence[4,5]. A key factor in this reactivation of cancer stem cells is TWIST1, a transcription factor that is required for normal early mesoderm development but silenced in most adult tissues[6,7,8]. TWIST1 is reactivated in many cancers, where it drives an epithelial to mesenchymal transition (EMT), leading to metastasis[8,9]. In a variety of tumour types, TWIST1 has also been linked to angiogenesis, resistance to apoptosis, and cancer cell stemness[10,11,12]. In ovarian cancer, TWIST1 protein is degraded in CSCs, maintaining CSCs in an epithelial state. However, once TWIST1 protein expression persists, CSCs undergo EMT, leading to proliferation and metastasis[5,13].

Despite its known role in activation of the stem cell pool, the direct role of TWIST1 in drug resistance in ovarian cancer is relatively unknown. Multiple downstream TWIST1 target genes have been implicated in drug resistance, including interleukin 8 and matrix metalloproteinases 2 and 9[14,15,16]. Additionally, TWIST1 has been shown to regulate Gli1, which upregulates the DNA repair protein ERCC1. ERCC1 is partially responsible for the repair of cisplatin-induced DNA crosslinks[17,18]. In other tumour types, TWIST1 has been linked to resistance to cisplatin, as well as paclitaxel and doxorubicin[19,20]. While the EMT process as a whole has previously been correlated with drug resistance in EOC, TWIST1 itself has never been causally linked[21]. The related transcription factor TWIST2 has been shown to lead to platinum resistance via Akt activation in another EOC model, but whether TWIST1 can function in the same manner is unknown[22]. Therefore, we sought to determine the distinct role of TWIST1 in cisplatin resistance in an EOC model. This study is the first to focus on the specific mechanisms by which TWIST1 confers cisplatin drug resistance in ovarian cancer, a novel function for a transcription factor that has previously primarily been only associated with tumour cell motility. Connecting TWIST1 and the EMT process as a whole to the dual malignant functions of increased cancerous cell proliferation and drug resistance makes it an especially attractive target for aggressive, drug-resistant carcinomas that require a combination of therapeutic approaches.

Results.

Figure 22A:
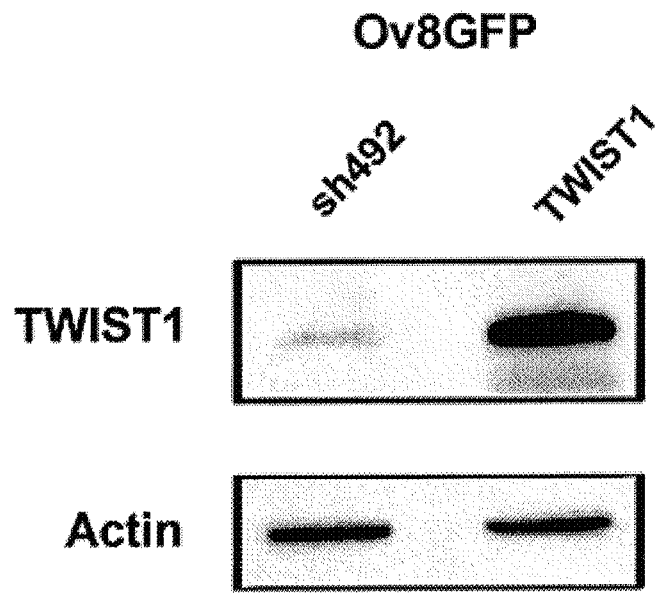
FIGS. 22A to 22D. TWIST1 overexpression leads to cisplatin resistance and enhanced tumour cell engraftment.
Figure 27A:
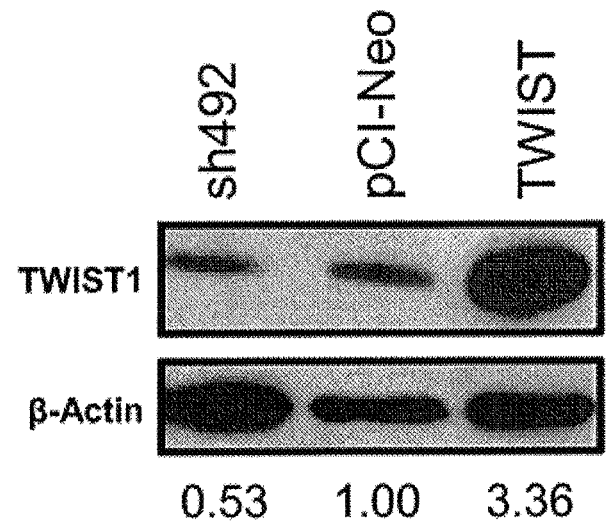
FIGS. 27A to 27B. Cells transfected with empty pCI-Neo vector exhibit intermediate phenotype.
Figure 27B:
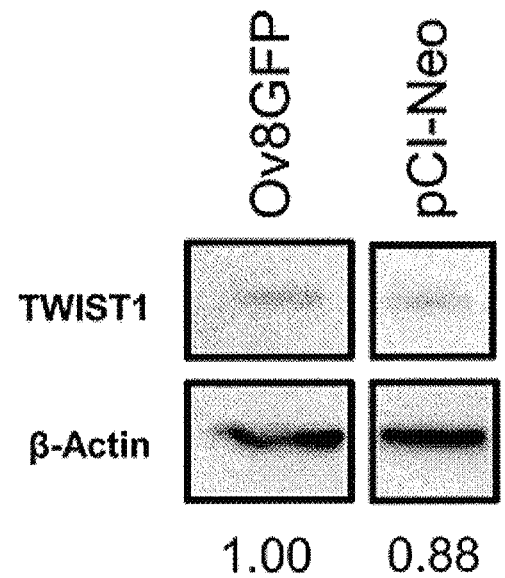
Figure 28:
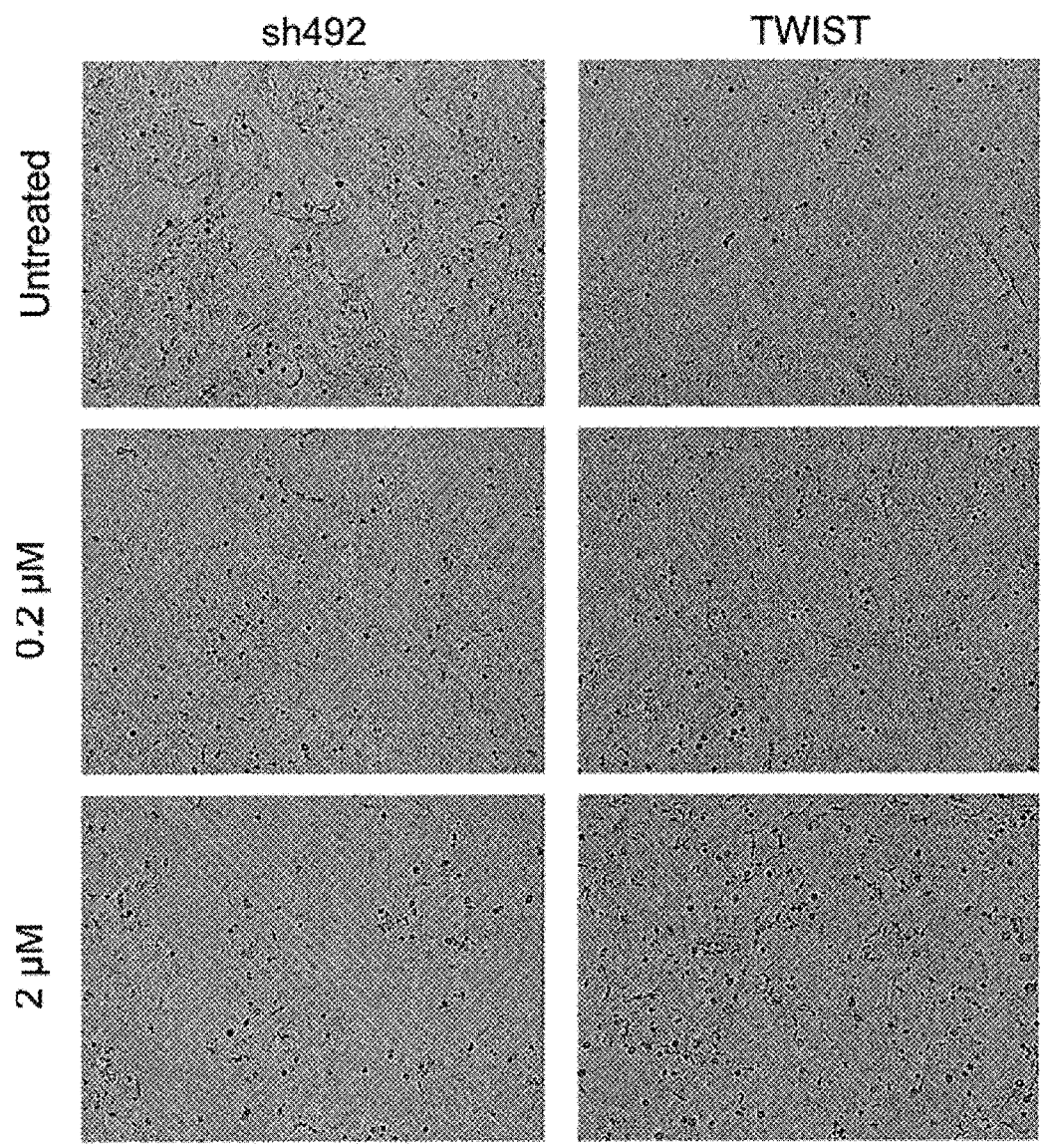
FIG. 28. Representative images of Ov8GFP-TWIST and Ov8GFP-sh492 cells acquired three days post treatment with the indicated doses of cisplatin. Images such as these were analyzed to determine confluence, which is graphed in FIG. 22C.

Creation of Ovcar8 derived stable lines with differential TWIST1 expression. The ovarian cancer cell line Ovcar8 was transfected with a viral construct encoding an enhanced GFP-firefly luciferase fusion protein (CMV-p:EGFP-ffluc pHIV7) to make the Ov8GFP cell line, as we have described for previous cell line models[23]. We then transfected Ov8GFP cells with either TWIST1 or sh492, a previously validated shRNA against TWIST[24,25], using the pCI-Neo G418-selectable plasmid vector system. Following G418 selection of cells with stably integrated plasmid, we verified that TWIST1 was differentially expressed in the two cell lines—referred to hereafter as Ov8GFP-TWIST1 and Ov8GFP-sh492—via western blot (FIG. 22A). Parental Ov8GFP cells express an intermediate level of TWIST1, thus an empty pCI-Neo vector resulted in intermediate TWIST1 expression, showing no substantial effect on TWIST1 from transfection alone (FIGS. 27A-27B). Reflecting their native TWIST1 expression, Ovcar8-derived lines exhibited mesenchymal morphology (FIG. 28).

Figure 22B:
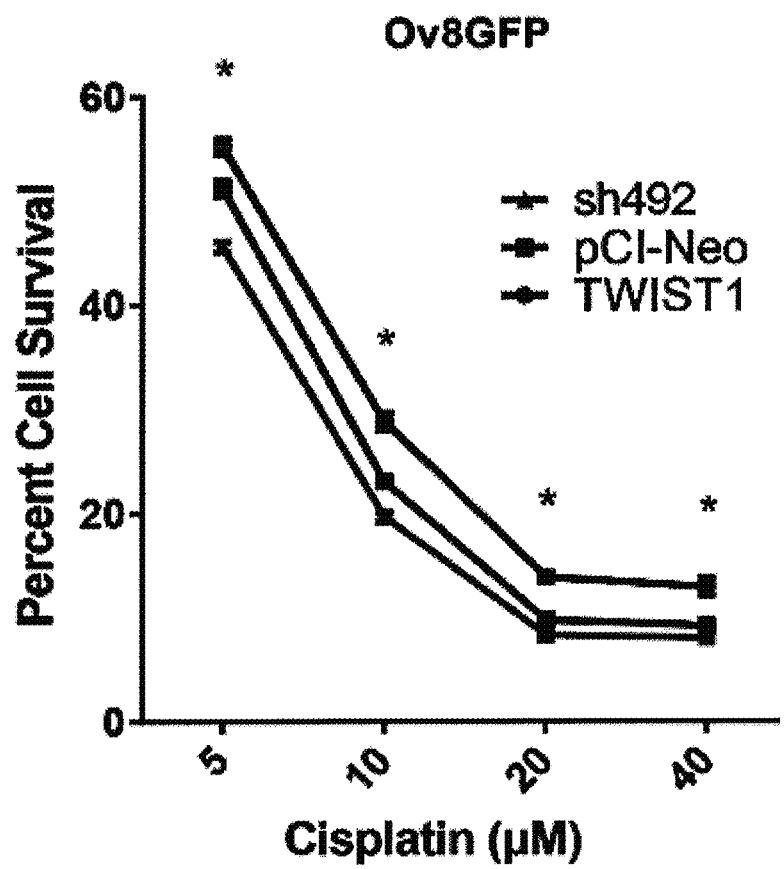
Figure 22C:
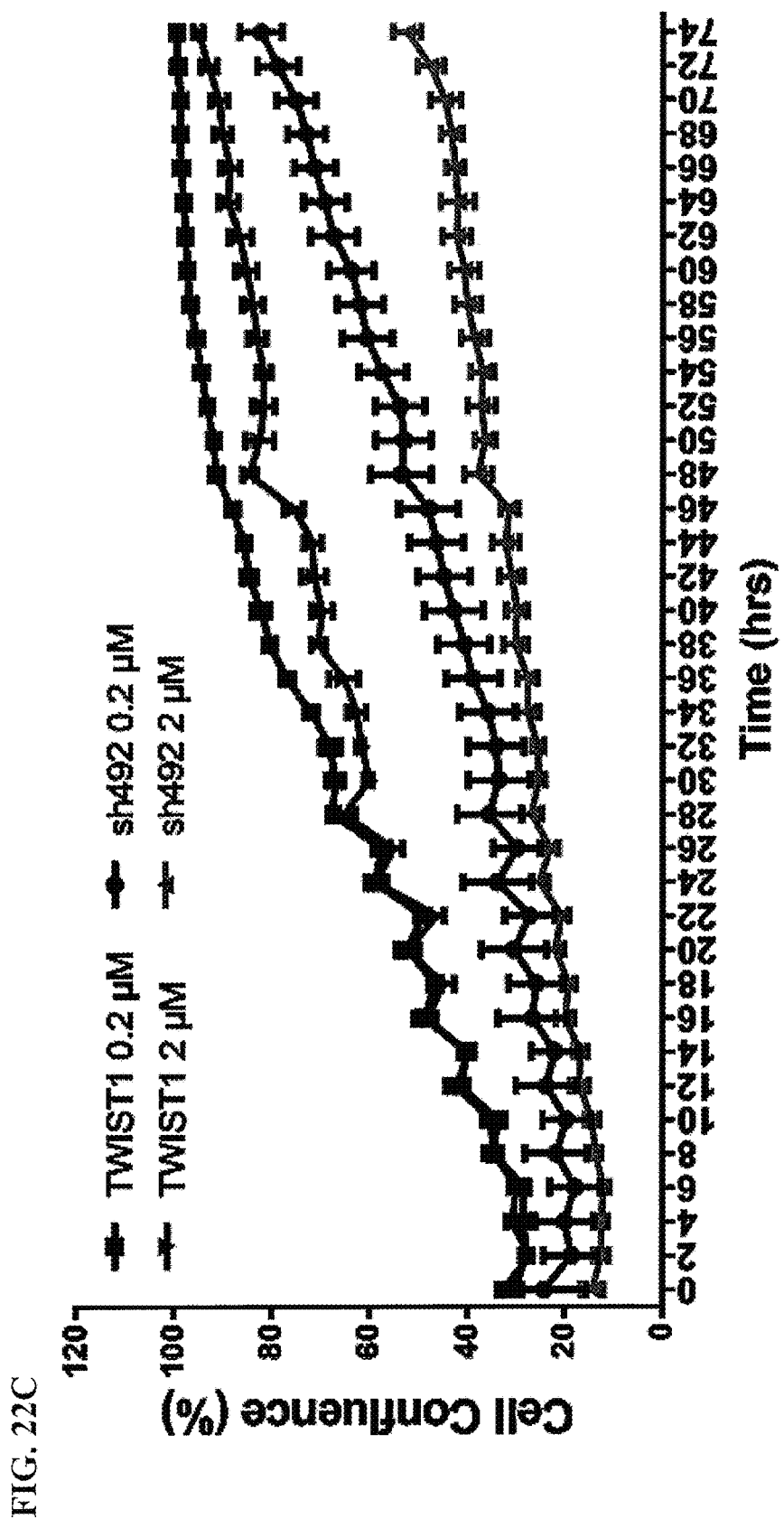

TWIST1 expressing cells are cisplatin resistant. We evaluated the effect of TWIST1 expression in response to cisplatin. Following 72 hr incubation with cisplatin, sulphorhodamine B (SRB) cell survival assays showed that TWIST1-overexpressing cells exhibited greater survival than TWIST1 knockdown cells, normalized to untreated cells of each line (FIG. 22B). Cells transfected with empty pCI-Neo vector had intermediate survival compared to TWIST1 and sh492, confirming dose dependence of TWIST1 on cisplatin resistance (FIG. 22B). TWIST1 also affected the kinetics of cell growth during cisplatin treatment. Monitoring of cell confluence at 2 hr intervals showed that Ov8GFP-TWIST1 cells proliferated more rapidly than their sh492 counterparts (compare slope of light blue vs light green and dark blue vs dark green plots) when treated with 0.2 or 2 μM cisplatin (FIGS. 22C and 28).

Figure 22D:
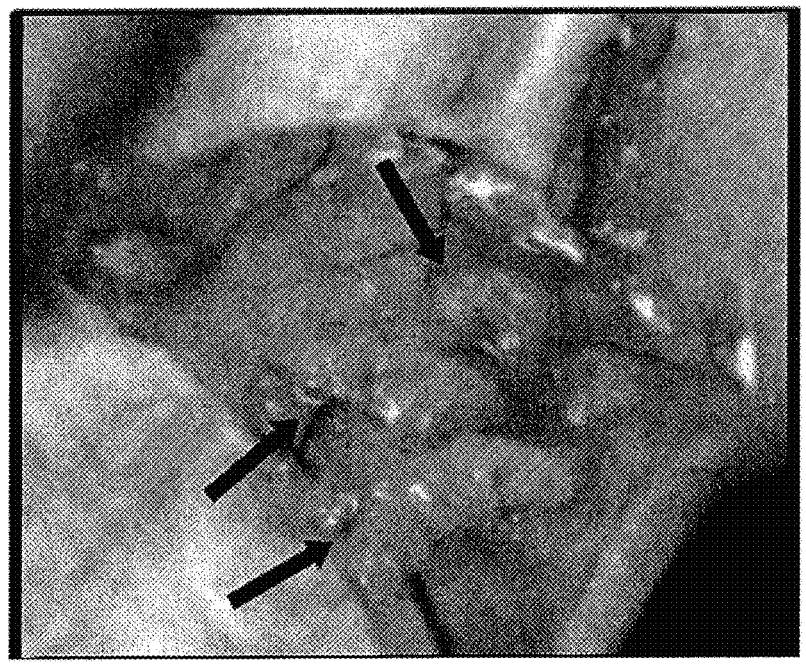
Figure 22D:

TWIST1-expressing cells show enhanced engraftment in mice. We next evaluated the pro-survival and proliferation phenotype of TWIST1-overexpressing cells in tumour engraftment. We injected either Ov8GFP-TWIST1 or Ov8GFP-sh492 cells intraperitoneally into NSG mice (n=4 per group). Seven weeks after the injection, tumour burden and distribution in these mice were evaluated via pathological examination of haematoxylin and eosin stained tissue sections and images of the peritoneal cavity obtained at necropsy. All four mice that received Ov8GFP-TWIST1 developed ovarian tumours were graded 4/4 by a certified veterinary pathologist. By contrast, only two mice given Ov8GFP-sh492 exhibited ovarian tumours, only one of which was graded a 4 (Table 1). Three mice that received Ov8GFP-TWIST1 had detectable tumour masses within intra-abdominal organs (i.e. parenchymal tumour metastases), compared to only one of four mice in the Ov8GFP-sh492 group (Table 1). Additionally, necropsy images of mice show that mice engrafted with Ov8GFP-TWIST1 had many disseminated tumour masses in the intra-abdominal peritoneal lining, which were absent in the peritoneum of the mice engrafted with Ov8GFP-sh492 (FIG. 22D). This disseminated tumour distribution parallels the peritoneal surface carcinomatosis found frequently in advanced stage ovarian cancer patients. Taken collectively, these data strongly suggest a critical role for TWIST1 in promoting survival, proliferation, and engraftment of tumour cells in the ovaries and peritoneal space.

RNA sequencing demonstrates differential expression of GAS6, L1CAM, and HMGA2. In order to determine which downstream pathways may be responsible for TWIST1-mediated proliferation, drug resistance, and cell survival, we performed RNA sequencing analysis. In addition to TWIST1 itself, a total of 51 genes were found to be differentially expressed between Ov8GFP-TWIST1 and —sh492 (>1.5 fold difference, p<0.05), 18 downregulated by TWIST1 and 33 upregulated. As expected given TWIST1's role in EMT during development and metastasis[8], gene ontology (GO) terms enriched amongst TWIST1 regulated genes included Cell Movement and Cell Morphology. Additional enriched GO terms included Cellular Growth/Proliferation and Cell Death and Survival. Ingenuity Pathway Analysis showed that apoptotic and migration signalling pathways intersect at TWIST1 and its target genes, including genes identified in our RNA sequencing results. This finding suggests that TWIST1 may act to promote both proliferation and migration of tumour cells. A full list of differentially expressed genes is given in Tables S1A-S1B following.

TABLE 1

List of differentially expressed genes output by RNA-seq analysis. Genes are ordered according to log2 fold change. Negative $\log_2$ indicates that gene is downregulated when TWIST1 is overexpressed and positive $\log_2$ indicates that gene is upregulated when TWIST1 is overexpressed.

| Gene | Expression sh492 | TWIST | Log2 Fold Change | p-Value | Function |
|---|---|---|---|---|---|
| HCLS1 | 1.9192 | 0.3462 | −2.4710 | 5.00E−05 | Antigen signaling |
| ESM1 | 19.8290 | 5.3762 | −1.8829 | 5.00E−05 | Proangiogenesic |
| GGT1 | 7.5759 | 2.6660 | −1.5068 | 5.00E−05 | Glutathione metabolism |
| TIE1 | 4.2598 | 1.5563 | −1.4526 | 5.00E−05 | Endothelial adhesion molecule |
| CCL20 | 21.4373 | 7.9192 | −1.4367 | 5.00E−05 | Downstream of IL6/NFkB/STAT3 - immune attractant |
| ABCA1 | 1.7954 | 0.7054 | −1.3478 | 5.00E−05 | Cholesterol homeostasis |
| SP4 | 10.2972 | 4.1698 | −1.3042 | 5.00E−05 | Primarily neural transcription factor |
| ARHGDIB | 8.3662 | 3.4472 | −1.2792 | 1.50E−04 | Microenvironmental communication to inhibit metastasis |
| LSAMP | 0.6617 | 0.2736 | −1.2739 | 2.50E−04 | Neuron growth |
| MIR484, NDE1 | 36.8636 | 15.6657 | −1.2346 | 1.50E−04 | MicroRNA |
| EDN1 | 11.9078 | 5.0866 | −1.2271 | 5.00E−05 | Endothelin |
| IL1A | 6.1556 | 2.7691 | −1.1525 | 2.00E−04 | Proinflammatory cytokine |
| CTPS2 | 10.0673 | 4.8606 | −1.0505 | 1.50E−04 | CTP synthase |
| SERPINB2 | 57.3030 | 28.1986 | −1.0230 | 5.00E−05 | Protease inhibitor, antiapoptotic |
| HMGA2 | 17.6553 | 8.9826 | −0.9749 | 1.00E−04 | DNA binding, chromosome condensation, DNA repair regulator |
| LOC643201 | 18.1145 | 9.4289 | −0.9420 | 1.50E−04 | Pseudogene |
| LPHN2 | 34.4611 | 18.9748 | −0.8609 | 1.50E−04 | Adhesion linked GPCR |
| CALB1 | 68.4107 | 38.3483 | −0.8351 | 1.00E−04 | Cytosol calcium buffering |
| FAM129A | 9.9252 | 17.6015 | 0.8265 | 2.50E−04 | ER stress response, regulates translation |
| DPYSL3 | 11.3916 | 20.8860 | 0.8746 | 5.00E−05 | L1CAM pathway member, putative migration function |
| GAS6 | 21.2476 | 39.7292 | 0.9029 | 1.00E−04 | Growth/adhesion/migration/survival. Interacts with Axl |
| CHN1 | 11.6973 | 22.1486 | 0.9210 | 5.00E−05 | Lipid stimulated GTPase |
| GREM1 | 24.7823 | 47.6102 | 0.9420 | 5.00E−05 | BMP inhib, proFGF signaling |
| SHISA9 | 7.0954 | 13.6759 | 0.9467 | 2.00E−04 | Synaptic protein |
| EPHB1 | 8.8684 | 17.2622 | 0.9609 | 1.00E−04 | Adhesion/migration signaling. ERK/JNK, possibly angiogenesis |
| RHOBTB1 | 1.7298 | 3.4910 | 1.0130 | 5.00E−05 | GTPase involved with actin skeleton |
| L1CAM | 17.3307 | 37.0653 | 1.0967 | 5.00E−05 | Cell adhesion, migration in drug resistant cancers |
| PCSK9 | 4.3111 | 9.2437 | 1.1004 | 5.00E−05 | Cholesterol homeostasis |
| OAS3 | 1.3659 | 2.9771 | 1.1240 | 1.50E−04 | RNA synthesis inhibitor |
| LOX | 4.5291 | 10.5536 | 1.2204 | 5.00E−05 | Crosslinks ECM |
| DOK7 | 8.9338 | 21.3466 | 1.2567 | 5.00E−05 | Neuromuscular interface |
| ID3 | 17.8285 | 43.0758 | 1.2727 | 5.00E−05 | Inhibitor of bHLH binding |
| LEPREL1 | 8.2163 | 21.0238 | 1.3555 | 5.00E−05 | Collagen assembly and linkage |
| CAPN6 | 2.0987 | 5.5978 | 1.4153 | 5.00E−05 | May inhibit apoptosis, promote angiogenesis |
| FN1 | 225.0440 | 620.2980 | 1.4628 | 1.50E−04 | Fibronectin |
| COL12A1 | 22.0742 | 61.1653 | 1.4704 | 5.00E−05 | Collagen 12 alpha 1 |
| AMIGO2 | 1.3070 | 3.9771 | 1.6055 | 5.00E−05 | Cell-cell communication, neg regulator of apoptosis |
| GALNT3 | 0.3538 | 1.1292 | 1.6743 | 1.50E−04 | Oligosaccharide biosynthesis |
| COL4A4 | 1.2217 | 4.2168 | 1.7873 | 5.00E−05 | Collagen alpha 4 |
| HOXA3 | 0.3283 | 1.1875 | 1.8548 | 5.00E−05 | Developmental transcription factor - angiogensis and patterning |
| ATOH8 | 0.2612 | 0.9560 | 1.8718 | 5.00E−05 | bHLH developmental TF |
| GDF6 | 0.4460 | 1.8793 | 2.0753 | 5.00E−05 | Bone development - BMP signal responsive |
| PXDNL | 0.5750 | 2.4422 | 2.0866 | 5.00E−05 | Oxidative stress responsive endonuclease |
| MIR1909, REXO1 | 12.5434 | 53.5919 | 2.0951 | 5.00E−05 | MicroRNA |
| MIR5193, UBA7 | 0.7722 | 5.1067 | 2.7254 | 5.00E−05 | MicroRNA |
| BDKRB1 | 0.4423 | 3.1086 | 2.8133 | 5.00E−05 | Receptor for bradykinin, an inflammatory vasodilator |

TABLE 1-continued

List of differentially expressed genes output by RNA-seq analysis. Genes
are ordered according to log2 fold change. Negative $\log_2$ indicates
that gene is downregulated when TWIST1 is overexpressed and positive
$\log_2$ indicates that gene is upregulated when TWIST1 is overexpressed.

| Gene | Expression | | Log2 Fold Change | p-Value | Function |
| --- | --- | --- | --- | --- | --- |
| | sh492 | TWIST | | | |
| LINC00452 | 0.2309 | 2.0640 | 3.1600 | 5.00E−05 | Noncoding RNA |
| TWIST1 | 20.2035 | 209.0290 | 3.3710 | 5.00E−05 | EMT, angiogenesis, metastasis, stem cell phenotype |
| MIR4324, SLC6A16 | 0.7451 | 21.5666 | 4.8552 | 5.00E−05 | MicroRNA |
| VIP | 0.0000 | 0.4792 | N/A | 5.00E−05 | Vasodilator, also involved in survival |
| DPT | 0.0000 | 1.2281 | N/A | 5.00E−05 | ECM protein involved with TGFb |
| KCNA10 | 0.0000 | 0.2646 | N/A | 5.00E−05 | Voltage gated potassium channel |

Figure 23A:
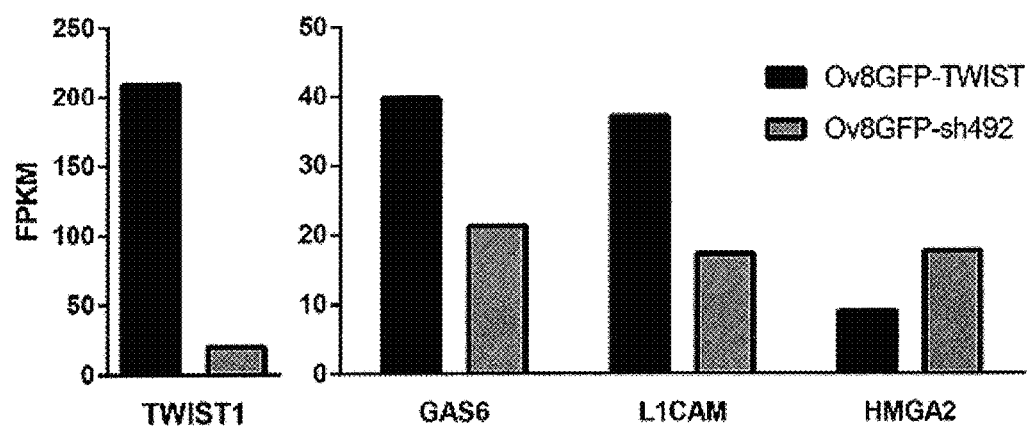
FIGS. 23A to 23C. RNA sequencing reveals differential expression of GAS6, L1CAM, and HMGA2.
Figure 23B:
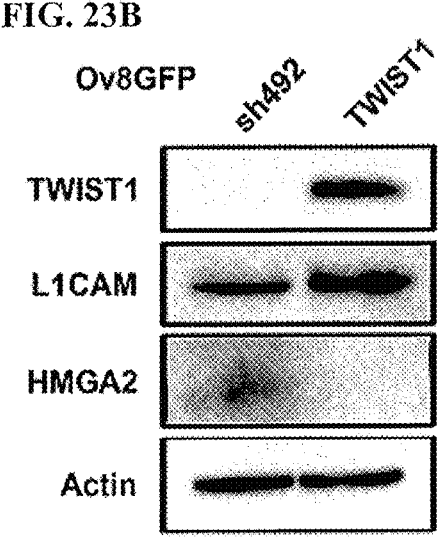
Figure 23C:
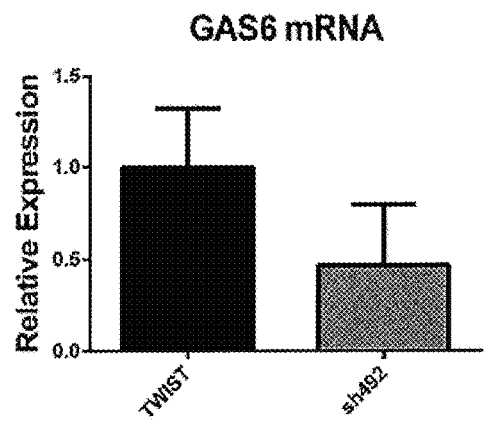
Figure 29:
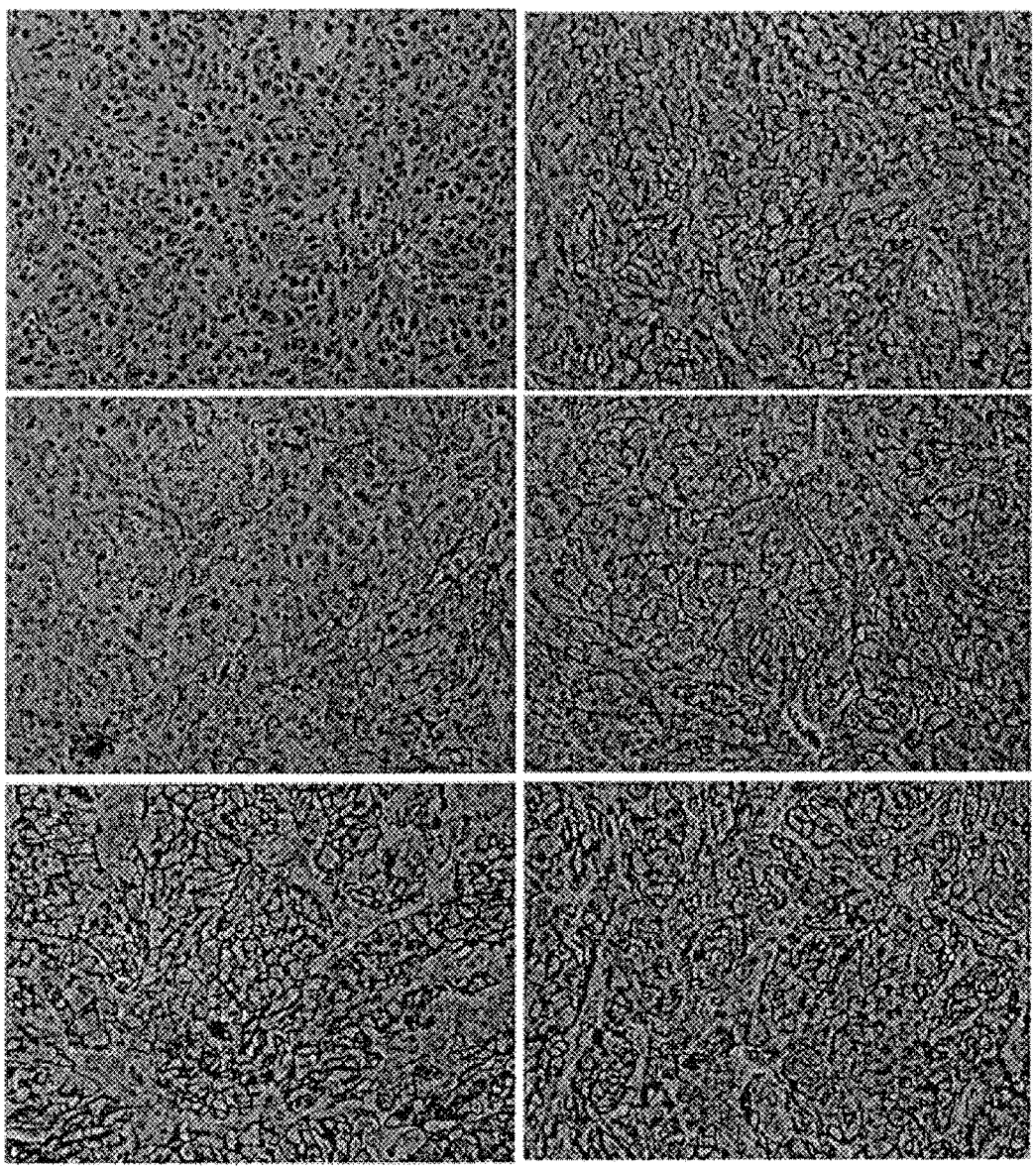
FIG. 29. Representative images of Ov8GFP-sh492 and Ov8GFP-TWIST1 tumours from mice, immunostained for cell surface L1CAM. Ov8GFP-sh492 tumours were heterogeneous, with different tumour masses displaying no staining (top), light staining (middle) or dark staining. TWIST1 tumours were stained more uniformly and were typically dark with some lighter areas.
Figure 30:
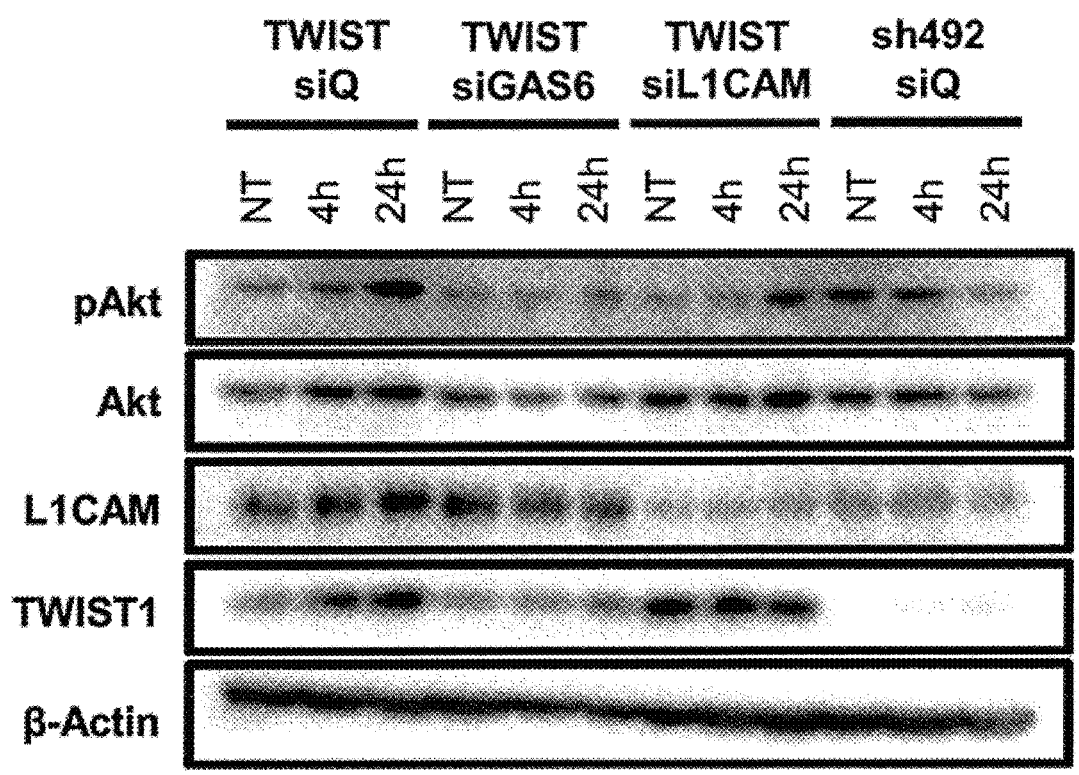
FIG. 30. Example of raw data for western blot graphs shown in FIGS. 25A-25C. Increases in total and activated Akt can be seen for TWIST siQ, and is abrogated in other conditions tested. Absence of L1CAM and TWIST1 can be observed in siL1CAM and sh492 lanes, respectively. All samples normalized to actin (bottom).
Figure 31A:
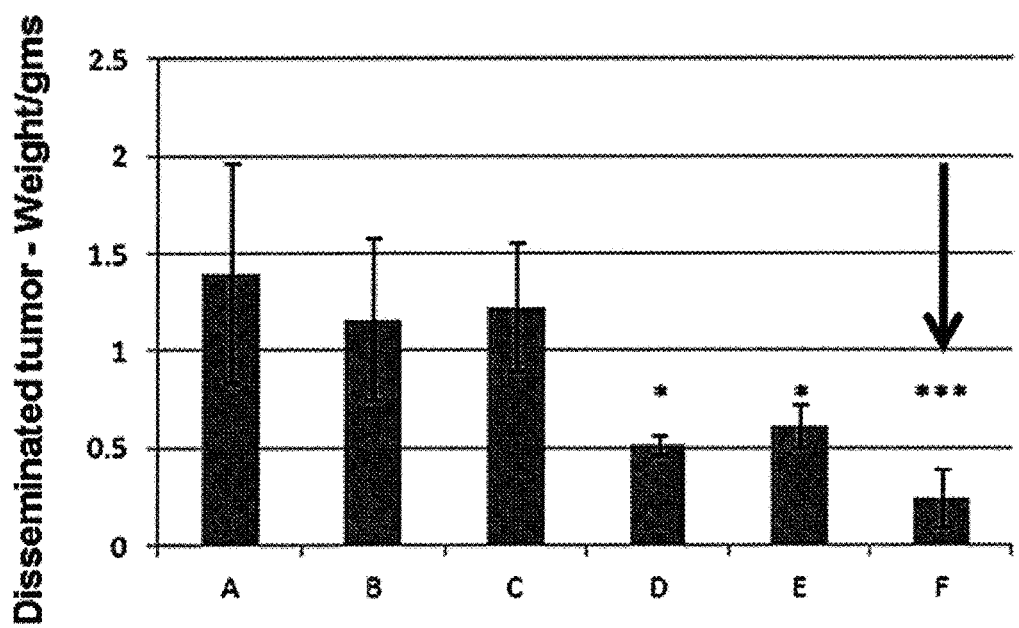
FIGS. 31A to 31B. NSG female mice were injected with OVCAR8-ip cells intraperitoneally, grown for two weeks, then treated IP with siRNA against Twist1 or control (siQ), and one week later treated with cisplatin IP. Results indicate significant reduction in weights of metastases when siRNA-TWIST was combined with cisplatin.
Figure 31B:
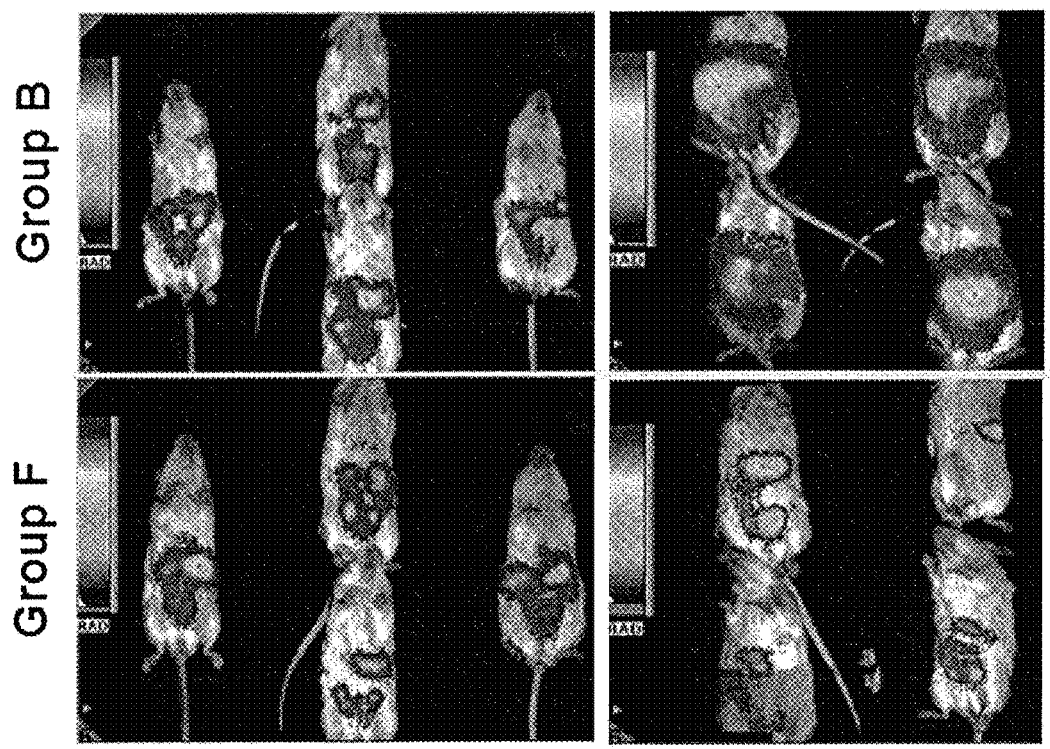
Figure 32:
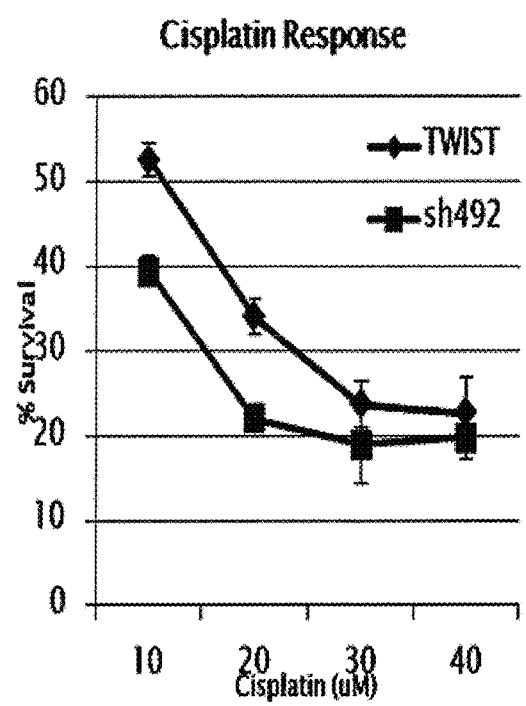
FIG. 32. Ovcar8-GFP-ffluc cells were stably transfected with CMV-driven shRNA against TWIST1 (sh492) or CMV-driven TWIST1. Ovcar8 TWIST cells treated for three days with cisplatin showed markedly higher survival compared to Ovcar8 sh492 cells, demonstrating a role for TWIST1 in cisplatin resistance.
Figure 33:
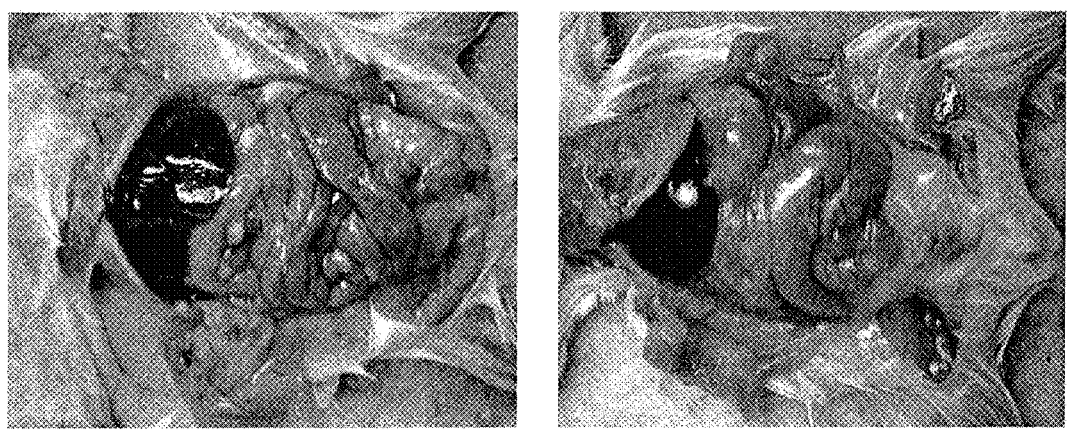
FIG. 33. Ovcar8-GFP-ffluc cells stably transfected with sh492 or TWIST were injected IP into NSG mice. After 7 weeks, TWIST expressing cells had given rise to carcinomatosis throughout the abdomen, whereas sh492 cells did not. sh492 cells also gave rise to smaller masses in the ovary.
Figure 34:
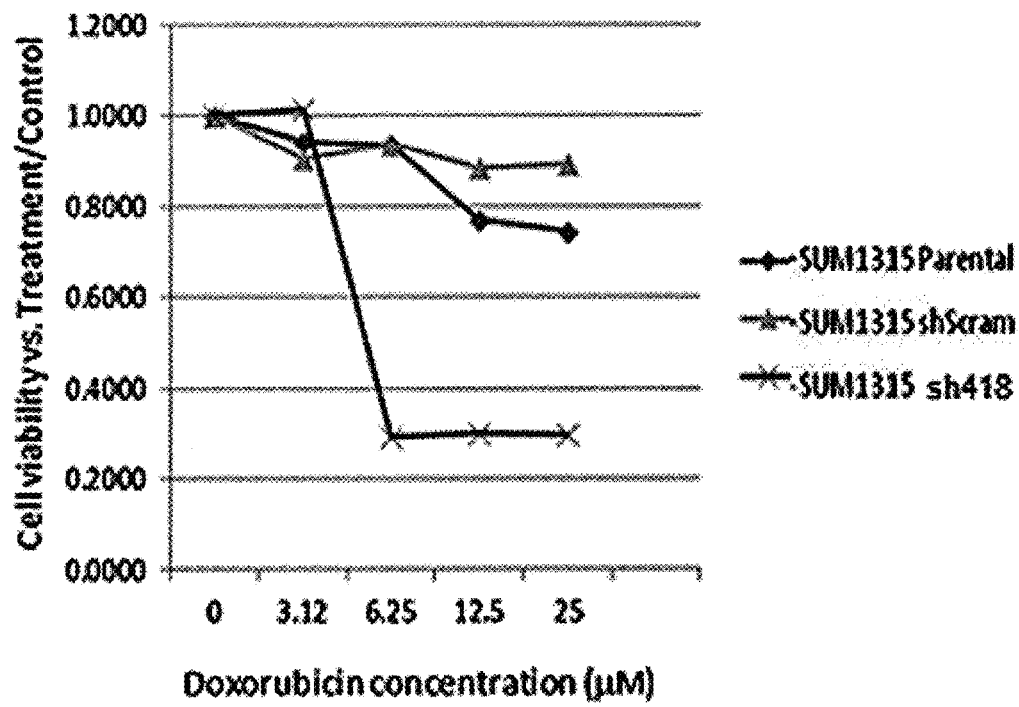
FIG. 34. Human SUM1315 cells become more sensitive to doxorubicin (top) and paclitaxel (bottom) treatment in vitro upon knockdown of TWIST, in this case by stable transfection with shRNA targeting TWIST (sh418). sh418 includes SEQ ID NO: 1 of anti-TWIST siRNA, and is used for establishing stable cell lines using adenoviral transduction.
Figure 34:
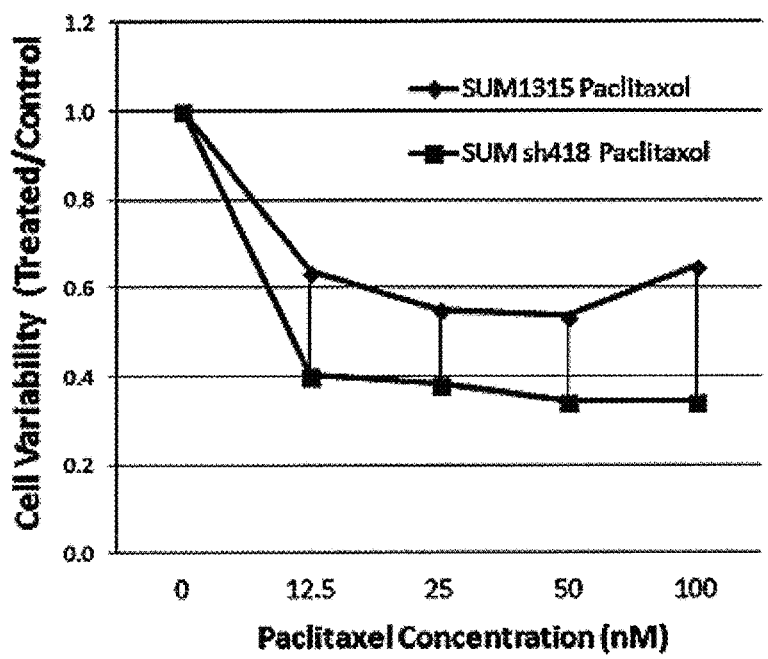
Figure 35:
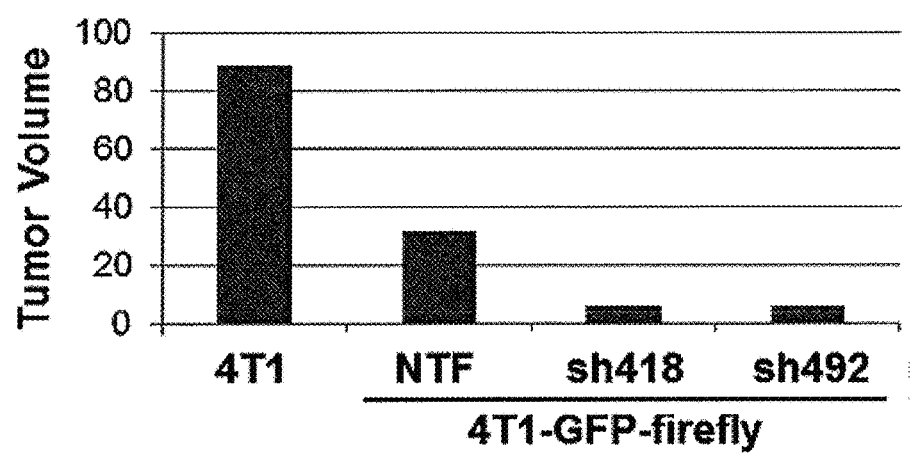
FIG. 35. Stable transfection of shRNA targeting TWIST led to reduced tumor volume in the 4T1 syngeneic mouse tumor in Balb/C mice (n=4). MSN transfection of 4T1 cells demonstrates knockdown of TWIST at one week post transfection in vitro.
Figure 35:
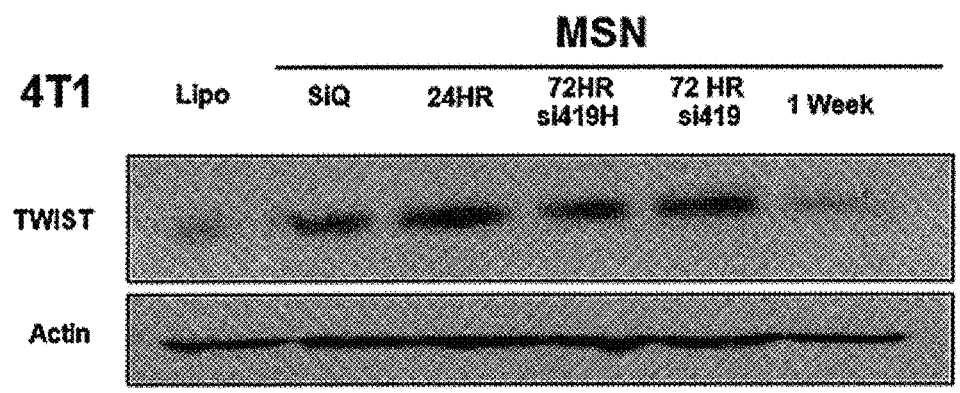

As we were focused on the role of TWIST1 in drug resistance, we did not study any gene whose known function related only to development or cell migration. On the contrary, on the basis of their function in regulating cell survival, cell proliferation, and DNA repair, we selected GAS6, L1CAM, and HMGA2 for further analysis. GAS6 and L1CAM were upregulated approximately two fold in Ov8GFP-TWIST1 cells, while HMGA2 was upregulated two fold in Ov8GFP-sh492 (FIG. 23A). We further verified that these genes were differentially expressed in our two cell lines. Western blot analysis confirmed that L1CAM was elevated and HMGA2 reduced in Ov8GFP-TWIST1 cells, as compared to Ov8GFP-sh492 (FIG. 23B). Because GAS6 is secreted from cells, its expression was confirmed by qRT-PCR rather than western. Despite variability in expression in both Ov8GFP-TWIST1 and —sh492 cells, TWIST1 expressing cells had two-fold higher levels of GAS6 mRNA on average (FIG. 23C). We also found that tumours from mice given Ov8GFP-TWIST1 cells showed uniform IHC staining for L1CAM. Tumours from sh492 mice were heterogeneous, with areas in which staining was entirely absent (FIG. 29).

Figure 24A:
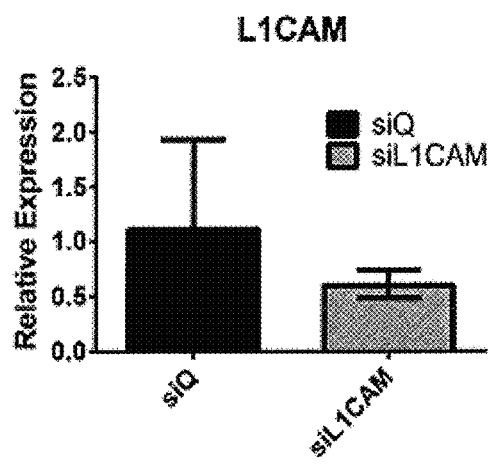
FIGS. 24A to 24F. Knockdown of GAS6 or L1CAM reverses drug resistance.
Figure 24B:
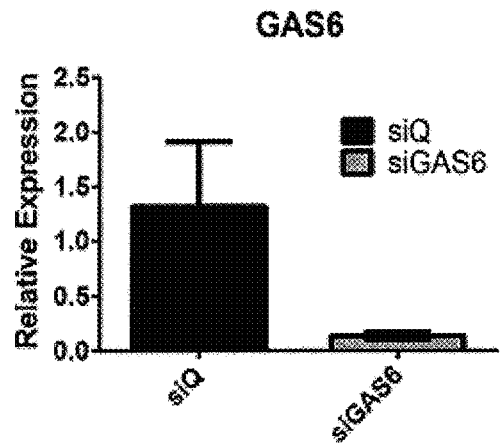
Figure 24C:
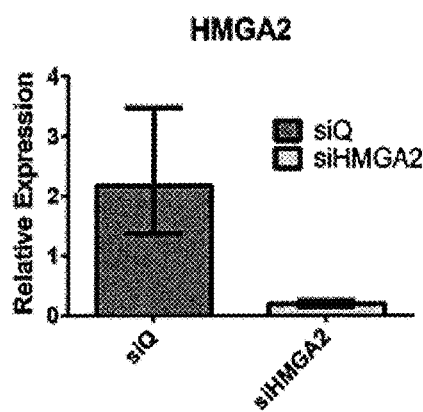
Figure 24D:
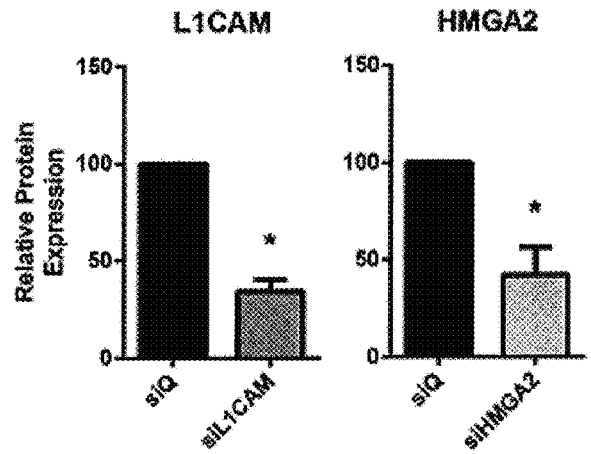

We next knocked down each of these three genes to observe their individual effects on TWIST1-driven cell survival. qRT-PCR showed that siRNA against L1CAM and GAS6 produced 46% and 90% knockdown of their target mRNAs, respectively, in Ov8GFP-TWIST1 cells compared to non-targeting control siRNA (siQ) (FIGS. 24A-24B). An siRNA pool against HMGA2 reduced HMGA2 mRNA levels by 91% on average in Ov8GFP-sh492 cells (FIG. 24C). Knockdown of L1CAM and HMGA2 by their respective siRNA sequences was also confirmed at the protein level via western blot (FIG. 24D).

Figure 24E:
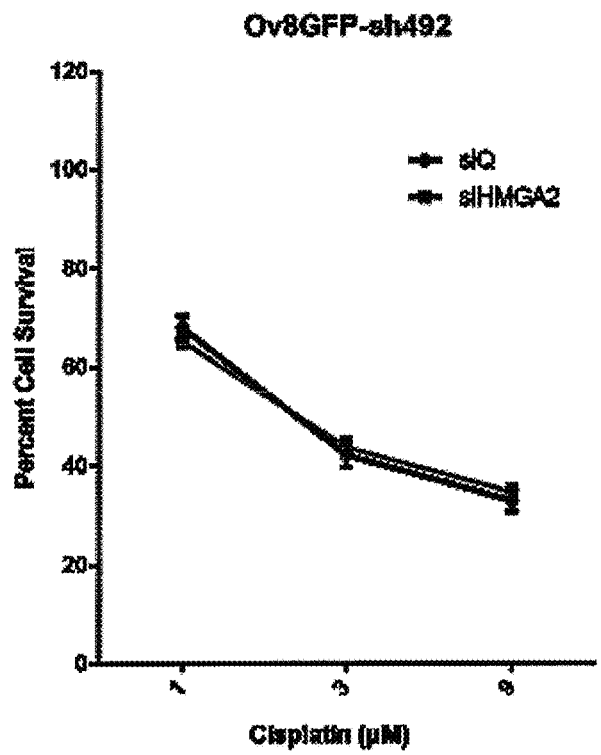

HMGA2 knockdown does not confer cisplatin resistance. As HMGA2 is a negative regulator of ERCC1[26], we hypothesized that knockdown of HMGA2 might upregulate the DNA repair pathway responsible for the repair of the DNA crosslinks caused by cisplatin. Thus, we expected that HMGA2 knockdown cells would show enhanced cisplatin resistance. However, an SRB cell survival assay showed that HMGA2 knockdown had no impact on the proportion of Ov8GFP-sh492 cells able to survive cisplatin treatment (FIG. 24E). This may be due to the redundancy of DNA repair pathways or the compensatory activation of ERCC1 by additional factors; however, further studies are needed to determine if this is truly the case.

Figure 24F:
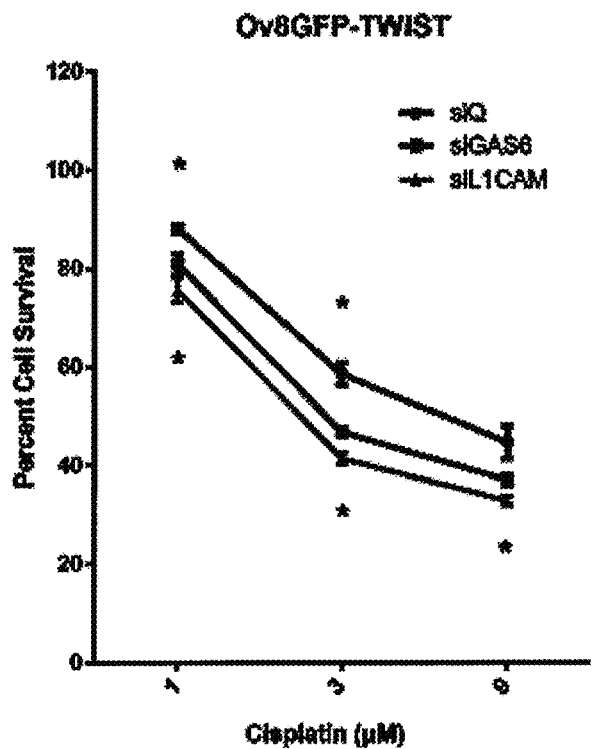

Knockdown of GAS6 or L1CAM sensitizes cells to cisplatin. We also hypothesized that knockdown of GAS6 or L1CAM might sensitize cells to cisplatin due to abrogated survival signalling downstream from these factors. In order to test this hypothesis, we performed an SRB assay on Ov8GFP-TWIST1 cells treated with siQ or siRNA pools against GAS6 or L1CAM. We found that knockdown of either gene was able to sensitize cells to cisplatin, with L1CAM knockdown reducing cell survival by up to 20% (FIG. 24F).

TWIST1, GAS6, and L1CAM upregulate expression and phosphorylation of Akt in response to cisplatin. Given that both GAS6 and L1CAM have been linked to Akt signalling[27,28], and that TWIST2-mediated activation of Akt has been previously implicated in acquired cisplatin resistance[22], we hypothesized that Akt may also be a key factor downstream from TWIST1, GAS6, and L1CAM. We also hypothesized that knockdown of GAS6 or L1CAM in TWIST1 overexpressing cells could inhibit upregulation and activation of Akt.

Figures 25A, 25B:
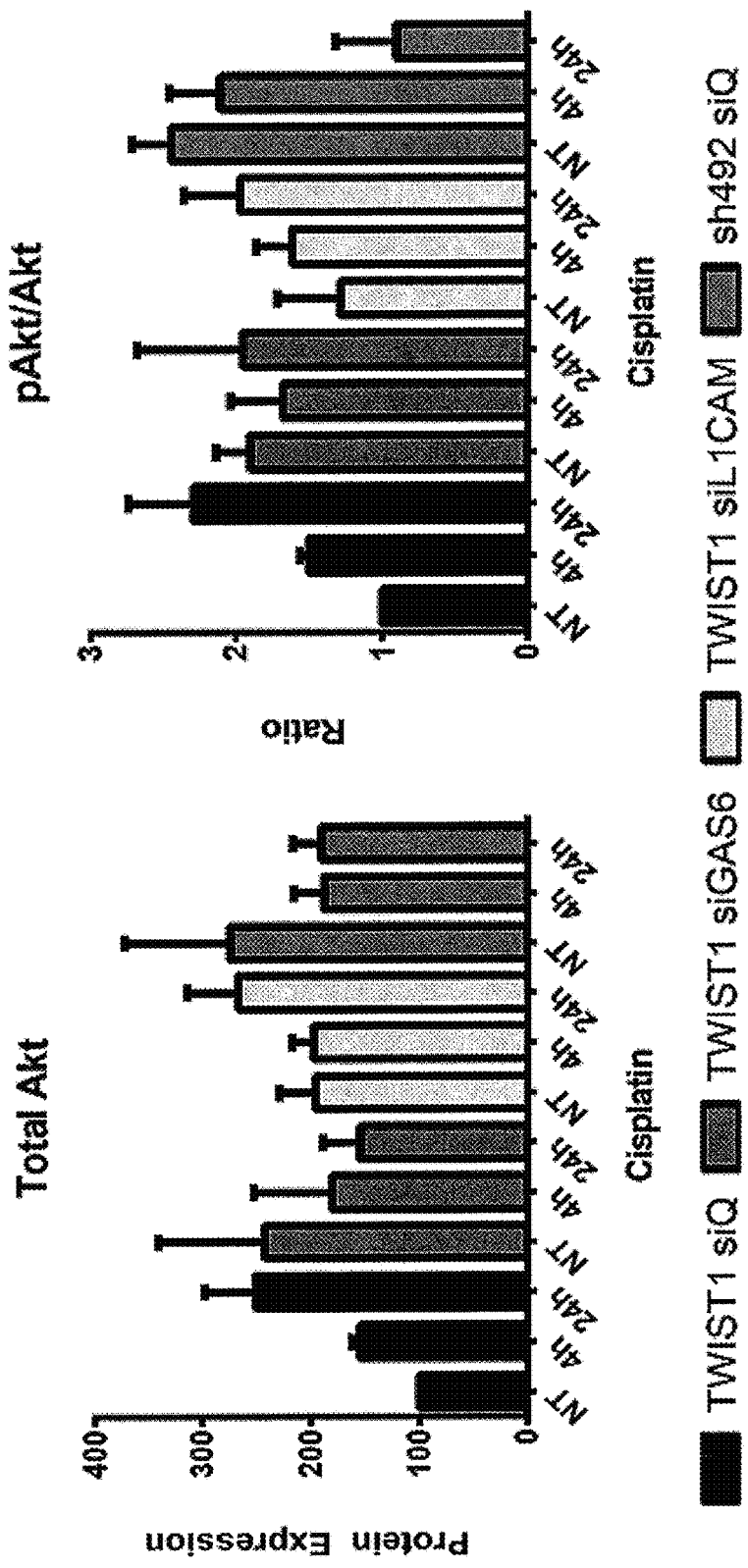
FIGS. 25A to 25D. TWIST1, GAS6, and L1CAM expression lead to upregulation of Akt signalling following cisplatin treatment.
Figure 25C:
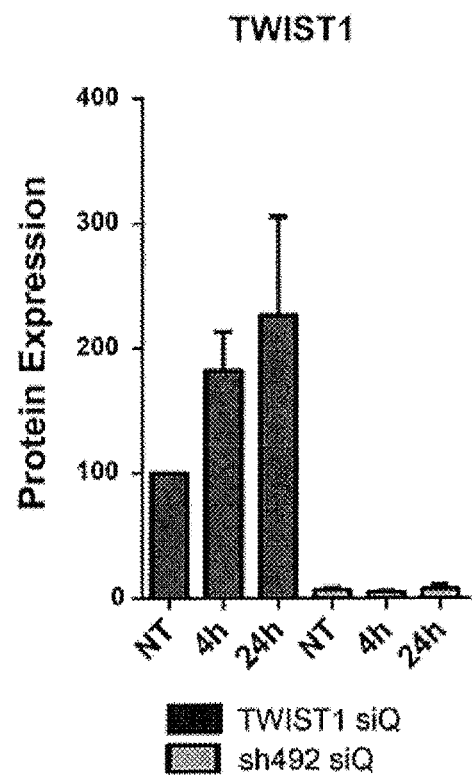

Following treatment of cells with siQ control siRNA or pooled siRNAs against GAS6 or L1CAM, western blotting of total Akt showed that while Ov8GFP-TWIST1 cells have lower initial Akt expression compared to OvGFP-sh492, continued exposure to 5 µM cisplatin led to a 150% increase in Akt levels in Ov8GFP-TWIST1 cells over the course of 24 hr (FIG. 25A). In Ov8GFP-sh492 cells, total Akt levels remain relatively constant over 24 hr of cisplatin exposure (FIG. 25A). Interestingly, the proportion of Akt in its active form (i.e. phosphorylated at Ser 473) increases 128% over the course of 24 hr in Ov8GFP-TWIST1 cells, even when normalized to total Akt expression at each time point (FIG. 25B). Conversely, OvGFP-sh492 cells show a 63% reduction in phosphorylated Akt over the same 24 hr period (FIG. 25B). The pattern of Akt activation in these cell lines mirrors the activation of TWIST1 itself in Ov8GFP-TWIST1 cells over 24 hours of cisplatin treatment, which is absent in sh492 cells (FIG. 25C).

Western blotting also revealed that knockdown of either GAS6 or L1CAM could partially prevent Akt upregulation, as It resulted in largely constant Akt levels over time (FIG. 25A). Similarly, knockdown of either GAS6 or L1CAM produced levels of Akt phosphorylation intermediate between those seen in Ov8GFP-TWIST1 and OvGFP-sh492 cells treated with siQ control. GAS6 knockdown kept the proportion of active Akt relatively constant, while loss of L1CAM led to increasing Akt activation at each time point, but only 53% over 24 hr, as compared to 128% for siQ treated Ov8GFP-TWIST1 cells (FIG. 25B).

Figure 25D:
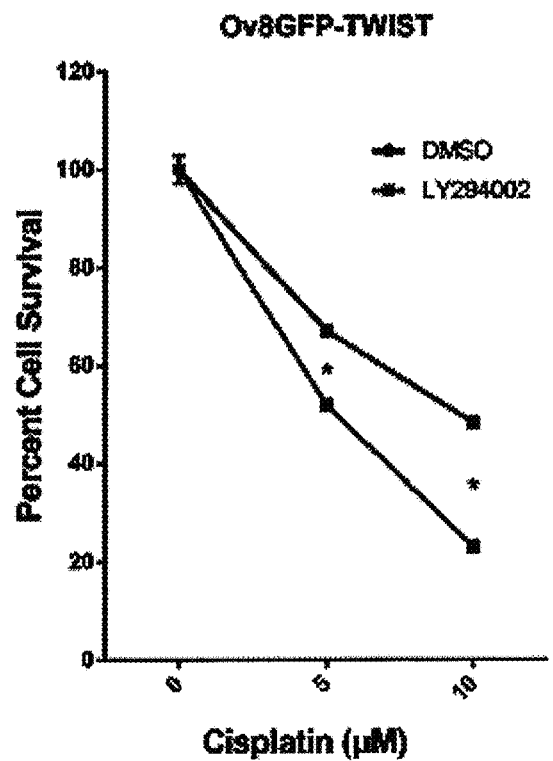

Inhibition of Akt activation sensitizes cells to cisplatin. In order to confirm that Akt mediates cisplatin resistance downstream of TWIST1 in our system, we treated Ov8GFP- TWIST1 cells with either cisplatin alone, or cisplatin plus the PI3K inhibitor LY294002, which prevents the phosphorylation of Akt by PI3K. Cells treated with the combination exhibited 15% greater cell death at 5 µM cisplatin and 25% greater cell death at 10 µM, compared to those treated with cisplatin alone, confirming that loss of Akt activation leads to cisplatin sensitivity in our model (FIG. 25D). This link between TWIST1 and Akt function, combined with the tumour engraftment data presented in FIGS. 22A-22D, suggests that TWIST1-mediated cisplatin resistance may be a part of an overall increase in cell growth and proliferation signalling.

Discussion.

Epithelial ovarian cancer is characterized by tumours that are widely disseminated throughout the peritoneal cavities of patients and that have a high tendency for recurrence. Both of these unwanted phenotypes are made possible by the presence of cancer stem cells. As these cells are quiescent, drugs such as paclitaxel and cisplatin that target rapidly proliferating cells have little efficacy. Unfortunately once the bulk of the tumour mass has been eliminated by surgery and chemotherapy, CSCs drive cancer recurrence by re-entering the cell cycle and differentiating. We have previously shown that during this process of re-entry, the CSCs lose expression of CD44 and MyD88 and acquire mesenchymal characteristics[5,13] due to the persistence of TWIST1 protein.

A growing body of studies link TWIST1 to many cancer processes outside of its traditionally studied roles in cell migration and metastasis. This current study examines additional cancer phenotypic impacts of TWIST1 in the context of differentiated EOC cells. We sought to determine the role TWIST1 plays in the acquisition of drug resistance in recurrent tumour cells. Prior studies have linked TWIST1 and the related protein TWIST2 to drug resistance in multiple tumour types, including ovarian, but the specific mechanism by which TWIST1 drives resistance in EOC is not well understood. To elucidate this mechanism, we created a pair of cell lines in the Ovcar8 background which differed in expression of TWIST1. We then employed SRB cell survival assays and IncuCyte cell growth studies to monitor the effects of TWIST1 and its target genes, providing both a static and dynamic measurement of cell proliferation, and using assays well suited to the Ovcar8 line.

In our EOC model, we found that sustained TWIST1 overexpression in EOC cells with a mesenchymal phenotype led to enhanced cell survival and proliferation, both in the in vivo tumour engraftment assays and in the presence of cisplatin in vitro (FIGS. 22A-22D). RNA-sequencing analysis of TWIST1-overexpressing and TWIST1-knockdown cells revealed 51 significantly differentially expressed genes. As expected given TWIST1's well documented role in modulating cell migration and cell-extracellular matrix interactions, several of the genes identified related to these processes (Tab S1). However, a number of genes also related to cell survival and proliferation signalling. Of these, we selected GAS6, L1CAM, and HMGA2 for further study. We verified differential expression of these genes in our Ov8GFP-TWIST1 and —sh492 cell lines (FIGS. 23A-23B), and validated a pool of siRNAs against each (FIGS. 24A-24F). HMGA2 has previously been linked to TWIST1, but in metastatic breast cancer, in which TWIST1 and HMGA2 are both targets of microRNA miR-33b[29]. HMGA2 is a negative regulator of the nucleotide excision repair (NER) protein ERCC1, which is involved in the repair of platinum-induced DNA crosslinks[18,26]. We therefore hypothesized that knockdown of HMGA2 would allow for cisplatin-induced upregulation of NER as previously reported[18], and that HMGA2 knockdown in Ov8GFP-sh492 cells would give rise to cisplatin resistance. However, we found that loss of HMGA2 did not have any effect on cell survival in response to cisplatin (FIG. 24E). This may be due to redundancy of DNA repair signalling, as multiple factors will likely regulate NER, including Gli1[18], and knockdown of a single regulatory protein may not be sufficient to impact NER function.

We next determined the impact of GAS6 and L1CAM in the response to cisplatin. We found that knockdown of either gene was able to sensitize TWIST1 overexpressing cells to cisplatin (FIG. 24F).

We next sought to determine if TWIST1, along with GAS6 and L1CAM, was acting via Akt. We found that expression of TWIST1 led to an increase in Akt expression and activation over the course of 24 hr of cisplatin treatment in vitro, while TWIST1 knockdown led to a decrease in Akt activity (FIGS. 25A-25B). Knockdown of GAS6 or L1CAM partially prevented Akt activation in Ov8GFP-TWIST1 cells (FIGS. 25A-25B). As expected, inhibition of Akt activation by the PI3K inhibitor LY294002 substantially sensitized OV8GFP-TWIST1 cells to cisplatin, even after correcting for the anti-proliferative effects of the inhibitor (FIG. 25C).

Figure 26:
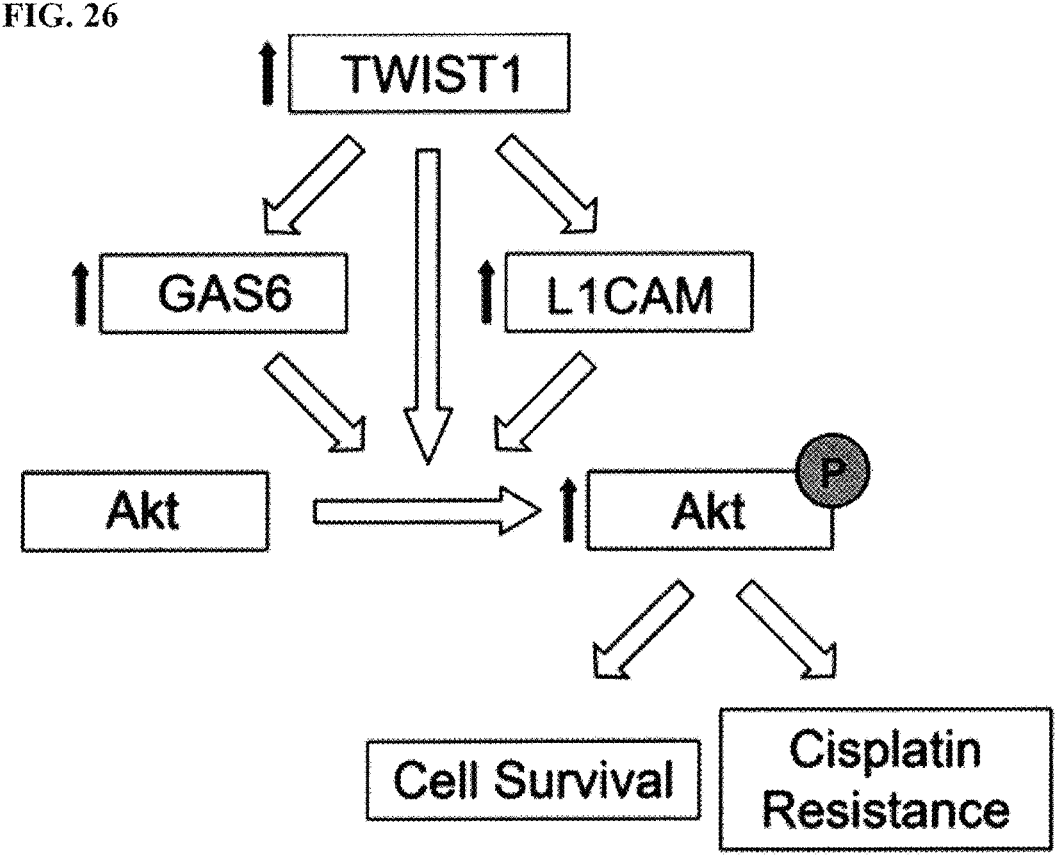
FIG. 26. Schematic representation of our proposed model. TWIST1 upregulates expression of GAS6 and L1CAM. TWIST1, GAS6, and L1CAM facilitate phosphorylation and activation of Akt, leading to increased proliferation. This in turn results in cisplatin resistance and greater tumour cell engraftment in vivo.

Taken together, our data suggest a model where TWIST1-mediated upregulation of L1CAM expression and GAS6/Axl signalling lead to higher throughput of Akt signalling. This increase in proliferation gives rise to greater cell survival during tumour cell engraftment assays. This model also suggests that TWIST1-mediated drug resistance is a result of increased proliferation, rather than direct inhibition of cisplatin activity by DNA repair proteins or upregulation of drug efflux, for example by downregulation of HMGA2 in TWIST1 overexpressing cells (FIG. 26). This is the first study on the role TWIST1 plays in acquired drug resistance in ovarian cancer.

Methods.

Cell lines. Ovcar8 cells were obtained from ATCC, and engineered to stably express a GFP-firefly luciferase fusion protein, using the CMV-p:EGFP-ffluc pHIV7 vector (a gift from Christine Brown at City of Hope, as has been described previously[23]) to make the Ov8GFP line. The TWIST1 gene or an shRNA targeting TWIST1, sh492, were cloned into the pCI-Neo vector from Promega (Madison, Wis.). Empty pCI-Neo vector was used as control. Lipofectamine 2000 (Thermo Fisher, Waltham, Mass.) was used to transfect the vectors into Ov8GFP cells and cells were treated with 0.8 mg/mL G418 (Sigma Aldrich, St. Louis, Mo.) to select for stable plasmid integration. Resulting cell lines are herein referred to as Ov8GFP-TWIST1, Ov8GFP-pCI-Neo, and Ov8GFP-sh492. sh492 includes an anti-TWIST siRNA sequence of 5'-GCGACGAGCUGGACUCCAA-3' (SEQ ID NO: 34), and is used for establishing stable cell lines using adenoviral transduction.

Cell culture. All cells were grown in RPMI 1640 medium (Genesee Scientific, San Diego, Calif.) supplemented with 10% foetal bovine serum and 1% penicillin/streptomycin, in a tissue culture incubator maintaining 37° C., 5% $CO_2$, 90% humidity. Ov8GFP-TWIST1, Ov8GFP-pCI-Neo, and Ov8GFP-sh492 were grown in 0.4 mg/mL G418 to maintain TWIST1/pCI-Neo/sh492 plasmid integration. Cells were passaged every 2-4 days. Confluent cells were washed with PBS, detached with 0.25% trypsin-EDTA (Genesee Scientific), and transferred to new dishes.

Gene knockdown. Small interfering RNA (siRNA) was used for knockdown of GAS6, L1CAM, and HMGA2. Lipofectamine 2000 was used to transfect siRNA into cells in OptiMEM medium (Thermo Fisher). Medium was changed to normal medium after 4 hr or on the following day. Non-targeting control siRNA, siQ, was AllStars Negative Control siRNA from Qiagen (Valencia, Calif.). Pooled siRNAs against GAS6, L1CAM, and HMGA2 were obtained from Santa Cruz Biotechnology (Dallas, Tex,; item numbers sc-35450, sc-43172, and sc-37994, respectively).

qRT-PCR. Total RNA was isolated from pelleted cells using the RNeasy Plus kit from Qiagen according to the manufacturer's protocol. cDNA was reverse transcribed using the iScript cDNA Synthesis kit from Bio-Rad (Hercules, Calif.). Real time PCR was run either on an Applied Biosystems StepOnePlus machine using SYBR Select Master Mix (Life Technologies, Carlsbad, Calif.) or on a Bio-Rad iQ5 system using SYBR master mix from Kapa Biosystems (Wilmington, Mass.) in 20 µL reactions, in triplicate. Melt curves were obtained for all reactions. β-Actin was used as the endogenous control. Expression was determined using the $2^{-\Delta\Delta Ct}$ method. Primers used were:

```
GAS6 Fwd
                                    (SEQ ID NO: 26)
5'-CTGCATCAACAAGTATGGGTCTCCGT-3',

GAS6 Rev
                                    (SEQ ID NO: 27)
5'-GTTCTCCTGGCTGCATTCGTTGA-3',

HMGA2 Fwd
                                    (SEQ ID NO: 28)
5'-CAGCGCCTCAGAAGAGAGGACG-3',

HMGA2 Rev
                                    (SEQ ID NO: 29)
5'-CCGTTTTTCTCCAGTGGCTTCTGCT-3',

L1CAM Fwd
                                    (SEQ ID NO: 30)
5'-GCAGCAAGGGCGGCAAATACTCA-3',

L1CAM Rev
                                    (SEQ ID NO: 31)
5'-CTTGATGTCCCCGTTGAGCGAT-3',

β-Actin Fwd
                                    (SEQ ID NO: 32)
5'-CCGCAAAGACCTGTACGCCAAC-3', β-Actin Rev
                                    (SEQ ID NO: 33)
5'-CCAGGGCAGTGATCTCCTTCTG-3'.
```

Western blotting. Cells were pelleted and washed once with phosphate buffered saline (PBS), then lysed in RIPA buffer. Protein concentration was determined using a BCA assay (Thermo Fisher). Equal masses of protein were run on 4% stacking, 10% resolving polyacrylamide gels, and then transferred to PVDF membrane (GE Healthcare Bio-Sciences, Pittsburgh, Pa.) using the Trans-Blot SD Semi-Dry Transfer Cell (Bio-Rad). Membranes were blocked in dry milk dissolved in PBS with shaking for 1 hr at room temperature or overnight at 4° C. 3% BSA was used for blocking prior to select pAkt blots to reduce background signal. Primary and secondary antibodies were diluted as indicated below in 5% dry milk in PBS with 0.1-0.2% Tween-20. Incubation was performed at room temperature for one hr or overnight at 4° C. for primary, and at room temperature for one hr for secondary. Each antibody incubation was followed by five 5 min washes in PBS with 0.1% Tween-20. FemtoGlow HRP substrate (Michigan Diagnostics, Royal Oak, Mich.) and the Pxi4 chemiluminescent imager (Syngene, Frederick, Md.) were used to acquire digital images. ECL 2 (Thermo Fisher) and Blue Devil Film (Genesee Scientific) were used to acquire film images. FemtoGlow was diluted 6-fold in water for imaging of actin bands. Membranes were stripped using Restore Western Blot Stripping Buffer (Thermo Fisher), rinsed twice in PBS, and the process was repeated for each protein tested. Antibodies used were TWIST1 (TWIST 2c1a, Santa Cruz Biotechnology sc-81417, 1:500), β-Actin (Sigma Aldrich A1978, 1:5,000), Phospho Akt (Ser473) (Cell Signaling Technology 9271, 1:1000), Akt (Cell Signaling Technology 9272, 1:1000), HMGA2 (HMGI-C 242106a, Santa Cruz Biotechnology sc-130024, 1:500), and L1CAM (NCAM-L1 D5, Santa Cruz Biotechnology sc-374046, 1:1000). For select digital and film westerns, bands were quantified using GeneTools software from Syngene or Image Studio Lite from LiCor (Lincoln, NB), respectively, and normalized to β-Actin.

RNA sequencing analysis. RNA from biological replicates of Ov8GFP-sh492 and —TWIST1 was obtained as described for qRT-PCR. Quality was verified by absorption spectra using a NanoDrop 1000 spectrophotometer (Thermo Fisher). RNA sequencing of two samples per cell line was performed in triplicate using the Illumina Hi-seq platform by the Integrative Genomics Core facility at City of Hope. Data were analysed using the online Galaxy platform. Pipeline consisted of the following algorithms: Tophat (for alignment of sequenced fragments to the human genome), Cufflinks (for the assembly of aligned fragments into transcripts), Cuffmerge (for the merging of several Cufflink assemblies into a single file), and Cuffdiff (for determining differences in expression using a two-sample t-test). Ingenuity Pathway Analysis was used to build relationships and potential links to canonical signalling pathways based on previously published publications.

Sulphorhodamine B assays. Cells were plated at 5,000 per well in normal medium in 96 well plates (100 µL/well), n=6 per drug concentration, per condition. Cells were allowed to adhere overnight, and then cisplatin was added. Cisplatin was prepared at 2× concentration in 100 µL normal medium, and then added to cells to yield 200 µL at 1×. Following 3 day incubation with cisplatin, medium was removed and cells were fixed with 10% trichloroacetic acid (TCA, 100 µL/well) at 4° C. for 1 hr. TCA was then removed and wells were rinsed with 200 µl water and allowed to air dry 10 min. Next, cells were incubated in 0.4% sulphorhodamine B (SRB) in 1% acetic acid at room temperature for 15 minutes, after which dye was discarded and wells were rinsed 3-4 times with 1% acetic acid until wash showed no further colour. Plates were air dried and excess SRB adhered to the walls of the wells was removed with a cotton swab. Finally, SRB was solubilized in 10 mM Tris base (200 µL/well) and absorbance was measured at 570 nm on a SpectraMax Plus plate reader (Molecular Devices, Sunnyvale, Calif.). Readings for each condition were normalized to untreated wells from the same condition. Cisplatin concentrations were adjusted to fit experimental demands. Lipofectamine transfected cells were more sensitive to cisplatin, thus a reduced cisplatin concentration across all conditions was required. For Akt studies, the PI3K inhibitor LY294002 was used to inhibit Akt activation (FIGS. 25A-25D), and was obtained from Cell Signaling Technology (Danvers, Mass.).

Real-time monitoring of cell confluence. In order to determine the effects of TWIST1 expression and cisplatin on the kinetics of cell growth, the IncuCyte ZOOM system (Essen BioScience, Ann Arbor, Mich.) was used as described previously [4,50,51]. Briefly, Ov8GFP-TWIST1 and Ov8GFP-sh492 cells were plated at 4,000 cells/well of a 96 well plate in quadruplicate overnight in normal medium. The following day, they were treated with 0.2 or 2 µM cisplatin (Teva Pharmaceuticals USA, Sellersville, Pa.) and imaged every two hr for 74 hr to determine cell confluence over time.

In vivo tumorigenesis study. To determine the effects of TWIST1 on tumour engraftment and proliferation in vivo, 3.2 million Ov8GFP-TWIST1 or Ov8GFP-sh492 cells were injected intraperitoneally into female NOD.Cg-Prkdc$^{scid}$Il2rg$^{tm1Wjl}$/SzJ (NSG) mice (The Jackson Laboratory, Bar Harbor, Me.). Four mice received each cell line. Tumours were allowed to grow for seven weeks, and tumour burden was evaluated at necropsy. Images were taken of mice, and peritoneal organs were harvested and fixed in formalin for evaluation by a board-certified veterinary pathologist with over 30 years of experience in pathology of experimental mouse models. Evaluation was done without knowledge of treatment group or experimental design. The amount of tumour growth within a tissue was graded using a progressive, semi-quantitative, tiered scale of 0-4, where 0=no tumour growth and 4=major portion of the tissue occupied by tumour growth. This study was conducted in accordance with a protocol approved by the Institutional Animal Care and Use Committee at the City of Hope Beckman Research Institute (Protocol no. 15002, approved 22 Mar. 2016). Care was taken to minimise the number of mice used and the pain and discomfort of mice in the study. Results of pathology analyses are tabulated in Table 2 following.

TABLE 2

Results of pathology analysis. TWIST1 overexpressing cells gave rise to large ovarian tumours in 4/4 mice, whereas sh492 expressing cells gave rise to tumours in 2/4 mice, with only one matching the severity seen in TWIST1 tumours (1/4 sh492 scored 4 vs 4/4 TWIST1 scored 4). 3/4 mice receiving TWIST1-expressing cells developed a metastatic lesion in their liver or spleen, compared to 1/4 sh492 mice. A, B, C, and D refer to individual mice. "0" reflects a tumour score of 0, while "—" denotes no sample collected.

| Mouse | Tumour Score | | | | |
|---|---|---|---|---|---|
| | Liver | Uterus | Ovary | Kidney | Spleen |
| sh492 A | 0 | 0 | 4 | 0 | 0 |
| sh492 B | 1 | 0 | 2 | 0 | 0 |
| sh492 C | 0 | 0 | 0 | 0 | 0 |
| sh492 D | 0 | — | — | 0 | 0 |
| TWIST1 A | 0 | 0 | 4 | 0 | 0 |
| TWIST1 B | 0 | — | 4 | 0 | 1 |
| TWIST1 C | 1 | 0 | 4 | 0 | 0 |
| TWIST1 D | 1 | 0 | 4 | 0 | 0 |

Statistics. Statistical significance between conditions for cytotoxicity assays was determined by a series of unpaired Student t-tests comparing TWIST1 to sh492 or comparing gene knockdown conditions to siQ control. The Holm-Sidak method was used to correct for multiple comparisons. No assumption of equal standard deviation was made. Knockdown of HMGA2 and L1CAM protein was analysed using paired, one-sided t-tests. All calculations were done using Prism 6 (GraphPad Software, La Jolla, Calif.). Asterisks denote statistical significance (p <0.05). Exact p-values and error bar parameters are given in figure legends. OneStep qPCR data, RNA-seq output, and slopes of IncuCyte graphs are not open to statistical analysis by our software, and so trends are numerically described in the text for these experiments.

REFERENCES (EXAMPLE 4)

[1] Siegel, R. L., Miller, K. D. & Jemal, A. Cancer statistics, 2016. CA: a cancer journal for clinicians 66, 7-30, doi:10.3322/caac.21332 (2016); [2] Khalil, I., Brewer, M. A., Neyarapally, T. & Runowicz, C. D. The potential of biologic network models in understanding the etiopathogenesis of ovarian cancer. Gynecol Oncol 116, 282-285, doi: 10.1016/j.ygyno.2009.10.085 (2010); [3] Visintin, I. et al. Diagnostic markers for early detection of ovarian cancer. Clin Cancer Res 14, 1065-1072, doi:10.1158/1078-0432.ccr-07-1569 (2008); [4] Alvero, A. B. et al. TRX-E-002-1 Induces c-Jun-Dependent Apoptosis in Ovarian Cancer Stem Cells and Prevents Recurrence In Vivo. Mol Cancer Ther 15, 1279-1290, doi:10.1158/1535-7163.mct-16-0005 (2016); [5] Yin, G. et al. TWISTing stemness, inflammation and proliferation of epithelial ovarian cancer cells through MIR199A2/214. Oncogene 29, 3545-3553, doi:10.1038/onc.2010.111 (2010); [6] Bildsoe, H. et al. Requirement for Twist1 in frontonasal and skull vault development in the mouse embryo. Developmental biology 331, 176-188, doi:10.1016/j.ydbio.2009.04.034 (2009); [7] Simpson, P. Maternal-Zygotic Gene Interactions during Formation of the Dorsoventral Pattern in Drosophila Embryos. Genetics 105, 615-632 (1983); [8] Yang, J. et al. Twist, a master regulator of morphogenesis, plays an essential role in tumor metastasis. Cell 117, 927-939, doi:10.1016/j.cell.2004.06.006 [doi] S0092867404005768 [pii] (2004); [9] Fu, J. et al. The TWIST/Mi2/NuRD protein complex and its essential role in cancer metastasis. Cell Res 21, 275-289, doi:cr2010118 [pii] 10.1038/cr.2010.118 [doi] (2011); [10] Vesuna, F., Lisok, A., Kimble, B. & Raman, V. Twist modulates breast cancer stem cells by transcriptional regulation of CD24 expression. Neoplasia 11, 1318-1328 (2009); [11] Finlay, J. et al. Mesoporous silica nanoparticle delivery of chemically modified siRNA against TWIST1 leads to reduced tumor burden. Nanomedicine: nanotechnology, biology, and medicine 11, 1657-1666, doi:10.1016/j.nano.2015.05.011 (2015); [12] Maestro, R. et al. Twist is a potential oncogene that inhibits apoptosis. Genes Dev 13, 2207-2217 (1999); [13] Yin, G. et al. Constitutive proteasomal degradation of TWIST-1 in epithelial-ovarian cancer stem cells impacts differentiation and metastatic potential. Oncogene 32, 39-49, doi:onc201233 [pii] 10.1038/onc.2012.33 [doi] (2013); [14] Chappell, N. P. et al. Mitochondrial proteomic analysis of cisplatin resistance in ovarian cancer. J Proteome Res 11, 4605-4614, doi:10.1021/pr300403d [doi] (2012); [15] Wang, Y. et al. Autocrine production of interleukin-8 confers cisplatin and paclitaxel resistance in ovarian cancer cells. Cytokine 56, 365-375, doi:S1043-4666(11)00182-7 [pii] 10.1016/j.cyto.2011.06.005 [doi] (2011); [16] Laios, A. et al. Pre-Treatment of Platinum Resistant Ovarian Cancer Cells with an MMP-9/MMP-2 Inhibitor Prior to Cisplatin Enhances Cytotoxicity as Determined by High Content Screening. Int J Mol Sci 14, 2085-2103, doi:ijms14012085 [pii] 10.3390/ijms14012085 [doi] (2013); [17] Villavicencio, E. H. et al. Cooperative E-box regulation of human GLI1 by TWIST and USF. Genesis 32, 247-258 (2002); [18] Kudo, K. et al. Inhibition of Gli1 results in altered c-Jun activation, inhibition of cisplatin-induced upregulation of ERCC1, XPD and XRCC1, and inhibition of platinum-DNA adduct repair. Oncogene 31, 4718-4724, doi:onc2011610 [pii] 10.1038/onc.2011.610 [doi] (2012); [19] Cheng, G. Z. et al. Twist transcriptionally up-regulates AKT2 in breast cancer cells leading to increased migration, invasion, and resistance to paclitaxel. Cancer Res 67, 1979-1987, doi:67/5/1979 [pii] 10.1158/0008-5472.CAN-06-1479 [doi] (2007); [20] Shiota, M. et al. Twist1 and Y-box-binding protein-1 promote malignant potential in bladder cancer cells. BJU international 108, E142-149, doi:10.1111/j.1464-

410X.2010.09810.x (2011); [21] Ahmed, N., Abubaker, K., Findlay, J. & Quinn, M. Epithelial mesenchymal transition and cancer stem cell-like phenotypes facilitate chemoresistance in recurrent ovarian cancer. *Curr Cancer Drug Targets* 10, 268-278 (2010); [22] Wang, T. et al. Twist2 contributes to cisplatin-resistance of ovarian cancer through the AKT/GSK-3beta signaling pathway. *Oncology letters* 7, 1102-1108, doi:10.3892/ol.2014.1816 (2014); [23] Brown, C. E. et al. Recognition and killing of brain tumor stem-like initiating cells by CD8+cytolytic T cells. *Cancer Res* 69, 8886-8893, doi:10.1158/0008-5472.can-09-2687 (2009); [24] Finlay, J. et al. RNA-based TWIST1 inhibition via dendrimer complex to reduce breast cancer cell metastasis. *BioMed research international* 2015, 382745, doi:10.1155/2015/382745 (2015); [25] Li, S. et al. TWIST1 associates with NF-kappaB subunit RELA via carboxyl-terminal WR domain to promote cell autonomous invasion through IL8 production. *BMC Biol* 10, 73, doi:1741-7007-10-73 [pii] 10.1186/1741-7007-10-73 [doi] (2012); [26] Borrmann, L. et al. High mobility group A2 protein and its derivatives bind a specific region of the promoter of DNA repair gene ERCC1 and modulate its activity. *Nucleic Acids Res* 31, 6841-6851 (2003); [27] Lee, W. P., Wen, Y., Varnum, B. & Hung, M. C. Akt is required for Axl-Gas6 signaling to protect cells from E1A-mediated apoptosis. *Oncogene* 21, 329-336, doi:10.1038/sj.onc.1205066 (2002); [28] Jung, J. et al. The cell adhesion molecule L1 promotes gallbladder carcinoma progression in vitro and in vivo. *Oncol Rep* 25, 945-952, doi:10.3892/or.2011.1181 (2011); [29] Lin, Y. et al. MicroRNA-33b Inhibits Breast Cancer Metastasis by Targeting HMGA2, SALL4 and Twist1. *Scientific reports* 5, 9995, doi:10.1038/srep09995 (2015); [30] Demarchi, F., Verardo, R., Varnum, B., Brancolini, C. & Schneider, C. Gas6 anti-apoptotic signaling requires NF-kappa B activation. *J Biol Chem* 276, 31738-31744, doi:10.1074/jbc.M104457200 (2001); [31] Melaragno, M. G. et al. Gas6 inhibits apoptosis in vascular smooth muscle: role of Axl kinase and Akt. *Journal of molecular and cellular cardiology* 37, 881-887, doi:10.1016/j.yjmcc.2004.06.018 (2004); [32] Gjerdrum, C. et al. Axl is an essential epithelial-to-mesenchymal transition-induced regulator of breast cancer metastasis and patient survival. *Proc Natl Acad Sci USA* 107, 1124-1129, doi:10.1073/pnas.0909333107 (2010); [33] Sharif, M. N. et al. Twist mediates suppression of inflammation by type I IFNs and Axl. *The Journal of experimental medicine* 203, 1891-1901, doi:10.1084/jem.20051725 (2006); [34] Buehler, M. et al. Meta-analysis of microarray data identifies GAS6 expression as an independent predictor of poor survival in ovarian cancer. *BioMed research international* 2013, 238284, doi:10.1155/2013/238284 (2013); [35] Rankin, E. B. et al. AXL is an essential factor and therapeutic target for metastatic ovarian cancer. *Cancer Res* 70, 7570-7579, doi:10.1158/0008-5472.can-10-1267 (2010); [36] Kiefel, H. et al. EMT-associated up-regulation of L1CAM provides insights into L1CAM-mediated integrin signalling and NF-kappaB activation. *Carcinogenesis* 33, 1919-1929, doi:10.1093/carcin/bgs220 (2012); [37] Weinspach, D. et al. Role of L1 cell adhesion molecule (L1CAM) in the metastatic cascade: promotion of dissemination, colonization, and metastatic growth. *Clin Exp Metastasis* 31, 87-100, doi:10.1007/s10585-013-9613-6 (2014); [38] Lund, K. et al. Slug-dependent upregulation of L1CAM is responsible for the increased invasion potential of pancreatic cancer cells following long-term 5-FU treatment. *PloS one* 10, e0123684, doi:10.1371/journal.pone.0123684 (2015); [39] Pfeifer, M. et al. L1CAM expression in endometrial carcinomas is regulated by usage of two different promoter regions. *BMC molecular biology* 11, 64, doi:10.1186/1471-2199-11-64 (2010); [40] Schafer, H. et al. TGF-beta1-dependent L1CAM expression has an essential role in macrophage-induced apoptosis resistance and cell migration of human intestinal epithelial cells. *Oncogene* 32, 180-189, doi:10.1038/onc.2012.44 (2013); [41] Sebens Muerkoster, S. et al. Drug-induced expression of the cellular adhesion molecule L1CAM confers anti-apoptotic protection and chemoresistance in pancreatic ductal adenocarcinoma cells. *Oncogene* 26, 2759-2768, doi:10.1038/sj.onc.1210076 (2007); [42] Stoeck, A. et al. L1-CAM in a membrane-bound or soluble form augments protection from apoptosis in ovarian carcinoma cells. *Gynecol Oncol* 104, 461-469, doi:10.1016/j.ygyno.2006.08.038 (2007); [43] Dellinger, T. H. et al. L1CAM is an independent predictor of poor survival in endometrial cancer—An analysis of The Cancer Genome Atlas (TCGA). *Gynecol Oncol* 141, 336-340, doi:10.1016/j.ygyno.2016.02.003 (2016); [44] Abdel Azim, S. et al. Clinical impact of L1CAM expression measured on the transcriptome level in ovarian cancer. *Oncotarget, doi:* 10.18632/oncotarget.9291 (2016); [45] Hahne, J. C. et al. Downregulation of AKT reverses platinum resistance of human ovarian cancers in vitro. *Oncol Rep* 28, 2023-2028, doi:10.3892/or.2012.2041 [doi] (2012); [46] Domcke, S., Sinha, R., Levine, D. A., Sander, C. & Schultz, N. Evaluating cell lines as tumour models by comparison of genomic profiles. *Nat Commun* 4, 2126, doi:10.1038/ncomms3126 (2013); [47] Imani, S., Hosseinifard, H., Cheng, J., Wei, C. & Fu, J. Prognostic Value of EMT-inducing Transcription Factors (EMT-TFs) in Metastatic Breast Cancer: A Systematic Review and Meta-analysis. *Scientific reports* 6, 28587, doi:10.1038/srep28587 (2016); [48] Yoon, N. A. et al. Tristetraprolin suppresses the EMT through the down-regulation of Twist1 and Snail in cancer cells. *Oncotarget* 7, 8931-8943, doi:10.18632/oncotarget.7094 (2016); [49] Cao, H. H. et al. Inhibition of the STAT3 signaling pathway contributes to apigenin-mediated anti-metastatic effect in melanoma. *Scientific reports* 6, 21731, doi:10.1038/srep21731 (2016); [50] Artymovich, K. & Appledorn, D. M. A multiplexed method for kinetic measurements of apoptosis and proliferation using live-content imaging. *Methods Mol Biol* 1219, 35-42, doi:10.1007/978-1-4939-1661-0_4 (2015); [51] Craveiro, V. et al. Phenotypic modifications in ovarian cancer stem cells following Paclitaxel treatment. *Cancer medicine* 2, 751-762, doi:10.1002/cam4.115 (2013).

What is claimed is:

1. A pharmaceutical composition comprising a nanoparticle and a pharmaceutically acceptable excipient, wherein the nanoparticle comprises a tumor targeting moiety on an outer surface thereof and a TWIST signaling inhibitor, wherein the tumor targeting moiety is hyaluronic acid (HA).

2. The composition of claim 1, wherein said TWIST signaling inhibitor is an siRNA inhibitor or a small molecule inhibitor.

3. The composition of claim 2, wherein said siRNA inhibitor is an anti-TWIST siRNA.

4. The composition of claim 3, wherein said anti-TWIST siRNA comprises a sequence of any one of SEQ ID Nos: 1-10, or a complementary sequence thereof.

5. The composition of claim 4, wherein said sequence comprises a nucleic acid modification.

6. The composition of claim 5, wherein said nucleic acid modification is a 2'-O-methyluracil or inverted abasic deoxyribose.

7. The composition of claim 5, wherein said modification is a 2-thio-deoxyuracil.

8. The composition of claim 1, wherein said nanoparticle is a mesoporous silica nanoparticle (MSN).

9. The composition of claim 8, wherein said MSN is bound to polyethyleneimine (PEI).

10. The composition of claim 1, wherein said nanoparticle is a dendrimer-based nanoparticle.

11. The composition of claim 10, wherein said dendrimer-based nanoparticle is YTZ3-15.

12. A method of reversing resistance to an anti-cancer drug in a subject, the method comprising administering a therapeutically effective amount of the pharmaceutical composition of claim 1 to said subject.

13. A method of treating cancer in a subject in need thereof, the method comprising administering to said subject a therapeutically effective amount of the pharmaceutical composition of claim 1.

14. A method of inhibiting metastasis in a subject in need thereof, the method comprising administering to said subject a therapeutically effective amount of the pharmaceutical composition of claim 1.

15. The pharmaceutical composition of claim 1, further comprising a chemotherapeutic agent.

16. The pharmaceutical composition of claim 15, wherein the chemotherapeutic agent is an antibiotic.

17. The pharmaceutical composition of claim 16, wherein the antibiotic is doxorubicin.

18. The pharmaceutical composition of claim 15, wherein the chemotherapeutic agent is an alkylating agent.

19. The pharmaceutical composition of claim 18, wherein the alkylating agent is cisplatin.

20. The pharmaceutical composition of claim 18, wherein the alkylating agent is carboplatin.

21. The pharmaceutical composition of claim 15, wherein the chemotherapeutic agent is a topoisomerase poison drug.

22. The pharmaceutical composition of claim 21, wherein the topoisomerase poison drug is camptothecin.

23. The pharmaceutical composition of claim 15, wherein the chemotherapeutic agent is a microtubule targeting drug.

24. The pharmaceutical composition of claim 23, wherein the microtubule targeting drug is a taxane.

25. The pharmaceutical composition of claim 24, wherein the taxane is paclitaxel.

26. A pharmaceutical composition comprising a chemotherapeutic agent, a nanoparticle, and a pharmaceutically acceptable excipient, wherein the nanoparticle comprises a TWIST signaling inhibitor, and wherein the chemotherapeutic agent is an antibiotic, an alkylating agent, or a microtubule targeting drug.

* * * * *

UNITED STATES PATENT AND TRADEMARK OFFICE
CERTIFICATE OF CORRECTION

PATENT NO.       : 10,519,442 B2
APPLICATION NO.  : 15/430372
DATED            : December 31, 2019
INVENTOR(S)      : Carlotta A. Glackin et al.

Page 1 of 1

It is certified that error appears in the above-identified patent and that said Letters Patent is hereby corrected as shown below:

In the Specification

At Column 1, Lines 18-21, change the following:
"This invention was made with Government support under Grant Numbers P30CA33572 and CA133697 awarded by the National Institutes of Health. The Government has certain rights in the invention."

To:
--This invention was made with government support under CA133697 and P30 CA033572 awarded by the National Institutes of Health. The government has certain rights in the invention.--

Signed and Sealed this
Twenty-sixth Day of September, 2023

Katherine Kelly Vidal
*Director of the United States Patent and Trademark Office*